(12) United States Patent
Yao et al.

(10) Patent No.: US 9,493,449 B2
(45) Date of Patent: Nov. 15, 2016

(54) CARBOXAMIDE DERIVATIVES AND USE THEREOF

(71) Applicant: Purdue Pharma L.P., Stamford, CT (US)

(72) Inventors: Jiangchao Yao, Princeton, NJ (US); Laykea Tafesse, Robbinsville, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/776,527

(22) PCT Filed: Mar. 13, 2014

(86) PCT No.: PCT/US2014/025644
§ 371 (c)(1),
(2) Date: Sep. 14, 2015

(87) PCT Pub. No.: WO2014/151393
PCT Pub. Date: Sep. 25, 2014

(65) Prior Publication Data
US 2016/0031873 A1  Feb. 4, 2016

Related U.S. Application Data

(60) Provisional application No. 61/789,502, filed on Mar. 15, 2013.

(51) Int. Cl.
| | | |
|---|---|---|
| *C07D 401/12* | (2006.01) | |
| *C07D 417/12* | (2006.01) | |
| *C07D 403/12* | (2006.01) | |
| *C07D 213/79* | (2006.01) | |
| *C07D 213/81* | (2006.01) | |
| *C07D 403/06* | (2006.01) | |
| *C07D 403/14* | (2006.01) | |
| *C07D 405/04* | (2006.01) | |
| *C07D 239/26* | (2006.01) | |
| *C07D 239/28* | (2006.01) | |
| *C07D 409/12* | (2006.01) | |
| *C07D 213/30* | (2006.01) | |

(52) U.S. Cl.
CPC ........... *C07D 417/12* (2013.01); *C07D 213/30* (2013.01); *C07D 213/79* (2013.01); *C07D 213/81* (2013.01); *C07D 239/26* (2013.01); *C07D 239/28* (2013.01); *C07D 401/12* (2013.01); *C07D 403/06* (2013.01); *C07D 403/12* (2013.01); *C07D 403/14* (2013.01); *C07D 405/04* (2013.01); *C07D 409/12* (2013.01)

(58) Field of Classification Search
CPC  C07D 417/12; C07D 213/30; C07D 213/79; C07D 213/81; C07D 239/26; C07D 239/28; C07D 401/12; C07D 403/06; C07D 403/12; C07D 403/14; C07D 405/04; C07D 409/12
See application file for complete search history.

(56) References Cited

U.S. PATENT DOCUMENTS

| | | |
|---|---|---|
| 6,281,211 B1 | 8/2001 | Cai et al. |
| 6,335,354 B2 | 1/2002 | Hogenkamp |
| 6,414,011 B1 | 7/2002 | Hogenkamp et al. |
| 6,479,484 B1 | 11/2002 | Lan et al. |
| 6,500,825 B2 | 12/2002 | Lan et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,737,418 B2 | 5/2004 | Hogenkamp et al. |
| 6,770,661 B2 | 8/2004 | Shao et al. |
| 6,867,210 B2 | 3/2005 | Hogenkamp et al. |
| 6,919,363 B2 | 7/2005 | Hogenkamp et al. |
| 7,022,714 B2 | 4/2006 | Sun et al. |
| 7,078,426 B2 | 7/2006 | Hogenkamp et al. |
| 7,091,210 B2 | 8/2006 | Lan et al. |
| 7,105,549 B2* | 9/2006 | Shao .................... C07D 213/81 514/341 |
| 7,169,782 B2 | 1/2007 | Sun et al. |
| 7,229,993 B2 | 6/2007 | Goehring et al. |

(Continued)

FOREIGN PATENT DOCUMENTS

| | | |
|---|---|---|
| EP | 1992361 | 5/2012 |
| KR | 2014-0107897 | 9/2014 |

(Continued)

OTHER PUBLICATIONS

Anger et al., Medicinal Chemistry of Neuronal Voltage-Gated Sodium Channel Blockers, J Med. Chem. 44:115-137 (2001).
Baker et al., Involvement of Na+ Channels in Pain Pathways, TRENDS in Pharmacological Sciences 22:27-31 (2001).
Black et al., Sensory Neuron-Specific Sodium Channel SNS is Abnormally Expressed in the Brains of Mice with Experimental Allergic Encephalomyelitis and Humans with Multiple Sclerosis, Proc. Natl. Acad. Sci. USA 97:11598-115602 (2000).
Brown et al., Neuroprotective Properties of Lifarizine Compared with Those of Other Agents in a Mouse Model of Focal Cerebral Ischaemia, British J. Pharmacol. 115:1425-1432 (1995).
Cannon, Spectrum of Sodium Channel Disturbances in the Nondystrophic Myotonias and Periodic Paralyses, Kidney Int. 57:772-779 (2000).

(Continued)

*Primary Examiner* — Alexander R Pagano
(74) *Attorney, Agent, or Firm* — Purdue Pharma L.P.; Alan L. Koller; Weiying Yang

(57) ABSTRACT

The present disclosure provides substituted pyridyl-, pyrimidinyl-, pyrazinyl-, pyridazinyl-, and triazinyl-based carboxamides of Formula I-A: $R^{10}$ Z-HET-E I-A and the pharmaceutically acceptable salts and solvates thereof, wherein Z, HET, $R^{10}$ and E are defined as set forth in the specification. The present disclosure is also directed to the use of compounds of Formula I-A to treat a disorder responsive to the blockade of sodium channels. Compounds of the present disclosure are especially useful for treating pain.

I-A

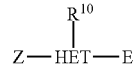

17 Claims, No Drawings

(56) References Cited

U.S. PATENT DOCUMENTS

| | | | |
|---|---|---|---|
| 7,393,872 B2 | 7/2008 | Lan | |
| 7,541,465 B2 | 6/2009 | Lan et al. | |
| 7,579,367 B2* | 8/2009 | Shao | C07D 213/81 514/355 |
| 7,872,127 B2 | 1/2011 | Lan et al. | |
| 7,943,643 B2* | 5/2011 | Shao | C07D 213/81 514/355 |
| 8,242,145 B2* | 8/2012 | Hutchinson | C07D 207/38 514/351 |
| 8,426,431 B2 | 4/2013 | Lan et al. | |
| 9,045,435 B2 | 6/2015 | Goehring et al. | |
| 9,056,832 B2* | 6/2015 | Ni | C07D 213/30 |
| 9,120,752 B2 | 9/2015 | Kyle et al. | |
| 9,120,786 B2 | 9/2015 | Tadesse et al. | |
| 9,133,131 B2 | 9/2015 | Shao | |
| 9,163,008 B2 | 10/2015 | Ni et al. | |
| 9,168,255 B2 | 10/2015 | Goehring et al. | |
| 9,181,185 B2 | 11/2015 | Yao | |
| 9,206,127 B2 | 12/2015 | Tafesse et al. | |
| 9,212,139 B2 | 12/2015 | Kyle et al. | |
| 9,340,504 B2 | 5/2016 | Park | |
| 2002/0037926 A1 | 3/2002 | Lan | |
| 2003/0055088 A1* | 3/2003 | Shao | C07D 213/81 514/340 |
| 2003/0225080 A1 | 12/2003 | Wang et al. | |
| 2004/0097569 A1 | 5/2004 | Sun et al. | |
| 2004/0152696 A1 | 8/2004 | Sun et al. | |
| 2004/0176364 A1 | 9/2004 | Sun et al. | |
| 2004/0192691 A1* | 9/2004 | Hogenkamp | C07D 213/81 514/242 |
| 2005/0043305 A1* | 2/2005 | Hogenkamp | C07D 213/81 514/241 |
| 2005/0222027 A1 | 10/2005 | Chiang et al. | |
| 2007/0010554 A1* | 1/2007 | Shao | C07D 213/81 514/318 |
| 2007/0088508 A1* | 4/2007 | Childs | A61K 9/145 702/19 |
| 2007/0275950 A1 | 11/2007 | Miyata et al. | |
| 2008/0318932 A1 | 12/2008 | Lan | |
| 2010/0048626 A1* | 2/2010 | Shao | C07D 213/81 514/318 |
| 2011/0098302 A1* | 4/2011 | Hutchinson | C07D 207/38 514/236.8 |
| 2013/0289044 A1 | 10/2013 | Goehring et al. | |
| 2013/0296281 A1 | 11/2013 | Kyle et al. | |
| 2013/0303526 A1 | 11/2013 | Ni et al. | |
| 2013/0303568 A1 | 11/2013 | Lan et al. | |
| 2013/0345211 A1 | 12/2013 | Kyle et al. | |
| 2014/0005212 A1 | 1/2014 | Ni et al. | |
| 2014/0249128 A1 | 9/2014 | Yu et al. | |
| 2014/0288092 A1 | 9/2014 | Yao et al. | |
| 2014/0303139 A1 | 10/2014 | Ni et al. | |
| 2014/0309228 A1 | 10/2014 | Engel | |
| 2015/0045397 A1 | 2/2015 | Tafesse et al. | |
| 2015/0057300 A1 | 2/2015 | Tafesse et al. | |
| 2015/0133500 A1 | 5/2015 | Tafesse et al. | |
| 2015/0141434 A1 | 5/2015 | Park | |
| 2015/0259293 A1 | 9/2015 | Ni et al. | |
| 2015/0284383 A1 | 10/2015 | Lynch et al. | |
| 2015/0335642 A1 | 11/2015 | Shao | |
| 2015/0336974 A1 | 11/2015 | Youngman | |
| 2015/0344465 A1 | 12/2015 | Kyle et al. | |
| 2016/0009659 A1 | 1/2016 | Lockman et al. | |
| 2016/0024022 A1 | 1/2016 | Ni et al. | |
| 2016/0052911 A1 | 2/2016 | Yao | |
| 2016/0145210 A1 | 5/2016 | Tafesse et al. | |

FOREIGN PATENT DOCUMENTS

| | | | |
|---|---|---|---|
| WO | WO-01/68612 | 9/2001 | |
| WO | WO 03022276 A1 * | 3/2003 | C07D 213/81 |
| WO | WO-2004/050857 | 6/2004 | |
| WO | WO-2004-111011 | 12/2004 | |
| WO | WO-2009/148004 | 12/2009 | |
| WO | WO-2010/100475 | 9/2010 | |
| WO | WO-2012/035421 | 3/2012 | |
| WO | WO-2014/016673 | 1/2014 | |
| WO | WO-2014/135955 | 9/2014 | |
| WO | WO-2015/031036 | 3/2015 | |
| WO | WO-2015/094443 | 6/2015 | |
| WO | WO-2015/099841 | 7/2015 | |
| WO | WO-2015/100174 | 7/2015 | |
| WO | WO-2015/112801 | 7/2015 | |

OTHER PUBLICATIONS

Catterall, Common Modes of Drug Action on Na+ Channels: Local Anesthetics, Antiarrhythmics and Anticonvulsants, Trends Pharmacol. Sci. 8:57-65 (1987).

Chahine et al., Voltage-Gated Sodium Channels in Neurological Disorders, CNS & Neurological Disorders—Drug Targets 7:144-158 (2008).

Clare et al., Voltage-Gated Sodium Channels as Therapeutic Targets, Drug Discovery Today 5:506-510 (2000).

Donaldson, Tegretol: A Double Blind Trial in Tinnitus, Laryngol. Otol. 95:947-951 (1981).

Graham et al., Neuroprotective Effects of a Use-Dependent Blocker of Voltage-Dependent Sodium Channels, BW619C89, in Rat Middle Cerebral Artery Occlusion, J. Pharmacol. Exp. Ther. 269:854-859 (1994).

Hubner et al., Ion Channel Disease, Hum. Mol. Genet. 11:2435-2445 (2002).

International Search Report from corresponding PCT Application No. PCT/US2014/025644 mailed on Oct. 27, 2014 with Written Opinion.

Kyle and Llyin, Sodium Channel Blockers, J. Med. Chem. 50:2583-2588 (2007).

Lai et al., The Role of Voltage-Gated Sodium Channels in Neuropathic Pain, Current Opinion in Neurobiology 13:291-297(2003).

Lai et al., Voltage-Gated Sodium Channels and Hyperalgesia, Annu. Rev. Pharmacol. Toxicol. 44:371-397 (2004).

Laird et al., Deficits in Visceral Pain and Referred Hyperalgesia in Nav1.8 (SNS/PN3)-Null Mice, J. Neurosci. 22:8352-8356 (2002).

Liu et al., Mutations in Cardiac Sodium Channels, Am. J. Pharmacogenomics 3:173-179 (2003).

Majumdar, B. et al., An Electrocochleographic Study of the Effects of Lignocaine on Patients with Tinnitus, Clin. Otolaryngol. 8:175-180 (1983).

Meisler and Kearney, Sodium Channel Mutations in Epilepsy and other Neurological Disorders, J. Clin. Invest. 115:2010-2017 (2005).

Moller, Similarities Between Chronic Pain and Tinnitus, Am. J. Otol. 18:577-585 (1997).

Nassar et al., Nociceptor-Specific Gene Deletion Reveals a Major Role for Nav 1.7 (PN1) in Acute and Inflammatory Pain, Proc Natl. Acad. Sci. USA 101:12706-12711 (2004).

Noble, Unraveling the Genetics and Mechanisms of Cardiac Arrhythmia, Proc. Natl. Acad. Sci. USA 99:5755-5756 (2002).

Simpson, et al., Recent Advances in Pharmacological Treatment of Tinnitus, TiP. 20:12-18 (1999).

Srivatsa et al., Mechanisms of Antiarrhythmic Drug Actions and Their Clinical Relevance for Controlling Disorders of Cardiac Rhythm, Curr. Cardiol. Rep. 4:401-410 (2002).

Taylor and Meldrum, Na+ Channels as Targets for Neuroprotective Drugs, Trends Pharmacol. Sci. 16:309-316 (1995).

Toledo-Aral et al., Identification of PN1, a Predominant Voltage-Dependent Sodium Channel Expressed Principally in Peripheral Neurons, Proc. Natl. Acad. Sci. USA 94:1527-1532 (1997).

Tonndorf, The Analogy Between Tinnitus and Pain: A Suggestion for a Physiological Basis of Chronic Tinnitus; Hear. Res. 28:271-275 (1987).

Wood et al., Voltage-Gated Sodium Channels and Pain Pathways, J. Neurobiol., 61:55-71 (2004).

Yogeeswari et al., Ion Channels as Important Targets for Antiepileptic Drug Design, Curr. Drug Target 5:589-602 (2004).

Shao B et al. "Phenoxyphenyl pyridines as Novel State-Dependent, High Potency Sodium Channel Inhibitors", 2004, J Med Chem, vol. 47 (17), pp. 4277-4285.

Office Action mailed Apr. 29, 2016 in corresponding Australian application No. 2014235063.

* cited by examiner

CARBOXAMIDE DERIVATIVES AND USE THEREOF

CROSS-REFERENCE TO RELATED APPLICATIONS

This application is the U.S. national phase, pursuant to 35 U.S.C. §371, of PCT International Application Ser. No. PCT/US2014/025644, filed Mar. 13, 2014, designating the United States and published in English on Sep. 25, 2014 as PCT Publication No. WO 2014/151393 A2, claiming priority to U.S. Provisional Application Ser. No. 61/789,502, filed Mar. 15, 2013. The contents of the afore-mentioned patent applications are incorporated herein by their entirety.

BACKGROUND OF THE INVENTION

1. Field of the Invention

This invention is in the field of medicinal chemistry. The invention provides novel substituted pyridyl-, pyrimidinyl-, pyrazinyl-, pyridazinyl-, and triazinyl-based carboxamides. In certain embodiments, the compounds are used as blockers of one or more voltage-gated sodium ($Na^+$) channels.

2. Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.,* 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and $Na_v$x.x (see TABLE 1, below). The VGSC family has been phylogenetically divided into two subfamilies $Na_v1.x$ (all but SCN6A) and $Na_v2.x$ (SCN6A). The $Na_v1.x$ subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v1.5$, H1) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v1.5$ have found clinical utility in treatment of such disorders (Srivatsa et al., *Curr. Cardiol. Rep.* 4:401-410 (2002)). The remaining TTX-resistant sodium channels, $Na_v1.8$ (SCN10A, PN3, SNS) and $Na_v1.9$ (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v1.8$ has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v1.8$-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
|---|---|---|---|---|---|
| $Na_v1.1$ | SCN1A | CNS/PNS | 10 | Epilepsy | Pain, seizures, neurodegeneration |
| $Na_v1.2$ | SCN2A | CNS | 10 | Epilepsy | Epilepsy, neurodegeneration |
| $Na_v1.3$ | SCN3A | CNS | 15 | — | Pain |
| $Na_v1.4$ | SCN4A | Skeletal muscle | 25 | Myotonia | Myotonia |
| $Na_v1.5$ | SCN5A | Heart muscle | 2,000 | Arrhythmia | Arrhythmia |
| $Na_v1.6$ | SCN8A | CNS/PNS | 6 | — | Pain, movement disorders |
| $Na_v1.7$ | SCN9A | PNS | 25 | Erythermalgia | Pain |
| $Na_v1.8$ | SCN10A | PNS | 50,000 | — | Pain |
| $Na_v1.9$ | SCN11A | PNS | 1,000 | — | Pain |

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v1.7$ plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc. Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenytoin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenytoin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

In one aspect, the present disclosure provides pyridyl-, pyrimidinyl-, pyrazinyl-, pyridazinyl-, and triazinyl-based carboxamides represented by Formulae I, I-A, II, II-A, III, III-A, and IV-VII, below, and the pharmaceutically acceptable salts and solvates thereof, collectively referred to herein as "Compounds of the Disclosure."

In another aspect, the present disclosure provides the use of Compounds of the Disclosure as blockers of one or more sodium ($Na^+$) channels.

In another aspect, the present disclosure provides compounds as synthetic intermediates that can be used to prepare blockers of one or more sodium ($Na^+$) channels.

In another aspect, the present disclosure provides a method for treating a disorder responsive to the blockade of one or more sodium channels in a mammal, comprising administering to the mammal an effective amount of a Compound of the Disclosure.

In another aspect, the present disclosure provides a method for treating pain (e.g., acute pain, chronic pain, which includes but is not limited to, neuropathic pain, postoperative pain, and inflammatory pain, or surgical pain), comprising administering an effective amount of a Compound of the Disclosure to a mammal in need of such treatment. Specifically, the present disclosure provides a method for preemptive or palliative treatment of pain by administering an effective amount of a Compound of the Disclosure to a mammal in need of such treatment.

In another aspect, the present disclosure provides a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, comprising administering an effective amount of a Compound of the Disclosure to a mammal in need of such treatment.

In another aspect, the present disclosure provides a pharmaceutical composition comprising a Compound of the Disclosure and one or more pharmaceutically acceptable carriers.

In another aspect, the present disclosure provides a pharmaceutical composition for treating a disorder responsive to the blockade of sodium ion channels, wherein the pharmaceutical composition comprises an effective amount of a Compound of the Disclosure in a mixture with one or more pharmaceutically acceptable carriers.

In another aspect, the present disclosure provides a method of modulating sodium channels in a mammal, comprising administering to the mammal an effective amount of at least one Compound of the Disclosure.

In another aspect, the present disclosure provides Compounds of the Disclosure for use in treating pain in a mammal, e.g., acute pain, chronic pain, which includes but is not limited to, neuropathic pain, postoperative pain, and inflammatory pain, or surgical pain.

In another aspect, the present disclosure provides Compounds of the Disclosure for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

In another aspect, the present disclosure provides a radiolabeled Compound of the Disclosure and the use of such compounds as radioligands in any appropriately selected competitive binding assays and screening methodologies. Thus, the present disclosure further provides a method for screening a candidate compound for its ability to bind to a sodium channel or sodium channel subunit using a radiolabeled Compound of the Disclosure. In certain embodiments, the compound is radiolabeled with $^3H$, $^{11}C$, or $^{14}C$. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

In another aspect, the present disclosure provides a Compound of the Disclosure for use in the manufacture of a medicament for treating pain in a mammal. In one embodiment, the present disclosure provides the use of a Compound of the Disclosure in the manufacture of a medicament for palliative or preemptive treatment of pain, such as acute pain, chronic pain, or surgical pain.

In another aspect, the present disclosure provides a Compound of the Disclosure for use in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the disclosure is based on the discovery of novel compounds as provided herein. In certain embodiments, the invention provides Compounds of the Disclosure as blockers of sodium (Na$^+$) channels. In other embodiments, the Compounds of the Disclosure are useful for treating disorders responsive to the blockade of sodium ion channels. In one embodiment, the Compounds of the Disclosure are useful for treating pain.

In one embodiment, Compounds of the Disclosure are compounds represented by Formula I-A:

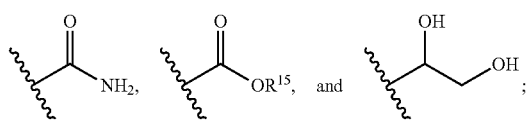

I-A and the pharmaceutically acceptable salts and solvates thereof, wherein:

Z is:

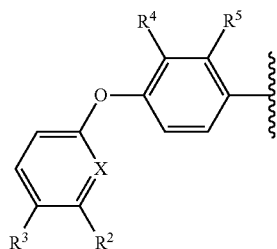

HET is a 6-membered nitrogen-containing heteroaryl, e.g., pyridyl, pyrimidinyl, pyrazinyl, pyridazinyl, or triazinyl;

E is selected from the group consisting of:

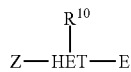

X is selected from the group consisting of N and CR$^1$;
R$^1$ is selected from the group consisting of:
a) hydrogen;
b) optionally substituted heteroaryl;
c) heteroalkyl;
d) (aralkylamino)alkyl
e) optionally-substituted (heterocyclo)alkyl;
f) optionally substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) optionally-substituted (carboxamido)alkyl;
q) (haloalkylamino)alkyl;
r) (hydroxy)(cyano)alkyl;
s) (amino)(cyano)alkyl;
t) (hydroxy)haloalkyl;
u) (heteroarylamino)alkyl;
v) (heteroaryl)alkyl;
w) COR$^{1a}$;
x) SO$_2$NR$^{8a}$R$^{8b}$;
y) COCONR$^{9a}$R$^{9b}$; and z) 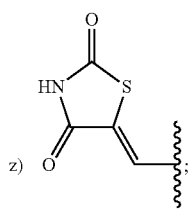

$R^{1a}$ is selected from the group consisting of hydroxy, alkoxy, and $NR^{7a}R^{7b}$;

$R^{7a}$ is selected from the group consisting of:
a) hydrogen;
b) alkyl;
c) hydroxyalkyl;
d) (amino)alkyl;
e) (alkylamino)alkyl;
f) (dialkylamino)alkyl;
g) aryl;
h) (heteroaryl)alkyl; and
i) heteroaryl;

$R^{7b}$ is selected from the group consisting of hydrogen and alkyl; or $R^{7a}$ and $R^{7b}$ are taken together form taken together to form a 3- to 8-membered optionally substituted heterocyclo;

$R^{8a}$ and $R^{8b}$ are each independently selected from the group consisting of hydrogen and alkyl; or $R^{8a}$ and $R^{8b}$ are taken together form taken together to form a 3- to 8-membered optionally substituted heterocyclo;

$R^{9a}$ and $R^{9b}$ are each independently selected from the group consisting of hydrogen and alkyl; or $R^{9a}$ and $R^{9b}$ are taken together form taken together to form a 3- to 8-membered optionally substituted heterocyclo;

$R^2$ is selected from the group consisting of:
a) hydrogen;
b) optionally substituted heteroaryl;
c) heteroalkyl;
d) (aralkylamino)alkyl;
e) optionally-substituted (heterocyclo)alkyl;
f) optionally-substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) (carboxamido)alkyl; and
q) (haloalkylamino)alkyl;

$R^3$ is selected from the group consisting of:
a) hydrogen;
b) halo;
c) cyano;
d) haloalkyl;
e) $C_1$-$C_4$ alkyl;
f) $C_{1-4}$ haloalkyl;
g) $C_{1-4}$ haloalkoxy; and
h) $C_{1-4}$ alkoxy;

$R^4$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl;

$R^5$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl;

$R^{10}$ is selected from the group consisting of:
a) hydrogen;
b) dihydroxyalkyl;
c) carboxy;
d) (heteroaryl)alkyl;
e) (acetoxy)alkyl;
f) —Y—$R^1$; and
g) carboxamido;

Y is —O— or —NH—;

$R^{11}$ is selected from the group consisting of:

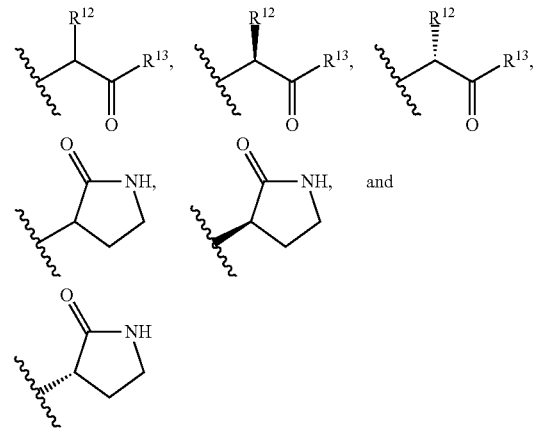

$R^{12}$ is selected from the group consisting of hydrogen, alkyl, and hydroxyalkyl;

$R^{13}$ is selected from the group consisting of hydroxy, alkoxy, and —$NR^{14a}R^{14b}$;

$R^{14a}$ is selected from the group consisting of:
a) hydrogen;
b) alkyl;
c) aralkyl;
d) (heterocyclo)alkyl;
e) (heteroaryl)alkyl;
f) (amino)alkyl;
g) (alkylamino)alkyl;
h) (dialkylamino)alkyl;
i) (carboxamido)alkyl;
j) (cyano)alkyl;
k) alkoxyalkyl;
l) hydroxyalkyl; and
m) heteroalkyl; and $R^{14b}$ is selected from the group consisting of hydrogen and alkyl; or $R^{14a}$ and $R^{14b}$ taken together with the nitrogen atom to which they are attached form a 3- to 8-membered optionally substituted heterocyclo.

It is appreciated that, in certain embodiments of Formula I-A, the E, Z, and $R^{10}$ groups are attached to the HET via separate carbon atoms.

In another embodiment, Compounds of the Disclosure are compounds represented by Formula I-A, and the pharmaceutically acceptable salts and solvates thereof, wherein:

1) when X is $CR^1$ and $R^1$ is hydrogen or hydroxyalkyl, then:
  i) $R^2$ is selected from the group consisting of optionally substituted heteroaryl; heteroalkyl; (aralkylamino)alkyl; optionally-substituted (heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl; or
  ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
  iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or 2) when X is $CR^1$ and $R^2$ is hydrogen, then:
  i) $R^1$ is selected from the group consisting of optionally substituted heteroaryl; heteroalkyl; (aralkylamino) alkyl; (heterocyclo)alkyl; optionally substituted aryl; (heterocycloalkylamino)alkyl; (heterocycloamino) alkyl; alkanolamine; (amino)alkyl; (alkylamino)alkyl; (dialkylamino)alkyl; (cycloalkylamino)alkyl; (nitro) alkyl; (carboxamido)alkyl; (haloalkylamino)alkyl; hydroxy)(cyano)alkyl; (amino)(cyano)alkyl; (hydroxy) haloalkyl; (heteroarylamino)alkyl; (heteroaryl)alkyl; $COR^{1a}$; $SO_2NR^{8a}R^{8b}$; $COCONR^{9a}R^{9b}$; and

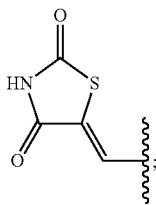

or
  ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
  iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl.

In certain embodiments, Compounds of the Disclosure are compounds represented by Formula I-A, and the pharmaceutically acceptable salts and solvates thereof, wherein when X is $CR^1$, then at least one of $R^1$ and $R^2$ is hydrogen, including embodiments, such as, those provided as follows:

1) when X is $CR^1$ and $R^2$ is hydrogen, then $R^1$ is selected from the group consisting of optionally substituted heteroaryl; heteroalkyl; (aralkylamino)alkyl; (heterocyclo) alkyl; optionally substituted aryl; (heterocycloalkylamino) alkyl; (heterocycloamino)alkyl; alkanolamine; (amino) alkyl; (alkylamino)alkyl; (dialkylamino)alkyl; (cycloalkylamino)alkyl; (nitro)alkyl; (carboxamido)alkyl; (haloalkylamino)alkyl; hydroxy)(cyano)alkyl; (amino)(cyano)alkyl; (hydroxy)haloalkyl; (heteroarylamino)alkyl; (heteroaryl)alkyl; $COR^{1a}$; $SO_2NR^{8a}R^{8b}$; $COCONR^{9a}R^{9b}$; and

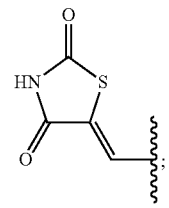 [SMILES: */C=C1\SC(=O)NC1=O]

or
1) when X is $CR^1$ and $R^1$ is hydrogen, then $R^2$ is selected from the group consisting of optionally substituted heteroaryl; heteroalkyl; (aralkylamino)alkyl(heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl.

In another embodiment, Compounds of the Disclosure are compounds represented by Formula I:

$$Z\text{-HET-E} \qquad \qquad I$$

and the pharmaceutically acceptable salts and solvates thereof, wherein:

Z is:

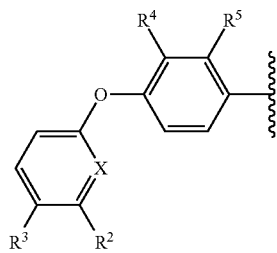

HET is a 6-membered nitrogen-containing heteroaryl, e.g., pyridyl, pyrimidinyl, pyrazinyl, pyridazinyl, or triazinyl;

E is selected from the group consisting of:

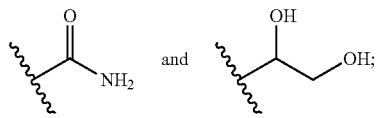

X is selected from the group consisting of N and $CR^1$;
$R^1$ is selected from the group consisting of:
a) hydrogen;
b) optionally substituted heteroaryl;
c) heteroalkyl;
d) (aralkylamino)alkyl
e) (heterocyclo)alkyl;
f) optionally substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;

p) (carboxamido)alkyl; and
q) (haloalkylamino)alkyl;
$R^2$ is selected from the group consisting of:
a) hydrogen;
b) optionally substituted heteroaryl;
c) heteroalkyl;
d) (aralkylamino)alkyl
e) (heterocyclo)alkyl;
f) optionally substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) (carboxamido)alkyl; and
q) (haloalkylamino)alkyl;
$R^3$ is selected from the group consisting of:
a) hydrogen;
b) halo;
c) cyano;
d) haloalkyl;
e) $C_1$-$C_4$ alkyl;
f) $C_{1-4}$ haloalkyl;
g) $C_{1-4}$ haloalkoxy; and
h) $C_{1-4}$ alkoxy;
$R^4$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl;
$R^5$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl.

In another embodiment, Compounds of the Disclosure are compounds represented by Formula I-A, and the pharmaceutically acceptable salts and solvates thereof, wherein E is

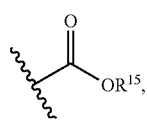

and all other variables are defined as those set forth in Formula I or I-A.

In compounds represented by Formula I or I-A, the E group and the Z group are attached to the HET via separate carbon atoms.

In another embodiment, Compounds of the Disclosure are compounds represented by Formula I or I-A, and the pharmaceutically acceptable salts and solvates thereof, wherein:
1) when X is $CR^1$ and $R^1$ is hydrogen or hydroxyalkyl, then:
  i) $R^2$ is selected from the group consisting of optionally substituted heteroaryl; heteroalkyl; (aralkylamino)alkyl (heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino) alkyl; (nitro)alkyl; (carboxamido)alkyl; and (haloalkylamino)alkyl; or
  ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
  iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
2) when X is $CR^1$ and $R^2$ is hydrogen, then:
  i) $R^1$ is selected from the group consisting of optionally substituted heteroaryl; heteroalkyl; (aralkylamino) alkyl; (heterocyclo)alkyl; optionally substituted aryl; (heterocycloalkylamino)alkyl; (heterocycloamino) alkyl; alkanolamine; (amino)alkyl; (alkylamino)alkyl; (dialkylamino)alkyl; (cycloalkylamino)alkyl; (nitro) alkyl; (carboxamido)alkyl; and (haloalkylamino)alkyl; or
  ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
  iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl.

In another embodiment, Compounds of the Disclosure are compounds represented by Formula I or I-A, and the pharmaceutically acceptable salts and solvates thereof, wherein at least one of $R^1$ and $R^2$ is hydrogen, e.g.,
1) when X is $CR^1$ and $R^2$ is hydrogen, then $R^1$ is selected from the group consisting of optionally substituted heteroaryl; heteroalkyl; (aralkylamino)alkyl(heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl; or
2) when X is $CR^1$ then $R^1$ is hydrogen, then $R^2$ is selected from the group consisting of optionally substituted heteroaryl; heteroalkyl; (aralkylamino)alkyl(heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl.

In another embodiment, Compounds of the Disclosure are compounds represented by Formula I or Formula I-A, and the pharmaceutically acceptable salts and solvates thereof, wherein Z-HET-E is selected from the group consisting of:

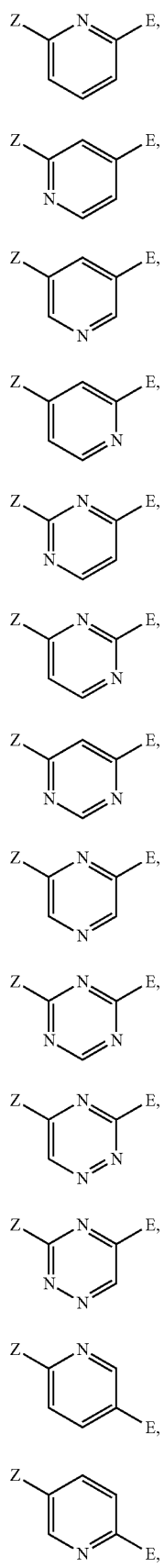
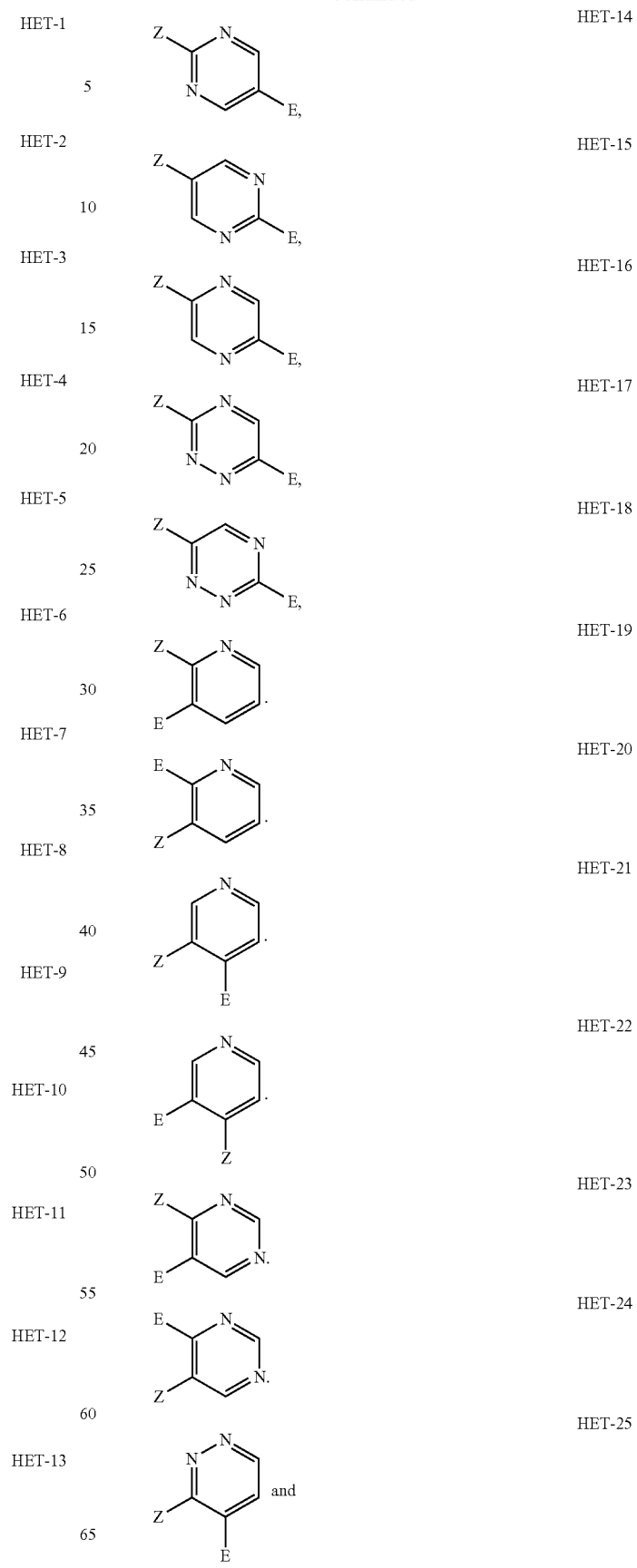

HET-26

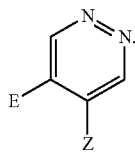

In another embodiment, Compounds of the Disclosure are compounds represented by Formula I or Formula I-A, and the pharmaceutically acceptable salts and solvates thereof, wherein HET is a pyridyl, and Z-HET-E is selected from the group consisting of HET-1, HET-2, HET-3, HET-4, HET-12, HET-13, HET-19, HET-20, HET-21, and HET-22.

In another embodiment, Compounds of the Disclosure are compounds represented by Formula I or Formula I-A, and the pharmaceutically acceptable salts and solvates thereof, wherein HET is a pyrimidinyl, and Z-HET-E is selected from the group consisting of HET-5, HET-6, HET-7, HET-14, HET-15, HET-23, and HET-24.

In another embodiment, Compounds of the Disclosure are compounds represented by Formula I or Formula I-A, and the pharmaceutically acceptable salts and solvates thereof, wherein HET is a pyrazinyl, and Z-HET-E is selected from the group consisting of HET-8 and HET-16.

In another embodiment, Compounds of the Disclosure are compounds represented by Formula I or Formula I-A, and the pharmaceutically acceptable salts and solvates thereof, wherein HET is a triazinyl, and Z-HET-E is selected from the group consisting of HET-9, HET-10, HET-11, HET-17, and HET-18.

In another embodiment, Compounds of the Disclosure are compounds represented by Formula I or Formula I-A, and the pharmaceutically acceptable salts and solvates thereof, wherein HET is a pyridazinyl, and Z-HET-E is selected from the group consisting of HET-25 and HET-26.

In another embodiment, Compounds of the Disclosure are compounds represented by Formula I or Formula I-A, and the pharmaceutically acceptable salts and solvates thereof, wherein Z-HET-E is selected from the group consisting of HET-1, HET-2, HET-3, HET-4, HET-5, HET-6, HET-7, HET-8, HET-9, HET-10, and HET-11.

In another embodiment, Compounds of the Disclosure are compounds represented by Formula I or Formula I-A, and the pharmaceutically acceptable salts and solvates thereof, wherein Z-HET-E is selected from the group consisting of HET-12, HET-13, HET-14, HET-15, HET-16, HET-17, and HET-18.

In another embodiment, Compounds of the Disclosure are compounds represented by Formula I or Formula I-A, and the pharmaceutically acceptable salts and solvates thereof, wherein Z-HET-E is selected from the group consisting of HET-19, HET-20, HET-21, HET-22, HET-23, HET-24, HET-25, and HET-26.

In another embodiment, Compounds of the Disclosure are compounds represented by Formula I or Formula I-A, and the pharmaceutically acceptable salts and solvates thereof, wherein Z-HET-E is selected from the group consisting of HET-1, HET-5, and HET-9.

In another embodiment, Compounds of the Disclosure are compounds represented by Formula I or Formula I-A, and the pharmaceutically acceptable salts and solvates thereof, wherein Z-HET-E is selected from the group consisting of HET-1 and HET-5.

In one embodiment, Compounds of the Disclosure are compounds represented by Formula I-A, and the pharmaceutically acceptable salts and solvates thereof, wherein $R^{10}$ is hydrogen.

In another embodiment, Compounds of the Disclosure are compounds represented by Formula I-A, and the pharmaceutically acceptable salts and solvates thereof, wherein $R^{10}$ is dihydroxyalkyl (e.g., 1,2-dihydroxyethyl).

In still another embodiment, Compounds of the Disclosure are compounds represented by Formula I-A, and the pharmaceutically acceptable salts and solvates thereof, wherein $R^{10}$ is —Y—$R^{11}$. In one embodiment, $R^{11}$ is selected from the group of

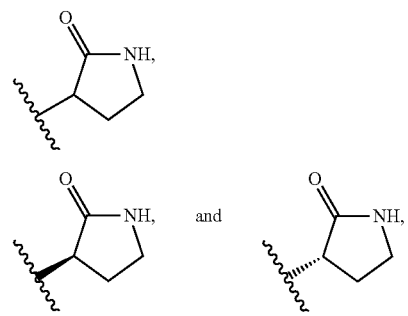

In another embodiment, $R^{11}$ is selected from the group of

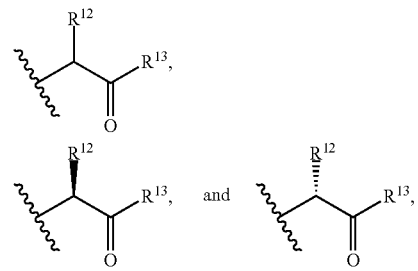

wherein $R^{12}$ is $C_1$-$C_4$ alkyl (e.g., methyl, ethyl, and propyl, etc.), and $R^{13}$ is and —$NR^{14a}R^{14b}$ (e.g., —$NH_2$).

In another embodiment, Compounds of the Disclosure are compounds represented by Formula II:

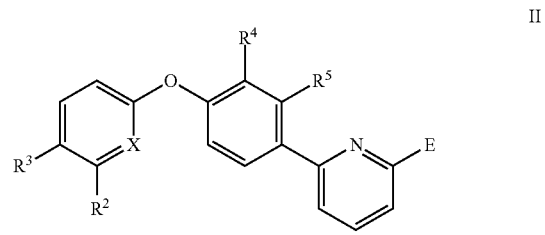

II and the pharmaceutically acceptable salts and solvates thereof, wherein E, X, $R^2$, $R^3$, $R^4$, and $R^5$ are as defined above in connection with Formula I or I-A. In a further embodiment, $R^5$ is selected from the group consisting of hydrogen; chloro; and $C_{1-4}$ haloalkyl.

In another embodiment, Compounds of the Disclosure are compounds represented by Formula II-A:

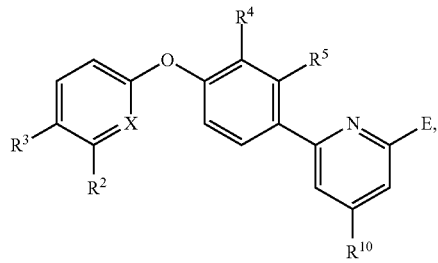

II-A and the pharmaceutically acceptable salts and solvates thereof, wherein E, X, $R^2$, $R^3$, $R^4$, $R^5$, and $R^{10}$ are as defined above in connection with Formula I-A.

In another embodiment, Compounds of the Disclosure are compounds represented by Formula III:

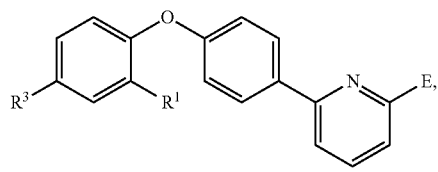

III and the pharmaceutically acceptable salts and solvates thereof, wherein:

$R^1$ is selected from the group consisting of:
a) optionally substituted heteroaryl;
b) heteroalkyl;
c) (aralkylamino)alkyl
d) (heterocyclo)alkyl;
e) optionally substituted aryl;
f) (heterocycloalkylamino)alkyl;
g) (heterocycloamino)alkyl;
h) alkanolamine;
i) (amino)alkyl;
j) (alkylamino)alkyl;
k) (dialkylamino)alkyl;
l) (cycloalkylamino)alkyl;
m) (nitro)alkyl; and
n) (carboxamido)alkyl; and E and $R^3$ are as defined above in connection with Formula I. In a further embodiment, $R^1$ is selected from the group consisting of optionally substituted heteroaryl; (heterocyclo)alkyl; and (dialkylamino)alkyl. In a further embodiment, $R^3$ is selected from the group consisting of halo, cyano, and haloalkyl.

In another embodiment, Compounds of the Disclosure are compounds represented by Formula III-A:

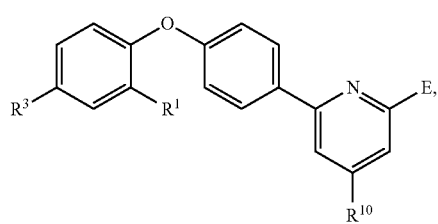

III-A and the pharmaceutically acceptable salts and solvates thereof, wherein:

$R^1$ is selected from the group consisting of:
a) optionally substituted heteroaryl;
b) heteroalkyl;
c) (aralkylamino)alkyl
d) optionally-substituted (heterocyclo)alkyl;
e) optionally substituted aryl;
f) (heterocycloalkylamino)alkyl;
g) (heterocycloamino)alkyl;
h) alkanolamine;
i) hydroxyalkyl;
j) (amino)alkyl;
k) (alkylamino)alkyl;
l) (dialkylamino)alkyl;
m) (cycloalkylamino)alkyl;
n) (nitro)alkyl;
o) (carboxamido)alkyl;
p) (haloalkylamino)alkyl;
q) (hydroxy)(cyano)alkyl;
r) (amino)(cyano)alkyl;
s) (hydroxy)haloalkyl;
t) (heteroarylamino)alkyl;
u) (heteroaryl)alkyl;
v) $COR^{1a}$;
w) $SO_2NR^{8a}R^{8b}$;
x) $COCONR^{9a}R^{9b}$; and y) 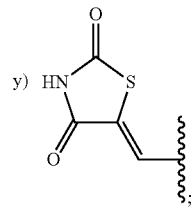 [SMILES: */C=C1\SC(=O)NC1=O]

and

E, $R^3$, and $R^{10}$ are as defined above in connection with Formula I-A.

In one embodiment of Formula III-A, $R^1$ is selected from the group consisting of:
a) optionally substituted heteroaryl;
b) (hydroxy)(cyano)alkyl;
c) (amino)(cyano)alkyl;
d) (hydroxy)haloalkyl;
e) (heteroarylamino)alkyl;
f) (heteroaryl)alkyl;
g) $COR^{1a}$;
h) $SO_2NR^{8a}R^{8b}$
i) $COCONR^{9a}R^{9b}$; and j) 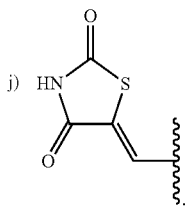 [SMILES: */C=C1\SC(=O)NC1=O]

In another embodiment of Formula III-A, $R^1$ is $COR^{1a}$. In one embodiment, $R^{1a}$ is $NR^{7a}R^{7b}$.

In another embodiment, Compounds of the Disclosure are compounds represented by Formula IV:

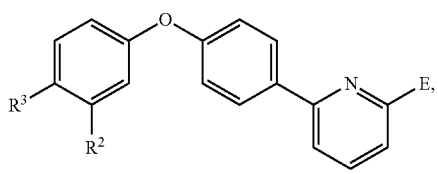

IV and the pharmaceutically acceptable salts and solvates thereof, wherein and E, $R^2$, and $R^3$ are as defined above in connection with Formula I or I-A. In a further embodiment, $R^2$ is selected from the group consisting of heteroaryl; (heterocyclo)alkyl; and (haloalkylamino)alkyl. In a further embodiment, $R^3$ is selected from the group consisting of halo, cyano, and haloalkyl.

In another embodiment, Compounds of the Disclosure are compounds represented by Formula V:

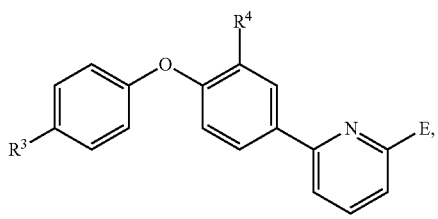

V and the pharmaceutically acceptable salts and solvates thereof, wherein $R^4$ is selected from the group consisting of:
a) arylamino;
b) (arylamino)alkyl;
c) (aryloxy)alkyl;
d) (dialkylamino)alkyl;
e) (heterocyclo)alkyl;
f) optionally substituted aryl; and
g) optionally substituted heteroaryl; and E and $R^3$ are as defined above in connection with Formula I or I-A. In a further embodiment, $R^3$ is fluoro.

In another embodiment, Compounds of the Disclosure are compounds represented by Formula VI:

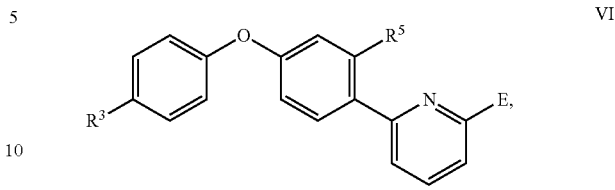

VI and the pharmaceutically acceptable salts and solvates thereof, wherein $R^5$ is selected from the group consisting of:
a) arylamino;
b) (arylamino)alkyl;
c) (aryloxy)alkyl;
d) (dialkylamino)alkyl;
e) (heterocyclo)alkyl;
f) optionally substituted aryl; and
g) optionally substituted heteroaryl; and E and $R^3$ are as defined above in connection with Formula I. In a further embodiment, $R^3$ is fluoro.

In another embodiment, Compounds of the Disclosure are compounds represented by Formula VII:

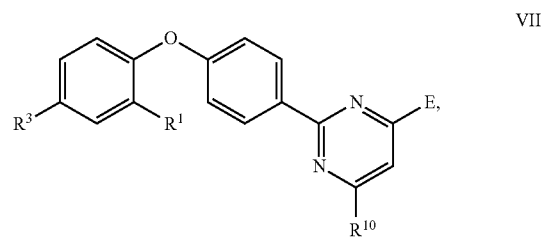

VII and the pharmaceutically acceptable salts and solvates thereof, wherein:
$R^1$ is selected from the group consisting of:
a) optionally substituted heteroaryl;
b) heteroalkyl;
c) (aralkylamino)alkyl
d) optionally-substituted (heterocyclo)alkyl;
e) optionally substituted aryl;
f) (heterocycloalkylamino)alkyl;
g) (heterocycloamino)alkyl;
h) alkanolamine;
i) hydroxyalkyl;
j) (amino)alkyl;
k) (alkylamino)alkyl;
l) (dialkylamino)alkyl;
m) (cycloalkylamino)alkyl;
n) (nitro)alkyl;
o) (carboxamido)alkyl;
p) (haloalkylamino)alkyl;
q) (hydroxy)(cyano)alkyl;
r) (amino)(cyano)alkyl;
s) (hydroxy)haloalkyl;
t) (heteroarylamino)alkyl;
u) (heteroaryl)alkyl;
v) $COR^{1a}$;
w) $SO_2NR^{8a}R^{8b}$;
x) $COCONR^{9a}R^{9b}$; and y)

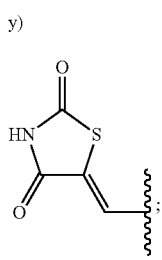

and

E, $R^3$, and $R^{10}$ are as defined above in connection with Formula I-A.

In one embodiment of Formula VII, $R^1$ is selected from the group consisting of optionally substituted heteroaryl, (heterocyclo)alkyl and (dialkylamino)alkyl. In a separate embodiment, $R^3$ is selected from the group consisting of halo, cyano, and haloalkyl.

In another embodiment, Compounds of the Disclosure are compounds represented by any one of Formulae I, II, III, IV, V, and VI, and the pharmaceutically acceptable salts and solvates thereof, wherein E is:

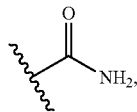 [SMILES: *C(N)=O]

In another embodiment, Compounds of the Disclosure are compounds represented by any one of Formulae I-A, II-A, III-A, and VII, and the pharmaceutically acceptable salts and solvates thereof, wherein E is:

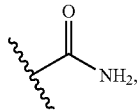

In another embodiment, Compounds of the Disclosure are compounds represented by any one of Formulae I, II, III, IV, V, and VI, and the pharmaceutically acceptable salts and solvates thereof, wherein E is selected from the group consisting of:

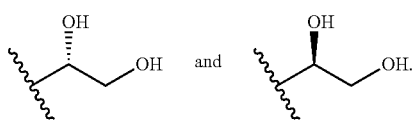 [SMILES: *[C@H](O)CO ; *[C@@H](O)CO]

In another embodiment, Compounds of the Disclosure are compounds represented by any one of Formulae I-A, II-A, III-A, and VII, and the pharmaceutically acceptable salts and solvates thereof, wherein E is selected from the group consisting of:

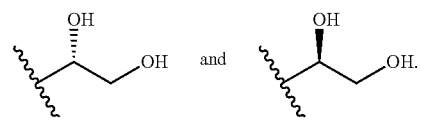 [SMILES: *[C@H](O)CO ; *[C@@H](O)CO]

In another embodiment, Compounds of the Disclosure are compounds represented by any one of Formulae I-A, II-A, III-A, and VII, and the pharmaceutically acceptable salts and solvates thereof, wherein $R^{10}$ is —Y—$R^{11}$, and Y is —O—.

In another embodiment, Compounds of the Disclosure are compounds represented by any one of Formulae I-A, II-A, III-A, and VII, and the pharmaceutically acceptable salts and solvates thereof, wherein $R^{10}$ is —Y—$R^{11}$, and Y is —NH—.

In another embodiment, Compounds of the Disclosure are compounds of represented by any one of Formulae I, I-A, II-A, III-A, or VII, and the pharmaceutically acceptable salts and solvates thereof, wherein $R^1$ is optionally substituted heteroaryl. In another embodiment, $R^1$ is an optionally substituted heteroaryl selected from the group consisting of:

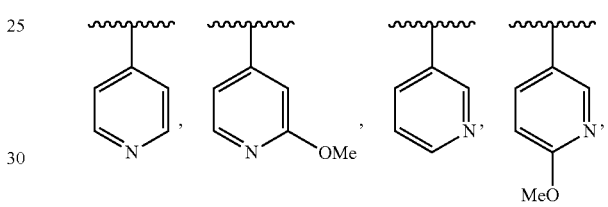

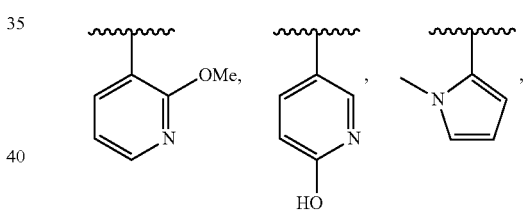

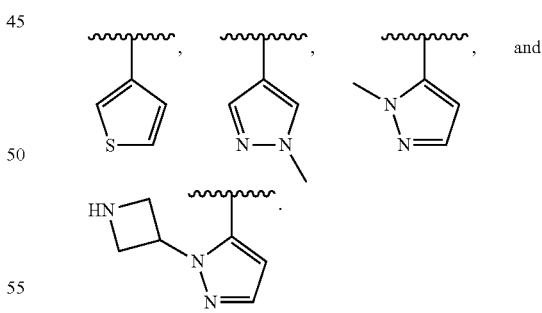

In another embodiment, Compounds of the Disclosure are compounds of represented by any one of Formulae I-A, II-A, III-A, or VII, and the pharmaceutically acceptable salts and solvates thereof, wherein $R^{10}$ is selected from the group consisting of:
a) hydrogen;
b) dihydroxyalkyl; and
c) —Y—$R^{11}$;
Y is —O— or —NH—;

$R^{11}$ is selected from the group consisting of:
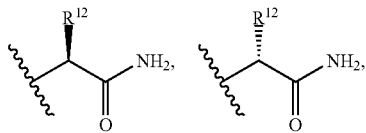
-continued
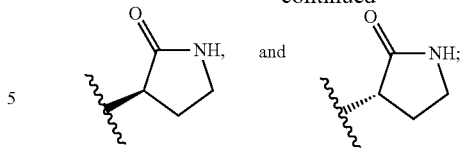
$R^{12}$ is $C_1$-$C_4$ alkyl (e.g., methyl).
In another embodiment, Compounds of the Disclosure are compounds of TABLE 2, and the pharmaceutically acceptable salts and solvates thereof.
TABLE 2
| Cpd. | Structure | Name |
|---|---|---|
| 15 | 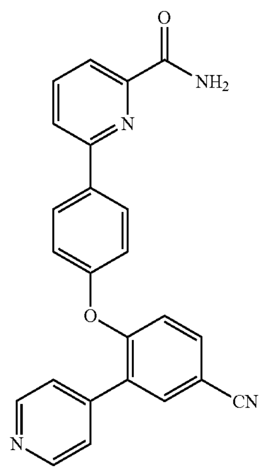 [SMILES: N#Cc1ccc(Oc2ccc(-c3cccc(C(N)=O)n3)cc2)c(-c2ccncc2)c1] | 6-(4-(4-cyano-2-(pyridin-4-yl)phenoxy)phenyl)picolinamide |
| 16 | 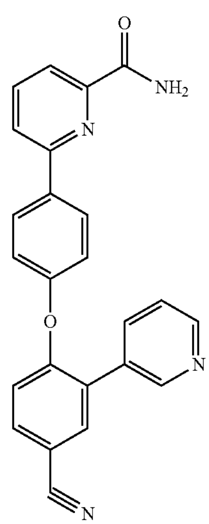 [SMILES: N#Cc1ccc(Oc2ccc(-c3cccc(C(N)=O)n3)cc2)c(-c2cccnc2)c1] | 6-(4-(4-cyano-2-(pyridin-3-yl)phenoxy)phenyl)picolinamide |

TABLE 2-continued

| Cpd. | Structure | Name |
|---|---|---|
| 17 | 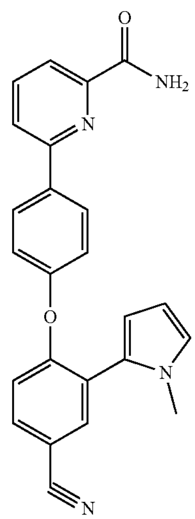 [SMILES: Cn1cccc1-c1cc(C#N)ccc1Oc1ccc(-c2cccc(C(N)=O)n2)cc1] | 6-(4-(4-cyano-2-(1-methyl-1H-pyrrol-2-yl)phenoxy)phenyl)-picolinamide |
| 18 | 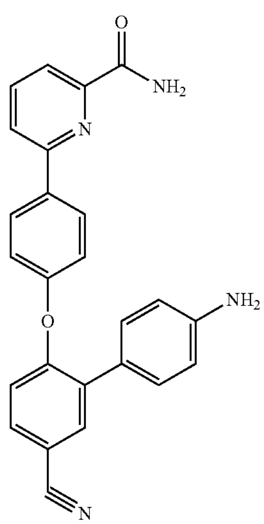 [SMILES: N#Cc1ccc(Oc2ccc(-c3cccc(C(N)=O)n3)cc2)c(-c2ccc(N)cc2)c1] | 6-(4-((4'-amino-5-cyano-[1,1'-biphenyl]-2-yl)oxy)phenyl)-picolinamide |
| 19 | 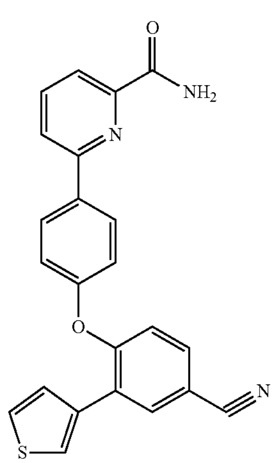 [SMILES: N#Cc1ccc(Oc2ccc(-c3cccc(C(N)=O)n3)cc2)c(-c2ccsc2)c1] | 6-(4-(4-cyano-2-(thiophen-3-yl)phenoxy)phenyl)picolinamide |

TABLE 2-continued
| Cpd. | Structure | Name |
|---|---|---|
| 20 | 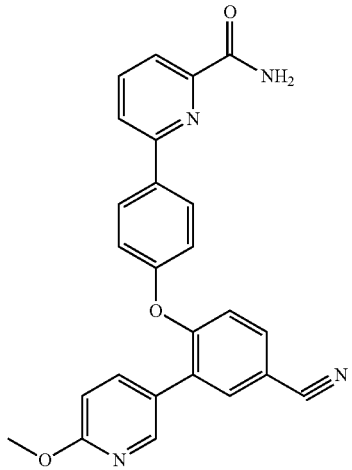 [SMILES: COc1ccc(-c2cc(C#N)ccc2Oc2ccc(-c3cccc(C(N)=O)n3)cc2)cn1] | 6-(4-(4-cyano-2-(6-methoxypyridin-3-yl)phenoxy)phenyl)picolinamide |
| 21 | 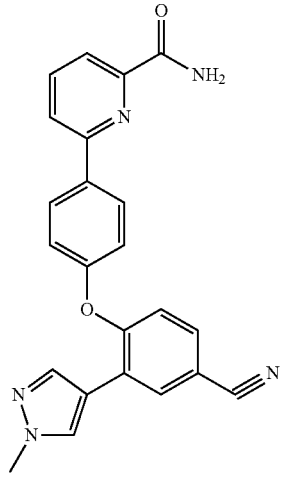 [SMILES: Cn1cc(-c2cc(C#N)ccc2Oc2ccc(-c3cccc(C(N)=O)n3)cc2)cn1] | 6-(4-(4-cyano-2-(1-methyl-1H-pyrazol-4-yl)phenoxy)phenyl)-picolinamide |
| 22 | 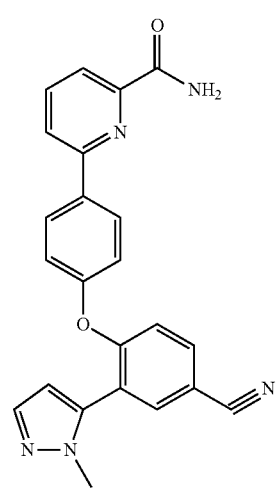 [SMILES: Cn1nccc1-c1cc(C#N)ccc1Oc1ccc(-c2cccc(C(N)=O)n2)cc1] | 6-(4-(4-cyano-2-(1-methyl-1H-pyrazol-5-yl)phenoxy)phenyl)picolinamide |

TABLE 2-continued

| Cpd. | Structure | Name |
|---|---|---|
| 23 | 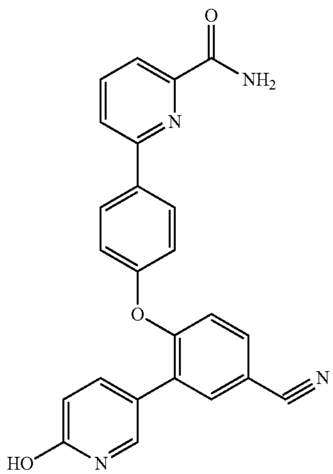 [SMILES: N#Cc1ccc(Oc2ccc(-c3cccc(C(N)=O)n3)cc2)c(-c2ccc(O)nc2)c1] | 6-(4-(4-cyano-2-(6-hydroxypyridin-3-yl)phenoxy)phenyl)picolinamide |
| 24 | 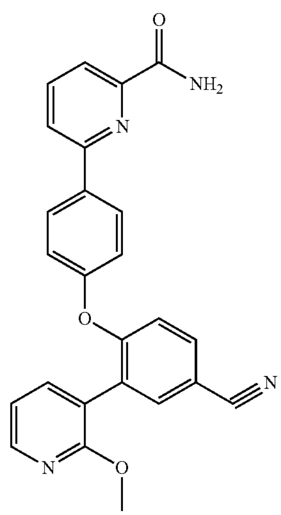 [SMILES: COc1ncccc1-c1cc(C#N)ccc1Oc1ccc(-c2cccc(C(N)=O)n2)cc1] | 6-(4-(4-cyano-2-(2-methoxypyridin-3-yl)phenoxy)phenyl)picolinamide |
| 25 | 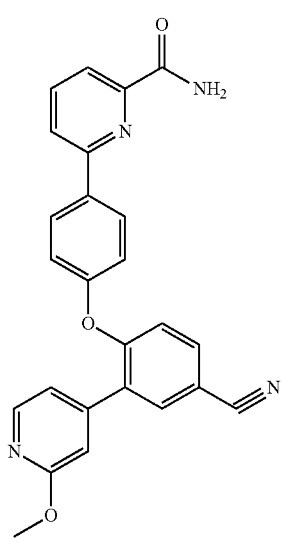 [SMILES: COc1cc(-c2cc(C#N)ccc2Oc2ccc(-c3cccc(C(N)=O)n3)cc2)ccn1] | 6-(4-(4-cyano-2-(2-methoxypyridin-4-yl)phenoxy)phenyl)picolinamide |

TABLE 2-continued

| Cpd. | Structure | Name |
|---|---|---|
| 26 | 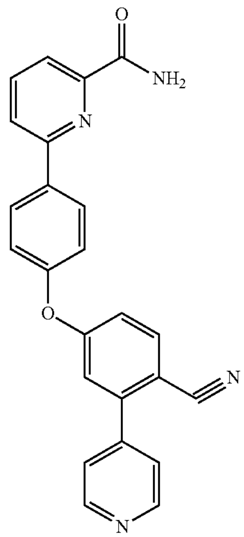 [SMILES: N#Cc1ccc(Oc2ccc(-c3cccc(C(N)=O)n3)cc2)cc1-c1ccncc1] | 6-(4-(4-cyano-3-(pyridin-4-yl)phenoxy)phenyl)picolinamide |
| 27 | 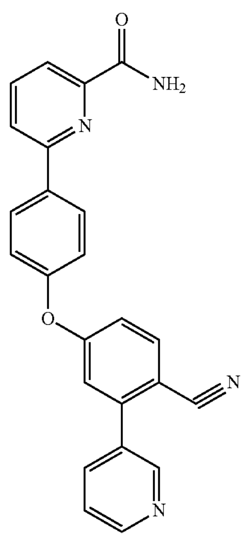 [SMILES: N#Cc1ccc(Oc2ccc(-c3cccc(C(N)=O)n3)cc2)cc1-c1cccnc1] | 6-(4-(4-cyano-3-(pyridin-3-yl)phenoxy)phenyl)picolinamide |
| 28 | 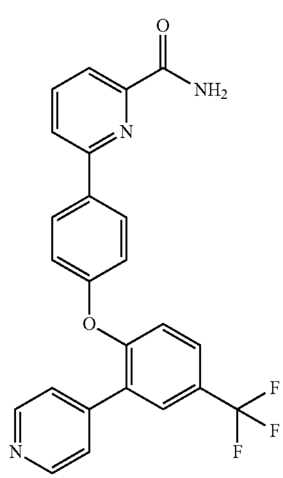 [SMILES: NC(=O)c1cccc(-c2ccc(Oc3ccc(C(F)(F)F)cc3-c3ccncc3)cc2)n1] | 6-(4-(2-(pyridin-4-yl)-4-(trifluoromethyl)phenoxy)phenyl)picolinamide |

TABLE 2-continued

| Cpd. | Structure | Name |
|---|---|---|
| 29 | 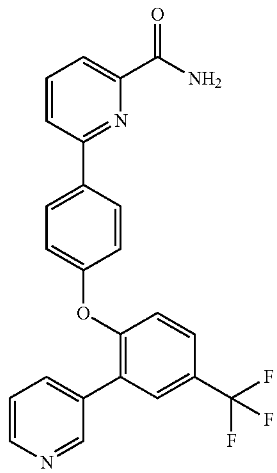 [SMILES: NC(=O)c1cccc(-c2ccc(Oc3ccc(C(F)(F)F)cc3-c3cccnc3)cc2)n1] | 6-(4-(2-(pyridin-3-yl)-4-(trifluoromethyl)phenoxy)phenyl)picolinamide |
| 30 | 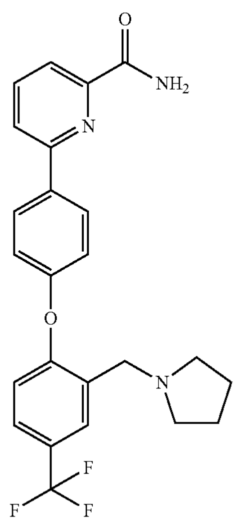 [SMILES: NC(=O)c1cccc(-c2ccc(Oc3ccc(C(F)(F)F)cc3CN3CCCC3)cc2)n1] | 6-(4-(2-(pyrrolidin-1-ylmethyl)-4-(trifluoromethyl)phenoxy)phenyl)picolinamide |
| 31 | 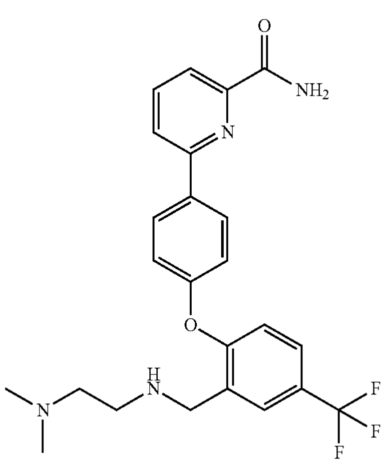 [SMILES: CN(C)CCNCc1cc(C(F)(F)F)ccc1Oc1ccc(-c2cccc(C(N)=O)n2)cc1] | 6-(4-(2-(((2-(dimethylamino)ethyl)amino)methyl)-4-(trifluoromethyl)phenoxy)phenyl)picolinamide |

TABLE 2-continued

| Cpd. | Structure | Name |
|---|---|---|
| 32 | 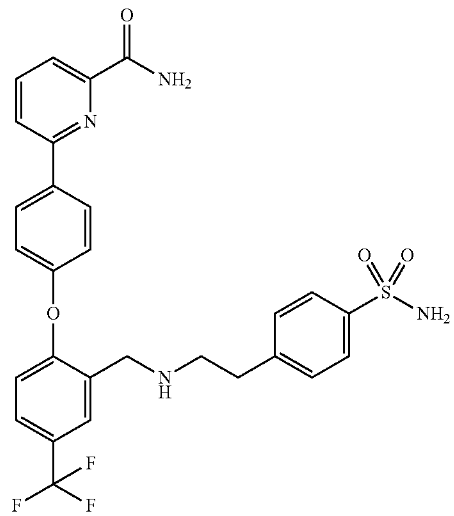 [SMILES: NC(=O)c1cccc(-c2ccc(Oc3ccc(C(F)(F)F)cc3CNCCc3ccc(S(N)(=O)=O)cc3)cc2)n1] | 6-(4-(2-(((4-sulfamoylphenethyl)-amino)methyl)-4-(trifluoromethyl)phenoxy)phenyl)picolinamide |
| 33 | 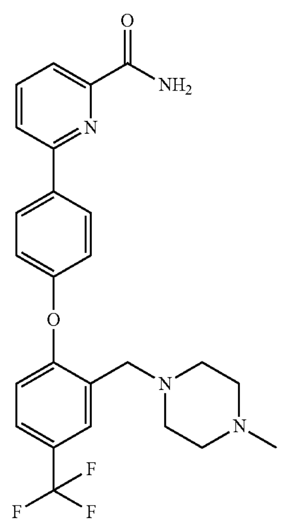 [SMILES: CN1CCN(Cc2cc(C(F)(F)F)ccc2Oc2ccc(-c3cccc(C(N)=O)n3)cc2)CC1] | 6-(4-(2-((4-methylpiperazin-1-yl)methyl)-4-(trifluoromethyl)-phenoxy)phenyl)picolinamide |
| 34 | 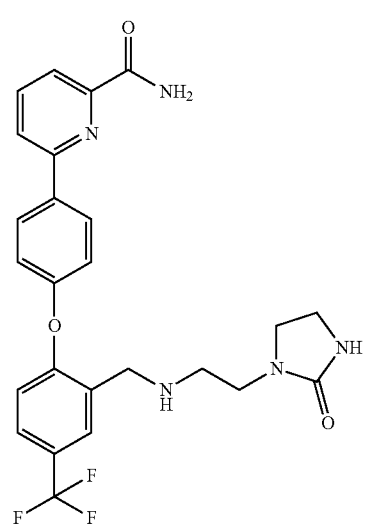 [SMILES: NC(=O)c1cccc(-c2ccc(Oc3ccc(C(F)(F)F)cc3CNCCN3CCNC3=O)cc2)n1] | 6-(4-(2-(((2-(2-oxoimidazolidin-1-yl)ethyl)amino)methyl)-4-(trifluoromethyl)phenoxy)phenyl)picolinamide |

TABLE 2-continued

| Cpd. | Structure | Name |
|---|---|---|
| 35 | 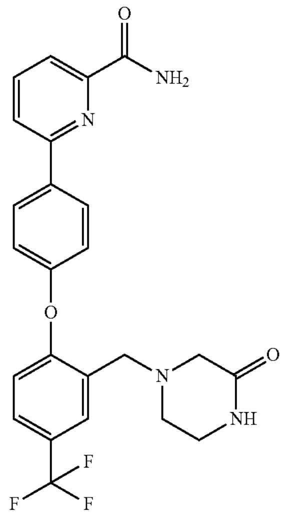 [SMILES: NC(=O)c1cccc(-c2ccc(Oc3ccc(C(F)(F)F)cc3CN3CCNC(=O)C3)cc2)n1] | 6-(4-(2-((3-oxopiperazin-1-yl)methyl)-4-(trifluoromethyl)phenoxy)phenyl)picolinamide |
| 36 | 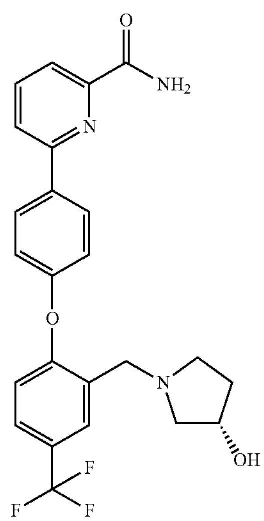 [SMILES: NC(=O)c1cccc(-c2ccc(Oc3ccc(C(F)(F)F)cc3CN3CC[C@H](O)C3)cc2)n1] | (S)-6-(4-(2-((3-hydroxypyrrolidin-1-yl)methyl)-4-(trifluoromethyl)phenoxy)phenyl)picolinamide |
| 37 | 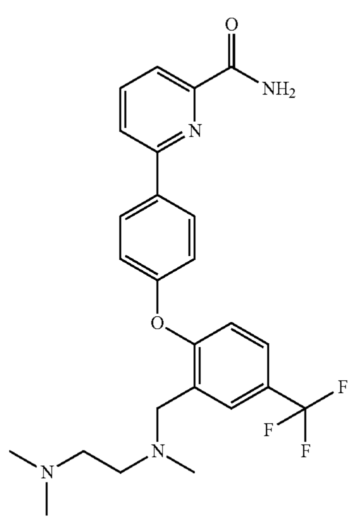 [SMILES: CN(C)CCN(C)Cc1cc(C(F)(F)F)ccc1Oc1ccc(-c2cccc(C(N)=O)n2)cc1] | 6-(4-(2-(((2-(dimethylamino)ethyl)(methyl)amino)methyl)-4-(trifluoromethyl)phenoxy)phenyl)picolinamide |

TABLE 2-continued

| Cpd. | Structure | Name |
|---|---|---|
| 38 | 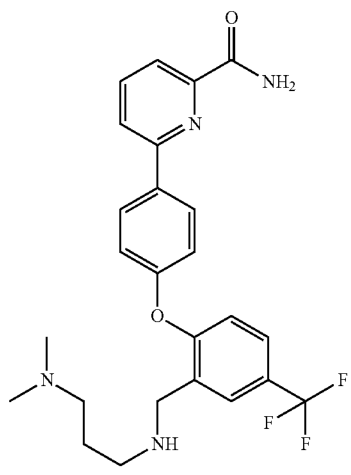 [SMILES: CN(C)CCCNCc1cc(C(F)(F)F)ccc1Oc1ccc(-c2cccc(C(N)=O)n2)cc1] | 6-(4-(2-(((3-(dimethylamino)-propyl)amino)methyl)-4-(trifluoromethyl)phenoxy)phenyl)picolinamide |
| 39 | 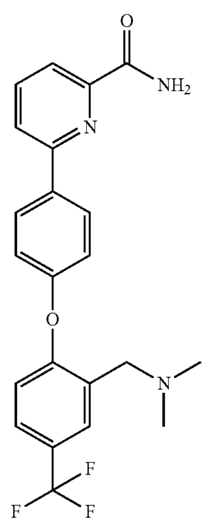 [SMILES: CN(C)Cc1cc(C(F)(F)F)ccc1Oc1ccc(-c2cccc(C(N)=O)n2)cc1] | 6-(4-(2-((dimethylamino)methyl)-4-(trifluoromethyl)phenoxy)-phenyl)picolinamide |
| 40 | 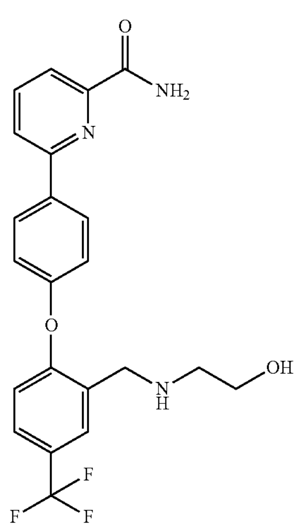 [SMILES: NC(=O)c1cccc(-c2ccc(Oc3ccc(C(F)(F)F)cc3CNCCO)cc2)n1] | 6-(4-(2-(((2-hydroxyethyl)-amino)methyl)-4-(trifluoromethyl)phenoxy)phenyl)picolinamide |

TABLE 2-continued

| Cpd. | Structure | Name |
|---|---|---|
| 41 | 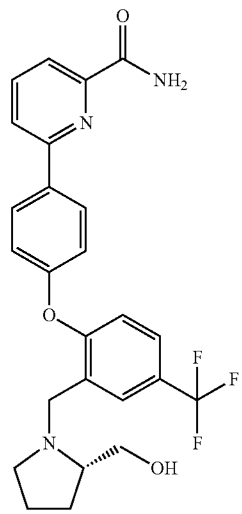 [SMILES: NC(=O)c1cccc(-c2ccc(Oc3ccc(C(F)(F)F)cc3CN3CCC[C@H]3CO)cc2)n1] | (S)-6-(4-(2-((2-(hydroxyl-methyl)pyrrolidin-1-yl)methyl)-4-(trifluoromethyl)phenoxy)phenyl)picolinamide |
| 42 | 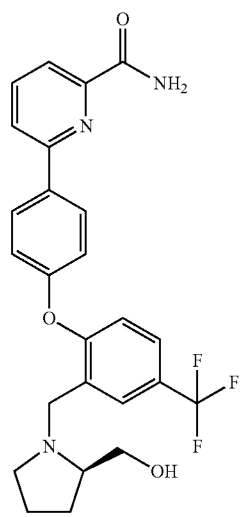 [SMILES: NC(=O)c1cccc(-c2ccc(Oc3ccc(C(F)(F)F)cc3CN3CCC[C@@H]3CO)cc2)n1] | (R)-6-(4-(2-((2-(hydroxyl-methyl)pyrrolidin-1-yl)methyl)-4-(trifluoromethyl)phenoxy)phenyl)picolinamide |
| 43 | 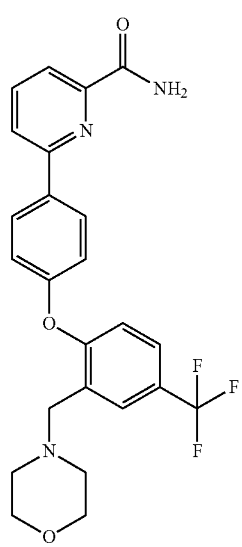 [SMILES: NC(=O)c1cccc(-c2ccc(Oc3ccc(C(F)(F)F)cc3CN3CCOCC3)cc2)n1] | 6-(4-(2-(morpholinomethyl)-4-(trifluoromethyl)phenoxy)phenyl)picolinamide |

TABLE 2-continued

| Cpd. | Structure | Name |
|---|---|---|
| 44 | 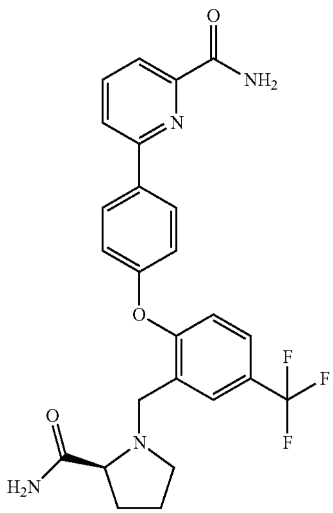 [SMILES: NC(=O)c1cccc(-c2ccc(Oc3ccc(C(F)(F)F)cc3CN3CCC[C@H]3C(N)=O)cc2)n1] | (S)-6-(4-(2-((2-carbamoyl-pyrrolidin-1-yl)methyl)-4-(trifluoromethyl)phenoxy)phenyl)picolinamide |
| 45 | 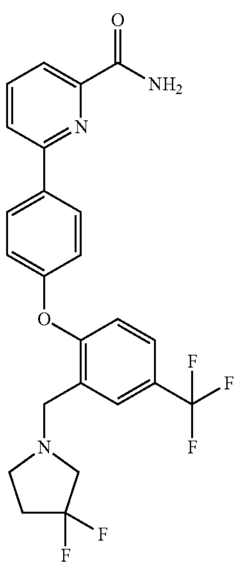 [SMILES: NC(=O)c1cccc(-c2ccc(Oc3ccc(C(F)(F)F)cc3CN3CCC(F)(F)C3)cc2)n1] | 6-(4-(2-((3,3-difluoropyrrolidin-1-yl)methyl)-4-(trifluoromethyl)phenoxy)phenyl)picolinamide |
| 46 | 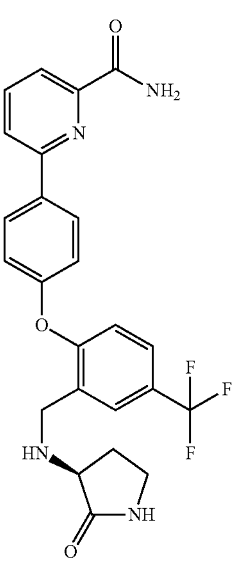 [SMILES: NC(=O)c1cccc(-c2ccc(Oc3ccc(C(F)(F)F)cc3CN[C@H]3CCNC3=O)cc2)n1] | (S)-6-(4-(2-(((2-oxopyrrolidin-3-yl)amino)methyl)-4-(trifluoromethyl)phenoxy)phenyl)picolinamide |

TABLE 2-continued
| Cpd. | Structure | Name |
|---|---|---|
| 47 | 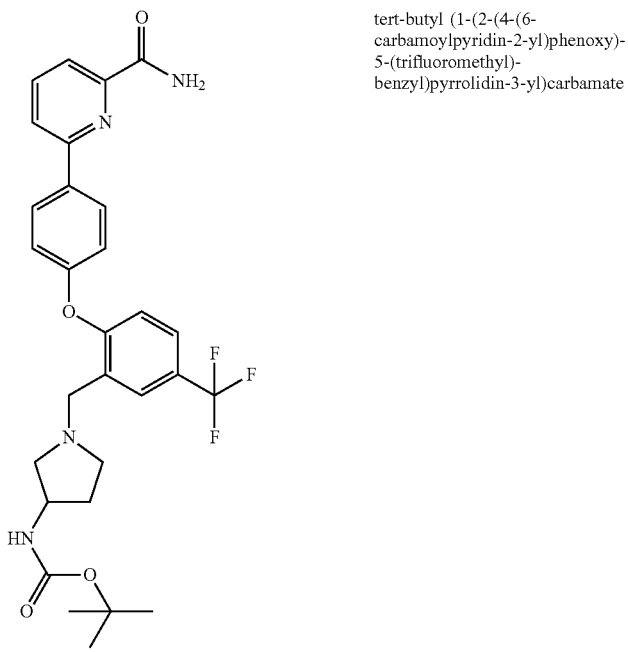 | tert-butyl (1-(2-(4-(6-carbamoylpyridin-2-yl)phenoxy)-5-(trifluoromethyl)benzyl)pyrrolidin-3-yl)carbamate |
| 48 | 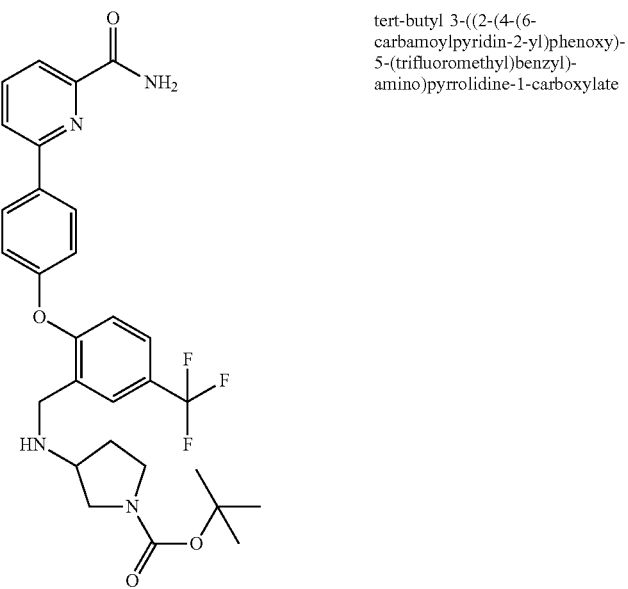 | tert-butyl 3-((2-(4-(6-carbamoylpyridin-2-yl)phenoxy)-5-(trifluoromethyl)benzyl)amino)pyrrolidine-1-carboxylate |

TABLE 2-continued
| Cpd. | Structure | Name |
|---|---|---|
| 49 | 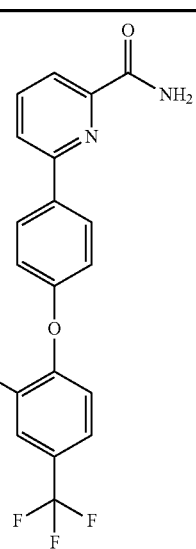 | 6-(4-(2-(piperidin-1-ylmethyl)-4-(trifluoromethyl)phenoxy)phenyl)picolinamide |
| 50 | 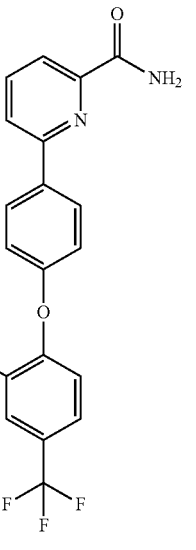 | 6-(4-(2-(azetidin-1-ylmethyl)-4-(trifluoromethyl)phenoxy)phenyl)picolinamide |
| 51 | 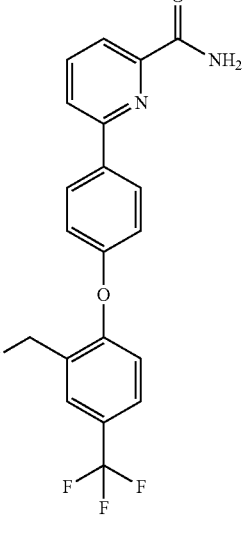 | 6-(4-(2-((3-hydroxypiperidin-1-yl)methyl)-4-(trifluoromethyl)-phenoxy)phenyl)picolinamide |

TABLE 2-continued
| Cpd. | Structure | Name |
|---|---|---|
| 52 | 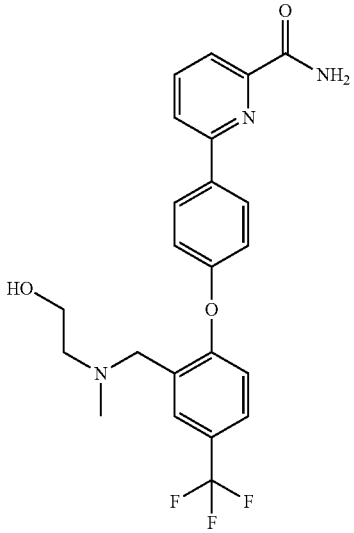 [SMILES: CN(CCO)Cc1cc(C(F)(F)F)ccc1Oc1ccc(-c2cccc(C(N)=O)n2)cc1] | 6-(4-(2-(((2-hydroxyethyl)-(methyl)amino)methyl)-4-(trifluoromethyl)phenoxy)phenyl)picolinamide |
| 53 | 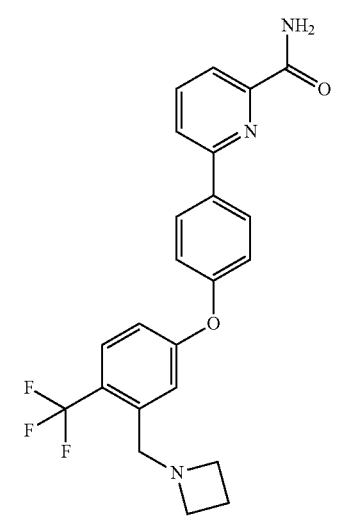 [SMILES: NC(=O)c1cccc(-c2ccc(Oc3ccc(C(F)(F)F)c(CN4CCC4)c3)cc2)n1] | 6-(4-(3-(azetidin-1-ylmethyl)-4-(trifluoromethyl)phenoxy)phenyl)picolinamide |
| 54 | 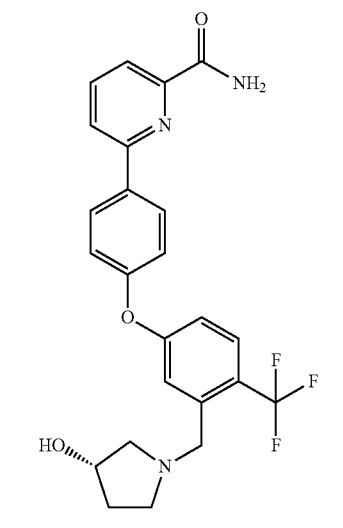 [SMILES: NC(=O)c1cccc(-c2ccc(Oc3ccc(C(F)(F)F)c(CN4CC[C@H](O)C4)c3)cc2)n1] | (S)-6-(4-(3-((3-hydroxy-pyrrolidin-1-yl)methyl)-4-(trifluoromethyl)phenoxy)-phenyl)picolinamide |

TABLE 2-continued

| Cpd. | Structure | Name |
|---|---|---|
| 55 | 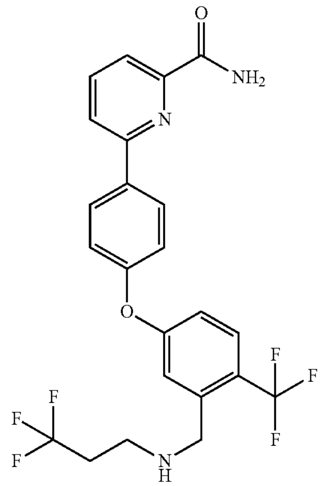 [SMILES: NC(=O)c1cccc(-c2ccc(Oc3ccc(C(F)(F)F)c(CNCCC(F)(F)F)c3)cc2)n1] | 6-(4-(4-(trifluoromethyl)-3-(((3,3,3-trifluoropropyl)amino)-methyl)phenoxy)phenyl)picolinamide |
| 56 | 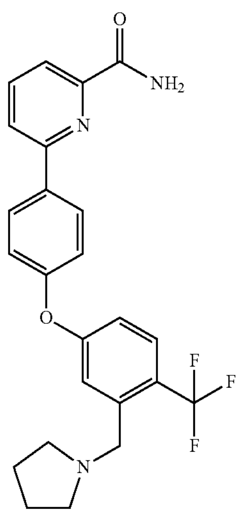 [SMILES: NC(=O)c1cccc(-c2ccc(Oc3ccc(C(F)(F)F)c(CN4CCCC4)c3)cc2)n1] | 6-(4-(3-(pyrrolidin-1-ylmethyl)-4-(trifluoromethyl)phenoxy)phenyl)picolinamide |
| 58 | 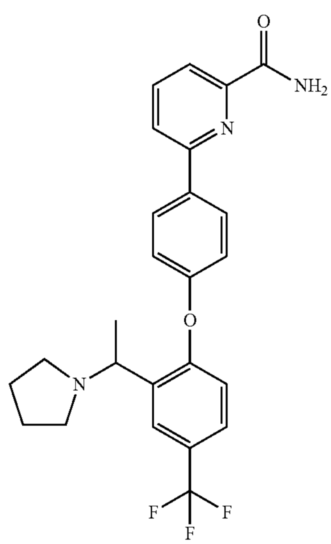 [SMILES: CC(c1cc(C(F)(F)F)ccc1Oc1ccc(-c2cccc(C(N)=O)n2)cc1)N1CCCC1] | 6-(4-(2-(1-(pyrrolidin-1-yl)ethyl)-4-(trifluoromethyl)phenoxy)-phenyl)picolinamide |

TABLE 2-continued

| Cpd. | Structure | Name |
|---|---|---|
| 59 | 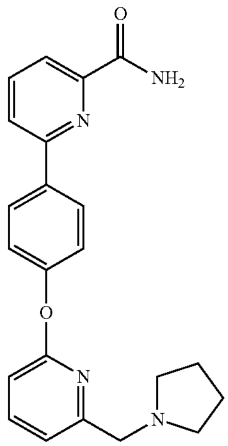 [SMILES: NC(=O)c1cccc(-c2ccc(Oc3cccc(CN4CCCC4)n3)cc2)n1] | 6-(4-((6-(pyrrolidin-1-ylmethyl)pyridin-2-yl)oxy)phenyl)picolinamide |
| 60 | 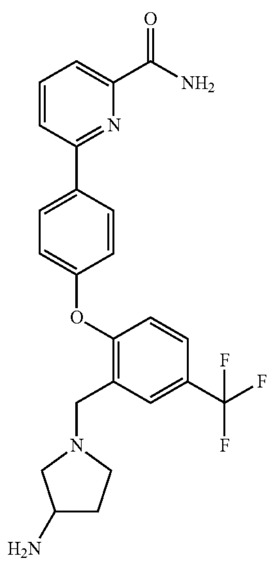 [SMILES: NC(=O)c1cccc(-c2ccc(Oc3ccc(C(F)(F)F)cc3CN3CCC(N)C3)cc2)n1] | 6-(4-(2-((3-aminopyrrolidin-1-yl)methyl)-4-(trifluoromethyl)-phenoxy)phenyl)picolinamide |
| 61 | 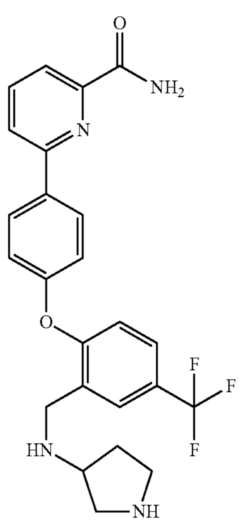 [SMILES: NC(=O)c1cccc(-c2ccc(Oc3ccc(C(F)(F)F)cc3CNC3CCNC3)cc2)n1] | 6-(4-(2-((pyrrolidin-3-ylamino)methyl)-4-(trifluoromethyl)phenoxy)phenyl)picolinamide |

TABLE 2-continued
| Cpd. | Structure | Name |
|---|---|---|
| 62 | 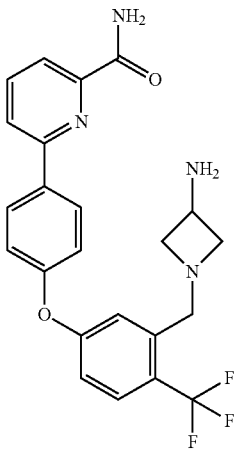 [SMILES: NC(=O)c1cccc(-c2ccc(Oc3ccc(C(F)(F)F)c(CN4CC(N)C4)c3)cc2)n1] | 6-(4-(3-((3-aminoazetidin-1-yl)methyl)-4-(trifluoromethyl)phenoxy)phenyl)picolinamide |
| 63 | 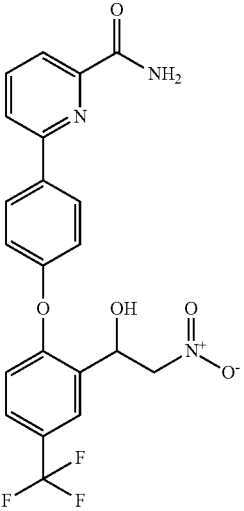 [SMILES: NC(=O)c1cccc(-c2ccc(Oc3ccc(C(F)(F)F)cc3C(O)C[N+](=O)[O-])cc2)n1] | 6-(4-(2-(1-hydroxy-2-nitroethyl)-4-(trifluoromethyl)phenoxy)-phenyl)picolinamide |
| 64 | 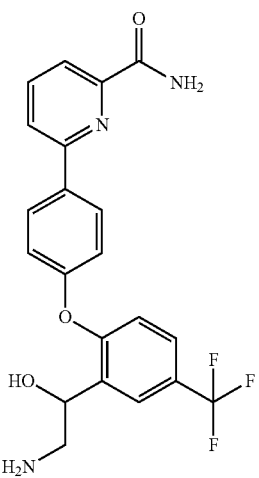 [SMILES: NCC(O)c1cc(C(F)(F)F)ccc1Oc1ccc(-c2cccc(C(N)=O)n2)cc1] | 6-(4-(2-(2-amino-1-hydroxy-ethyl)-4-(trifluoromethyl)-phenoxy)phenyl)picolinamide |

TABLE 2-continued

| Cpd. | Structure | Name |
|---|---|---|
| 65 | 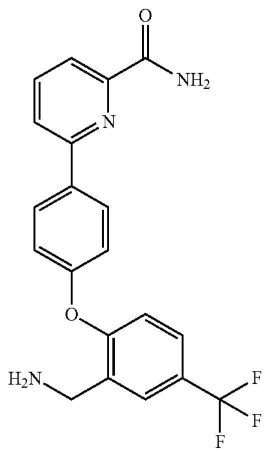 [SMILES: NCc1cc(C(F)(F)F)ccc1Oc1ccc(-c2cccc(C(N)=O)n2)cc1] | 6-(4-(2-(aminomethyl)-4-(trifluoromethyl)phenoxy)phenyl)picolinamide |
| 74 | 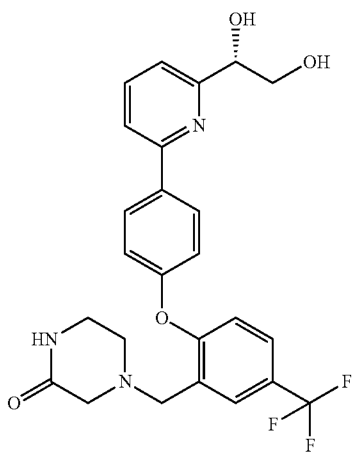 [SMILES: O=C1CN(Cc2cc(C(F)(F)F)ccc2Oc2ccc(-c3cccc([C@H](O)CO)n3)cc2)CCN1] | (S)-4-(2-(4-(6-(1,2-dihydroxyethyl)pyridin-2-yl)phenoxy)-5-(trifluoromethyl)benzyl)piperazin-2-one |
| 75 | 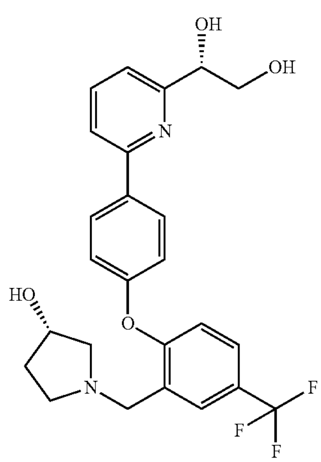 [SMILES: OC[C@@H](O)c1cccc(-c2ccc(Oc3ccc(C(F)(F)F)cc3CN3CC[C@H](O)C3)cc2)n1] | (S)-1-(6-(4-(2-(((S)-3-hydroxypyrrolidin-1-yl)methyl)-4-(trifluoromethyl)phenoxy)phenyl)pyridin-2-yl)ethane-1,2-diol |

| Cpd. | Structure | Name |
|---|---|---|
| 77 | 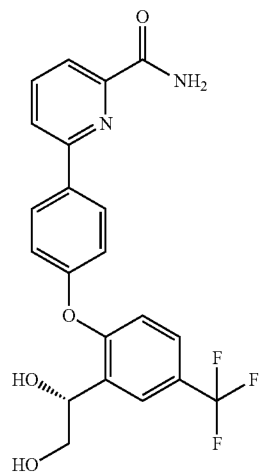 [SMILES: NC(=O)c1cccc(-c2ccc(Oc3ccc(C(F)(F)F)cc3[C@@H](O)CO)cc2)n1] | (R)-6-(4-(2-(1,2-dihydroxyethyl)-4-(trifluoromethyl)-phenoxy)phenyl)picolinamide |
| 79 | 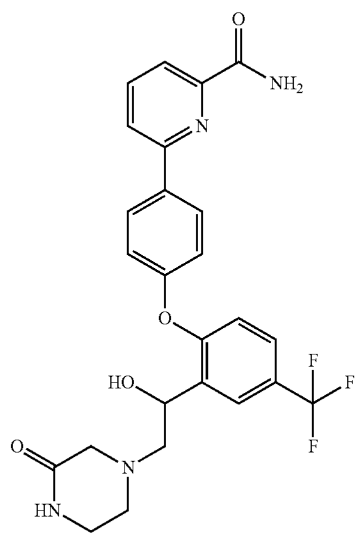 [SMILES: NC(=O)c1cccc(-c2ccc(Oc3ccc(C(F)(F)F)cc3C(O)CN3CCNC(=O)C3)cc2)n1] | 6-(4-(2-(1-hydroxy-2-(3-oxopiperazin-1-yl)ethyl)-4-(trifluoromethyl)phenoxy)phenyl)picolinamide |
| 81 | 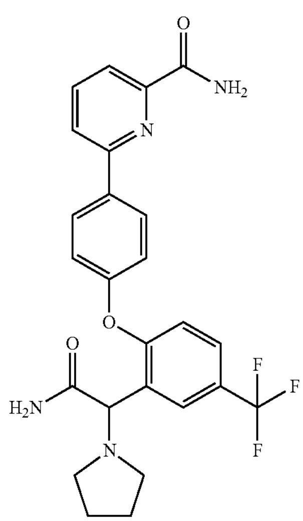 [SMILES: NC(=O)c1cccc(-c2ccc(Oc3ccc(C(F)(F)F)cc3C(C(N)=O)N3CCCC3)cc2)n1] | 6-(4-(2-(2-amino-2-oxo-1-(pyrrolidin-1-yl)ethyl)-4-(trifluoromethyl)phenoxy)phenyl)picolinamide |

TABLE 2-continued
| Cpd. | Structure | Name |
|---|---|---|
| 82 | 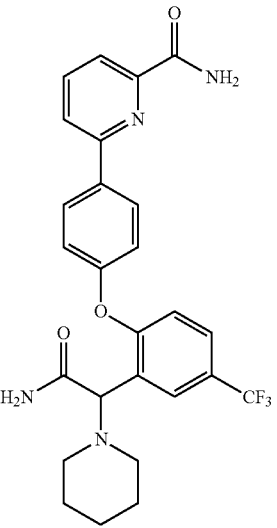 [SMILES: NC(=O)c1cccc(-c2ccc(Oc3ccc(C(F)(F)F)cc3C(C(N)=O)N3CCCCC3)cc2)n1] | 6-(4-(2-(2-amino-2-oxo-1-(piperidin-1-yl)ethyl)-4-(trifluoromethyl)phenoxy)phenyl)picolinamide |
| 83 | 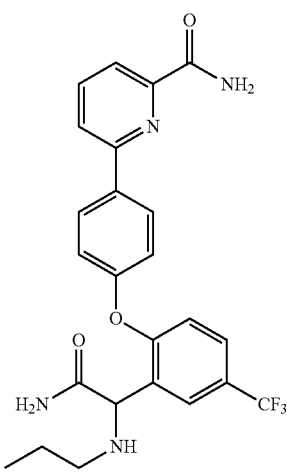 [SMILES: CCCNC(C(N)=O)c1cc(C(F)(F)F)ccc1Oc1ccc(-c2cccc(C(N)=O)n2)cc1] | 6-(4-(2-(2-amino-2-oxo-1-(propylamino)ethyl)-4-(trifluoromethyl)phenoxy)phenyl)picolinamide |
| 84 | 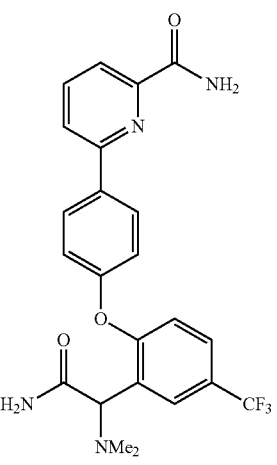 | 6-(4-(2-(2-amino-1-(dimethylamino)-2-oxoethyl)-4-(trifluoromethyl)phenoxy)phenyl)picolinamide |

TABLE 2-continued

| Cpd. | Structure | Name |
|---|---|---|
| 85 | 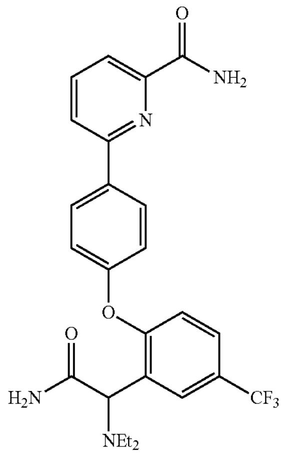 | 6-(4-(2-(2-amino-1-(diethylamino)-2-oxoethyl)-4-(trifluoromethyl)phenoxy)phenyl)picolinamide |
| 86 | 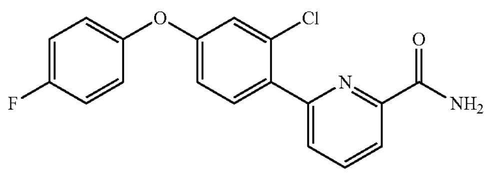 [SMILES: NC(=O)c1cccc(-c2ccc(Oc3ccc(F)cc3)cc2Cl)n1] | 6-(2-chloro-4-(4-fluorophenoxy)-phenyl)picolinamide |
| 87 | 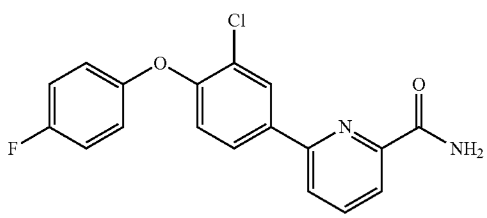 [SMILES: NC(=O)c1cccc(-c2ccc(Oc3ccc(F)cc3)c(Cl)c2)n1] | 6-(3-chloro-4-(4-fluorophenoxy)-phenyl)picolinamide |
| 89 | 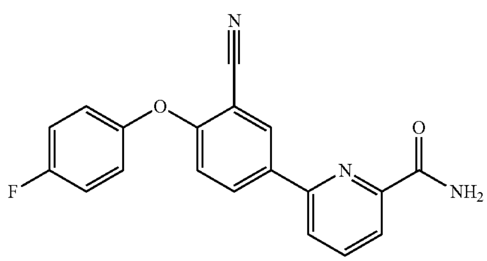 [SMILES: N#Cc1cc(-c2cccc(C(N)=O)n2)ccc1Oc1ccc(F)cc1] | 6-(3-cyano-4-(4-fluorophenoxy-phenyl)picolinamide |
| 90 | 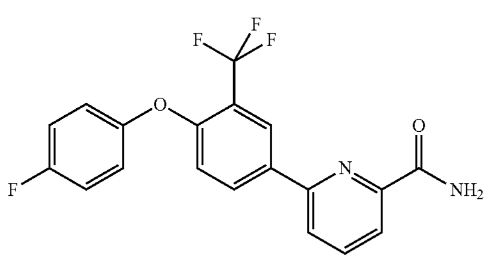 [SMILES: NC(=O)c1cccc(-c2ccc(Oc3ccc(F)cc3)c(C(F)(F)F)c2)n1] | 6-(4-(4-fluorophenoxy)-3-(trifluoromethyl)phenyl)picolinamide |
| 91 | 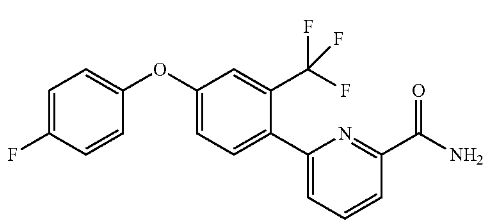 [SMILES: NC(=O)c1cccc(-c2ccc(Oc3ccc(F)cc3)cc2C(F)(F)F)n1] | 6-(4-(4-fluorophenoxy)-2-(trifluoromethyl)phenyl)picolinamide |

TABLE 2-continued

| Cpd. | Structure | Name |
|---|---|---|
| 92 | 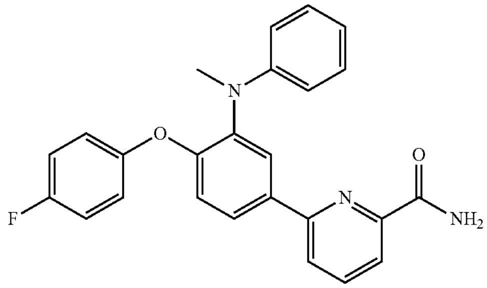 [SMILES: CN(c1ccccc1)c1cc(-c2cccc(C(N)=O)n2)ccc1Oc1ccc(F)cc1] | 6-(4-(4-fluorophenoxy)-3-(methyl(phenyl)amino)phenyl)picolinamide |
| 93 | 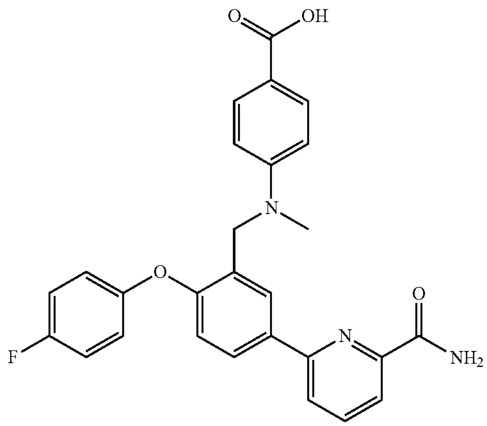 [SMILES: CN(Cc1cc(-c2cccc(C(N)=O)n2)ccc1Oc1ccc(F)cc1)c1ccc(C(=O)O)cc1] | 4-((5-(6-carbamoylpyridin-2-yl)-2-(4-fluorophenoxy)benzyl)-(methyl)amino)benzoic acid |
| 94 | 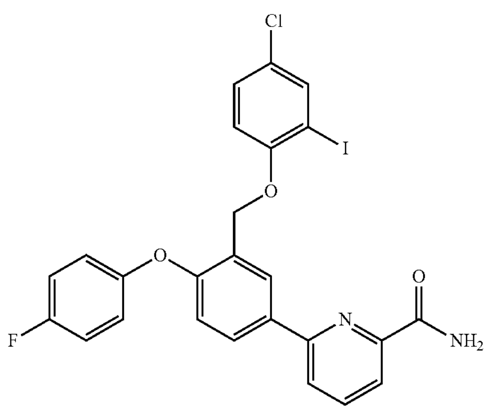 [SMILES: NC(=O)c1cccc(-c2ccc(Oc3ccc(F)cc3)c(COc3ccc(Cl)cc3I)c2)n1] | 6-(3-((4-chloro-2-iodophenoxy)methyl)-4-(4-fluorophenoxy)phenyl)picolinamide |
| 95 | 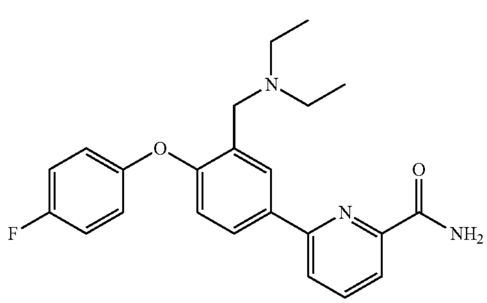 [SMILES: CCN(CC)Cc1cc(-c2cccc(C(N)=O)n2)ccc1Oc1ccc(F)cc1] | 6-(3-((diethylamino)methyl)-4-(4-fluorophenoxy)phenyl)picolinamide |

TABLE 2-continued

| Cpd. | Structure | Name |
|---|---|---|
| 96 | 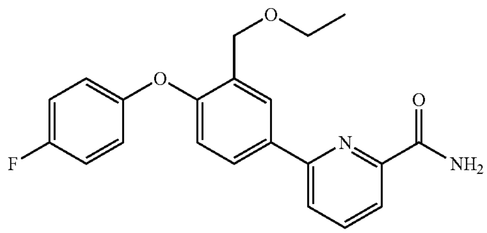 [SMILES: CCOCc1cc(-c2cccc(C(N)=O)n2)ccc1Oc1ccc(F)cc1] | 6-(3-(ethoxymethyl)-4-(4-fluorophenoxy)phenyl)picolinamide |
| 97 | 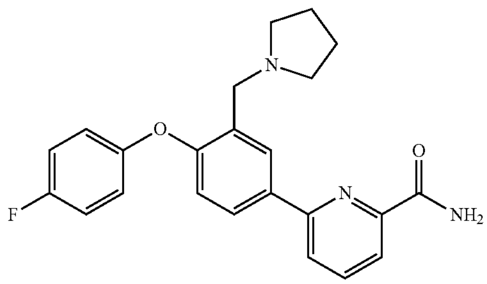 [SMILES: NC(=O)c1cccc(-c2ccc(Oc3ccc(F)cc3)c(CN3CCCC3)c2)n1] | 6-(4-(4-fluorophenoxy)-3-(pyrrolidin-1-ylmethyl)phenyl)-picolinamide |
| 98 | 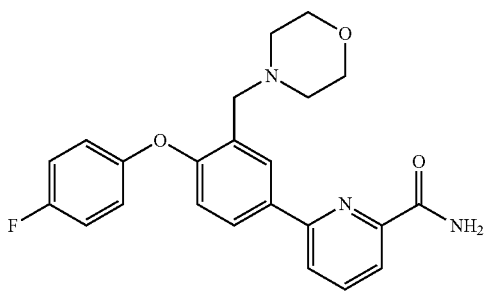 [SMILES: NC(=O)c1cccc(-c2ccc(Oc3ccc(F)cc3)c(CN3CCOCC3)c2)n1] | 6-(4-(4-fluorophenoxy)-3-(morpholinomethyl)phenyl)picolinamide |
| 99 | 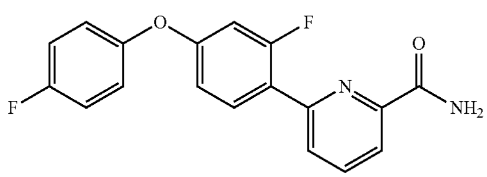 [SMILES: NC(=O)c1cccc(-c2ccc(Oc3ccc(F)cc3)cc2F)n1] | 6-(2-fluoro-4-(4-fluorophenoxy)-phenyl)picolinamide |
| 100 | 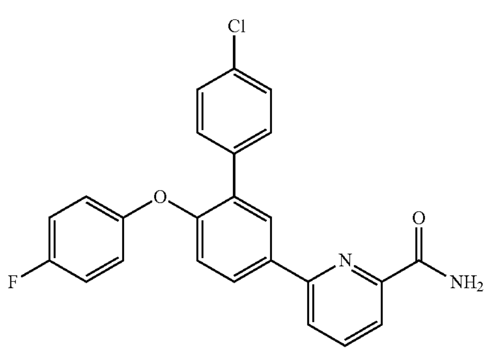 [SMILES: NC(=O)c1cccc(-c2ccc(Oc3ccc(F)cc3)c(-c3ccc(Cl)cc3)c2)n1] | 6-(4'-chloro-6-(4-fluorophenoxy)-[1,1'-biphenyl]-3-yl)picolinamide |

TABLE 2-continued
| Cpd. | Structure | Name |
|---|---|---|
| 101 | 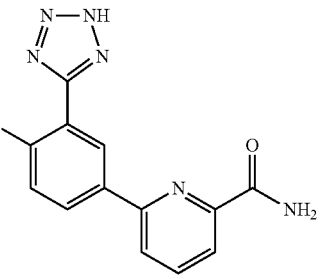 | 6-(4-(4-fluorophenoxy)-3-(2H-tetrazol-5-yl)phenyl)picolinamide |
| 102 | 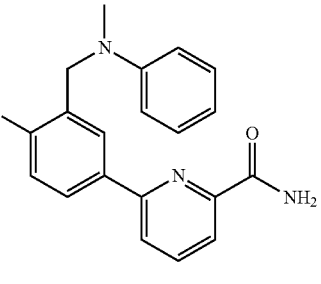 | 6-(4-(4-fluorophenoxy)-3-((methyl(phenyl)amino)methyl)phenyl)picolinamide |
| 103 | 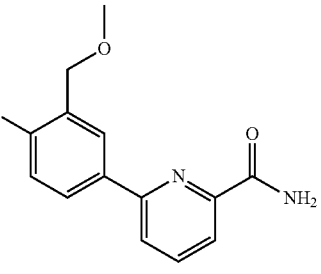 | 6-(4-(4-fluorophenoxy)-3-(methoxymethyl)phenyl)picolinamide |

TABLE 2-continued

| Cpd. | Structure | Name |
|---|---|---|
| 104 | 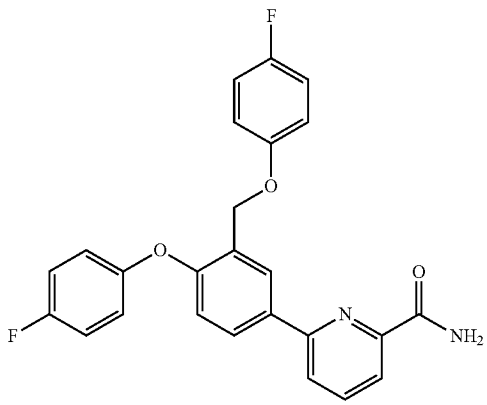 [SMILES: NC(=O)c1cccc(-c2ccc(Oc3ccc(F)cc3)c(COc3ccc(F)cc3)c2)n1] | 6-(4-(4-fluorophenoxy)-3-((4-fluorophenoxy)methyl)phenyl)picolinamide |
| 105 | 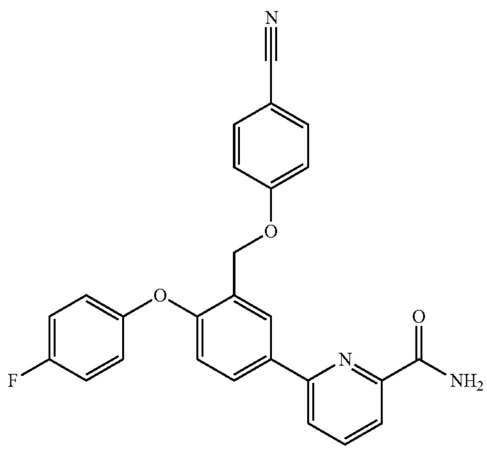 [SMILES: N#Cc1ccc(OCc2cc(-c3cccc(C(N)=O)n3)ccc2Oc2ccc(F)cc2)cc1] | 6-(3-((4-cyanophenoxy)methyl)-4-(4-fluorophenoxy)phenyl)picolinamide |
| 106 | 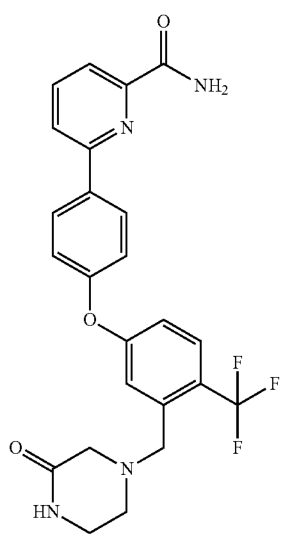 [SMILES: NC(=O)c1cccc(-c2ccc(Oc3ccc(C(F)(F)F)c(CN4CCNC(=O)C4)c3)cc2)n1] | 6-(4-(3-((3-oxopiperazin-1-yl)methyl)-4-(trifluoromethyl)phenoxy)phenyl)picolinamide |

In another embodiment, Compounds of the Disclosure are compounds of TABLE 2A, and the pharmaceutically acceptable salts and solvates thereof.
TABLE 2A
| Cpd. | Structure | Name |
| --- | --- | --- |
| 107 | 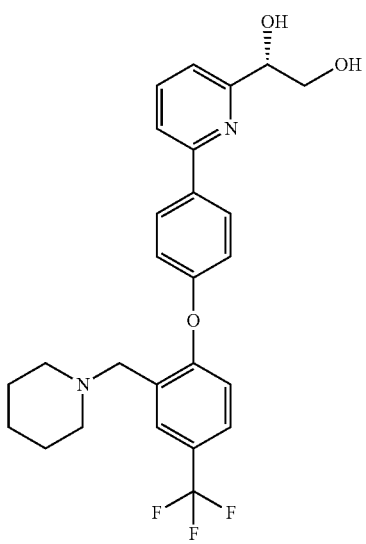 [SMILES: OC[C@@H](O)c1cccc(-c2ccc(Oc3ccc(C(F)(F)F)cc3CN3CCCCC3)cc2)n1] | (S)-1-(6-(4-(2-(piperidin-1-ylmethyl)-4-(trifluoromethyl)phenoxy)phenyl)pyridin-2-yl)ethane-1,2-diol |
| 108 | 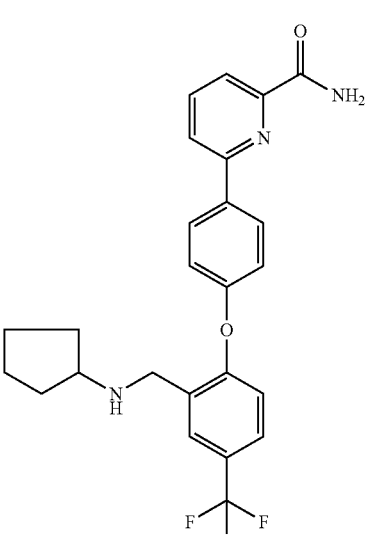 | 6-(4-(2-((cyclopentylamino)-methyl)-4-(trifluoromethyl)-phenoxy)phenyl)picolinamide |

TABLE 2A-continued
| Cpd. | Structure | Name |
|---|---|---|
| 109 | 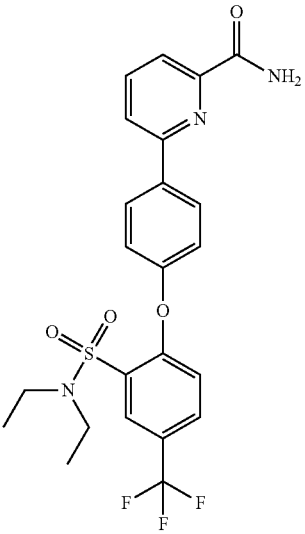 [SMILES: CCN(CC)S(=O)(=O)c1cc(C(F)(F)F)ccc1Oc1ccc(-c2cccc(C(N)=O)n2)cc1] | 6-(4-(2-(N,N-diethylsulfamoyl)-4-(trifluoromethyl)phenoxy)phenyl)picolinamide |
| 111 | 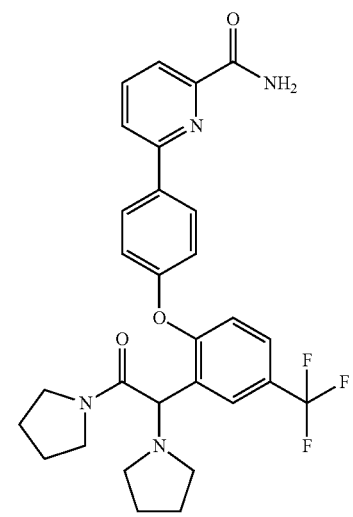 [SMILES: NC(=O)c1cccc(-c2ccc(Oc3ccc(C(F)(F)F)cc3C(C(=O)N3CCCC3)N3CCCC3)cc2)n1] | 6-(4-(2-(2-oxo-1,2-di(pyrrolidin-1-yl)ethyl)-4-(trifluoromethyl)phenoxy)phenyl)picolinamide |
| 112 | 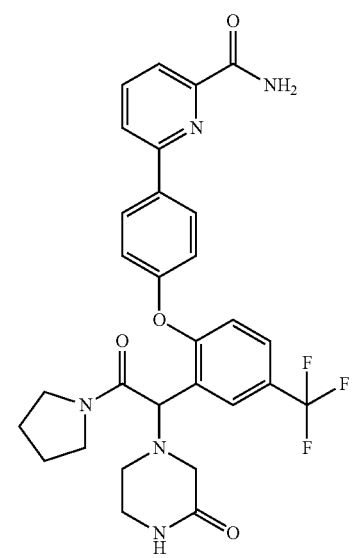 [SMILES: NC(=O)c1cccc(-c2ccc(Oc3ccc(C(F)(F)F)cc3C(C(=O)N3CCCC3)N3CCNC(=O)C3)cc2)n1] | 6-(4-(2-(2-oxo-1-(3-oxopiperazin-1-yl)-2-(pyrrolidin-1-yl)ethyl)-4-(trifluoromethyl)phenoxy)phenyl)picolinamide |

| Cpd. | Structure | Name |
|---|---|---|
| 113 | 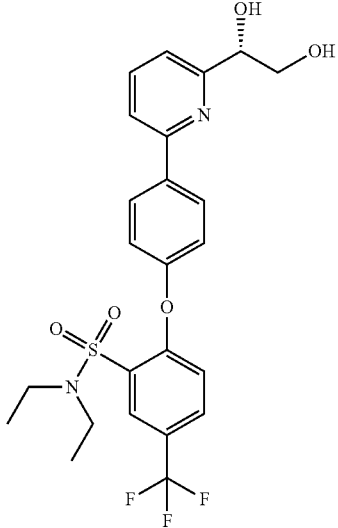 [SMILES: CCN(CC)S(=O)(=O)c1cc(C(F)(F)F)ccc1Oc1ccc(-c2cccc([C@H](O)CO)n2)cc1] | (S)-2-(4-(6-(1,2-dihydroxyethyl)pyridin-2-yl)phenoxy)-N,N-diethyl-5-(trifluoromethyl)benzenesulfonamide |
| 114 | 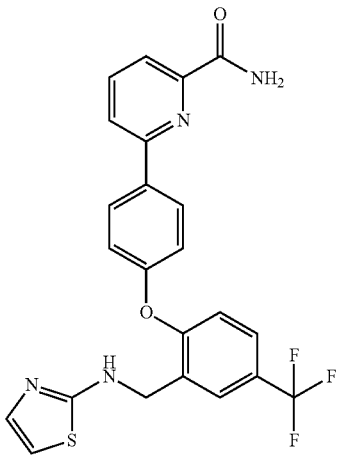 [SMILES: NC(=O)c1cccc(-c2ccc(Oc3ccc(C(F)(F)F)cc3CNc3nccs3)cc2)n1] | 6-(4-(2-((thiazol-2-ylamino)methyl)-4-(trifluoromethyl)phenoxy)phenyl)picolinamide |
| 115 | 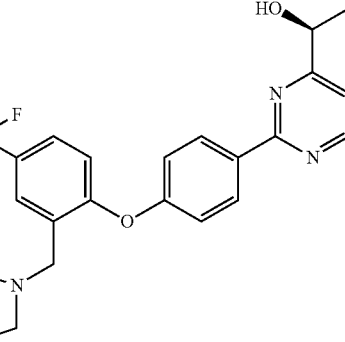 | (R)-1-(2-(4-(2-(pyrrolidin-1-ylmethyl)-4-(trifluoromethyl)phenoxy)phenyl)pyrimidin-4-yl)ethane-1,2-diol |

TABLE 2A-continued

| Cpd. | Structure | Name |
|---|---|---|
| 116 | 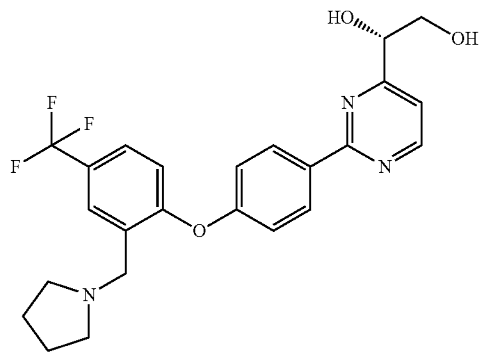 [SMILES: OC[C@@H](O)c1ccnc(-c2ccc(Oc3ccc(C(F)(F)F)cc3CN3CCCC3)cc2)n1] | (S)-1-(2-(4-(2-(pyrrolidin-1-ylmethyl)-4-(trifluoromethyl)phenoxy)phenyl)pyrimidin-4-yl)ethane-1,2-diol |
| 117 | 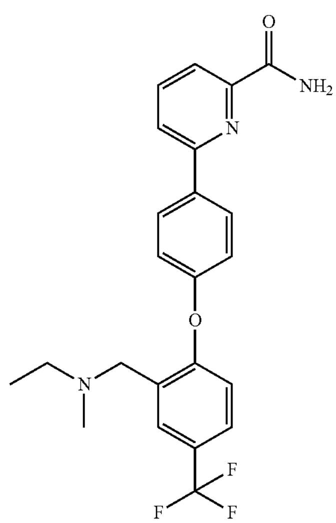 [SMILES: CCN(C)Cc1cc(C(F)(F)F)ccc1Oc1ccc(-c2cccc(C(N)=O)n2)cc1] | 6-(4-(2-((ethyl(methyl)amino)methyl)-4-(trifluoromethyl)phenoxy)phenyl)picolinamide |
| 118 | 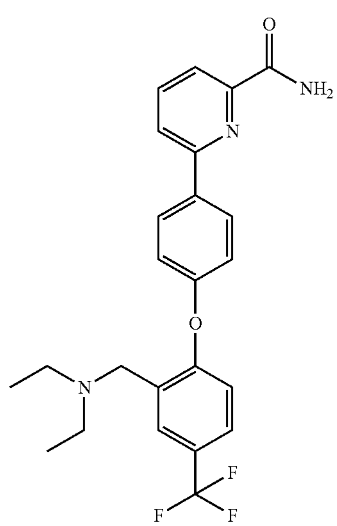 [SMILES: CCN(CC)Cc1cc(C(F)(F)F)ccc1Oc1ccc(-c2cccc(C(N)=O)n2)cc1] | 6-(4-(2-((diethylamino)methyl)-4-(trifluoromethyl)phenoxy)phenyl)picolinamide |

TABLE 2A-continued
| Cpd. | Structure | Name |
|---|---|---|
| 119 | 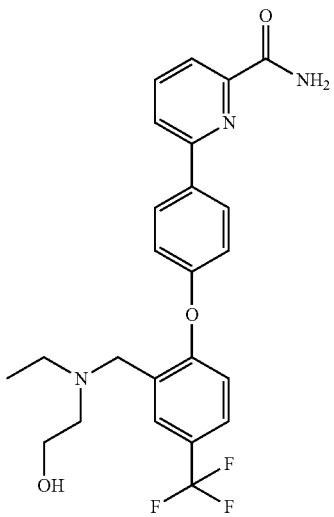 [SMILES: CCN(CCN(C)C)Cc1cc(C(F)(F)F)ccc1Oc1ccc(-c2cccc(C(N)=O)n2)cc1] | 6-(4-(2-((ethyl(2-hydroxyethyl)amino)methyl)-4-(trifluoromethyl)phenoxy)phenyl)picolinamide |
| 120 | 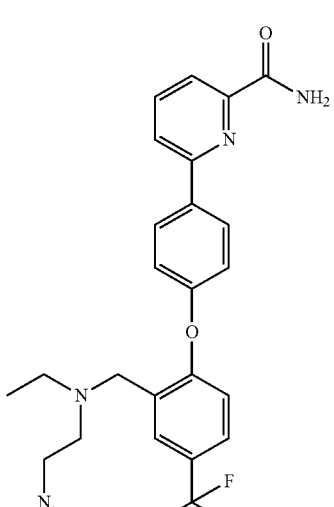 | 6-(4-(2-(((2-(dimethylamino)ethyl)(ethyl)amino)methyl)-4-(trifluoromethyl)phenoxy)phenyl)picolinamide |
| 121 | 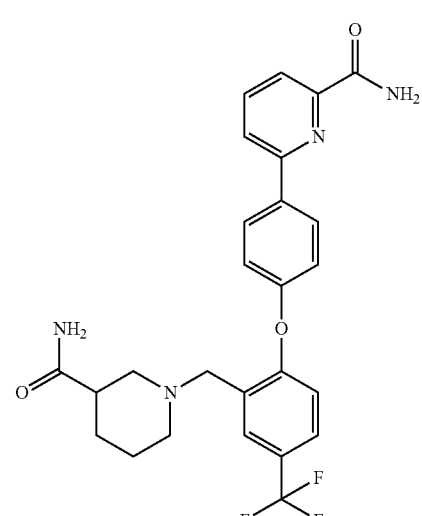 | 6-(4-(2-((3-carbamoylpiperidin-1-yl)methyl)-4-(trifluoromethyl)phenoxy)phenyl)picolinamide |

TABLE 2A-continued

| Cpd. | Structure | Name |
|---|---|---|
| 122 | 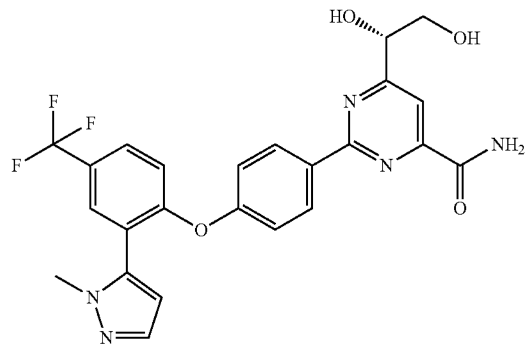 [SMILES: Cn1nccc1-c1cc(C(F)(F)F)ccc1Oc1ccc(-c2nc(C(N)=O)cc([C@H](O)CO)n2)cc1] | (S)-6-(1,2-dihydroxyethyl)-2-(4-(2-(1-methyl-1H-pyrazol-5-yl)-4-(trifluoromethyl)phenoxy)phenyl)pyrimidine-4-carboxamide |
| 123 | 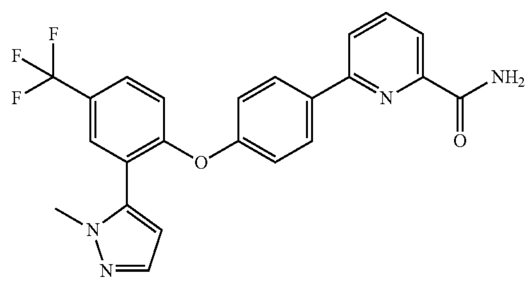 [SMILES: Cn1nccc1-c1cc(C(F)(F)F)ccc1Oc1ccc(-c2cccc(C(N)=O)n2)cc1] | 6-(4-(2-(1-methyl-1H-pyrazol-5-yl)-4-(trifluoromethyl)phenoxy)phenyl)picolinamide |
| 124 | 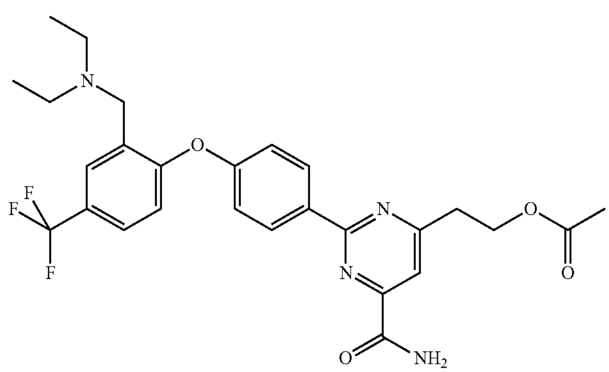 [SMILES: CCN(CC)Cc1cc(C(F)(F)F)ccc1Oc1ccc(-c2nc(CCOC(C)=O)cc(C(N)=O)n2)cc1] | 2-(6-carbamoyl-2-(4-(2-((diethylamino)methyl)-4-(trifluoromethyl)phenoxy)phenyl)pyrimidin-4-yl)ethyl acetate |
| 125 | 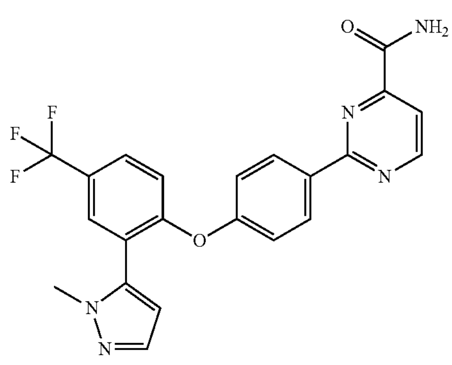 [SMILES: Cn1nccc1-c1cc(C(F)(F)F)ccc1Oc1ccc(-c2nccc(C(N)=O)n2)cc1] | 2-(4-(2-(1-methyl-1H-pyrazol-5-yl)-4-(trifluoromethyl)phenoxy)phenyl)pyrimidine-4-carboxamide |

TABLE 2A-continued

| Cpd. | Structure | Name |
|---|---|---|
| 126 | 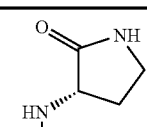 | (S)-2-(4-(2-(1-methyl-1H-pyrazol-5-yl)-4-(trifluoromethyl)phenoxy)phenyl)-6-((2-oxopyrrolidin-3-yl)amino)pyrimidine-4-carboxamide |
| 127 | 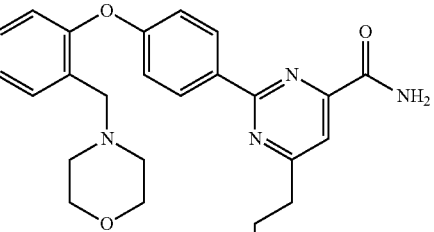 | 6-(2-(1H-imidazol-1-yl)ethyl)-2-(4-(2-(morpholinomethyl)-4-(trifluoromethyl)phenoxy)phenyl)pyrimidine-4-carboxamide |
| 128 | 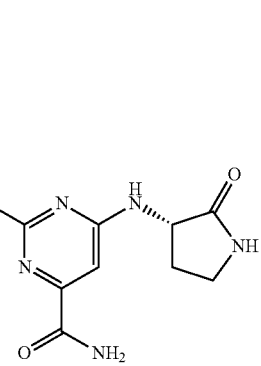 | (S)-2-(4-(2-(2-(dimethylamino)pyrimidin-5-yl)-4-(trifluoromethyl)phenoxy)phenyl)-6-((2-oxopyrrolidin-3-yl)amino)pyrimidine-4-carboxamide |
| 129 | 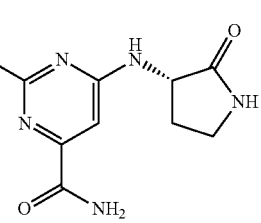 | (S)-2-(4-(2-(5-(dimethylamino)pyrazin-2-yl)-4-(trifluoromethyl)phenoxy)phenyl)-6-((2-oxopyrrolidin-3-yl)amino)pyrimidine-4-carboxamide |

| Cpd. | Structure | Name |
|---|---|---|
| 130 | 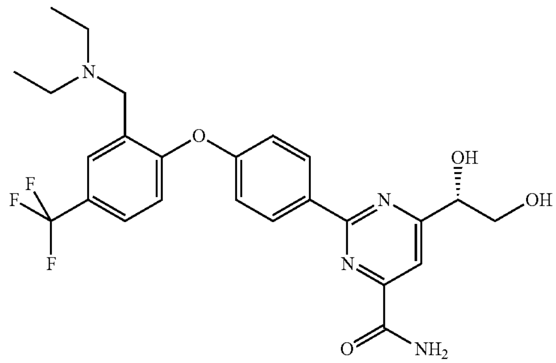 [SMILES: CCN(CC)Cc1cc(C(F)(F)F)ccc1Oc1ccc(-c2nc(C(N)=O)cc([C@H](O)CO)n2)cc1] | (S)-2-(4-(2-((diethylamino)methyl)-4-(trifluoromethyl)phenoxy)phenyl)-6-(1,2-dihydroxyethyl)pyrimidine-4-carboxamide |
| 131 | 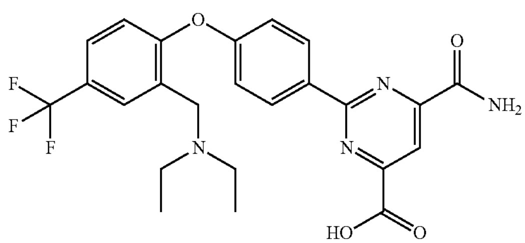 [SMILES: CCN(CC)Cc1cc(C(F)(F)F)ccc1Oc1ccc(-c2nc(C(N)=O)cc(C(=O)O)n2)cc1] | 6-carbamoyl-2-(4-(2-((diethylamino)methyl)-4-(trifluoromethyl)phenoxy)phenyl)pyrimidine-4-carboxylic acid |
| 132 | 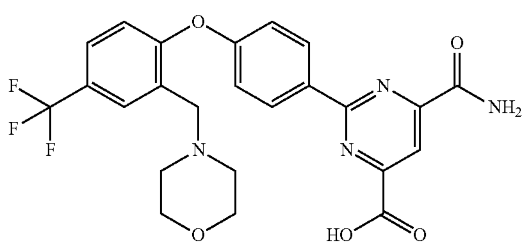 [SMILES: NC(=O)c1cc(C(=O)O)nc(-c2ccc(Oc3ccc(C(F)(F)F)cc3CN3CCOCC3)cc2)n1] | 6-carbamoyl-2-(4-(2-(morpholinomethyl)-4-(trifluoromethyl)phenoxy)phenyl)pyrimidine-4-carboxylic acid |
| 133 | 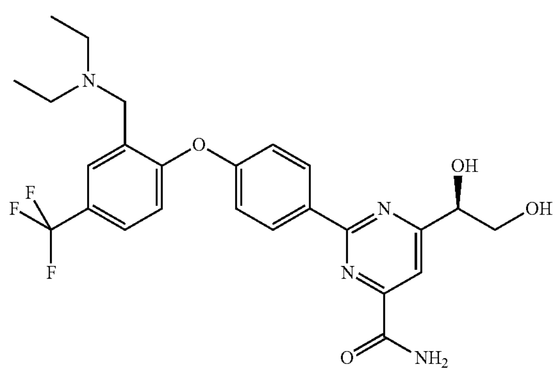 | (R)-2-(4-(2-((diethylamino)methyl)-4-(trifluoromethyl)phenoxy)phenyl)-6-(1,2-dihydroxyethyl)pyrimidine-4-carboxamide |

TABLE 2A-continued

| Cpd. | Structure | Name |
|---|---|---|
| 134 | 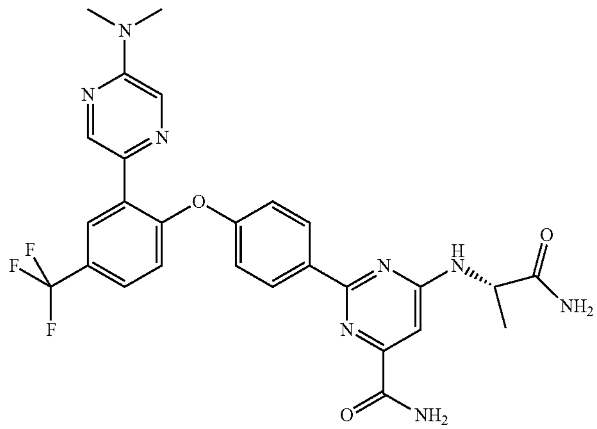 [SMILES: C[C@H](Nc1cc(C(N)=O)nc(-c2ccc(Oc3ccc(C(F)(F)F)cc3-c3cnc(N(C)C)cn3)cc2)n1)C(N)=O] | (S)-6-((1-amino-1-oxopropan-2-yl)amino)-2-(4-(2-(5-(dimethylamino)pyrazin-2-yl)-4-(trifluoromethyl)phenoxy)phenyl)pyrimidine-4-carboxamide |
| 135 | 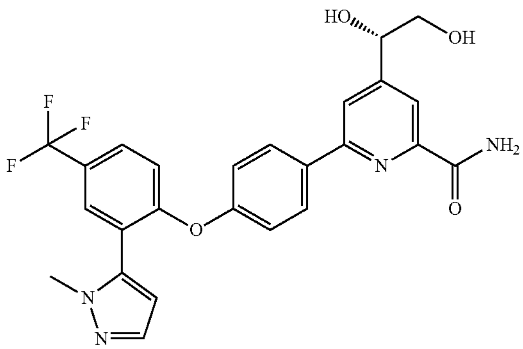 [SMILES: Cn1nccc1-c1cc(C(F)(F)F)ccc1Oc1ccc(-c2cc([C@H](O)CO)cc(C(N)=O)n2)cc1] | (S)-4-(1,2-dihydroxyethyl)-6-(4-(2-(1-methyl-1H-pyrazol-5-yl)-4-(trifluoromethyl)phenoxy)phenyl)picolinamide |
| 136 | 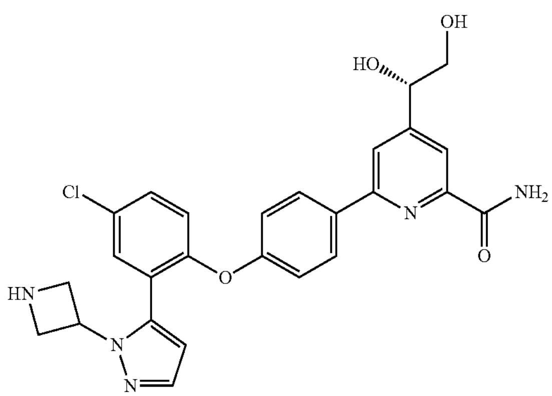 [SMILES: NC(=O)c1cc([C@H](O)CO)cc(-c2ccc(Oc3ccc(Cl)cc3-c3ccnn3C3CNC3)cc2)n1] | (S)-6-(4-(2-(1-(azetidin-3-yl)-1H-pyrazol-5-yl)-4-chlorophenoxy)phenyl)-4-(1,2-dihydroxyethyl)picolinamide |
| 137 | 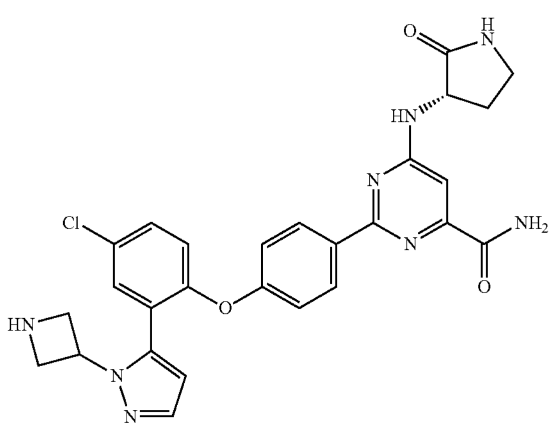 [SMILES: NC(=O)c1cc(N[C@H]2CCNC2=O)nc(-c2ccc(Oc3ccc(Cl)cc3-c3ccnn3C3CNC3)cc2)n1] | (S)-2-(4-(2-(1-(azetidin-3-yl)-1H-pyrazol-5-yl)-4-chlorophenoxy)phenyl)-6-((2-oxopyrrolidin-3-yl)amino)pyrimidine-4-carboxamide |

TABLE 2A-continued

| Cpd. | Structure | Name |
|---|---|---|
| 138 | 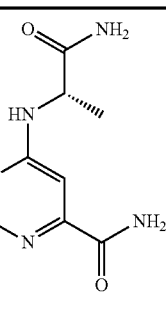 | (S)-6-((1-amino-1-oxopropan-2-yl)amino)-2-(4-(2-(1-methyl-1H-pyrazol-5-yl)-4-(trifluoromethyl)phenoxy)phenyl)pyrimidine-4-carboxamide |
| 139 | 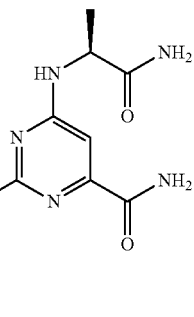 | (S)-6-((1-amino-1-oxopropan-2-yl)amino)-2-(4-(2-(1-methyl-1H-pyrazol-5-yl)phenoxy)phenyl)-pyrimidine-4-carboxamide |
| 140 | 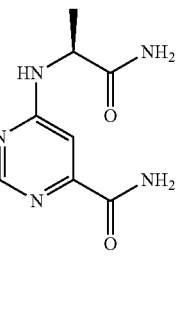 | (S)-6-((1-amino-1-oxopropan-2-yl)amino)-2-(4-(2-(1-methyl-1H-pyrazol-5-yl)phenoxy)phenyl)-pyrimidine-4-carboxamide |
| 141 | 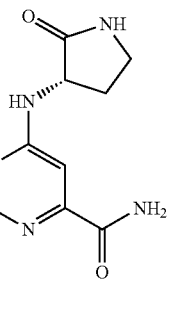 | (S)-2-(4-(4-chloro-2-(1-methyl-1H-pyrazol-5-yl)phenoxy)phenyl)-6-((2-oxopyrrolidin-3-yl)amino)-pyrimidine-4-carboxamide |

TABLE 2A-continued
| Cpd. | Structure | Name |
|---|---|---|
| 144 | 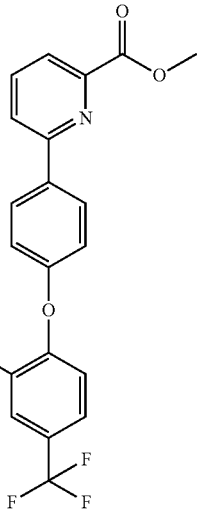 | methyl 6-(4-(2-(cyano(hydroxy)methyl)-4-(trifluoromethyl)phenoxy)phenyl)picolinate |
| 145 | 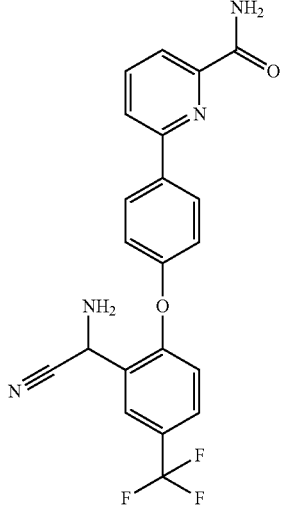 [SMILES: N#CC(N)c1cc(C(F)(F)F)ccc1Oc1ccc(-c2cccc(C(N)=O)n2)cc1] | 6-(4-(2-(amino(cyano)methyl)-4-(trifluoromethyl)phenoxy)phenyl)picolinamide |
| 155 | 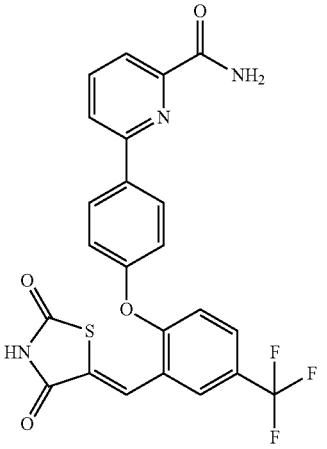 [SMILES: NC(=O)c1cccc(-c2ccc(Oc3ccc(C(F)(F)F)cc3/C=C3\SC(=O)NC3=O)cc2)n1] | (Z)-6-(4-(2-((2,4-dioxothiazolidin-5-ylidene)methyl)-4-(trifluoromethyl)phenoxy)phenyl)picolinamide |

TABLE 2A-continued
| Cpd. | Structure | Name |
|---|---|---|
| 156 | 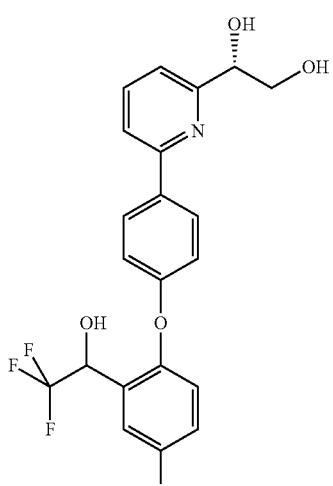 | (1S)-1-(6-(4-(4-fluoro-2-(2,2,2-trifluoro-1-hydroxyethyl)-phenoxy)phenyl)pyridin-2-yl)ethane-1,2-diol |
| 157 | 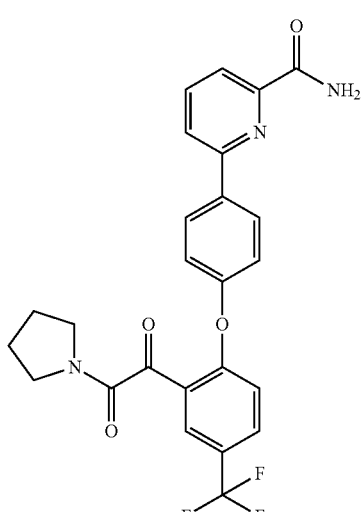 | 6-(4-(2-(2-oxo-2-(pyrrolidin-1-yl)acetyl)-4-(trifluoromethyl)-phenoxy)phenyl)picolinamide |
| 158 | 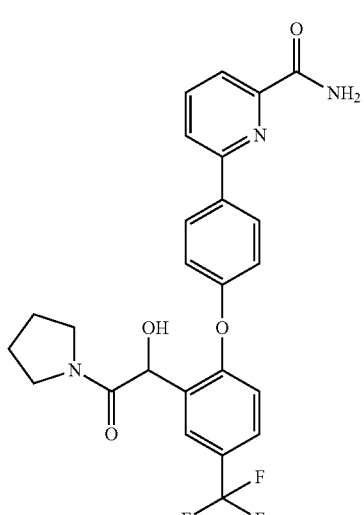 | 6-(4-(2-(1-hydroxy-2-oxo-2-(pyrrolidin-1-yl)ethyl)-4-(trifluoromethyl)phenoxy)phenyl)picolinamide |

TABLE 2A-continued
| Cpd. | Structure | Name |
|---|---|---|
| 159 | 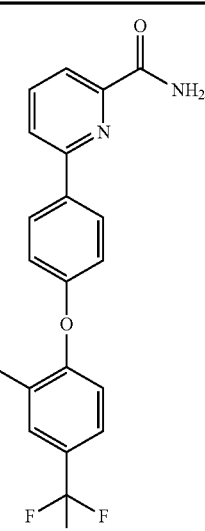 | 2-(4-(6-carbamoylpyridin-2-yl)phenoxy)-5-(trifluoromethyl)benzoic acid |
| 160 | 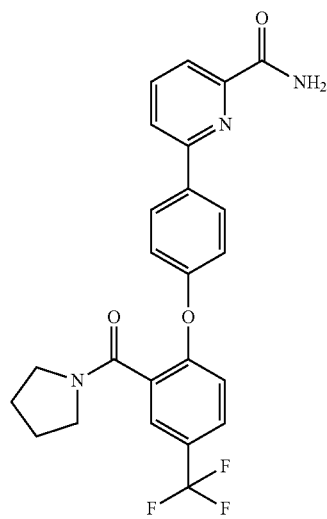 [SMILES: NC(=O)c1cccc(-c2ccc(Oc3ccc(C(F)(F)F)cc3C(=O)N3CCCC3)cc2)n1] | 6-(4-(2-(pyrrolidine-1-carbonyl)-4-(trifluoromethyl)phenoxy)phenyl)picolinamide |
| 161 | 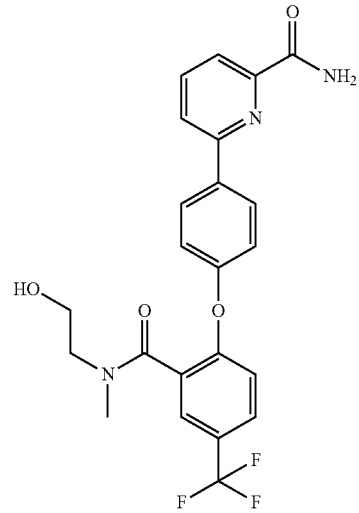 [SMILES: CN(CCO)C(=O)c1cc(C(F)(F)F)ccc1Oc1ccc(-c2cccc(C(N)=O)n2)cc1] | 6-(4-(2-((2-hydroxyethyl)-(methyl)carbamoyl)-4-(trifluoromethyl)phenoxy)phenyl)picolinamide |

TABLE 2A-continued
| Cpd. | Structure | Name |
|---|---|---|
| 162 | 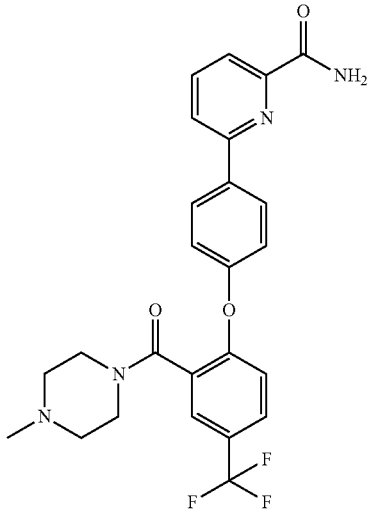 [SMILES: CN1CCN(C(=O)c2cc(C(F)(F)F)ccc2Oc2ccc(-c3cccc(C(N)=O)n3)cc2)CC1] | 6-(4-(2-(4-methylpiperazine-1-carbonyl)-4-(trifluoromethyl)phenoxy)phenyl)picolinamide |
| 163 | 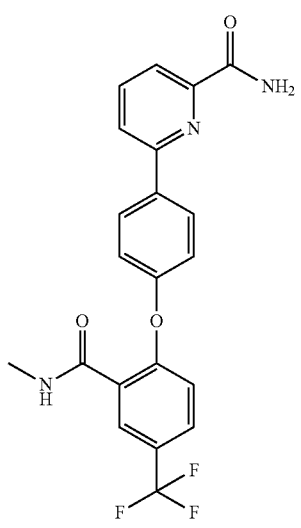 [SMILES: CNC(=O)c1cc(C(F)(F)F)ccc1Oc1ccc(-c2cccc(C(N)=O)n2)cc1] | 6-(4-(2-(methylcarbamoyl)-4-(trifluoromethyl)phenoxy)phenyl)picolinamide |
| 164 | 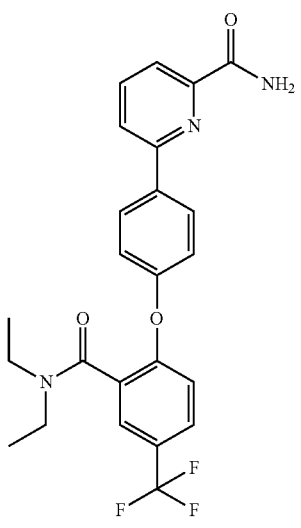 [SMILES: CCN(CC)C(=O)c1cc(C(F)(F)F)ccc1Oc1ccc(-c2cccc(C(N)=O)n2)cc1] | 6-(4-(2-(diethylcarbamoyl)-4-(trifluoromethyl)phenoxy)phenyl)picolinamide |

TABLE 2A-continued
| Cpd. | Structure | Name |
|---|---|---|
| 165 | 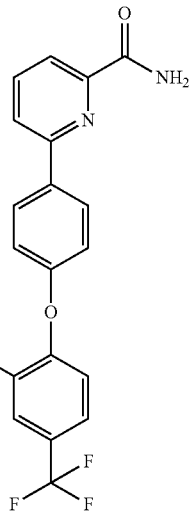 | 6-(4-(2-(3-oxopiperazine-1-carbonyl)-4-(trifluoromethyl)-phenoxy)phenyl)picolinamide |
| 167 | 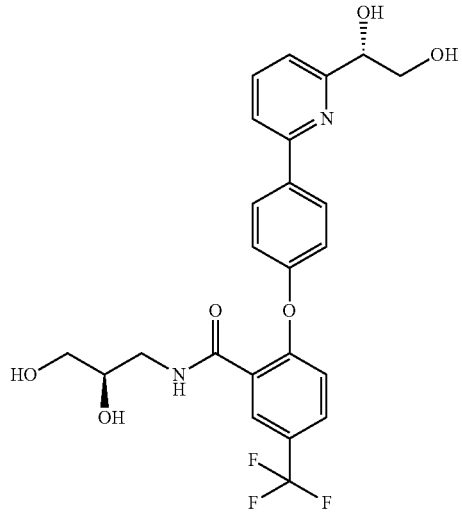 [SMILES: O=C(NC[C@@H](O)CO)c1cc(C(F)(F)F)ccc1Oc1ccc(-c2cccc([C@H](O)CO)n2)cc1] | 2-(4-(6-((S)-1,2-dihydroxyethyl)pyridin-2-yl)phenoxy)-N-((R)-2,3-dihydroxypropyl)-5-(trifluoromethyl)benzamide |
| 168 | 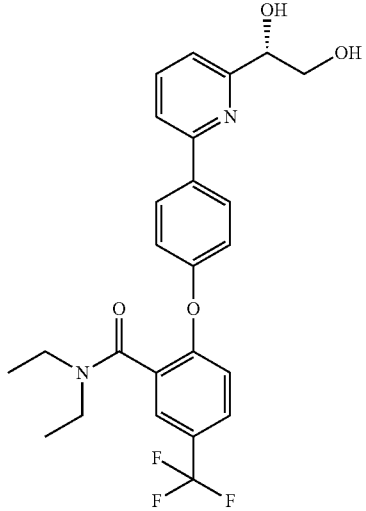 [SMILES: CCN(CC)C(=O)c1cc(C(F)(F)F)ccc1Oc1ccc(-c2cccc([C@H](O)CO)n2)cc1] | (S)-2-(4-(6-(1,2-dihydroxyethyl)pyridin-2-yl)phenoxy)-N,N-diethyl-5-(trifluoromethyl)benzamide |

| Cpd. | Structure | Name |
|---|---|---|
| 169 | 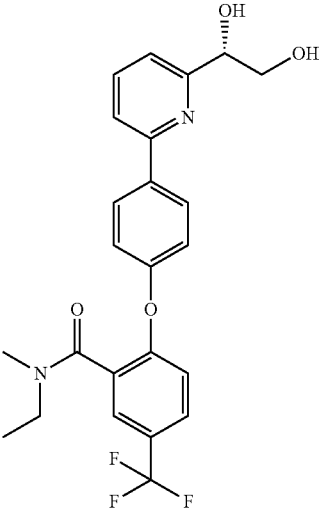 [SMILES: CCN(C)C(=O)c1cc(C(F)(F)F)ccc1Oc1ccc(-c2cccc([C@H](O)CO)n2)cc1] | (S)-2-(4-(6-(1,2-dihydroxy-ethyl)pyridin-2-yl)phenoxy)-N-ethyl-N-methyl-5-(trifluoro-methyl)benzamide |
| 170 | 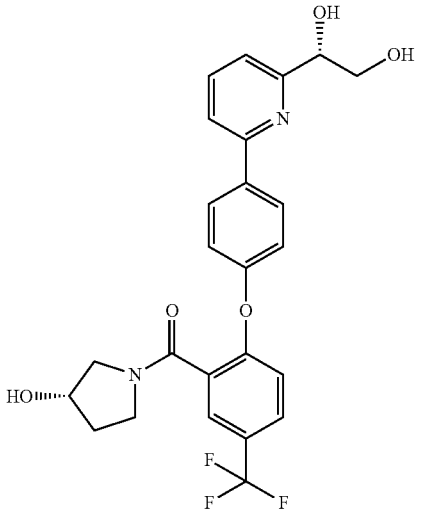 [SMILES: O=C(c1cc(C(F)(F)F)ccc1Oc1ccc(-c2cccc([C@H](O)CO)n2)cc1)N1CC[C@H](O)C1] | (2-(4-(6-((S)-1,2-dihydroxyethyl)pyridin-2-yl)phenoxy)-5-(trifluoromethyl)phenyl)((S)-3-hydroxypyrrolidin-1-yl)methanone |
| 171 | 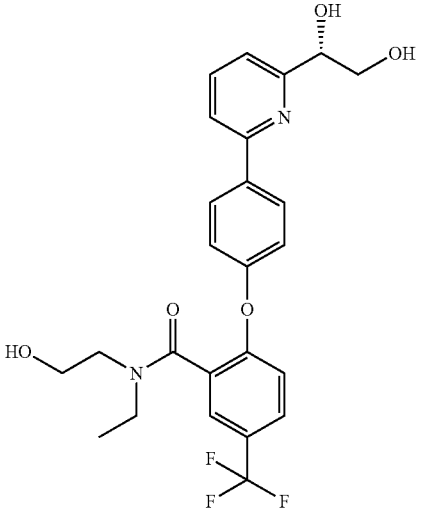 [SMILES: CCN(CCO)C(=O)c1cc(C(F)(F)F)ccc1Oc1ccc(-c2cccc([C@H](O)CO)n2)cc1] | (S)-2-(4-(6-(1,2-dihydroxyethyl)pyridin-2-yl)phenoxy)-N-ethyl-N-(2-hydroxyethyl)-5-(trifluoro-methyl)benzamide |

TABLE 2A-continued
| Cpd. | Structure | Name |
|---|---|---|
| 172 | 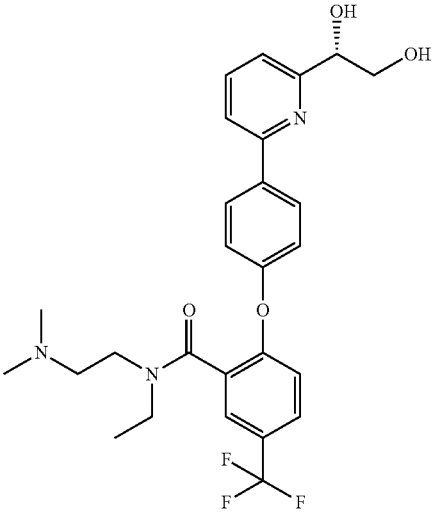 [SMILES: CCN(CCN(C)C)C(=O)c1cc(C(F)(F)F)ccc1Oc1ccc(-c2cccc([C@H](O)CO)n2)cc1] | (S)-2-(4-(6-(1,2-dihydroxyethyl)pyridin-2-yl)phenoxy)-N-(2-(dimethylamino)ethyl)-N-ethyl-5-(trifluoromethyl)benzamide |
| 173 | 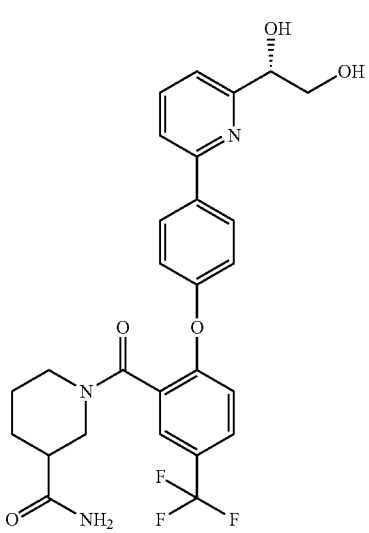 [SMILES: NC(=O)C1CCCN(C(=O)c2cc(C(F)(F)F)ccc2Oc2ccc(-c3cccc([C@H](O)CO)n3)cc2)C1] | 1-(2-(4-(6-((S)-1,2-dihydroxyethyl)pyridin-2-yl)phenoxy)-5-(trifluoromethyl)benzoyl)piperidine-3-carboxamide |
| 174 | 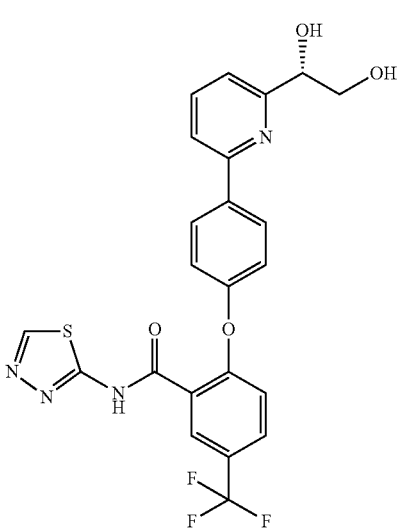 [SMILES: O=C(Nc1nncs1)c1cc(C(F)(F)F)ccc1Oc1ccc(-c2cccc([C@H](O)CO)n2)cc1] | (S)-2-(4-(6-(1,2-dihydroxyethyl)pyridin-2-yl)phenoxy)-N-(1,3,4-thiadiazol-2-yl)-5-(trifluoromethyl)-benzamide |

TABLE 2A-continued
| Cpd. | Structure | Name |
|---|---|---|
| 174 | 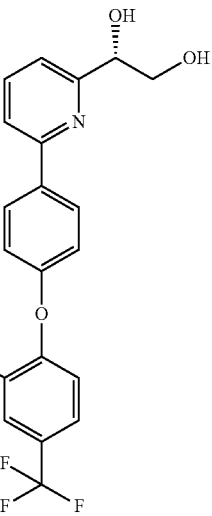 | (S)-2-(4-(6-(1,2-dihydroxyethyl)pyridin-2-yl)phenoxy)-N-(1,3,4-thiadiazol-2-yl)-5-(trifluoromethyl)-benzamide |
| 175 | 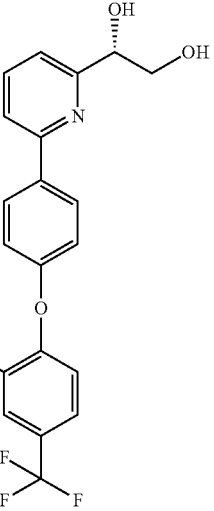 | (S)-2-(4-(6-(1,2-dihydroxyethyl)pyridin-2-yl)phenoxy)-N-(thiazol-2-yl)-5-(trifluoromethyl)benzamide |
| 176 | 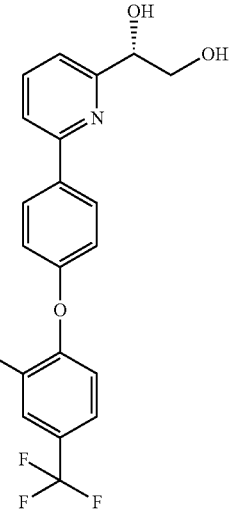 | (S)-N-((1H-tetrazol-5-yl)methyl)-2-(4-(6-(1,2-dihydroxyethyl)-pyridin-2-yl)phenoxy)-5-(trifluoromethyl)benzamide |

In one aspect, the present disclosure is drawn to the following particular embodiments:

Embodiment I

A compound having Formula I-A:

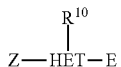

I-A and the pharmaceutically acceptable salts and solvates thereof, wherein:
Z is:

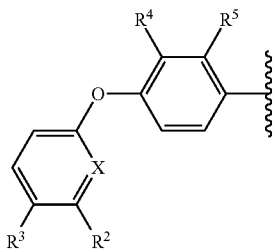

HET is a 6-membered nitrogen-containing heteroaryl, e.g., pyridyl, pyrimidinyl, pyrazinyl, pyridazinyl, or triazinyl;
E is selected from the group consisting of:

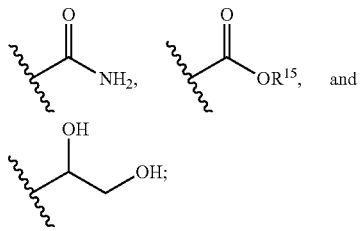

X is selected from the group consisting of N and $CR^1$;
$R^1$ is selected from the group consisting of:
a) hydrogen;
b) optionally substituted heteroaryl;
c) heteroalkyl;
d) (aralkylamino)alkyl
e) optionally-substituted (heterocyclo)alkyl;
f) optionally substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) optionally-substituted (carboxamido)alkyl;
q) (haloalkylamino)alkyl;
r) (hydroxy)(cyano)alkyl;
s) (amino)(cyano)alkyl;
t) (hydroxy)haloalkyl;
u) (heteroarylamino)alkyl;
v) (heteroaryl)alkyl;
w) $COR^{1a}$;
x) $SO_2NR^{8a}R^{8b}$;
y) $COCONR^{9a}R^{9b}$; and z)

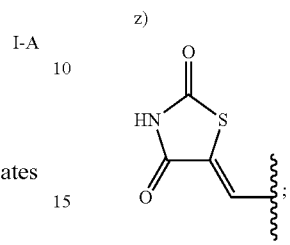

$R^{1a}$ is selected from the group consisting of hydroxy, alkoxy, and $NR^{7a}R^{7b}$;
$R^{7a}$ is selected from the group consisting of:
a) hydrogen;
b) alkyl;
c) hydroxyalkyl;
d) (amino)alkyl;
e) (alkylamino)alkyl;
f) (dialkylamino)alkyl;
g) aryl;
h) (heteroaryl)alkyl; and
i) heteroaryl;
$R^{7b}$ is selected from the group consisting of hydrogen and alkyl; or
$R^{7a}$ and $R^{7b}$ are taken together form taken together to form a 3- to 8-membered optionally substituted heterocyclo;
$R^{8a}$ and $R^{8b}$ are each independently selected from the group consisting of hydrogen and alkyl; or
$R^{8a}$ and $R^{8b}$ are taken together form taken together to form a 3- to 8-membered optionally substituted heterocyclo;
$R^{9a}$ and $R^{9b}$ are each independently selected from the group consisting of hydrogen and alkyl; or
$R^{9a}$ and $R^{9b}$ are taken together form taken together to form a 3- to 8-membered optionally substituted heterocyclo;
$R^2$ is selected from the group consisting of:
a) hydrogen;
b) optionally substituted heteroaryl;
c) heteroalkyl;
d) (aralkylamino)alkyl;
e) optionally-substituted (heterocyclo)alkyl;
f) optionally-substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) (carboxamido)alkyl; and
q) (haloalkylamino)alkyl;
$R^3$ is selected from the group consisting of:
a) hydrogen;
b) halo;
c) cyano;
d) haloalkyl;
e) $C_1$-$C_4$ alkyl;
f) $C_{1-4}$ haloalkyl;

g) $C_{1-4}$ haloalkoxy; and
h) $C_{1-4}$ alkoxy;
$R^4$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl;
$R^5$ is selected from the group consisting of:
a) hydrogen;
b) chloro;
c) cyano;
d) $C_{1-4}$ haloalkyl;
e) arylamino;
f) (arylamino)alkyl;
g) (aryloxy)alkyl;
h) (dialkylamino)alkyl;
i) alkoxyalkyl;
j) (heterocyclo)alkyl;
k) optionally substituted aryl; and
l) optionally substituted heteroaryl;
$R^{10}$ is selected from the group consisting of:
a) hydrogen;
b) dihydroxyalkyl;
c) carboxy;
d) (heteroaryl)alkyl;
e) (acetoxy)alkyl;
f) —Y—$R^{11}$; and
g) carboxamido;
Y is —O— or —NH—;
$R^{11}$ is selected from the group consisting of:

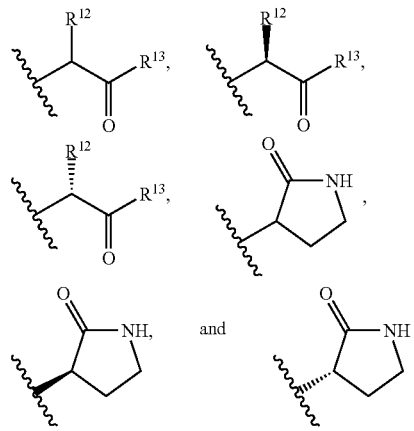

$R^{12}$ is selected from the group consisting of hydrogen, alkyl, and hydroxyalkyl;
$R^{13}$ is selected from the group consisting of hydroxy, alkoxy, and —$NR^{4a}R^{14b}$;
$R^{14a}$ is selected from the group consisting of:
a) hydrogen;
b) alkyl;
c) aralkyl;
d) (heterocyclo)alkyl;

e) (heteroaryl)alkyl;
f) (amino)alkyl;
g) (alkylamino)alkyl;
h) (dialkylamino)alkyl;
i) (carboxamido)alkyl;
j) (cyano)alkyl;
k) alkoxyalkyl;
l) hydroxyalkyl; and
m) heteroalkyl; and
$R^{14b}$ is selected from the group consisting of hydrogen and alkyl; or
$R^{14a}$ and $R^{14b}$ taken together with the nitrogen atom to which they are attached form a 3- to 8-membered optionally substituted heterocyclo.

Embodiment II

The compound of Embodiment I, and the pharmaceutically acceptable salts and solvates thereof, wherein when X is $CR^1$ and $R^1$ is hydrogen or hydroxyalkyl, then:
i) $R^2$ is selected from the group consisting of optionally substituted heteroaryl; heteroalkyl; (aralkylamino)alkyl(heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl; or
ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl.

Embodiment III

The compound of Embodiment I, and the pharmaceutically acceptable salts and solvates thereof, wherein when X is $CR^1$ and $R^2$ is hydrogen, then:
i) $R^1$ is selected from the group consisting of optionally substituted heteroaryl; heteroalkyl; (aralkylamino)alkyl; (heterocyclo)alkyl; optionally substituted aryl; (heterocycloalkylamino)alkyl; (heterocycloamino)alkyl; alkanolamine; (amino)alkyl; (alkylamino)alkyl; (dialkylamino)alkyl; (cycloalkylamino)alkyl; (nitro)alkyl; (carboxamido)alkyl; (haloalkylamino)alkyl; hydroxy)(cyano)alkyl; (amino)(cyano)alkyl; (hydroxy)haloalkyl; (heteroarylamino)alkyl; (heteroaryl)alkyl; $COR^{1a}$; $SO_2NR^{8a}R^{8b}$; $COCONR^{9a}R^{9b}$; and

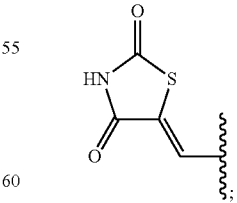

or
ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl.

Embodiment IV

The compound of any one of Embodiments I to III, or a pharmaceutically acceptable salt or solvate thereof, wherein Z-HET-E is selected from the group consisting of:

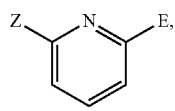  HET-1

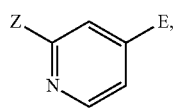  HET-2

HET-3

HET-4

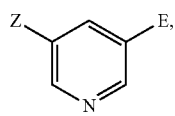  HET-5

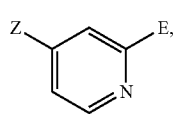  HET-6

HET-7

HET-8

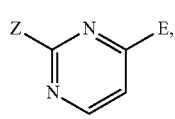  HET-9

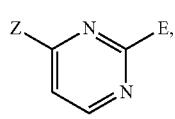  HET-10

HET-11

-continued

HET-12

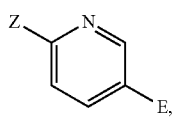  HET-13

HET-14

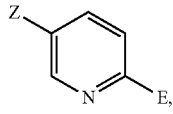  HET-15

HET-16

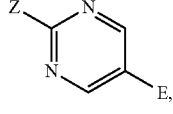  HET-17

HET-18

HET-19

HET-20

HET-21

HET-22

HET-23

-continued

HET-24

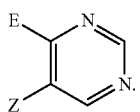

HET-25

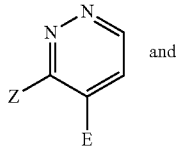 and

HET-26

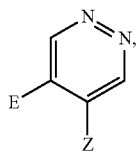

wherein each of the above Z-HET-E groups is further substituted by $R^{10}$ (as set forth in Formula I-A).

Embodiment V

The compound of any one of Embodiments I-IV, or a pharmaceutically acceptable salt or solvate thereof, wherein $R^{10}$ is hydrogen.

Embodiment VI

The compound of any one of Embodiments I-V, or a pharmaceutically acceptable salt or solvate thereof, wherein $R^1$ is selected from the group consisting of:
a) hydrogen;
b) optionally substituted heteroaryl;
c) heteroalkyl;
d) (aralkylamino)alkyl
e) optionally substituted (heterocyclo)alkyl;
f) optionally substituted aryl;
g) (heterocycloalkylamino)alkyl;
h) (heterocycloamino)alkyl;
i) alkanolamine;
j) hydroxyalkyl;
k) (amino)alkyl;
l) (alkylamino)alkyl;
m) (dialkylamino)alkyl;
n) (cycloalkylamino)alkyl;
o) (nitro)alkyl;
p) (carboxamido)alkyl; and
q) (haloalkylamino)alkyl.

Embodiment VII

The compound of Embodiments I-V, or a pharmaceutically acceptable salt or solvate thereof, wherein $R^1$ is selected from the group consisting of:
a) (hydroxy)(cyano)alkyl;
b) (amino)(cyano)alkyl;
c) (hydroxy)haloalkyl;
d) (heteroarylamino)alkyl;
e) (heteroaryl)alkyl;
f) $COR^{1a}$;
g) $SO_2NR^{8a}R^{8b}$;
h) $COCONR^{9a}R^{9b}$; and i) 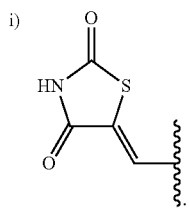 [SMILES: */C=C1\SC(=O)NC1=O]

Embodiment VIII

The compound of any one of Embodiments I-VII, or a pharmaceutically acceptable salt or solvate thereof, wherein Z-HET-E is selected from the group consisting of HET-1, HET-2, HET-3, HET-4, HET-12, HET-13, HET-19, HET-20, HET-21, and HET-22.

Embodiment IX

The compound of any one of Embodiments I-VII, or a pharmaceutically acceptable salt or solvate thereof, wherein Z-HET-E is selected from the group consisting of HET-5, HET-6, HET-7, HET-14, HET-15, HET-23, and HET-24.

Embodiment X

The compound of any one of Embodiments I-VII, or a pharmaceutically acceptable salt or solvate thereof, wherein Z-HET-E is selected from the group consisting of HET-8 and HET-16.

Embodiment XI

The compound of any one of Embodiments I-VII, or a pharmaceutically acceptable salt or solvate thereof, wherein Z-HET-E is selected from the group consisting of HET-9, HET-10, HET-11, HET-17, and HET-18.

Embodiment XII

The compound of any one of Embodiments I-VII, or a pharmaceutically acceptable salt or solvate thereof, wherein Z-HET-E is selected from the group consisting of HET-25 and HET-26.

Embodiment XIII

The compound of any one of Embodiments I-VII, or a pharmaceutically acceptable salt or solvate thereof, wherein Z-HET-E is selected from the group consisting of HET-1, HET-2, HET-3, HET-4, HET-5, HET-6, HET-7, HET-8, HET-9, HET-10, and HET-11.

Embodiment XIV

The compound of any one of Embodiments I-VII, or a pharmaceutically acceptable salt or solvate thereof, wherein Z-HET-E is selected from the group consisting of HET-12, HET-13, HET-14, HET-15, HET-16, HET-17, and HET-18.

Embodiment XV

The compound of any one of Embodiments I-VII, or a pharmaceutically acceptable salt or solvate thereof, wherein Z-HET-E is selected from the group consisting of HET-19, HET-20, HET-21, HET-22, HET-23, HET-24, HET-25, and HET-26.

Embodiment XVI

The compound of any one of Embodiments I-VIII or XIII having Formula II-A:

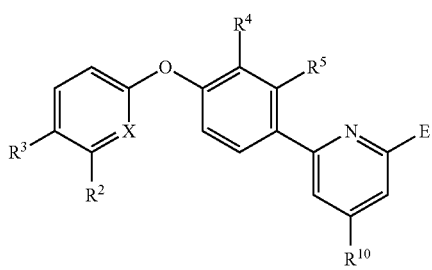

II-A or a pharmaceutically acceptable salt or solvate thereof.

Embodiment XVII

The compound of Embodiment XVI, or a pharmaceutically acceptable salt or solvate thereof, wherein $R^5$ is selected from the group consisting of hydrogen; halogen (e.g., fluoro, chloro, and bromo); and $C_{1-4}$ haloalkyl.

Embodiment XVIII

The compound of any one of Embodiments I-VIII or XIII, or a pharmaceutically acceptable salt or solvate thereof, having Formula III-A:

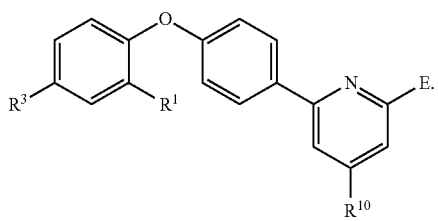

III-A

Embodiment XIX

The compound of Embodiment XVIII, or a pharmaceutically acceptable salt or solvate thereof, wherein $R^1$ is selected from the group consisting of:
  a) optionally substituted heteroaryl (e.g., pyrrolyl, 1H-pyrazol-5-yl, 1H-pyrazol-4-yl, thiophenyl, and pyridyl);
  b) heteroalkyl;
  c) (aralkylamino)alkyl
  d) optionally-substituted (heterocyclo)alkyl;
  e) optionally substituted aryl;
  f) (heterocycloalkylamino)alkyl;
  g) (heterocycloamino)alkyl;
  h) alkanolamine;
  i) hydroxyalkyl;
  j) (amino)alkyl;
  k) (alkylamino)alkyl;
  l) (dialkylamino)alkyl;
  m) (cycloalkylamino)alkyl;
  n) (nitro)alkyl;
  o) (carboxamido)alkyl;
  p) (haloalkylamino)alkyl;
  q) (hydroxy)(cyano)alkyl;
  r) (amino)(cyano)alkyl;
  s) (hydroxy)haloalkyl;
  t) (heteroarylamino)alkyl;
  u) (heteroaryl)alkyl;
  v) $COR^{1a}$;
  w) $SO_2NR^{8a}R^{8b}$
  x) $COCONR^{9a}R^{9b}$; and y) 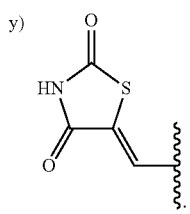 [SMILES: */C=C1\SC(=O)NC1=O]

Embodiment XX

The compound of Embodiment XIX, or a pharmaceutically acceptable salt or solvate thereof, wherein $R^1$ is selected from the group consisting of:
  a) optionally substituted heteroaryl;
  b) heteroalkyl;
  c) (aralkylamino)alkyl
  d) optionally substituted (heterocyclo)alkyl;
  e) optionally substituted aryl;
  f) (heterocycloalkylamino)alkyl;
  g) (heterocycloamino)alkyl;
  h) alkanolamine;
  i) (amino)alkyl;
  j) (alkylamino)alkyl;
  k) (dialkylamino)alkyl;
  l) (cycloalkylamino)alkyl;
  m) (nitro)alkyl; and
  n) (carboxamido)alkyl.

Embodiment XXI

The compound of Embodiment XIX, or a pharmaceutically acceptable salt or solvate thereof, wherein $R^1$ is selected from the group consisting of optionally substituted heteroaryl, (heterocyclo)alkyl, and (dialkylamino)alkyl.

Embodiment XXII

The compound of Embodiment XVIII, or a pharmaceutically acceptable salt or solvate thereof, wherein $R^1$ is selected from the group consisting of:
  a) (hydroxy)(cyano)alkyl;
  b) (amino)(cyano)alkyl;
  c) (hydroxy)haloalkyl;
  d) (heteroarylamino)alkyl;
  e) (heteroaryl)alkyl;
  f) $COR^{1a}$;
  g) $SO_2NR^{8a}R^{8b}$;
  h) $COCONR^{9a}R^{9b}$; and i) 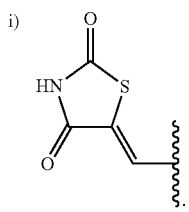 [SMILES: */C=C1\SC(=O)NC1=O]

Embodiment XXIV

The compound of Embodiment XXIII, or a pharmaceutically acceptable salt or solvate thereof, wherein $R^1$ is $COR^{1a}$.

Embodiment XXV

The compound of Embodiment XXIV, or a pharmaceutically acceptable salt or solvate thereof, wherein $R^{1a}$ is $NR^{7a}R^{7b}$.

Embodiment XXVI

The compound of any one of Embodiments I-VIII or XIII, or a pharmaceutically acceptable salt or solvate thereof, having Formula IV:

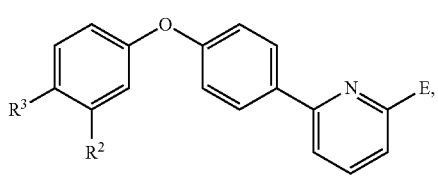

IV wherein $R^2$ is selected from the group consisting of heteroaryl, (heterocyclo)alkyl, and (haloalkylamino)alkyl.

Embodiment XXVII

The compound of any one of Embodiments I-VIII or XIII, or a pharmaceutically acceptable salt or solvate thereof, having Formula V:

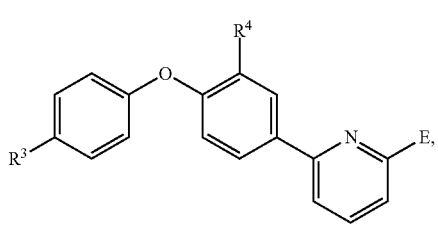

V wherein $R^4$ is selected from the group consisting of:
a) arylamino;
b) (arylamino)alkyl;
c) (aryloxy)alkyl;
d) (dialkylamino)alkyl;
e) (heterocyclo)alkyl;
f) optionally substituted aryl; and
g) optionally substituted heteroaryl.

Embodiment XXVIII

The compound any one of Embodiments I-VIII or XIII, or a pharmaceutically acceptable salt or solvate thereof, having Formula VI:

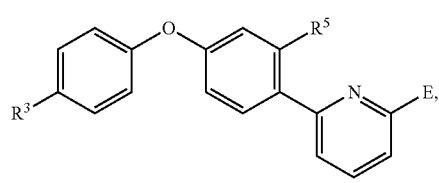

VI wherein $R^5$ is selected from the group consisting of:
a) arylamino;
b) (arylamino)alkyl;
c) (aryloxy)alkyl;
d) (dialkylamino)alkyl;
e) (heterocyclo)alkyl;
f) optionally substituted aryl; and
g) optionally substituted heteroaryl.

Embodiment XXIX: The compound of any one of Embodiments I-VIII or XIII, or a pharmaceutically acceptable salt or solvate thereof, having Formula VII:

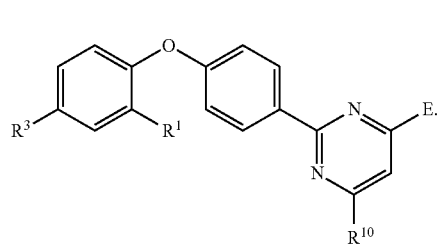

VII

Embodiment XXX

The compound of Embodiment XXIX, or a pharmaceutically acceptable salt or solvate thereof, wherein $R^1$ is selected from the group consisting of:
a) optionally substituted heteroaryl;
b) heteroalkyl;
c) (aralkylamino)alkyl
d) (heterocyclo)alkyl;
e) optionally substituted aryl;
f) (heterocycloalkylamino)alkyl;
g) (heterocycloamino)alkyl;
h) alkanolamine;
i) hydroxyalkyl;
j) (amino)alkyl;
k) (alkylamino)alkyl;
l) (dialkylamino)alkyl;
m) (cycloalkylamino)alkyl;
n) (nitro)alkyl;
o) (carboxamido)alkyl;
p) (haloalkylamino)alkyl;
q) (hydroxy)(cyano)alkyl;
r) (amino)(cyano)alkyl;
s) (hydroxy)haloalkyl;

t) (heteroarylamino)alkyl;
u) (heteroaryl)alkyl;
v) COR$^{1a}$;
w) SO$_2$NR$^{8a}$R$^{8b}$;
x) COCONR$^{9a}$R$^{9b}$; and y) 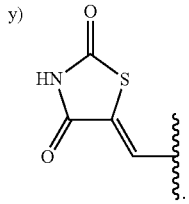 [SMILES: */C=C1\SC(=O)NC1=O]

Embodiment XXXI

The compound of any one of Embodiments I, XVIII, or XXX, or a pharmaceutically acceptable salt or solvate thereof, wherein R$^1$ is optionally substituted heteroaryl.

Embodiment XXXII

The compound of any one of Embodiments I-XXI, or a pharmaceutically acceptable salt or solvate thereof, wherein:
R$^{10}$ is selected from the group consisting of hydrogen, dihydroxyalkyl and —Y—R$^{11}$;
R$^{11}$ is selected from the group consisting of:

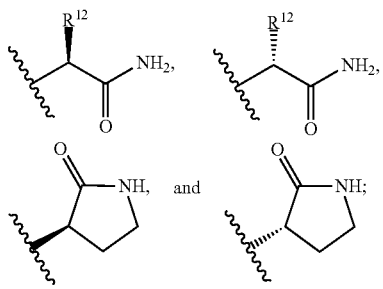

and R$^{12}$ is C$_1$-C$_4$ alkyl.

Embodiment XXXIII

The compound of Embodiment XXXII, or a pharmaceutically acceptable salt or solvate thereof, wherein R$^{10}$ is —Y—R$^{11}$.

Embodiment XXXIV

The compound of Embodiment XXXIII, or a pharmaceutically acceptable salt or solvate thereof, wherein Y is —NH—.

Embodiment XXXV

The compound of Embodiment XXXIII, or a pharmaceutically acceptable salt or solvate thereof, wherein Y is —O—.

Embodiment XXXVI

The compound of Embodiment XXXII, or a pharmaceutically acceptable salt or solvate thereof, wherein R$^{10}$ is dihydroxyalkyl.

Embodiment XXXVII

The compound of Embodiment XXXVI, or a pharmaceutically acceptable salt or solvate thereof, wherein R$^{10}$ is dihydroxyalkyl selected from the group consisting of:

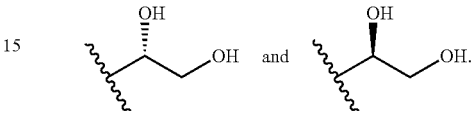

Embodiment XXXVIII

The compound of any one of Embodiments I-XXXVII, or a pharmaceutically acceptable salt or solvate thereof, wherein E is:

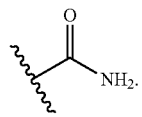

Embodiment XXXIX

The compound of any one of Embodiments I-XXXVII, or a pharmaceutically acceptable salt or solvate thereof, wherein E is selected from the group consisting of:

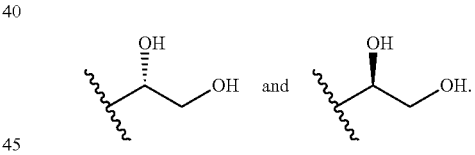

Embodiment XL

The compound of any one of Embodiments I-XXX, or a pharmaceutically acceptable salt or solvate thereof, wherein R$^3$ is selected from the group consisting of halo, cyano, and haloalkyl.

Embodiment XLI

The compound of Embodiment I, or a pharmaceutically acceptable salt or solvate thereof, selected from the group consisting of:
(S)-1-(6-(4-(2-(piperidin-1-ylmethyl)-4-(trifluoromethyl)phenoxy)phenyl)pyridin-2-yl)ethane-1,2-diol;
6-(4-(2-(2-oxo-2-(pyrrolidin-1-yl)acetyl)-4-(trifluoromethyl)phenoxy)phenyl) picolinamide;
6-(4-(2-((cyclopentylamino)methyl)-4-(trifluoromethyl) phenoxy)phenyl)picolinamide methyl 6-(4-(2-(cyano(hydroxy)methyl)-4-(trifluoromethyl)phenoxy)phenyl) picolinate;

6-(4-(2-((2-hydroxyethyl)(methyl)carbamoyl)-4-(trifluoromethyl)phenoxy)phenyl) picolinamide;
6-(4-(2-(pyrrolidine-1-carbonyl)-4-(trifluoromethyl)phenoxy)phenyl)picolinamide;
6-(4-(2-(4-methylpiperazine-1-carbonyl)-4-(trifluoromethyl) phenoxy)phenyl) picolinamide;
6-(4-(2-(methylcarbamoyl)-4-(trifluoromethyl)phenoxy)phenyl)picolinamide;
6-(4-(2-(diethylcarbamoyl)-4-(trifluoromethyl)phenoxy)phenyl)picolinamide;
6-(4-(2-(3-oxopiperazine-1-carbonyl)-4-(trifluoromethyl)phenoxy)phenyl)picolinamide;
6-(4-(2-(1-hydroxy-2-oxo-2-(pyrrolidin-1-yl)ethyl)-4-(trifluoromethyl)phenoxy)phenyl) picolinamide;
(Z)-6-(4-(2-((2,4-dioxothiazolidin-5-ylidene)methyl)-4-(trifluoromethyl)phenoxy)phenyl)picolinamide;
2-(4-(6-carbamoylpyridin-2-yl)phenoxy)-5-(trifluoromethyl)benzoic acid;
6-(4-(2-(2-oxo-1,2-di(pyrrolidin-1-yl)ethyl)-4-(trifluoromethyl)phenoxy)phenyl) picolinamide;
(1S)-1-(6-(4-(4-fluoro-2-(2,2,2-trifluoro-1-hydroxyethyl)phenoxy)phenyl)pyridin-2-yl)ethane-1,2-diol;
6-(4-(2-(2-oxo-1-(3-oxopiperazin-1-yl)-2-(pyrrolidin-1-yl)ethyl)-4-(trifluoromethyl) phenoxy)phenyl)picolinamide;
6-(4-(2-(amino(cyano)methyl)-4-(trifluoromethyl)phenoxy)phenyl)picolinamide;
6-(4-(2-((thiazol-2-ylamino)methyl)-4-(trifluoromethyl)phenoxy)phenyl)picolinamide;
(S)-2-(4-(6-(1,2-dihydroxyethyl)pyridin-2-yl)phenoxy)-N,N-diethyl-5-(trifluoromethyl)benzenesulfonamide;
6-(4-(2-(N,N-diethylsulfamoyl)-4-(trifluoromethyl)phenoxy)phenyl)picolinamide;
(R)-1-(2-(4-(2-(pyrrolidin-1-ylmethyl)-4-(trifluoromethyl)phenoxy)phenyl)pyrimidin-4-yl)ethane-1,2-diol;
(S)-1-(2-(4-(2-(pyrrolidin-1-ylmethyl)-4-(trifluoromethyl)phenoxy)phenyl)pyrimidin-4-yl)ethane-1,2-diol;
6-(4-(2-((ethyl(methyl)amino)methyl)-4-(trifluoromethyl)phenoxy)phenyl)picolinamide
6-(4-(2-((diethylamino)methyl)-4-(trifluoromethyl)phenoxy)phenyl) picolinamide;
6-(4-(2-((ethyl(2-hydroxyethyl)amino)methyl)-4-(trifluoromethyl)phenoxy)phenyl)picolinamide;
6-(4-(2-(((2-(dimethylamino)ethyl)(ethyl)amino)methyl)-4-(trifluoromethyl)phenoxy)phenyl)picolinamide;
6-(4-(2-((3-carbamoylpiperidin-1-yl)methyl)-4-(trifluoromethyl)phenoxy)phenyl) picolinamide;
2-(4-(6-((S)-1,2-dihydroxyethyl)pyridin-2-yl)phenoxy)-N—((R)-2,3-dihydroxypropyl)-5-(trifluoromethyl)benzamide;
(S)-2-(4-(6-(1,2-dihydroxyethyl)pyridin-2-yl)phenoxy)-N,N-diethyl-5-(trifluoromethyl)benzamide;
(S)-2-(4-(6-(1,2-dihydroxyethyl)pyridin-2-yl)phenoxy)-N-ethyl-N-methyl-5-(trifluoromethyl)benzamide;
(2-(4-(6-((S)-1,2-dihydroxyethyl)pyridin-2-yl)phenoxy)-5-(trifluoromethyl)phenyl)((S)-3-hydroxypyrrolidin-1-yl)methanone;
(S)-2-(4-(6-(1,2-dihydroxyethyl)pyridin-2-yl)phenoxy)-N-ethyl-N-(2-hydroxyethyl)-5-(trifluoromethyl)benzamide;
(S)-2-(4-(6-(1,2-dihydroxyethyl)pyridin-2-yl)phenoxy)-N-(2-(dimethylamino)ethyl)-N-ethyl-5-(trifluoromethyl)benzamide;
1-(2-(4-(6-((S)-1,2-dihydroxyethyl)pyridin-2-yl)phenoxy)-5-(trifluoromethyl)benzoyl)piperidine-3-carboxamide;
(S)-2-(4-(6-(1,2-dihydroxyethyl)pyridin-2-yl)phenoxy)-N-(1,3,4-thiadiazol-2-yl)-5-(trifluoromethyl)benzamide;
(S)-2-(4-(6-(1,2-dihydroxyethyl)pyridin-2-yl)phenoxy)-N-(thiazol-2-yl)-5-(trifluoromethyl)benzamide;
(S)—N-((1H-tetrazol-5-yl)methyl)-2-(4-(6-(1,2-dihydroxyethyl)pyridin-2-yl)phenoxy)-5-(trifluoromethyl)benzamide;
(S)-6-(1,2-dihydroxyethyl)-2-(4-(2-(1-methyl-1H-pyrazol-5-yl)-4-(trifluoromethyl)phenoxy)phenyl)pyrimidine-4-carboxamide;
6-(4-(2-(1-methyl-1H-pyrazol-5-yl)-4-(trifluoromethyl)phenoxy)phenyl)picolinamide;
2-(6-carbamoyl-2-(4-(2-((diethylamino)methyl)-4-(trifluoromethyl)phenoxy)phenyl)pyrimidin-4-yl)ethyl acetate;
2-(4-(2-(1-methyl-1H-pyrazol-5-yl)-4-(trifluoromethyl)phenoxy)phenyl)pyrimidine-4-carboxamide;
(S)-2-(4-(2-(1-methyl-1H-pyrazol-5-yl)-4-(trifluoromethyl)phenoxy)phenyl)-6-((2-oxopyrrolidin-3-yl)amino)pyrimidine-4-carboxamide;
6-(2-(1H-imidazol-1-yl)ethyl)-2-(4-(2-(morpholinomethyl)-4-(trifluoromethyl)phenoxy)phenyl)pyrimidine-4-carboxamide;
(S)-2-(4-(2-(2-(dimethylamino)pyrimidin-5-yl)-4-(trifluoromethyl)phenoxy)phenyl)-6-((2-oxopyrrolidin-3-yl)amino)pyrimidine-4-carboxamide;
(S)-2-(4-(2-(5-(dimethylamino)pyrazin-2-yl)-4-(trifluoromethyl)phenoxy)phenyl)-6-((2-oxopyrrolidin-3-yl)amino)pyrimidine-4-carboxamide;
(S)-2-(4-(2-((diethylamino)methyl)-4-(trifluoromethyl)phenoxy)phenyl)-6-(1,2-dihydroxyethyl)pyrimidine-4-carboxamide;
6-carbamoyl-2-(4-(2-((diethylamino)methyl)-4-(trifluoromethyl)phenoxy)phenyl) pyrimidine-4-carboxylic acid;
6-carbamoyl-2-(4-(2-(morpholinomethyl)-4-(trifluoromethyl)phenoxy)phenyl) pyrimidine-4-carboxylic acid;
(R)-2-(4-(2-((diethylamino)methyl)-4-(trifluoromethyl)phenoxy)phenyl)-6-(1,2-dihydroxyethyl)pyrimidine-4-carboxamide;
(S)-6-((1-amino-1-oxopropan-2-yl)amino)-2-(4-(2-(5-(dimethylamino)pyrazin-2-yl)-4-(trifluoromethyl)phenoxy)phenyl)pyrimidine-4-carboxamide;
(S)-4-(1,2-dihydroxyethyl)-6-(4-(2-(1-methyl-1H-pyrazol-5-yl)-4-(trifluoromethyl) phenoxy)phenyl)picolinamide;
(S)-4-(1,2-dihydroxyethyl)-6-(4-(2-(1-methyl-1H-pyrazol-5-yl)-4-(trifluoromethyl)phenoxy)phenyl)picolinamide;
(S)-6-(4-(2-(1-(azetidin-3-yl)-1H-pyrazol-5-yl)-4-chlorophenoxy)phenyl)-4-(1,2-dihydroxyethyl)picolinamide;
(S)-6-(4-(2-(1-(azetidin-3-yl)-1H-pyrazol-5-yl)-4-chlorophenoxy)phenyl)-4-(1,2-dihydroxyethyl)picolinamide;
(S)-2-(4-(2-(1-(azetidin-3-yl)-1H-pyrazol-5-yl)-4-chlorophenoxy)phenyl)-6-((2-oxopyrrolidin-3-yl)amino)pyrimidine-4-carboxamide;
(S)-6-((1-amino-1-oxopropan-2-yl)amino)-2-(4-(2-(1-methyl-1H-pyrazol-5-yl)-4-(trifluoromethyl)phenoxy)phenyl)pyrimidine-4-carboxamide;
(S)-6-((1-amino-1-oxopropan-2-yl)amino)-2-(4-(2-(1-methyl-H-pyrazol-5-yl)phenoxy)phenyl)pyrimidine-4-carboxamide;
(S)-6-((1-amino-1-oxopropan-2-yl)amino)-2-(4-(2-(1-methyl-1H-pyrazol-5-yl) phenoxy)phenyl)pyrimidine-4-carboxamide;
(S)-2-(4-(4-chloro-2-(1-methyl-1H-pyrazol-5-yl)phenoxy)phenyl)-6-((2-oxopyrrolidin-3-yl)amino)pyrimidine-4-carboxamide, or a pharmaceutically acceptable salt or solvate thereof.

Embodiment XLII

A pharmaceutical composition comprising the compound of any one of Embodiments I-XLI, or a pharmaceutically acceptable salt or solvate thereof, and a pharmaceutically acceptable carrier.

Embodiment XLIII

A method of treating a disorder responsive to the blockade of sodium channels in a mammal suffering from said disorder, comprising administering to a mammal in need of such treatment an effective amount of a compound of any one of Embodiments I-XLI, or a pharmaceutically acceptable salt or solvate thereof.

Embodiment XLIV

The method of Embodiment XLIII, wherein a disorder responsive to the blockade of TTX resistant sodium channels is treated.

Embodiment XLV

The method of Embodiment XLIV, wherein a disorder responsive to the blockade of TTX sensitive sodium channels is treated.

Embodiment XLVI

The method of Embodiment XLV, wherein a disorder responsive to the blockade of Nav1.7 sodium channels is treated.

Embodiment XLVII

A method for treating stroke, neuronal damage resulting from head trauma, epilepsy, seizures, neuronal loss following global and focal ischemia, pain, migraine, primary erythromelalgia, paroxysmal extreme pain disorder, cerebellar atrophy, ataxia, mental retardation, a neurodegenerative disorder, manic depression, tinnitus, myotonia, a movement disorder, or cardiac arrhythmia, or providing local anesthesia in a mammal, comprising administering an effective amount of a compound of any one of Embodiments I-XLI, or a pharmaceutically acceptable salt or solvate thereof, to a mammal in need of such treatment.

Embodiment XLVIII

The method of Embodiment XLVII, wherein said method is for treating pain.

Embodiment XLIX

The method of Embodiment XLVIII, wherein said method is for preemptive or palliative treatment of pain.

Embodiment L

The method of Embodiment XLIX, wherein said pain is selected from the group consisting of chronic pain, inflammatory pain, neuropathic pain, acute pain, and surgical pain.

Embodiment LI

A method of modulating sodium channels in a mammal, comprising administering to the mammal at least one compound of any one of Embodiments I-XLI, or a pharmaceutically acceptable salt or solvate thereof.

Embodiment LII

The method of Embodiment LI, wherein the Nav1.7 sodium channel is modulated.

Embodiment LIII

A pharmaceutical composition, comprising the compound of any one of Embodiments I-XLI, or a pharmaceutically acceptable salt or solvate thereof, for treating a disorder responsive to the blockade of sodium ion channels.

Embodiment LIV

A compound of any one of Embodiments I-XLI, or a pharmaceutically acceptable salt or solvate thereof, for use in treating a disorder responsive to the blockade of sodium ion channels.

Embodiment LV

A method of preparing a pharmaceutical composition, comprising admixing a therapeutically effective amount of a compound of any one of Embodiments I-XLI, or a pharmaceutically acceptable salt or solvate thereof, with a pharmaceutically acceptable carrier.

The present disclosure further provides the compound as defined in any one of Embodiments I-XLI, or a pharmaceutically acceptable salt or solvate thereof, for use in treating a disorder responsive to the blockade of sodium ion channels.

For the purpose of the present disclosure, the term "alkyl" as used by itself or as part of another group refers to a straight- or branched-chain aliphatic hydrocarbon containing one to twelve, i.e., i.e. 1, 2, 3, 4, 5, 6, 7, 8, 9, 10, 11 or 12, carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. Non-limiting exemplary $C_{1-10}$ alkyl groups include methyl, ethyl, propyl, isopropyl, butyl, sec-butyl, tert-butyl, isobutyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —$CH_2CH_2NO_2$, —$CH_2CH_2CO_2H$, —$CH_2CH_2SO_2CH_3$, —$CH_2CH_2COPh$, —$CH_2C_6H_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In one embodiment, the cycloalkyl group is a saturated cyclic aliphatic hydrocarbon containing one or two rings, preferably one ring, and having 3, 4, 5, 6, 7, 8, 9, 10, 11 or 12 carbon atoms. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

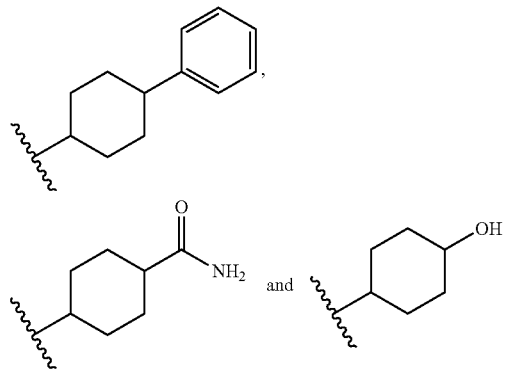

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group having 4, 5, 6, 7, or 8 carbon atoms. Exemplary cycloalkenyl groups include cyclopentenyl, cyclohexenyl and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group having 2, 3, 4, 5 or 6 carbon atoms. In another embodiment, the alkenyl group is chosen from a $C_{2-4}$ alkenyl group having 2, 3, or 4 carbon atoms. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group having 2, 3, 4, 5 or 6 carbon atoms. In another embodiment, the alkynyl group is chosen from a $C_{2-4}$ alkynyl group having 2, 3 or 4 carbon atoms. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "(hydroxy)haloalkyl" as used by itself or as part of another group refers to an alkyl group substituted by one or more halogen atoms and one hydroxy group. A non-limiting exemplary (hydroxy)haloalkyl group is $-CH(OH)CF_3$.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "(cycloalkyl)alkyl" as used by itself or as part of another group refers to an alkyl group substituted with at least one optionally substituted cycloalkyl group. Non-limiting exemplary (cycloalkyl)alkyl groups include:

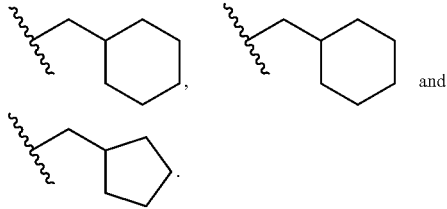

For the purpose of the present disclosure, the term "hydroxy(cycloalkyl)alkyl" as used by itself or as part of another group refers to (cycloalkyl)alkyl group substituted with at least one hydroxy group. The hydroxy group(s) can be at any available position. Non-limiting exemplary hydroxy(cycloalkyl)alkyl groups include:

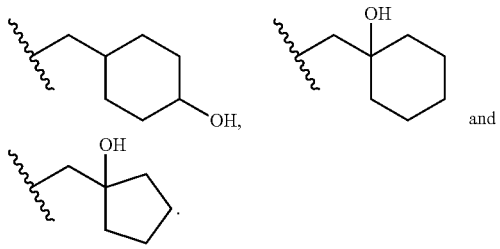

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include $-SCH_3$, and $-SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable straight or branched chain hydrocarbon radical containing 1 to 10, i.e. 1, 2, 3, 4, 5, 6, 7, 8, 9, or 10, carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include $-CH_2OCH_2CH_2OCH_3$, $-OCH_2CH_2OCH_2CH_2OCH_3$, $-CH_2NHCH_2CH_2OCH_2$, $-OCH_2CH_2NH_2$, and $-NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen, i.e. 6, 7, 8, 9, 10, 11, 12, 13 or 14, carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, heteroaryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (cycloalkylamino)alkyl, ($C_1$-$C_4$ haloalkoxy)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include

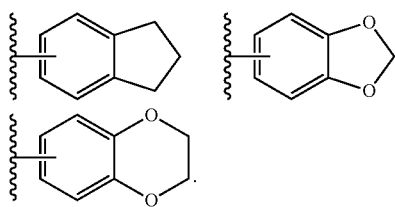

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom. Non-limiting exemplary heteroaryloxy groups include:

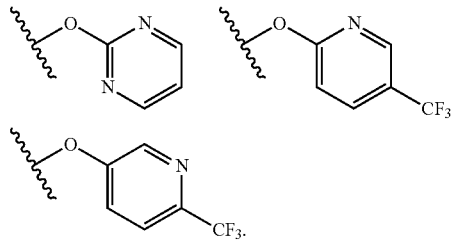

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3-, 4-, 5-, 6-, 7-, 8-, 9-, 10-, 11-, 12-, 13- or 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, and the like. Substitution may occur on any available carbon or nitrogen atom, and may form a spirocycle. Non-limiting exemplary optionally substituted heterocyclo groups include:

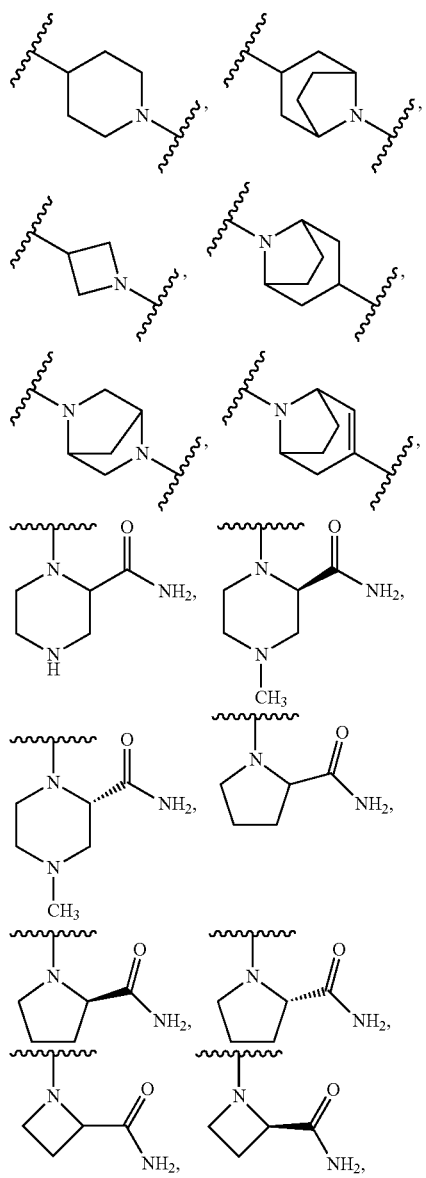

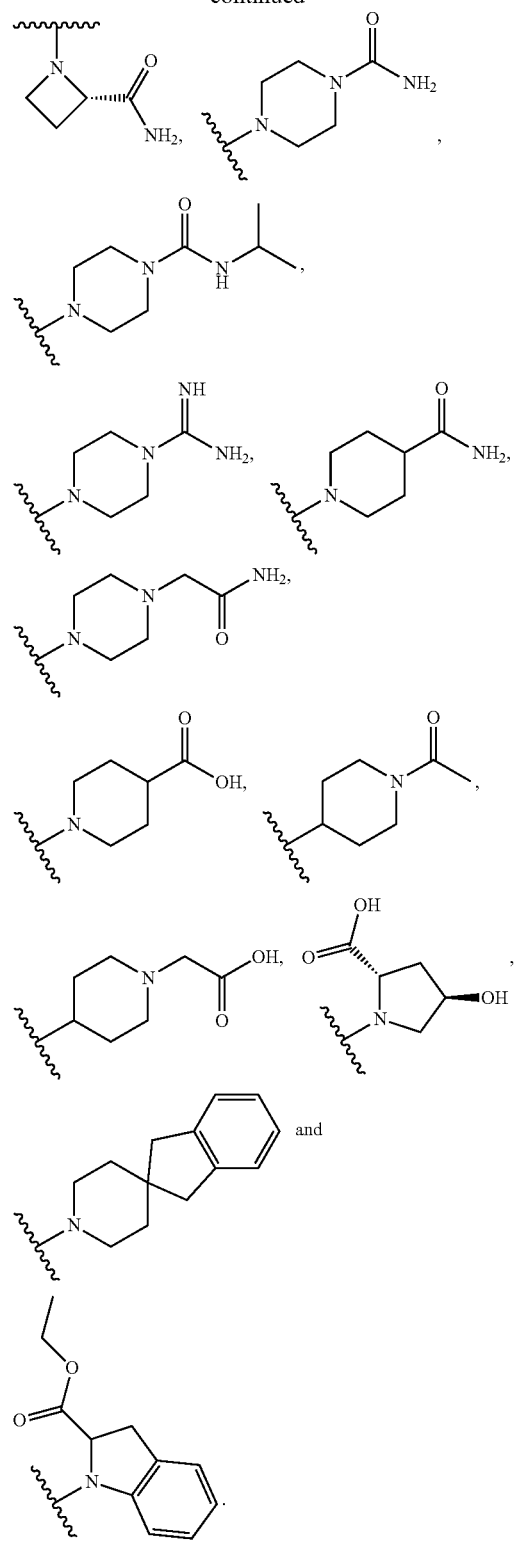

Preferably, the term "optionally substituted heterocyclo" also covers a heterocycle, which is substituted with one to four substituents independently selected from the above listed substituents further including a fused benzo group, wherein the benzo group is optionally substituted with one or more halogen atoms, and further including oxo (=O).

For the purpose of the present disclosure, the term "amino" as used by itself or as part of another group refers to —$NH_2$.

For the purpose of the present disclosure, the term "alkylamino" as used by itself or as part of another group refers to —$NHR^{15}$, wherein $R^{15}$ is alkyl.

For the purpose of the present disclosure, the term "dialkylamino" as used by itself or as part of another group refers to —$NR^{16a}R^{16b}$, wherein $R^{16a}$ and $R^{16b}$ are each independently alkyl or $R^{16a}$ and $R^{16b}$ are taken together to form a 3- to 8-membered optionally substituted heterocyclo.

For the purpose of the present disclosure, the term "hydroxyalkylamino" as used by itself or as part of another group refers to —$NHR^{17}$, wherein $R^{17}$ is hydroxyalkyl.

For the purpose of the present disclosure, the term "arylamino" as used by itself or as part of another group refers to —$NR^{18a}R^{18b}$, wherein $R^{18a}$ is optionally substituted aryl and $R^{18b}$ is hydrogen or alkyl.

For the purpose of the present disclosure, the term "cycloalkylamino" as used by itself or as part of another group refers to —$NR^{19a}R^{19b}$, wherein $R^{19a}$ is optionally substituted cycloalkyl and $R^{19b}$ is hydrogen or alkyl.

For the purpose of the present disclosure, the term "heteroarylamino" as used by itself or as part of another group refers to —$NR^{20a}R^{20b}$ wherein $R^{20a}$ is optionally substituted heteroaryl and $R^{20b}$ is hydrogen or alkyl.

For the purpose of the present disclosure, the term "heterocycloamino" as used by itself or as part of another group refers to —$NR^{21a}R^{21b}$ wherein $R^{21a}$ is optionally substituted heterocyclo and $R^{21b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include —$CH_2CH_2NH_2$, —$CH_2CH_2CH_2NH_2$, —$CH_2CH_2CH_2CH_2NH_2$ and the like.

For the purpose of the present disclosure, the term "diaminoalkyl" as used by itself or as part of another group refers to an alkyl group substituted with two amino groups. A non-limiting exemplary diaminoalkyl includes —$CH_2CH(NH_2)CH_2CH_2NH_2$.

For the purpose of the present disclosure, the term "(alkylamino)alkyl" as used by itself or as part of another group refers to an alkyl group substituted with an alkylamino group. A non-limiting exemplary (alkylamino)alkyl group is —$CH_2CH_2N(H)CH_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —$CH_2CH_2N(CH_3)_2$.

For the purpose of the present disclosure, the term "(cycloalkylamino)alkyl" as used by itself or as part of another group refers to an alkyl group substituted by a cycloalkylamino group. Non-limiting exemplary (cycloalkylamino)alkyl groups include —$CH_2N(H)$cyclopropyl, —$CH_2N(H)$cyclobutyl, and —$CH_2N(H)$cyclohexyl.

For the purpose of the present disclosure, the term "($C_1$-$C_4$ haloalkoxy)alkyl" as used by itself or as part of another group refers to an alkyl group substituted by a $C_1$-$C_4$ haloalkoxy group. Non-limiting exemplary ($C_1$-$C_4$ haloalkoxy)alkyl groups include —$CH_2OCH_2CF_3$ and —$CH_2OCF_3$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —$CH_2CH_2CN$, —$CH_2CH_2CH_2CN$, and —$CH_2CH_2CH_2CH_2CN$.

For the purpose of the present disclosure, the term "(hydroxy)(cyano)alkyl" as used by itself or as part of another group refers to an alkyl group substituted with a cyano group and a hydroxy group. A non-limiting exemplary (hydroxy)(cyano)alkyl group is —CH(OH)CN.

For the purpose of the present disclosure, the term "(amino)(cyano)alkyl" as used by itself or as part of another group refers to an alkyl group substituted with a cyano group and an amino group. A non-limiting exemplary (amino)(cyano)alkyl group is —$CH(NH_2)CN$.

For the purpose of the present disclosure, the term "(heteroarylamino)alkyl" as used by itself or as part of another group refers to an alkyl group substituted with one heteroarylamino group. A non-limiting exemplary (heteroarylamino)alkyl group is:

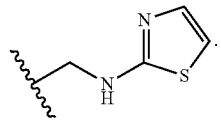 [SMILES: *CNc1nccs1]

For the purpose of the present disclosure, the term "carboxamido" as used by itself or as part of another group refers to a radical of formula —$C(=O)NR^{24a}R^{24b}$, wherein $R^{24a}$ and $R^{24b}$ are each independently hydrogen, optionally substituted alkyl, optionally substituted aryl, or optionally substituted heteroaryl, or $R^{24a}$ and $R^{24b}$ taken together with the nitrogen to which they are attached from a 3- to 8-membered heterocyclo group. In one embodiment, $R^{24a}$ and $R^{24b}$ are each independently hydrogen or optionally substituted alkyl. Non-limiting exemplary carboxamido groups include —$CONH_2$, —$CON(H)CH_3$, $CON(CH_3)_2$, and $CON(H)Ph$.

For the purpose of the present disclosure, the term "sulfonamido" as used by itself or as part of another group refers to a radical of the formula —$SO_2NR^{23a}R^{23b}$, wherein $R^{23a}$ and $R^{23b}$ are each independently hydrogen, optionally substituted alkyl, or optionally substituted aryl, or $R^{23a}$ and $R^{23b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

For the purpose of the present disclosure, the term "alkylcarbonyl" as used by itself or as part of another group refers to a carbonyl group, i.e., —$C(=O)$—, substituted by an alkyl group. A non-limiting exemplary alkylcarbonyl group is —$COCH_3$.

For the purpose of the present disclosure, the term "arylcarbonyl" as used by itself or as part of another group refers to a carbonyl group, i.e., —$C(=O)$—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

For the purpose of the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "acetoxy" as used by itself or as part of another group refers to a radical of the formula CH$_3$(C=O)—O—.

For the purpose of the present disclosure, the term "(acetoxy)alkyl" as used by itself or as part of another group refers to an alkyl group substituted with an acetoxy group. A non-limiting exemplary (acetoxy)alkyl is —CH$_2$CH$_2$—O—(C=O)CH$_3$.

For the purpose of the present disclosure, the term "aralkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, and —CH(4-F-Ph)$_2$.

For the purpose of the present disclosure, the term "ureido" as used by itself or as part of another group refers to a radical of the formula —NR$^{22a}$—C(=O)—NR$^{22b}$R$^{22c}$, wherein R$^{22a}$ is hydrogen, alkyl, or optionally substituted aryl, and R$^{22b}$ and R$^{22c}$ are each independently hydrogen, alkyl, or optionally substituted aryl, or R$^{22b}$ and R$^{22c}$ taken together with the nitrogen to which they are attached form a 4-, 5-, 6-, 7-, or to 8-membered heterocyclo group. Non-limiting exemplary ureido groups include —NH—C(C=O)—NH$_2$ and —NH—C(C=O)—NHCH$_3$.

For the purpose of the present disclosure, the term "guanidino" as used by itself or as part of another group refers to a radical of the formula —NR$^{25a}$—C(=NR$^{26}$)—NR$^{25b}$R$^{25c}$, wherein R$^{25a}$, R$^{25b}$, and R$^{25c}$ are each independently hydrogen, alkyl, or optionally substituted aryl, and R$^{26}$ is hydrogen, alkyl, cyano, alkylsulfonyl, alkylcarbonyl, carboxamido, or sulfonamido. Non-limiting exemplary guanidino groups include —NH—C(=NH)—NH$_2$, —NH—C(=NCN)—NH$_2$, —NH—C(=NH)—NHCH$_3$ and the like.

For the purpose of the present disclosure, the term "azido" as used by itself or as part of another group refers to a radical of the formula —N$_3$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a C$_{1-4}$ alkyl substituted with one optionally substituted heterocyclo group. Non-limiting exemplary (heterocyclo)alkyl groups include:

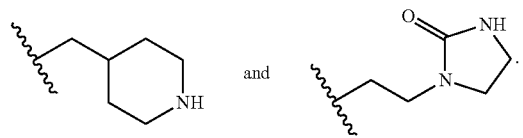 [SMILES: *CC1CCNCC1 ; *CCN1CCNC1=O]

For the purpose of the present disclosure, the term "optionally-substituted (heterocyclo)alkyl" as used by itself or as part of another group refers to a (heterocyclo)alkyl group which is optionally substituted at the heterocyclo and/or alkyl moieties with one, two, three, four, five, or six same or different substituents. Suitable optional substituents include those for an alkyl group and those for a heterocyclo group (as above defined).

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a C$_{1-4}$ alkyl substituted with one optionally substituted heteroaryl group. Non-limiting exemplary (heteroaryl)alkyl groups include:

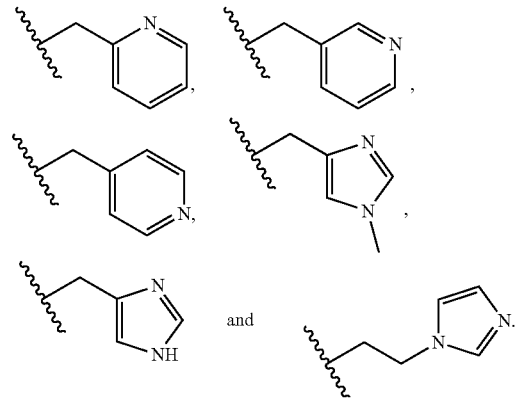

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

For the purpose of the present disclosure, the term "heteroalkyl" as used by itself or part of another group refers to a stable straight or branched chain hydrocarbon radical containing 1 to 10, i.e. 1, 2, 3, 4, 5, 6, 7, 8, 9, or 10, carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position or terminal position of the heteroalkyl group, or at a position at which the heteroalkyl group is attached to the remainder of the molecule. In one embodiment, the heteroalkyl group contains two oxygen atoms. In another embodiment, the heteroalkyl group contains two nitrogen atoms. In other embodiment, the heteroalkyl group contains one nitrogen atom and one oxygen atom. Non-limiting exemplary heteroalkyl groups include:
—CH$_2$N(H)CH$_2$CH$_2$N(CH$_3$)$_2$; —CH$_2$N(CH$_3$)CH$_2$CH$_2$N(CH$_3$)$_2$; —CH$_2$N(H)CH$_2$CH$_2$N(CH$_3$)$_2$; —CH$_2$N(H)CH$_2$CH$_2$OH; —CH$_2$N(CH$_3$)CH$_2$CH$_2$OH;

—CH₂OCH₂CH₂OCH₃,   —OCH₂CH₂OCH₂CH₂OCH₃;
—CH₂NHCH₂CH₂OCH₂;   —OCH₂CH₂NH₂;   and
—NHCH₂CH₂N(H)CH₃.

For the purpose of the present disclosure, the term "(heterocyclo)alkyl" as used by itself or as part of another group refers to an alkyl group substituted with one optionally substituted heterocyclo group, and optionally one hydroxy group. In one embodiment, the (heterocyclo)alkyl is a C₁₋₄ alkyl substituted with one optionally substituted heterocyclo group and one hydroxy group. In another embodiment, the (heterocyclo)alkyl is a C₁₋₄ alkyl substituted with one optionally substituted heterocyclo group. Non-limiting exemplary (heterocyclo)alkyl groups include:

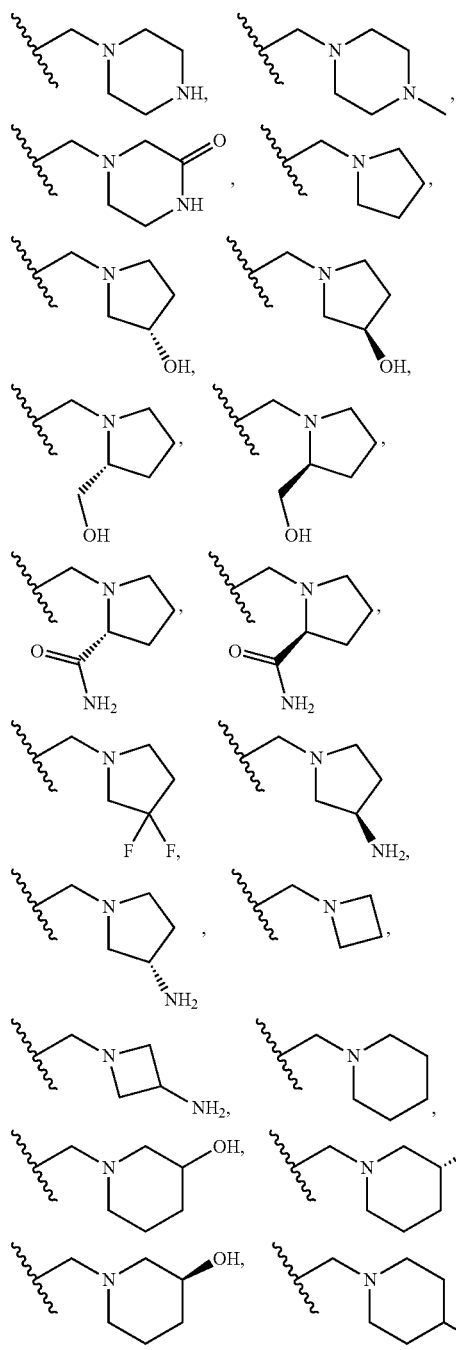
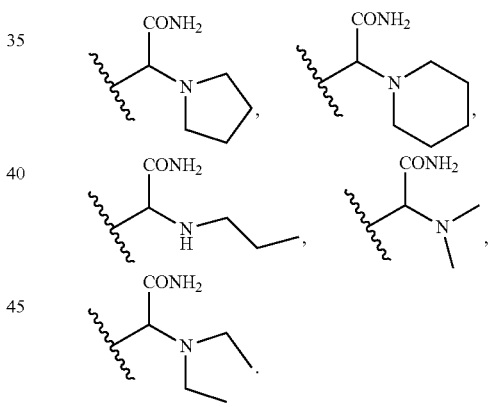

For the purpose of the present disclosure, the term "(carboxamido)alkyl" as used by itself or as part of another group refers to an alkyl group substituted with one carboxamido group, and optionally one heterocyclo, amino, alkylamino, or dialkylamino group. In one embodiment, the (carboxamido)alkyl is a C₁₋₄ alkyl substituted with one carboxamido group, and optionally one heterocyclo, amino, alkylamino, or dialkylamino group. In another embodiment, the (carboxamido)alkyl is a C₁₋₄ alkyl substituted with one carboxamido group and one heterocyclo, amino, alkylamino, or dialkylamino group. Non-limiting exemplary (carboxamido)alkyl groups include —CH₂CONH₂, —C(H)CH₃—CONH₂, —CH₂CON(H)CH₃, For the purpose of the present disclosure, the term "heterocycloalkylamino" as used by itself or as part of another group refers to —NHR¹⁷ᵃ, wherein R¹⁷ᵃ is heterocycloalkyl. A non-limiting exemplary heterocycloalkylamino group is:

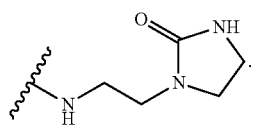 [SMILES: *NCCN1CCNC1=O]

For the purpose of the present disclosure, the term "(heterocycloalkylamino)alkyl" as used by itself or as part of another group refers to an alkyl group substituted with one heterocycloalkylamino group. In one embodiment, (heterocycloalkylamino)alkyl is a C₁₋₄ alkyl substituted with one heterocycloalkylamino group. A non-limiting exemplary (heterocycloalkylamino)alkyl group is:

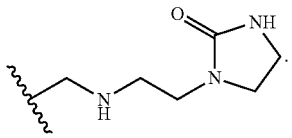 [SMILES: *CNCCN1CCNC1=O]

For the purpose of the present disclosure, the term "(heterocycloamino)alkyl" as used by itself or as part of another group refers to an alkyl group substituted with one heterocycloamino group. In one embodiment, the (heterocycloamino)alkyl is a $C_{1-4}$ alkyl substituted with one heterocycloamino group. Non-limiting exemplary (heterocyclo)alkyl groups include:

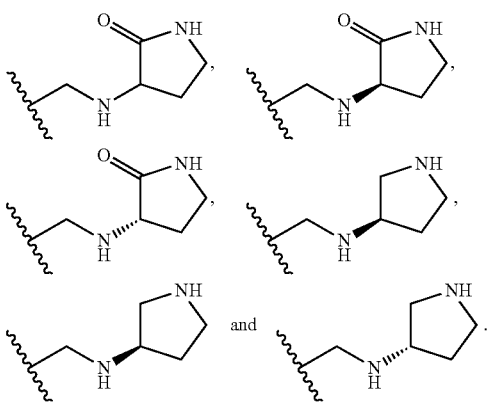

For the purpose of the present disclosure, the term "aralkylamino" as used by itself or as part of another group refers to —NR$^{19c}$R$^{19d}$ wherein R$^{19c}$ is any aralkyl group as "aralkyl" is defined above and R$^{19d}$ is hydrogen or any alkyl group as "alkyl" is defined above. Non-limiting exemplary aralkylamino groups include:

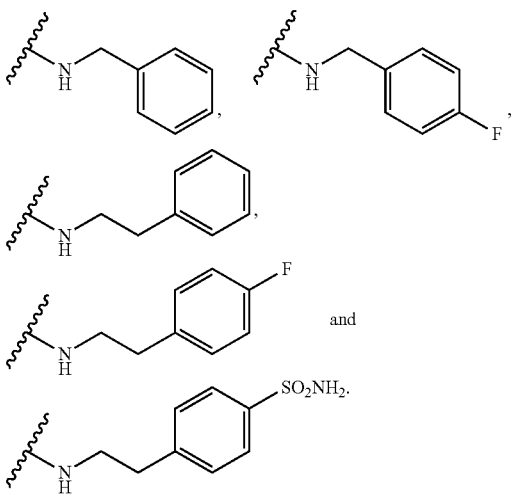

For the purpose of the present disclosure, the term "(aralkylamino)alkyl" as used by itself or as part of another group refers to an alkyl group substituted with one aralkylamino group. In one embodiment, the (aralkylamino)alkyl is a $C_{1-4}$ alkyl substituted with one aralkylamino group. Non-limiting exemplary (aralkylamino)alkyl groups include:

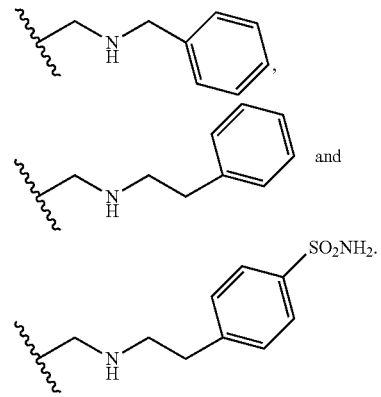

For the purpose of the present disclosure, the term "alkanolamine" as used by itself or part of another group refers to an alkyl group substituted with one hydroxyl group and one amino, alkylamino, or dialkylamino group. The alkanolamine is optionally linked to the rest of the molecule through a carbon atom. In one embodiment, the alkanolamine is an ethanolamine. Non-limiting exemplary alkanolamine groups include:

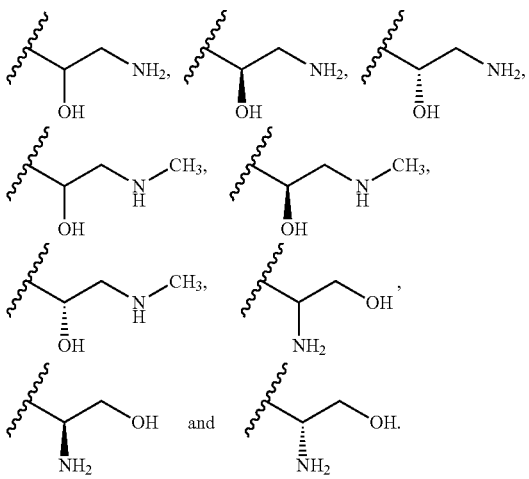

For the purpose of the present disclosure, the term "(nitro)alkyl" as used by itself or as part of another group refers to an alkyl group substituted with one nitro (—NO$_2$) group, and optionally one hydroxy group. In one embodiment, the (nitro)alkyl is a $C_{1-4}$ alkyl substituted with one nitro group, and optionally one hydroxy group. Non-limiting exemplary (nitro)alkyl groups include —CH$_2$CH$_2$NO$_2$ and —CH(OH)CH$_2$NO$_2$.

For the purpose of the present disclosure, the term "haloalkylamino" as used by itself or as part of another group refers to —N(H)R$^{19f}$ wherein R$^{19f}$ is any heteroalkyl group as "heteroalkyl" is defined above. Non-limiting exemplary haloalkylamino groups include —N(H)CH$_2$CH$_2$F and —N(H)CH$_2$CH$_2$CF$_3$.

For the purpose of the present disclosure, the term "(haloalkylamino)alkyl" as used by itself or as part of another group refers to an alkyl group substituted with one haloalkylamino group. In one embodiment, the (haloalkylamino)alkyl is a $C_{1-4}$ alkyl substituted with one haloalkylamino group. Non-limiting exemplary haloalkylamino groups include —$CH_2N(H)CH_2CH_2F$ and —$CH_2N(H)$ $CH_2CH_2CF_3$.

For the purpose of the present disclosure, the term "(arylamino)alkyl" as used by itself or as part of another group refers to an alkyl group substituted with one arylamino group. In one embodiment, the (arylamino)alkyl is a $C_{1-4}$ alkyl substituted with one arylamino group. Non-limiting exemplary (arylamino)alkyl groups include —$CH_2N(H)Ph$ and —$CH_2N(CH_3)Ph$.

For the purpose of the present disclosure, the term "(aryloxy)alkyl" as used by itself or as part of another group refers to an alkyl group substituted with one aryloxy group. In one embodiment, the (aryloxy)alkyl is a $C_{1-4}$ alkyl substituted with one aryloxy group. Non-limiting exemplary (aryloxy)alkyl groups include —$CH_2OPh$, —$CH_2O$-4-F-Ph, and —$CH_2O$-4-CN-Ph.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. Isotopically-labeled Compounds of the Disclosure can be prepared by methods known in the art.

The present disclosure encompasses $^3H$, $^{11}C$, or $^{14}C$ radiolabeled Compounds of the Disclosure and the use of any such compounds as radioligands for their ability to bind to the sodium channel. For example, one use of the labeled compounds of the present disclosure is the characterization of specific receptor binding. Another use of a labeled Compound of the Disclosure is an alternative to animal testing for the evaluation of structure-activity relationships. For example, the receptor assay can be performed at a fixed concentration of a labeled Compound of the Disclosure and at increasing concentrations of a test compound in a competition assay. For example, a tritiated Compound of the Disclosure can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a compound of the present disclosure for the purposes of amelioration or cure, including preemptive and palliative treatment. In one embodiment, the term "treat," "treating" or "treatment" is meant to encompass administering to a subject a compound of the present disclosure for the purposes of amelioration or cure.

The term "about," as used herein in connection with a measured quantity, refers to the normal variations in that measured quantity, as expected by the skilled artisan making the measurement and exercising a level of care commensurate with the objective of measurement and the precision of the measuring equipment.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.,* 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Disclosure are blockers of sodium ($Na^+$) channels, a number of diseases and conditions mediated by sodium ion influx can be treated by employing these compounds. The present disclosure is thus directed generally to a method for treating a disorder responsive to the blockade of sodium channels in an animal suffering from, or at risk of suffering from, said disorder, said method comprising administering to the animal an effective amount of one or more Compounds of the Disclosure.

The present disclosure is further directed to a method of modulating sodium channels in an animal in need thereof, said method comprising administering to the animal a modulating-effective amount of at least one Compound of the Disclosure.

More specifically, the present disclosure provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the disclosure provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a Compound of the Disclosure that is therapeutically effective in achieving said treatment. In one embodiment, the amount of such compound is the amount that is effective to block sodium channels in vitro. In one embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 18:387-391 (2000)).

The inflammatory process is a complex series of biochemical and cellular events activated in response to tissue injury or the presence of foreign substances (Levine, *Inflammatory Pain, In: Textbook of Pain,* Wall and Melzack eds., $3^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogeneous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present disclosure is also directed to the use of a Compound of the Disclosure in the manufacture of a medicament for treating a disorder responsive to the blockade of sodium channels (e.g., any of the disorders listed above) in an animal suffering from said disorder.

General Synthesis of Compounds

Compounds of the Disclosure are prepared using methods known to those skilled in the art in view of this disclosure, or by the illustrative method shown in the General Schemes below.

General Scheme 1

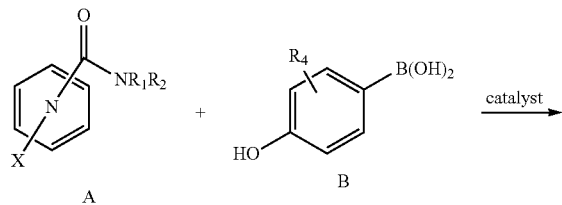

 = pyridine, pyrimidine, pyrazine, pyridazine, or triazine

A compound having Formula A is converted to a compound having Formula C by reaction with a suitable boron reagent such a compound having Formula B in the presence of a suitable catalyst such as Pd(Ph$_3$P)$_2$Cl$_2$ in the presence of a suitable base such as K$_2$CO$_3$ in a suitable solvent such as DMF.

General Scheme 2

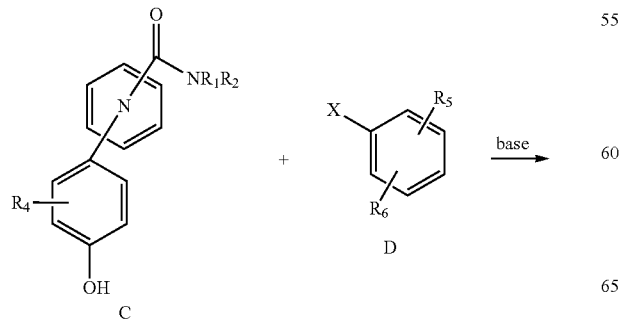

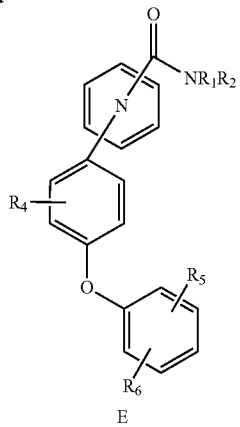

A compound having Formula C is converted to a compound having Formula E by reaction with a compound having Formula D in the presence of a suitable base such as K$_2$CO$_3$ in a suitable solvent such as DMF.

General Scheme 3

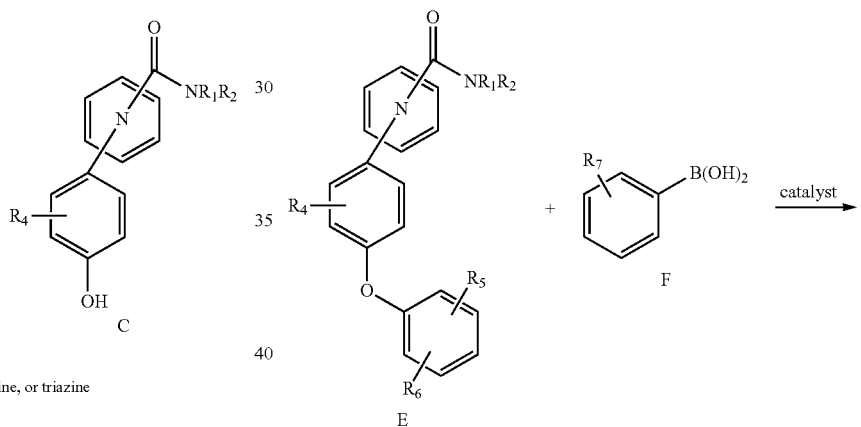

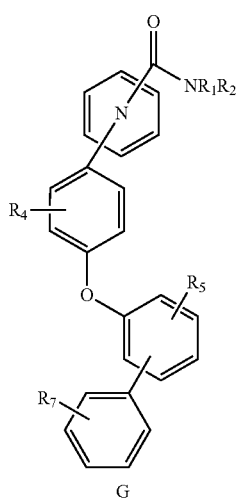

A compound having Formula d E, where R$_6$ is a suitable group such as a halogen, mesylate, or triflate, is converted to a compound having Formula G by reaction with a suitable boron reagent such as a compound having Formula F in the presence of a suitable catalyst such as Pd(Ph₃P)₂Cl₂ in the presence of a suitable base such as K₂CO₃ in a suitable solvent such as DMF.

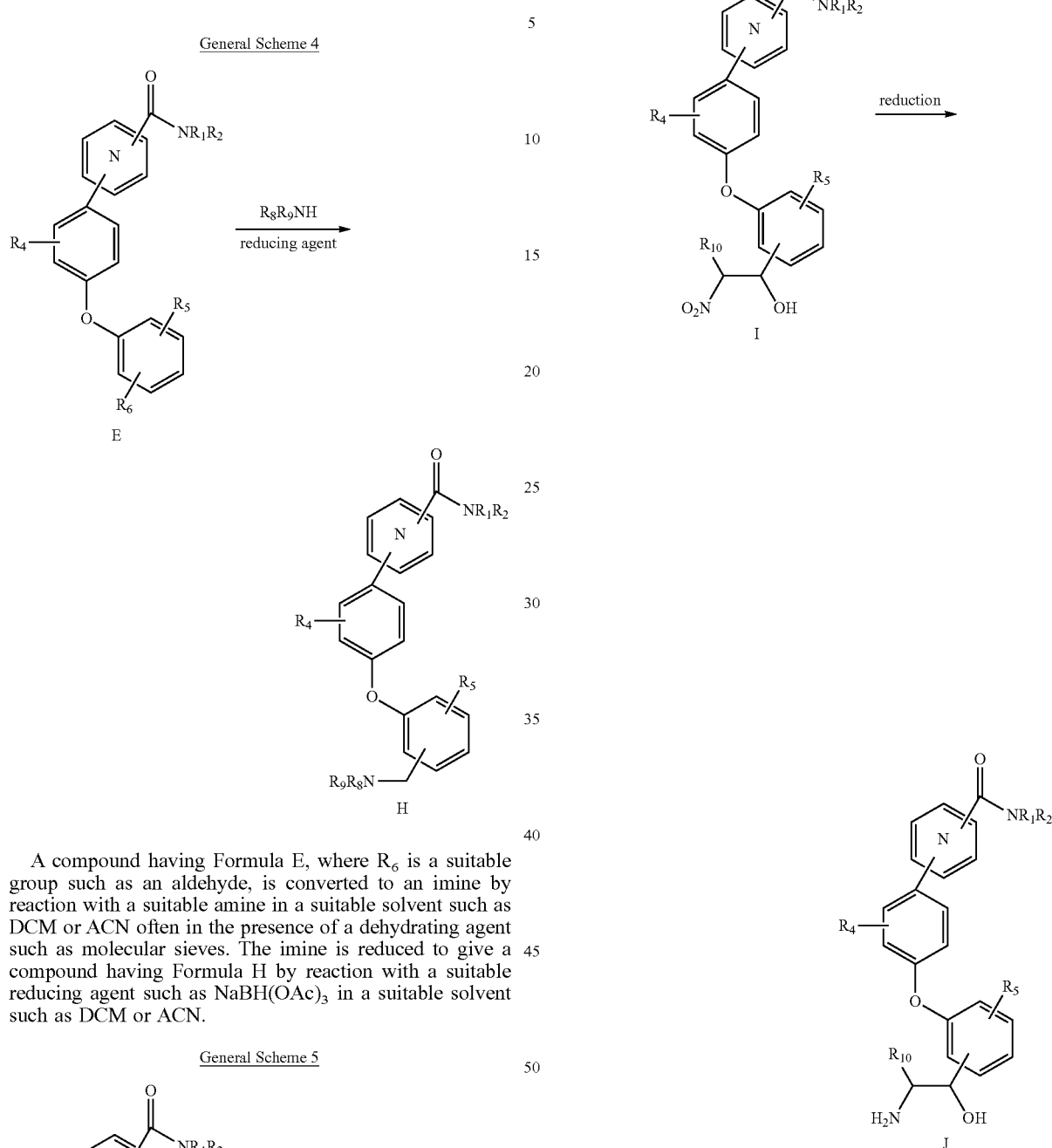

A compound having Formula E, where $R_6$ is a suitable group such as an aldehyde, is converted to an imine by reaction with a suitable amine in a suitable solvent such as DCM or ACN often in the presence of a dehydrating agent such as molecular sieves. The imine is reduced to give a compound having Formula H by reaction with a suitable reducing agent such as NaBH(OAc)₃ in a suitable solvent such as DCM or ACN.

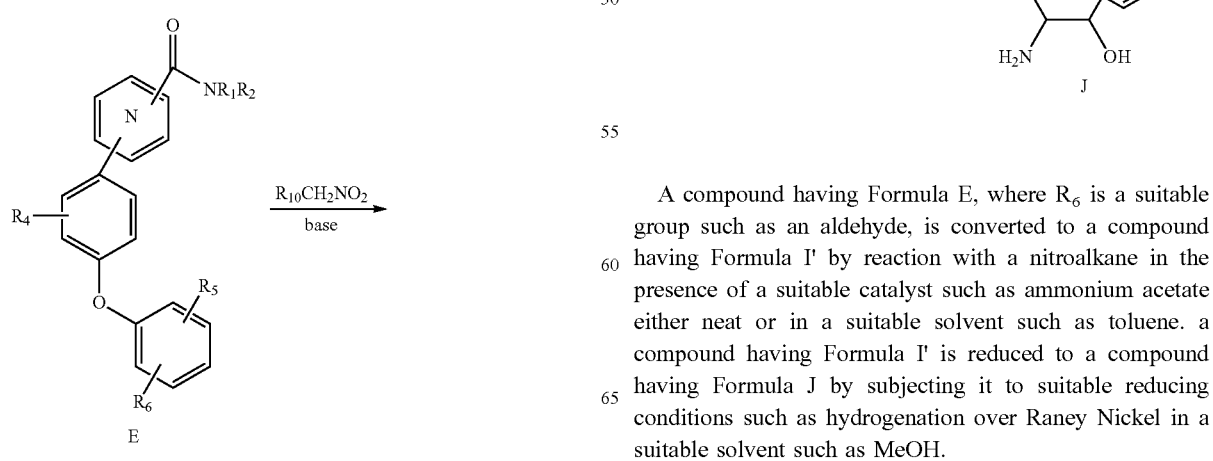

A compound having Formula E, where $R_6$ is a suitable group such as an aldehyde, is converted to a compound having Formula I' by reaction with a nitroalkane in the presence of a suitable catalyst such as ammonium acetate either neat or in a suitable solvent such as toluene. a compound having Formula I' is reduced to a compound having Formula J by subjecting it to suitable reducing conditions such as hydrogenation over Raney Nickel in a suitable solvent such as MeOH.

General Scheme 6

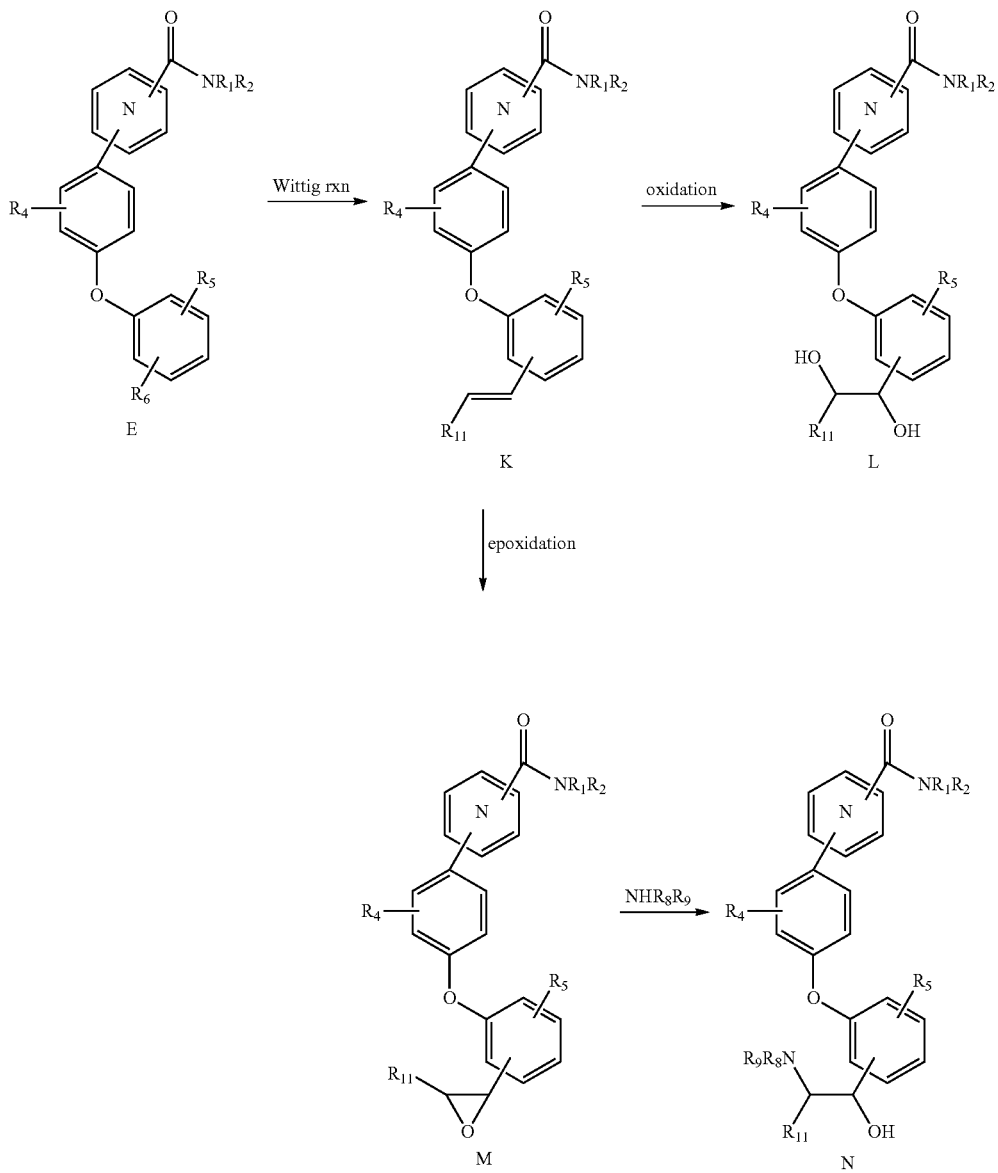

A compound having Formula E, where $R_6$ is a suitable group such as an aldehyde, is converted to a compound having Formula K by reaction with a suitable Wittig reagent (e.g. Maercker, A. *Org. React.* 14:270-490 (1965)0, or other such reagent, in a suitable solvent such as THF. A compound having Formula K is converted to a compound having Formula L by reaction with a suitable oxidizing reagent such as osmium tetroxide, either alone or in conjunction with an additive such as sodium periodate or as part of a chiral reagent such as Ad-Mix-alpha or beta. A compound having Formula K is converted to a compound having Formula M by reaction with a suitable reagent such as mCPBA in a suitable solvent such as chloroform. A compound having Formula M is converted to a compound having Formula N by treatment with a suitable amine in a suitable solvent such as EtOH.

General Scheme 7

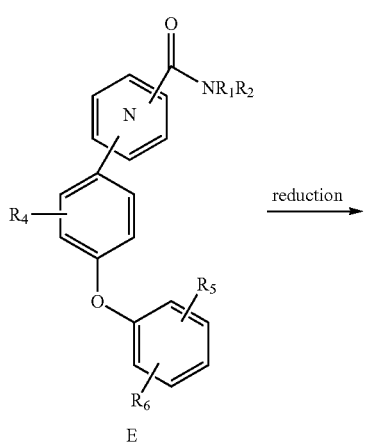

General Scheme 9

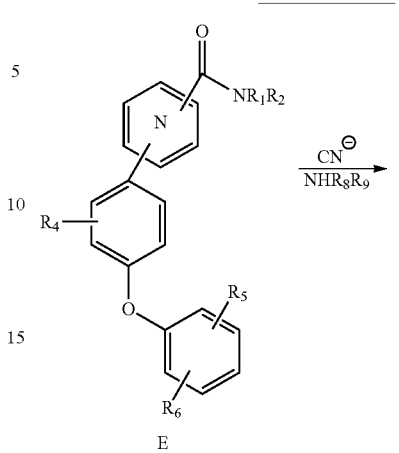

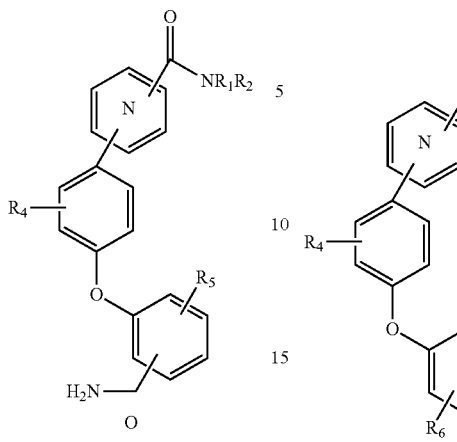

A compound having Formula E, where $R_6$ is a suitable group such as a nitrile, is reduced to a compound having Formula O by subjecting it to suitable reducing conditions such as hydrogenation over Raney Nickel in a suitable solvent such as ammonia in MeOH.

General Scheme 8

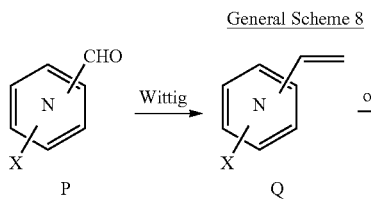

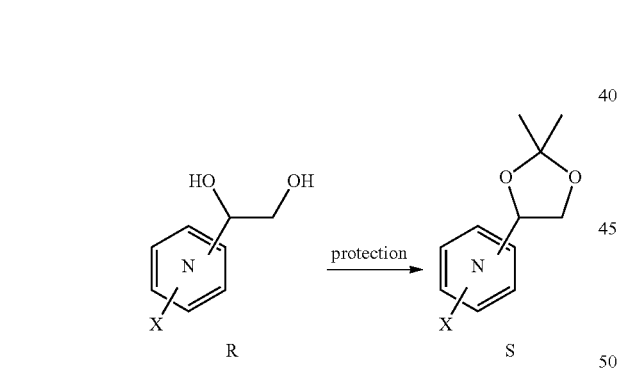

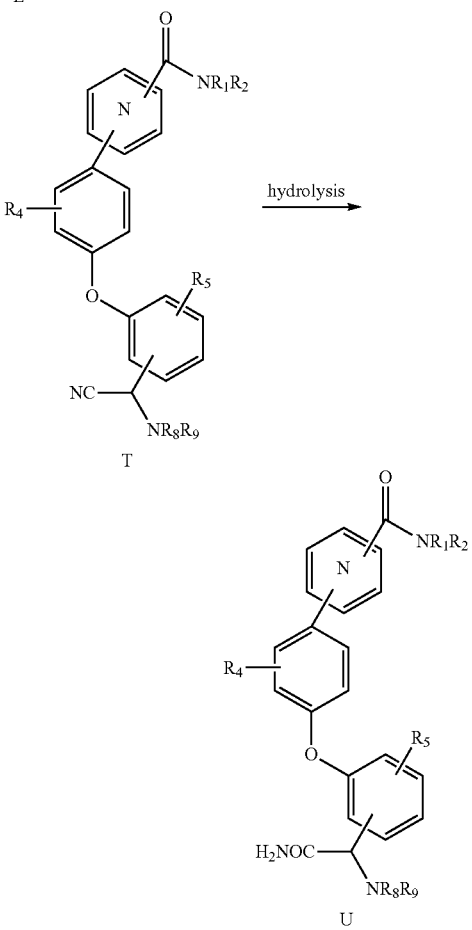

A compound having Formula P is converted to a compound having Formula Q by reaction with a suitable Wittig reagent, or other such reagent, in a suitable solvent such as THF. A compound having Formula Q is converted to a compound having Formula R by reaction with a suitable oxidizing reagent such as osmium tetroxide, either alone or in conjunction with an additive such as sodium periodate or as part of a chiral reagent such as Ad-Mix-alpha or beta. The diol in a compound having Formula R is protected by treatment with a suitable reagent such as 2,2-dimethoxypropane in the presence of a suitable acid catalyst such as PTSA in a suitable solvent such as chloroform to give Compound S, which can be reacted further in a manner similar to that described for a compound having Formula A in General Scheme 1 and subsequent General Schemes.

A compound having Formula E, where $R_6$ is a suitable group such as an aldehyde, is subjected to Strecker aminonitrile synthesis conditions (e.g., Shibasaki, M., et al. *Org. React.* 70:1 (2008)) by treatment with a suitable amine and suitable cyanide such as $Zn(CN)_2$ in a suitable solvent such as an EtOH/AcOH mixture to give a compound having Formula T. A compound having Formula T can be converted to a compound having Formula U by reaction with a suitable reagent such as hydrogen peroxide in DMSO.

Testing of Compounds

Compounds of the Disclosure were assessed by sodium mobilization and/or electrophysiological assays for sodium channel blocker activity. One aspect of the present disclosure is based on the use of the Compounds of the Disclosure as sodium channel blockers. Based upon this property, Compounds of the Disclosure are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. Compounds of the Disclosure are also expected to be effective in treating pain, e.g., acute pain, chronic pain, which includes but is not limited to, neuropathic pain, postoperative pain, and inflammatory pain, or surgical pain.

More specifically, the present disclosure is directed to Compounds of the Disclosure that are blockers of sodium channels. According to the present disclosure, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 µM or less, e.g., about 50 µM or less, about 25 µM or less, about 10 µM or less, about 5 µM or less, or about 1 µM or less, in sodium mobilization and/or electrophysiological assays. In certain embodiments, Compounds of the Disclosure exhibit an $IC_{50}$ for $Na_v1.7$ of 100 µM or less, about 50 µM or less, about 25 µM or less, about 10 µM or less, about 5 µM or less, about 1 µM or less, about 0.5 µM or less, about 0.1 µM or less, about 0.05 µM or less, or about 0.01 µM or less. Compounds of the Disclosure can be tested for their $Na^+$ channel blocking activity using methods known in the art and by the following fluorescence imaging and electrophysiological in vitro assays and/or in vivo assays.

In one embodiment, Compounds of the Disclosure demonstrate substantially no penetration across the CNS blood-brain barrier in a mammal. Such compounds are referred to as "peripherally restricted" as a means to designate their PNS versus CNS tissue selectivity.

In one embodiment, the PNS:CNS concentration ratio of a peripherally restricted Compound of the Disclosure is about 5:1, about 10:1, about 20:1, about 30:1; about 50:1; about 100:1, about 250:1, about 500:1, about 1000:1, about 5,000:1, about 10,000:1, or more. Compounds of the Disclosure can be tested for their ability to penetrate the central nervous system using in vitro and in vivo methods known in the art.

In Vitro Assay Protocols

FLIPR® Assays

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, J. Neurosci. 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-Recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, Nav1.2 (rBIIa), expressed in HEK293 host cells (Ilyin et al., Br. J. Pharmacol. 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 µg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., Proc. Soc. Exp. Biol. Med. 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., J. Biol. Chem. 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer, to a stock concentration of 10 mM in DMSO. It was then diluted in the assay buffer to a 4× concentrated working solution, so that the final concentration of dye in the cell loading buffer was 5 μM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 μM (veratridine) and 10 μg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 μM, 3.333 μM, 1.111 μM, 370 μM, 123 μM, 41 μM, 14 μM, 4.6 μM, 1.5 M and 0.5 μM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 μM, 6.7 μM, 2.2 μM, 0.74 μM, 0.25 M and 0.08 μM, 0.03 μM, 0.01 μM, 0.003 M and 0.001 μM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism Program, version 4.0 or higher (available from GraphPad Software, San Diego, Calif.) to determine the $IC_{50}$ value for the test article. At least one standard reference compound was evaluated during each experiment.

FLIPR® or FLIPR$^{TETA®}$ Sodium Dye Assay with KCl and Test Article Pre-Incubation:

Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 l/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) finally, a solution of 180 mM KCl (2×) was prepared by diluting a 2M stock solution into assay buffer and the solution was added to the cells at 100 l/well. The cells were incubated at 25° C. in the dark for 30 min. before their fluorescence was measured.

The plates containing dye-loaded cells were then flicked to remove the pre-incubation components and washed once with 100 μM/well assay buffer. A 100 μM/well aliquot of assay buffer was added back to the plate, and the real-time assay was commenced. The fluorescence of cells was measured using a fluorescence plate reader (FLIPR$^{TETRA®}$ or FLIPR384®, MDS, Molecular Devices, Sunnyvale, Calif.) Samples were excited by either a laser or a PMT light source (Excitation wavelength=470-495 nM) and the emissions are filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen were typically profiled more exhaustively (multiple times), subjected to dose-response or competition assays and tested in counter screens against other voltage-gated sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% CO$_2$, 95% humidity, in preparation for the assay (see, e.g., Benjamin et. al., J. Biomol. Screen 10(4): 365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 µL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 µL/well; 2) membrane potential dye is diluted from the stock solution in assay buffer (4× concentrate) and added to the plate at 50 µL/well; and 3) finally, a solution of 180 mM KCl (2×) is prepared by diluting a 2M stock solution into assay buffer and the solution added to the cells at 100 µL/well. The cells are incubated at 37° C. in the dark for 30-60 min. before their fluorescence is measured.

The plates containing dye-loaded cells are then flicked to remove the pre-incubation components and washed once with 50 µL/well assay buffer. A 50 µL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 µM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% CO$_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 µL/well assay buffer (1× Hank's balanced salt solution without sodium bicarbonate or phenol red, 20 mM Hepes, pH 7.3). Membrane potential dye is then added to each well of the 96-well plate (50 µL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 µL/well from a 4× stock plate) and then the channel activators (later, 100 µL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10

μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells are plated on 35 mm culture dishes pre-coated with poly-D-lysine in standard DMEM culture media (Mediatech, Inc., Herndon, Va.) and incubated in a 5% $CO_2$ incubator at 37° C. Cultured cells are used approximately 12-48 h after plating.

Electrophysiology:

On the day of experimentation, the 35 mm dish is placed on the stage of an inverted microscope equipped with a perfusion system that continuously perfuses the culture dish with fresh recording media. A gravity driven superfusion system is used to apply test solutions directly to the cell under evaluation. This system consists of an array of glass pipette glass connected to a motorized horizontal translator. The outlet of the shooter is positioned approximately 100 m from the cell of interest.

Whole cell currents are recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals are formed and the whole-cell configuration is established in voltage clamp mode, and membrane currents generated by hNa$_v$1.7 are recorded in gap-free mode. Borosilicate glass pipettes have resistance values between 1.5 and 2.0 MΩ when filled with pipette solution and series resistance (<5 MΩ) is compensated 75-80%. Signals are sampled at 50 kHz and low pass filtered at 3 kHz.

Voltage Protocols:

After establishing the whole-cell configuration in voltage clamp mode, two voltage protocols are run to establish: 1) the holding potential; and 2) the test potential for each cell.

Resting Block:

To determine a membrane potential at which the majority of channels are in the resting state, a standard steady-state inactivation (SSIN) protocol is run using 100 ms prepulses× 10 mV depolarizing steps. The holding potential for testing resting block (Vh$_1$) is 20 mV more hyperpolarized than the first potential where inactivation is observed with the inactivation protocol.

From this holding potential a standard I-V protocol is run to determine the potential at which the maximal current (Imax) was elicited. This potential is the test potential (Vt).

The compound testing protocol is a series of 10 ms depolarizations from the Vh$_1$ (determined from the SSIN) to the Vt (determined from the I-V protocol) repeated every 10-seconds. After a stable baseline is established, a high concentration of a test compound (highest concentration solubility permits or that which provides ~50% block) is applied and block of the current assessed. Washout of the compound is attempted by superfusing with control solution once steady-state block was observed. The fractional response is calculated as follows:

$$FR=I(\text{after drug})/I(\text{control}),$$

where I is the peak current amplitude and is used for estimating resting block dissociation constant, $K_r$:

$$K_r=[\text{drug}]*\{FR/(1-FR)\},$$

where [drug] is the concentration of a drug.

Block of Inactivated Channels:

To assess the block of inactivated channels the holding potential is depolarized such that 20-50% of the current amplitude is reduced when pulsed to the same Vt as above. The magnitude of this depolarization depends upon the initial current amplitude and the rate of current loss due to slow inactivation. This is the second holding potential (Vh$_2$). The current reduction is recorded to determine the fraction of available channels at this potential (h).

$$h=I@Vh_2/I\text{max}.$$

At this membrane voltage a proportion of channels are in the inactivated state, and thus inhibition by a blocker includes interaction with both resting and inactivated channels.

To determine the potency of the test compound on inactivated channels, a series of currents are elicited by 10 ms voltage steps from Vh$_2$ to V$_t$ every 10-15 seconds. After establishing a stable baseline, the low concentration of the compound is applied. Multiple cumulative concentrations may have to be applied to identify a concentration that will block between 40-60% of the current. Washout is attempted to re-establish baseline. Fractional responses were measured with respect to a projected baseline to determine $K_{app}$.

$$K_{app}=[\text{drug}]*\{FR/(1-FR)\},$$

where [drug] is the concentration of a drug.

This $K_{app}$ value, along with the calculated $K_r$ and h values, are used to calculate the affinity of the compound for the inactivated channels ($K_i$) using the following equation:

$$K_i=(1-h)/((1/K_{app})-(h/K_r)).$$

Solutions and Chemicals:

For electrophysiological recordings the external solution is either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), CaCl$_2$ (1), MgCl$_2$ (5), EGTA (11), HEPES (10: pH 7.4, 305 mOsm). Compounds are prepared first as a series of stock solutions in DMSO and then dissolved in external solution; DMSO content in final dilutions did not exceed 0.3%. At this concentration, DMSO did not affect sodium currents. Vehicle solution used to establish base line also contained 0.3% DMSO.

Data Analysis:

Data is analyzed off-line using Clampfit™ software (pClamp, v. 8; Axon Instruments) and graphed using Graph-Pad Prizm® (v. 4.0 or higher) software.

In Vivo Assay for Pain

Compounds of the Disclosure can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of the experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 h before dosing. A control group acts as a comparison to rats treated with a Compound of the Disclosure. The control group is administered the carrier as used for the test compound. The volume of carrier administered to the control group is the same as the volume of carrier and test compound administered to the test group.

Inflammatory Pain:

To assess the actions of Compounds of the Disclosure on the treatment of inflammatory pain, the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). Prior to the injury, the animal is assessed for response to noxious mechanical stimuli by determining the paw withdrawal threshold (PWT), or to noxious thermal stimuli by determining paw withdrawal latency (PWL), as described below (baseline PWT or PWL). Then, the left hind paw of each animal is administered a 50 µL intraplantar injection of 50% FCA. 24 hour post injection, the PWT or PWL is again assessed (pre-administration PWT or PWL). Rats are then administered a single injection of either a test compound or 30 mg/Kg of a positive control compound (e.g., indomethacin). Responses to noxious mechanical or thermal stimuli are then determined 1, 3, 5 and 24 hours post administration (post-administration PWT or PWL). Percentage reversal of hyperalgesia for each animal is defined as:

$$\% \text{ reversal} = \frac{\begin{bmatrix} \text{(post administration } PWT \text{ or } PWL) - \\ \text{(pre-administration } PWT \text{ or } PWL) \end{bmatrix}}{\begin{bmatrix} \text{(baseline } PWT \text{ or } PWL) - \\ \text{(pre-administration } PWT \text{ or } PWL) \end{bmatrix}} \times 100$$

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., Pain 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after administration of either drug or vehicle, for the ipsilateral (injured side) rear paw of the animal. Percentage reversal of neuropathic hyperalgesia is defined as:

$$\% \text{ reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation (SNL) model of neuropathic pain is used to produce mechanical hyperalgesia, thermal hyperalgesia, and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Disclosure or vehicle, for the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Representative Compounds of the Disclosure can be tested in the SNL-induced mechanical hyperalgesia model in rats. Sensitivity to noxious mechanical stimuli are measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and a punctate weight was applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

In Vivo Assay for Anticonvulsant Activity

Compounds of the Disclosure can be tested for in vivo anticonvulsant activity after i.v., p.o., or i.p. injection using any of a number of anticonvulsant tests in mice or rats, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Compounds of the Disclosure can be administered to a mammal in the form of a raw chemical without any other components present. Compounds of the Disclosure can also be administered to a mammal as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A pharmaceutical composition of the present disclosure can be administered to any animal that may experience the beneficial effects of a Compound of the Disclosure. Foremost among such animals are mammals, e.g., humans and companion animals, although the disclosure is not intended to be so limited.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally and is formulated into tablets, dragees, capsules or an oral liquid preparation. In one embodiment, the oral formulation comprises extruded multiparticulates comprising the Compound of the Disclosure.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, and preferably from about 0.25 to 75 percent by weight, of active compound(s).

A method of the present disclosure, such as a method for treating a disorder responsive to the blockade of sodium channels in an animal in need thereof, can further comprise administering a second therapeutic agent to the animal in combination with a Compound of the Disclosure. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

Compounds of the Disclosure (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a Compound of the Disclosure is administered concurrently with a second therapeutic agent; for example, a single composition comprising both an effective amount of a Compound of the Disclosure and an effective amount of the second therapeutic agent can be administered. Accordingly, the present disclosure further provides a pharmaceutical composition comprising a combination of a Compound of the Disclosure, the second therapeutic agent, and a pharmaceutically acceptable carrier. Alternatively, a first pharmaceutical composition comprising an effective amount of a Compound of the Disclosure and a second pharmaceutical composition comprising an effective amount of the second therapeutic agent can be concurrently administered. In another embodiment, an effective amount of a Compound of the Disclosure is administered prior or subsequent to administration of an effective amount of the second therapeutic agent. In this embodiment, the Compound of the Disclosure is administered while the second therapeutic agent exerts its therapeutic effect, or the second therapeutic agent is administered while the Compound of the Disclosure exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-(PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions, and methods of the present disclosure. Suitable modifications and adaptations of the variety of conditions and parameters normally encountered in clinical therapy and which are obvious to those skilled in the art in view of this disclosure are within the spirit and scope of the disclosure.

EXAMPLES

The abbreviations set forth in TABLE 3 are used in the following examples:

TABLE 3

| ACN | acetonitrile |
|---|---|
| AcOH | acetic acid |
| aq. | aqueous |
| atm | atmosphere(s) |
| ° C. | degrees Celcius |
| d | day(s) |
| DCM | dichloromethane |
| DMF | dimethylformamide |
| DMSO | dimethylsulfoxide |
| EtOAc | ethyl acetate |
| EtOH | ethanol |
| h | hour(s) |
| HPLC | high pressure liquid chromatography |
| mCPBA | meta-chloroperoxybenzoic acid |
| MeOH | methanol |
| min | minute(s) |
| Pd(Ph$_3$P)$_2$Cl$_2$ | bis(triphenylphosphine)palladium(II) dichloride |
| (Ph)$_3$P | triphenylphosphine |
| PTSA | p-toluenesulfonic acid |
| RT | room temperature |
| t-BuOH | tert-butyl alcohol |
| TFA | trifluoroacetic acid |
| THF | tetrahydrofuran |

Example 1

Synthesis of Compound 4

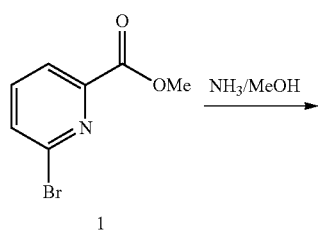

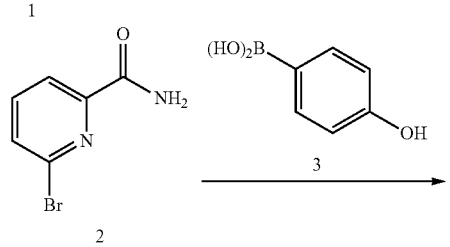

A mixture of Compound 1 (20.0 g, 92.0 mmol) and NH$_4$Cl (10.0 g) in 200 mL of NH$_3$ (7M in MeOH) was heated at 70° C. for 4 h. After cooling to RT the solvent was removed under vacuum and the residue was washed with water and dried to afford Compound 2 as white solid (15.0 g).

A suspension of Compound 2 (5.0 g, 25.0 mmol), Compound 3 (3.5 g, 25.0 mmol), K$_2$CO$_3$ (8.0 g) and Pd(Ph$_3$P)$_2$Cl$_2$ (0.8 g) in DMF (100 mL)/water (0.05 mL) was heated at 80° C. under argon for 18 h. After cooling to RT the reaction was quenched with water (200 mL) and extracted with EtOAc (2×150 mL). The combined organic layers were washed with water (2×50 mL) and brine (100 mL), concentrated and purified by flash chromatography (SiO$_2$, 33% EtOAc/hexanes) to give Compound 4 as white solid (4.0 g). Yield 75%. $^1$H NMR (400 MHz, CD$_3$OD): δ 7.88-8.02 (m, 5H), 6.95 (d, J=8.8 Hz, 2H).

Example 2

Synthesis of Compound 6

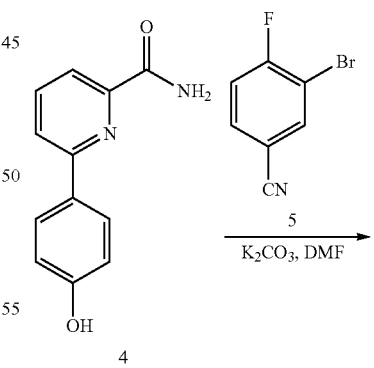

6

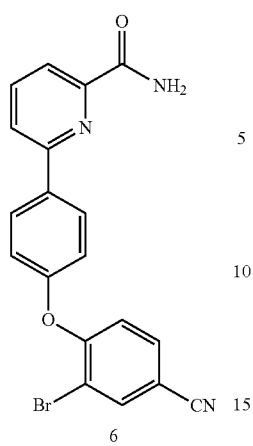

A mixture of Compound 5 (3.20 g, 16 mmol, ACROS), Compound 4 (3.50 g, 16 mmol), and K$_2$CO$_3$ (2.50 g, 16 mmol) in DMF (30 mL) was heated at 90° C. under nitrogen for 4 h. The reaction mixture was cooled with ice-water, and slowly added water (30 mL). The solid was collected and suspended in ACN (25 mL)/water (10 mL) at 0° C. for 15 min. The solid was collected and dried to give Compound 6 as white solid (6.0 g). Yield 93%. $^1$H NMR (400 MHz, CD$_3$OD): δ 8.19 (dd, J=1.0, 7.7 Hz, 1H), 8.08 (d, J=8.8 Hz, 2H), 7.94-7.98 (m, 3H), 7.89 (dd, J=1.0, 7.8 Hz, 1H), 7.55 (dd, J=1.9, 8.5 Hz, 1H), 7.18 (d, J=8.8 Hz, 2H), 6.96 (d, J=8.6 Hz, 1H), 5.68 (brs, 1H).

In a similar manner the following compounds were prepared:

7

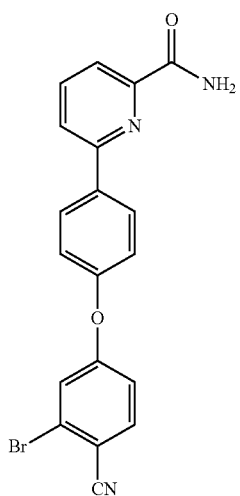

8

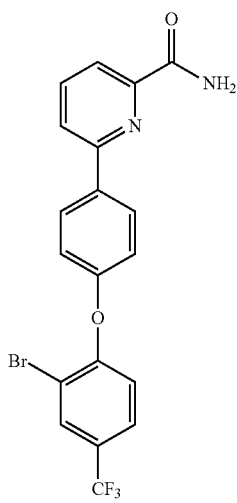

9

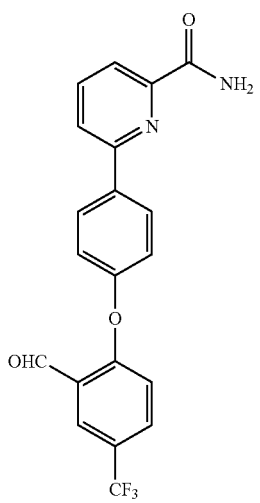

10

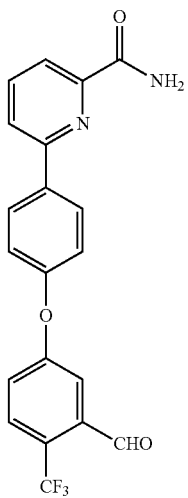

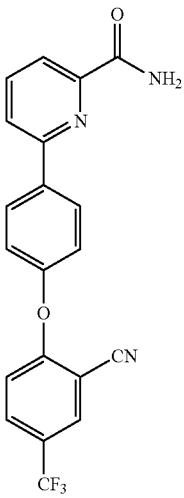

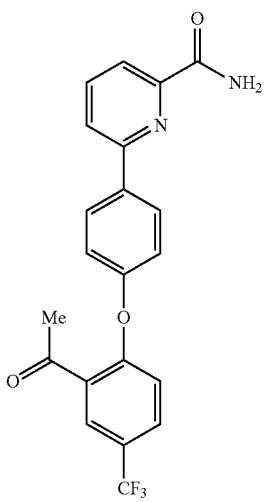

Compound 7. ¹H NMR (400 MHz, CD₃OD): δ 8.20 (dd, J=1.0, 7.7 Hz, 1H), 8.10 (d, J=8.9 Hz, 2H), 7.97 (dd, J=7.6, 7.7 Hz, 2H), 7.91 (dd, J=1.3, 8.1 Hz, 1H), 7.62 (d, J=8.6 Hz, 1H), 7.28 (d, J=2.4 Hz, 1H), 7.21 (d, J=8.9 Hz, 2H), 7.05 (dd, J=2.4, 8.5 Hz, 1H), 5.75 (brs, 1H).

Compound 8. LC/MS: m/z=437.0/439.0 [M+H]⁺ (Calc: 437.2).

6-(4-(2-Formyl-4-(trifluoromethyl)phenoxy)phenyl)picolinamide (Compound 9): ¹H NMR (400 MHz, CDCl₃): δ 10.60 (s, 1H), 8.25 (d, J=2.4 Hz, 1H), 8.20 (dd, J=0.8, 7.4 Hz, 1H), 8.12 (d, J=8.8 Hz, 2H), 7.90-8.00 (m, 2H), 7.91 (dd, J=1.0, 8.1 Hz, 1H), 7.75 (dd, J=2.4, 7.6 Hz, 1H), 7.25 (d, J=8.3 Hz, 2H), 7.04 (d, J=8.6 Hz, 1H), 5.80 (brs, 1H).

Compound 10. ¹H NMR (600 MHz, CDCl₃): δ 10.40 (s, 1H), 8.20 (d, J=7.8 Hz, 1H), 8.10 (d, J=7.8 Hz, 2H), 7.97-8.00 (m, 2H), 7.92 (d, J=7.8 Hz, 1H), 7.81 (d, J=8.4 Hz, 1H), 7.73 (s, 1H), 7.35 (d, J=7.8 Hz, 1H), 7.21 (d, J=7.8 Hz, 2H), 5.80 (brs, 1H).

Compound 11. LC/MS: m/z=384.2 [M+H]⁺ (Calc: 383.3).

Compound 12. LC/MS: m/z=401.2 [M+H]⁺ (Calc: 400.4).

Compound 13. LC/MS: m/z=320.0 [M+H]⁺ (Calc: 319.3).

Example 3

Synthesis of 6-(4-(4-cyano-2-(pyridin-4-yl)phenoxy)phenyl)picolinamide (Compound 15)

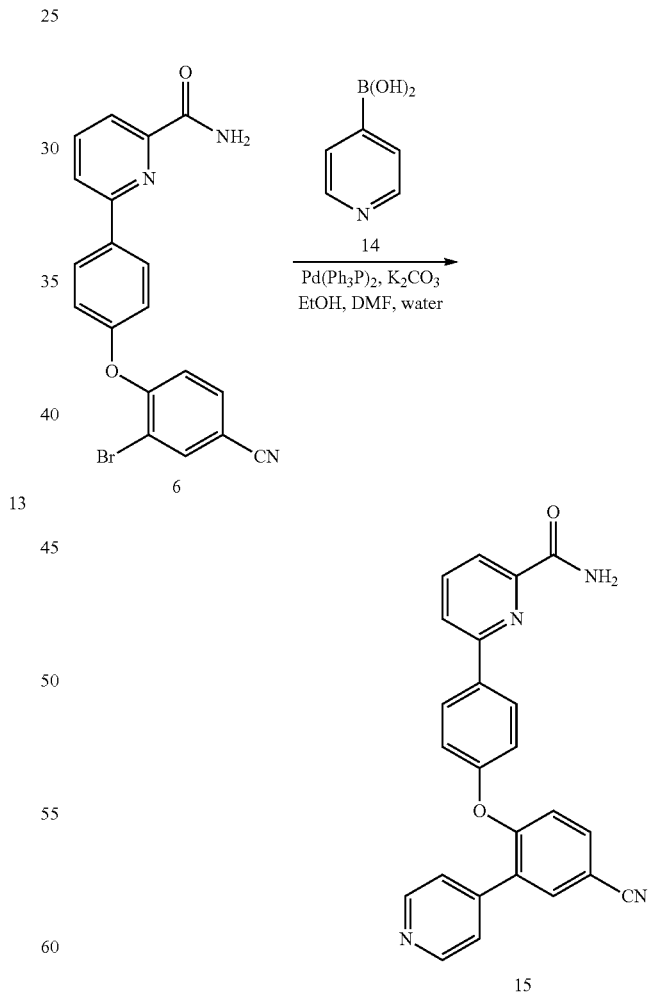

A mixture of Compound 6 (0.22 g, 0.55 mmol), Compound 14 (0.12 g, 0.9 mmol), K₂CO₃ (0.30 g, 2.3 mmol), and Pd(PPh₃)₂Cl₂ (80 mg, 0.11 mmol) in EtOH/DMF (1/1) (8 mL) and water (0.1 mL) was flushed with argon. The reaction mixture was sealed and microwaved at 130° C. for 1 h. After cooling to RT the reaction mixture was quenched with water (20 mL) and extracted with EtOAc (40 mL). The organic layer was washed with brine, concentrated and purified by reverse-phase prep HPLC (C18, 0-100% 0.1% TFA in water/0.1% TFA in ACN) to give Compound 15 as the TFA salt (0.15 g). $^1$H NMR (400 MHz, CD$_3$OD): δ 8.78-8.81 (m, 2H), 8.21 (d, J=6.8 Hz, 2H), 8.18 (d, J=8.9 Hz, 2H), 8.05 (d, J=1.7 Hz, 1H), 7.9-7.98 (m, 3H), 7.78 (dd, J=2.2, 8.9 Hz, 1H), 7.16 (d, J=8.9 Hz, 2H), 7.07 (d, J=8.8 Hz, 1H). LC/MS, m/z=393.2 [M+H]$^+$ (Calc: 392.4).

In a similar manner the following compounds were prepared:

6-(4-(4-cyano-2-(pyridin-3-yl)phenoxy)phenyl)picolinamide (Compound 16). LC/MS: m/z=393.2 [M+H]$^+$ (Calc: 392.4).

6-(4-(4-cyano-2-(1-methyl-1H-pyrrol-2-yl)phenoxy)phenyl)picolinamide (Compound 17). LC/MS: m/z=395.2 [M+H]$^+$ (Calc: 394.4).

6-(4-((4'-amino-5-cyano-[1,1'-biphenyl]-2-yl)oxy)phenyl)picolinamide (Compound 18). LC/MS: m/z=407.1 [M+H]$^+$ (Calc: 406.4).

6-(4-(4-cyano-2-(thiophen-3-yl)phenoxy)phenyl)picolinamide (Compound 19). LC/MS: m/z=398.2 [M+H]$^+$ (Calc: 397.4).

6-(4-(4-cyano-2-(6-methoxypyridin-3-yl)phenoxy)phenyl)picolinamide (Compound 20). LC/MS: m/z=423.2 [M+H]$^+$ (Calc: 422.4).

6-(4-(4-cyano-2-(1-methyl-1H-pyrazol-4-yl)phenoxy)phenyl)picolinamide (Compound 21). LC/MS: m/z=396.2 [M+H]$^+$ (Calc: 395.4).

6-(4-(4-cyano-2-(1-methyl-1H-pyrazol-5-yl)phenoxy)phenyl)picolinamid (Compound 22). LC/MS: m/z=396.2 [M+H]$^+$ (Calc: 395.4).

6-(4-(4-cyano-2-(6-hydroxypyridin-3-yl)phenoxy)phenyl)picolinamide (Compound 23). LC/MS: m/z=409.2 [M+H]$^+$ (Calc: 408.4).

6-(4-(4-cyano-2-(2-methoxypyridin-3-yl)phenoxy)phenyl)picolinamide (Compound 24). LC/MS: m/z=423.1 [M+H]$^+$ (Calc: 422.4).

6-(4-(4-cyano-2-(2-methoxypyridin-4-yl)phenoxy)phenyl)picolinamide (Compound 25). LC/MS: m/z=423.1 [M+H]$^+$ (Calc: 422.4).

6-(4-(4-cyano-3-(pyridin-4-yl)phenoxy)phenyl)picolinamide (Compound 26). LC/MS: m/z=393.1 [M+H]$^+$ (Calc: 392.4).

6-(4-(4-cyano-3-(pyridin-3-yl)phenoxy)phenyl)picolinamide (Compound 27, V122186). LC/MS: m/z=393.1 [M+H]$^+$ (Calc: 392.4).

6-(4-(2-(pyridin-4-yl)-4-(trifluoromethyl)phenoxy)phenyl)picolinamide (Compound 28). LC/MS: m/z=436.0 [M+H]$^+$ (Calc: 435.4).

6-(4-(2-(pyridin-3-yl)-4-(trifluoromethyl)phenoxy)phenyl)picolinamide (Compound 29). LC/MS: m/z=436.0 [M+H]$^+$ (Calc: 435.4).

Example 4

Synthesis of 6-(4-(2-(pyrrolidin-1-ylmethyl)-4-(trifluoromethyl)phenoxy)phenyl)picolinamide (Compound 30)

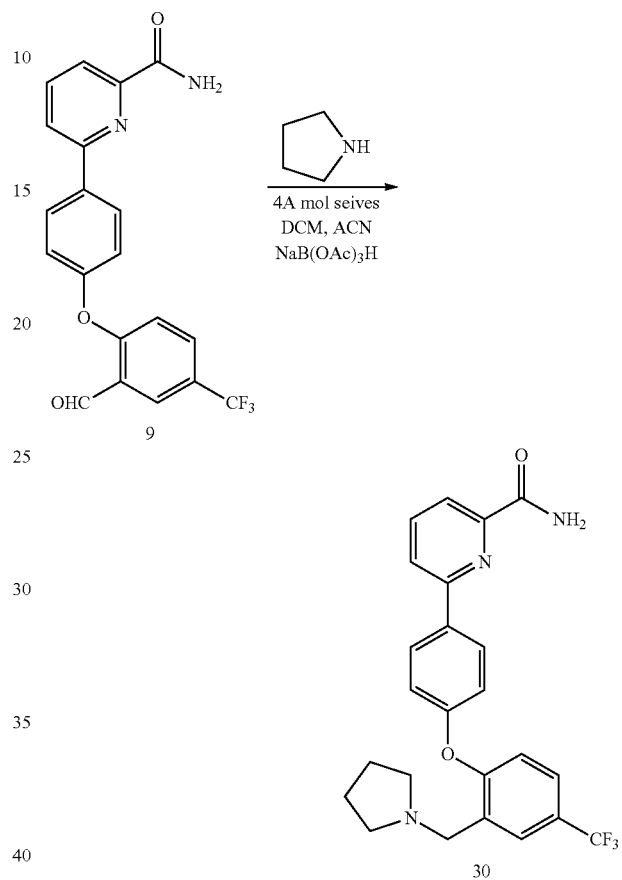

A mixture of Compound 9 (0.10 g, 0.26 mmol), pyrrolidine (0.028 g, 0.39 mmol) and 4A molecular sieves in DCM/ACN (1/1) (2 mL) was shaken at RT for 1 h. NaBH(OAc)$_3$ (110 mg, 0.50 mmol) was added at RT and the reaction mixture was shaken at RT for 24 h. The reaction was quenched with water (2 mL) and extracted with CHCl$_3$ (6 mL). The organic layer was washed with brine, concentrated and purified by reverse-phase prep HPLC (C18, 0-100% 0.1% TFA in water/0.1% TFA in ACN) to give Compound 30 as the TFA salt as a white solid. LC/MS: m/z=442.2 [M+H]$^+$ (Calc: 441.4).

In a similar manner the following compounds were prepared.

6-(4-(2-(((2-(dimethylamino)ethyl)amino)methyl)-4-(trifluoromethyl)phenoxy)phenyl)picolinamide (Compound 31) LC/MS: m/z=459.2 [M+H]$^+$ (Calc: 458.5).

6-(4-(2-(((4-sulfamoylphenethyl)amino)methyl)-4-(trifluoromethyl)phenoxy)phenyl) picolinamide (Compound 32). LC/MS: m/z=571.2 [M+H]$^+$ (Calc: 570.6).

6-(4-(2-((4-methylpiperazin-1-yl)methyl)-4-(trifluoromethyl)phenoxy)phenyl) picolinamide (Compound 33). LC/MS: m/z=471.2 [M+H]$^+$ (Calc: 470.5).

6-(4-(2-(((2-(2-oxoimidazolidin-1-yl)ethyl)amino)methyl)-4-(trifluoromethyl) phenoxy)phenyl)picolinamide (Compound 34). LC/MS: m/z=500.2 [M+H]$^+$ (Calc: 499.5).

6-(4-(2-((3-oxopiperazin-1-yl)methyl)-4-(trifluoromethyl)phenoxy)phenyl) picolinamide (Compound 35). LC/MS: m/z=471.2 [M+H]+ (Calc: 470.4).

(S)-6-(4-(2-((3-hydroxypyrrolidin-1-yl)methyl)-4-(trifluoromethyl)phenoxy)phenyl)picolinamide (Compound 36). LC/MS: m/z=458.2 [M+H]+ (Calc: 457.4).

6-(4-(2-(((2-(dimethylamino)ethyl)(methyl)amino)methyl)-4-(trifluoromethyl) phenoxy)phenyl)picolinamide (Compound 37). LC/MS: m/z=473.2 [M+H]+ (Calc: 472.5).

6-(4-(2-(((3-(dimethylamino)propyl)amino)methyl)-4-(trifluoromethyl) phenoxy)phenyl)picolinamide (Compound 38). LC/MS: m/z=473.2 [M+H]+ (Calc: 472.5).

6-(4-(2-((dimethylamino)methyl)-4-(trifluoromethyl)phenoxy)phenyl)picolinamide (Compound 39). LC/MS: m/z=416.2 [M+H]+ (Calc: 415.4).

6-(4-(2-(((2-hydroxyethyl)amino)methyl)-4-(trifluoromethyl)phenoxy)phenyl)picolinamide (Compound 40). LC/MS: m/z=432.2 [M+H]+ (Calc: 431.4).

(S)-6-(4-(2-((2-(hydroxymethyl)pyrrolidin-1-yl)methyl)-4-(trifluoromethyl) phenoxy)phenyl)picolinamide (Compound 41). LC/MS: m/z=472.2 [M+H]+ (Calc: 471.5).

(R)-6-(4-(2-((2-(hydroxymethyl)pyrrolidin-1-yl)methyl)-4-(trifluoromethyl) phenoxy)phenyl)picolinamide (Compound 42). LC/MS: m/z=472.2 [M+H]+ (Calc: 471.5).

6-(4-(2-(morpholinomethyl)-4-(trifluoromethyl)phenoxy)phenyl)picolinamide (Compound 43). LC/MS: m/z=458.2 [M+H]+ (Calc: 457.4).

(S)-6-(4-(2-((2-carbamoylpyrrolidin-1-yl)methyl)-4-(trifluoromethyl)phenoxy)phenyl)picolinamide (Compound 44). LC/MS: m/z=485.2 [M+H]+ (Calc: 484.5).

6-(4-(2-((3,3-difluoropyrrolidin-1-yl)methyl)-4-(trifluoromethyl)phenoxy)phenyl)picolinamide (Compound 45, V122263). LC/MS: m/z=478.2 [M+H]+ (Calc: 477.4).

(S)-6-(4-(2-(((2-oxopyrrolidin-3-yl)amino)methyl)-4-(trifluoromethyl)phenoxy)phenyl)picolinamide (Compound 46). LC/MS: m/z=471.2 [M+H]+ (Calc: 470.4).

tert-butyl(1-(2-(4-(6-carbamoylpyridin-2-yl)phenoxy)-5-(trifluoromethyl)benzyl)pyrrolidin-3-yl)carbamate (Compound 47, V122269). LC/MS: m/z=557.2 [M+H]+ (Calc: 556.6).

tert-butyl 3-((2-(4-(6-carbamoylpyridin-2-yl)phenoxy)-5-(trifluoromethyl)benzyl)-amino)pyrrolidine-1-carboxylate (Compound 48). LC/MS: m/z=557.2 [M+H]+ (Calc: 556.6).

6-(4-(2-(piperidin-1-ylmethyl)-4-(trifluoromethyl)phenoxy)phenyl)picolinamide (Compound 49). LC/MS: m/z=456.2 [M+H]+ (Calc: 455.5).

6-(4-(2-(azetidin-1-ylmethyl)-4-(trifluoromethyl)phenoxy)phenyl)picolinamide (Compound 50). LC/MS: m/z=557.2 [M+H]+ (Calc: 427.4).

6-(4-(2-((3-hydroxypiperidin-1-yl)methyl)-4-(trifluoromethyl)phenoxy)phenyl) picolinamide (Compound 51). LC/MS: m/z=472.2 [M+H]+ (Calc: 471.5).

6-(4-(2-(((2-hydroxyethyl)(methyl)amino)methyl)-4-(trifluoromethyl)phenoxy)phenyl)picolinamide (Compound 52). LC/MS: m/z=446.2 [M+H]+ (Calc: 445.4).

6-(4-(3-(azetidin-1-ylmethyl)-4-(trifluoromethyl)phenoxy)phenyl)picolinamide (Compound 53). LC/MS: m/z=428.0 [M+H]+ (Calc: 427.4).

(S)-6-(4-(3-((3-hydroxypyrrolidin-1-yl)methyl)-4-(trifluoromethyl)phenoxy)phenyl)picolinamide (Compound 54). LC/MS: m/z=458.0 [M+H]+ (Calc: 457.4).

6-(4-(4-(trifluoromethyl)-3-(((3,3-trifluoropropyl)amino)methyl)phenoxy)phenyl)picolinamide (Compound 55). LC/MS: m/z=484.0 [M+H]+ (Calc: 483.4).

6-(4-(3-(pyrrolidin-1-ylmethyl)-4-(trifluoromethyl)phenoxy)phenyl) picolinamide (Compound 56). LC/MS: m/z=442.0 [M+H]+ (Calc: 441.4).

6-(4-(2-(1-(pyrrolidin-1-yl)ethyl)-4-(trifluoromethyl)phenoxy)phenyl) picolinamide (Compound 58). LC/MS: m/z=456.2 [M+H]+ (Calc: 455.5).

6-(4-((6-(pyrrolidin-1-ylmethyl)pyridin-2-yl)oxy)phenyl) picolinamide (Compound 59). LC/MS: m/z=375.2 [M+H]+ (Calc: 374.4).

Example 5

Synthesis of 6-(4-(2-((3-aminopyrrolidin-1-yl)methyl)-4-(trifluoromethyl)phenoxy)phenyl)picolinamide (Compound 60)

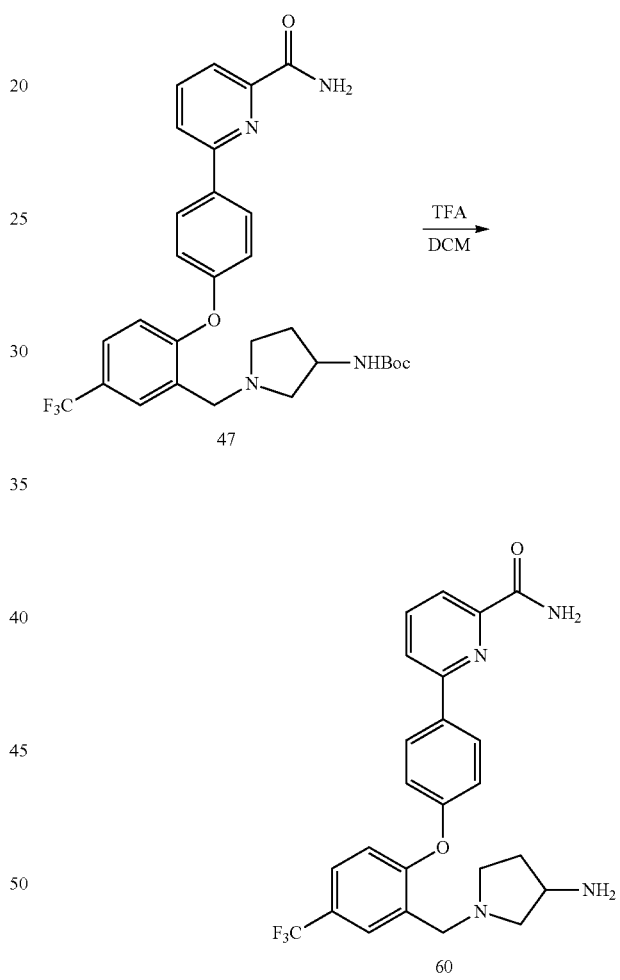

TFA (1 mL) was added to a solution of Compound 47 (20.0 mg, 0.035 mmol) in DCM (4 mL) at 0° C. The reaction mixture was stirred at 0° C. for 2 h. The solvent was evaporated under vacuum and the residue purified by reverse-phase prep HPLC (C18, 0-100% 0.1% TFA in water/0.1% TFA in ACN) to give Compound 60 as the TFA salt as a white solid (15 mg). $^1$H NMR (600 MHz, CD$_3$OD): δ 8.20 (d, J=8.4 Hz, 2H), 7.93-8.01 (m, 3H), 7.89 (s, 1H), 7.62 (d, J=8.9 Hz, 1H), 7.18 (d, J=8.8 Hz, 2H), 6.99 (d, J=8.8 Hz, 1H), 4.34 (s, 2H), 3.95 (s, 1H), 3.50-3.53 (m, 2H), 3.27-3.51 (m, 2H), 2.42-2.50 (m, 1H), 1.95-2.04 (m, 1H). LC/MS: m/z=457.2 [M+H]+ (Calc: 456.5).

In a similar manner the following compounds were prepared:

6-(4-(2-((pyrrolidin-3-ylamino)methyl)-4-(trifluoromethyl)phenoxy)phenyl) picolinamide (Compound 61). LC/MS: m/z=457.2 [M+H]$^+$ (Calc: 456.5).

6-(4-(3-((3-aminoazetidin-1-yl)methyl)-4-(trifluoromethyl)phenoxy)phenyl) picolinamide (Compound 62). LC/MS: m/z=443.1 [M+H]$^+$ (Calc: 442.4).

Example 6

Synthesis of 6-(4-(2-(1-hydroxy-2-nitroethyl)-4-(trifluoromethyl)phenoxy)phenyl) picolinamide (Compound 63)

and 6-(4-(2-(2-amino-1-hydroxyethyl)-4-(trifluoromethyl)phenoxy)phenyl)picolinamide (Compound 64)

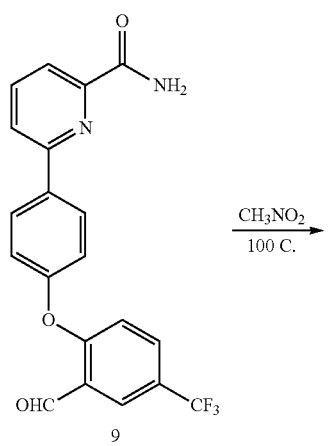

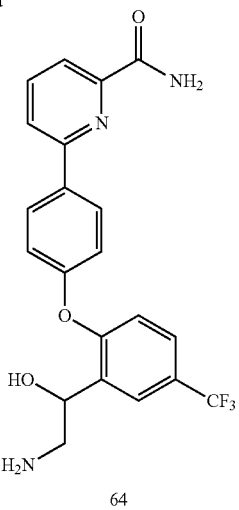

A mixture of Compound 9 (0.20 g, 0.50 mmol), nitromethane (1.5 mL), THF (0.4 mL) and a catalytic amount of ammonium acetate (0.30 mmol) was heated in a microwave at 100° C. for 40 min. The solvent was evaporated under vacuum and the mixture purified by reverse-phase prep HPLC (C18, 0-100% 0.1% TFA in water/0.1% TFA in ACN) to give Compound 63 as a white solid (50 mg). Yield 22%. $^1$H NMR (600 MHz, CD$_3$OD): δ 8.19 (d, J=8.9 Hz, 2H), 7.99 (d, J=7.2 Hz, 1H), 7.93-7.96 (m, 2H), 7.90 (s, 1H), 7.52 (d, J=8.9 Hz, 1H), 7.15 (d, J=8.9 Hz, 2H), 6.93 (d, J=9.1 Hz, 1H), 5.72 (dd, J=3, 9.6 Hz, 1H), 4.76 (dd, J=3, 12.6 Hz, 1H), 4.49 (dd, J=9, 12.6 Hz, 1H). LC/MS: m/z=448.0 [M+H]$^+$ (Calc: 447.4).

A solution of Compound 63 (40.0 mg) in MeOH (40 mL) was passed through H-Cube (Raney Nickel, 1 atm, 30° C., 1 mL/min) at RT for 30 min. The solvent was evaporated, and the product purified by reverse-phase prep HPLC (C18, 0-100% 0.1% TFA in water/0.1% TFA in ACN) to give Compound 64 as the TFA salt as a white solid (40 mg). LC/MS: m/z=418.2 [M+H]$^+$ (Calc: 417.4).

Example 7

Synthesis of 6-(4-(2-(aminomethyl)-4-(trifluoromethyl)phenoxy)phenyl)picolinamide (Compound 65)

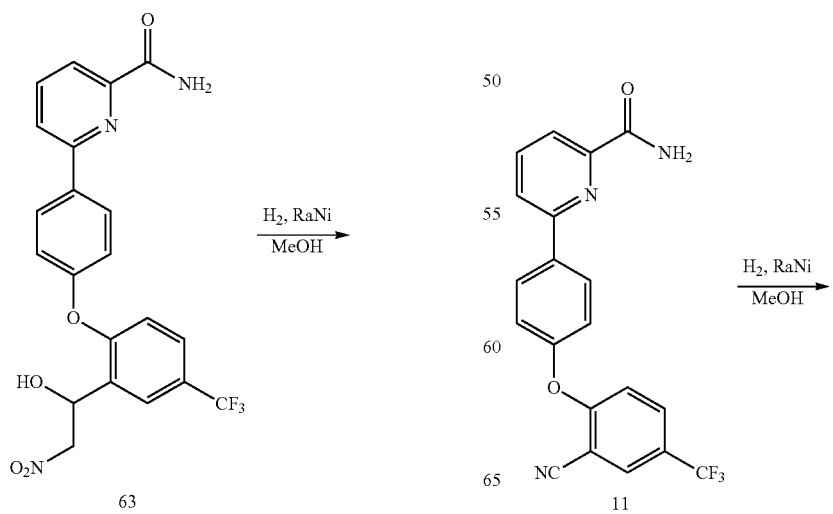

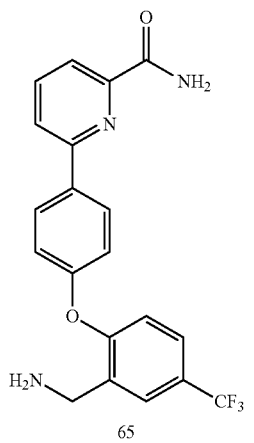

A solution of Compound 11 (0.10 g, 0.26 mmol) in 2N NH₃ in MeOH (20 mL) was passed through H-Cube (Raney Nickel, 5 atm, 30° C., 1 mL/min) for 30 min. The solvent was evaporated and the product purified by reverse-phase prep HPLC (C18, 0-100% 0.1% TFA in water/0.1% TFA in ACN) to give Compound 65 as the TFA salt as a white solid (90 mg). ¹H NMR (600 MHz, CD₃OD): δ 8.22 (d, J=9.0 Hz, 2H), 8.01 (d, J=7.2 Hz, 1H), 7.93-7.98 (m, 2H), 7.80 (s, 1H), 7.62 (d, J=9.0 Hz, 1H), 7.23 (d, J=9.6 Hz, 2H), 6.97 (d, J=8.4 Hz, 1H), 4.26 (s, 2H). LC/MS: m/z=388.2 [M+H]⁺ (Calc: 387.4).

Example 8

Synthesis of (S)-4-(2-(4-(6-(1,2-dihydroxyethyl)pyridin-2-yl)phenoxy)-5-(trifluoromethyl)benzyl)piperazin-2-one (Compound 74)

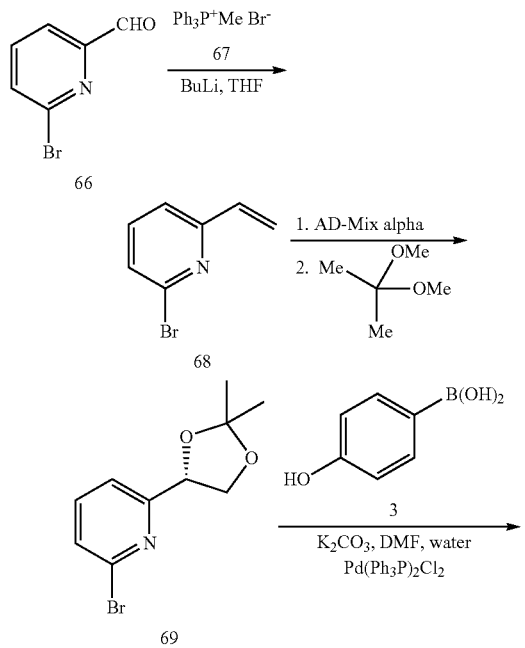

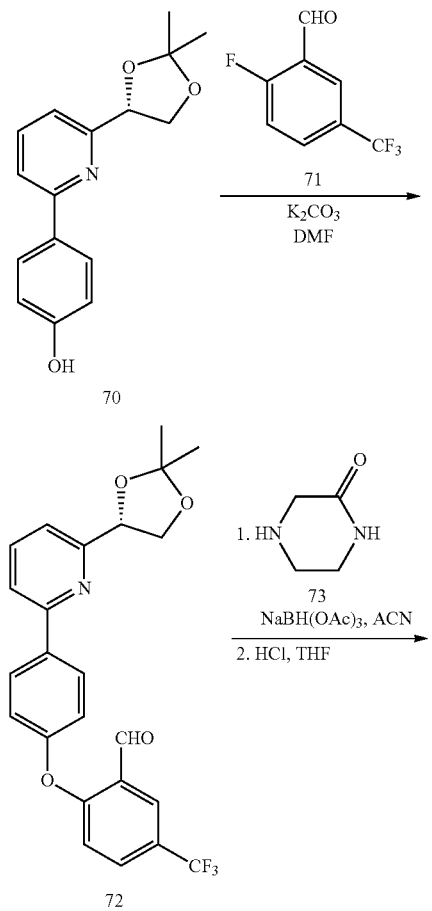

n-BuLi (22 mL, 2.5 N in hexane, 55.0 mmol) was added to a suspension of Compound 67 (19.0 g, 53 mmol) in THF (300 mL) at −30° C. The mixture was stirred under argon at −20° C. for 1 h to give a yellow solution. A solution of Compound 66 (10.0 g, 53 mmol, Accela Chembio) in THF (50 mL) was added over 5 min. The reaction mixture was warmed to RT over 1 h and heated at 35° C. for 10 h. The reaction was quenched with water (150 mL) and extracted with CHCl₃ (3×150 mL). The combined organic layers were concentrated and purified by flash chromatography (SiO₂, 33% CHCl₃/hexanes) to give Compound 68 as a colorless oil (7.0 g). ¹H NMR (400 MHz, CDCl₃): δ 7.42 (dd, 7.6, 7.8

Hz, 1H), 7.27 (d, 7.6 Hz, 1H), 7.2 (dd, 0.7, 7.6 Hz, 1H), 6.66 (dd, 10.2, 17.5 Hz, 1H), 6.17 (dd, 1.0, 17.3 Hz, 1H), 5.44 (dd, 0.8, 17.3 Hz, 1H).

Ad-Mix-alpha (18 g, Aldrich) was added to a solution of Compound 68 (3.60 g, 19.5 mmol) in t-BuOH/water (1/1) (150 mL) at 0° C. The reaction was warmed to RT and stirred for 24 h. The reaction mixture was concentrated under vacuum, water (200 mL) was added and extracted with EtOAc (2×100 mL). The organic layer was washed with brine and concentrated to give a yellow oil which was dissolved in acetone/CHCl$_3$ (1/1) (20 mL). To this solution, was added 2,2-dimethoxypropane (4 mL, excess) and PTSA (0.37 g, 1.9 mmol). The reaction mixture was stirred at RT for 72 h. The reaction was quenched with water (30 mL) and 2N NaOH (2 mL) and extracted with EtOAc (2×100 mL). The combined organic layer was washed with brine, concentrated and purified by flash chromatography (SiO$_2$, 10% EtOAc/hexanes) to give Compound 69 as brown oil (4.0 g). Yield 79%. $^1$H NMR (400 MHz, CDCl$_3$): δ 7.57 (dd, J=7.6, 7.7 Hz, 1H), 7.50-7.52 (m, 1H), 7.39 (ddd, J=0.6, 0.9, 7.6 Hz, 1H), 5.16 (t, J=6.6 Hz, 1H), 4.47 (dd, J=6.6, 8.3 Hz, 1H), 3.95 (dd, J=6.1, 8.5 Hz, 1H), 1.53 (s, 3H), 1.48 (s, 3H).

A mixture of Compound 69 (1.0 g, 3.8 mmol), Compound 3 (0.6 g, 4.3 mmol), K$_2$CO$_3$ (1.0 g) and Pd(PPh$_3$)$_2$Cl$_2$ (30 mg, 0.043 mmol) were placed in a mixture of DMF (10 mL) and water (0.1 mL) and purged with argon. After heating at 100° C. for 3 h the reaction was quenched with water (40 mL), extracted with EtOAc (100 mL), concentrated and purified by flash chromatography (SiO$_2$, 0-50% MeOH/CHCl$_3$). to give Compound 70 as a brown oil (0.8 g). LC/MS: m/z=272.2 [M+H]$^+$ (Calc: 271.3).

A mixture of Compound 71 (0.78 g, 3.7 mmol), Compound 70 (1.0 g, 3.7 mmol) and K$_2$CO$_3$ (1.0 g, 7.4 mmol) in DMF (20 mL) was heated at 90° C. under nitrogen for 4 h. The reaction mixture was cooled to RT, quenched with water (40 mL) and extracted with EtOAc (150 mL). The organic layer was washed with brine, concentrated and purified by flash chromatography (SiO$_2$, 25% EtOAc/hexanes) to give Compound 72 as a yellow oil (1.5 g). Yield 92%. $^1$H NMR (400 MHz, CDCl$_3$): δ 10.60 (s, 1H), 8.25 (s, 1H), 8.11 (d, J=8.2 Hz, 2H), 7.82 (dd, J=7.6, 8.2 Hz, 1H), 7.75 (d, J=8.1 Hz, 1H), 7.65 (d, J=8.6 Hz, 1H), 7.53 (d, J=7.8 Hz, 1H), 7.23 (d, J=8.2 Hz, 2H), 7.02 (d, J=7.9 Hz, 1H), 5.29 (t, J=7.2 Hz, 1H), 4.54 (dd, J=7.8, 8.4 Hz, 1H), 4.09-4.16 (m, 1H), 1.59 (s, 3H), 1.55 (s, 3H).

A mixture of Compound 72 (0.10 g, 0.23 mmol) and piperazin-2-one (Compound 73) (33 mg, 0.34 mmol) in ACN (2 mL) was shaken at RT for 2 h. NaBH(OAc)$_3$. (96 mg, 0.45 mmol) was added and the mixture shaken at RT for 24 h. The reaction mixture was quenched with water (2 mL), extracted with CHCl$_3$ (2×4 mL) and concentrated to give an oil. After dissolving in THF (5 mL), 1N HCl (2 mL) was added and the resulting mixture shaken at RT for 2 h. The reaction was quenched with water (2 mL), extracted with CHCl$_3$, concentrated and purified by reverse-phase prep HPLC (C18, 0-100% 0.1% TFA in water/0.1% TFA in ACN) to give Compound 74 as the TFA salt as a white solid (60 mg). $^1$H NMR (400 MHz, CD$_3$OD): δ 8.02 (d, J=7.6 Hz, 2H), 7.96 (dd, J=7.2, 8 Hz, 1H), 7.89 (d, J=2 Hz, 1H), 7.78 (d, J=8.0 Hz, 1H), 7.67 (dd, J=2, 8.6 Hz, 2H), 7.55 (d, J=7.6 Hz, 1H), 7.21 (d, J=8.4 Hz, 2H), 7.02 (d, J=8.8 Hz, 1H), 4.81 (t, J=5.2 Hz, 1H), 4.39 (s, 2H), 3.7-3.84 (m, 4H), 3.36-3.45 (m, 4H). LC/MS: m/z=488.2 [M+H]$^+$ (Calc: 487.4).

In a similar manner, the following compounds were prepared:

(S)-1-(6-(4-(2-(((S)-3-hydroxypyrrolidin-1-yl)methyl)-4-(trifluoromethyl) phenoxy)phenyl)pyridin-2-yl)ethane-1,2-diol (Compound 75). LC/MS: m/z=475.0 [M+H]$^+$ (Calc: 474.5).

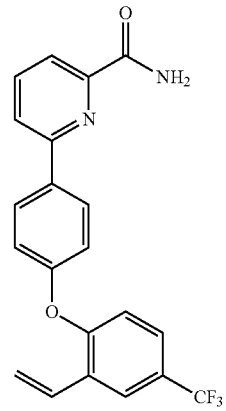

76

Compound 76. LC/MS: m/z=385.2 [M+H]$^+$ (Calc: 384.4).

(R)-6-(4-(2-(1,2-dihydroxyethyl)-4-(trifluoromethyl)phenoxy)phenyl) picolinamide (Compound 77). Prepared from Compound 76 using Ad-Mix-beta (Aldrich). $^1$H NMR (400 MHz, CD$_3$OD): δ 8.15 (d, J=8.4 Hz, 2H), 7.98 (d, J=7.8 Hz, 1H), 7.92-7.96 (m, 2H), 7.87 (s, 1H), 7.45 (d, J=8.4 Hz, 1H), 7.08 (d, J=8.9 Hz, 2H), 6.92 (d, J=8.4 Hz, 1H), 5.09-5.11 (m, 1H), 3.73 (dd, J=3, 11.5 Hz, 1H), 3.50 (dd, J=7.2, 12 Hz, 1H). LC/MS: m/z=419.1 [M+H]$^+$ (Calc: 418.4).

Example 9

6-(4-(2-(1-hydroxy-2-(3-oxopiperazin-1-yl)ethyl)-4-(trifluoromethyl)phenoxy)phenyl) picolinamide (Compound 79)

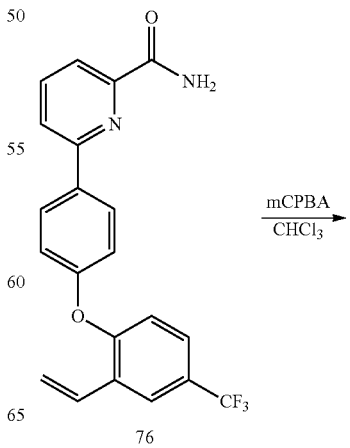

76

185
-continued

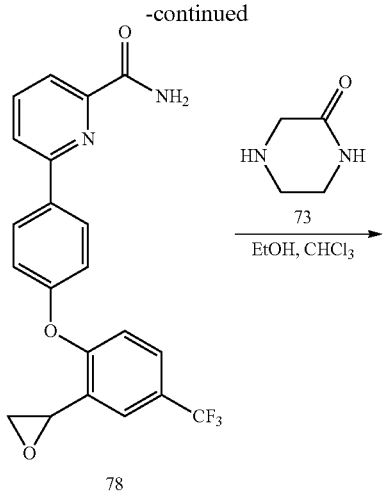

186
Example 10

6-(4-(2-(2-amino-2-oxo-1-(pyrrolidin-1-yl)ethyl)-4-(trifluoromethyl)phenoxy)phenyl) picolinamide
(Compound 81)

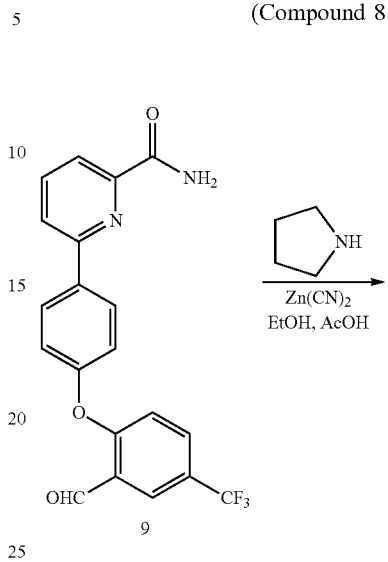

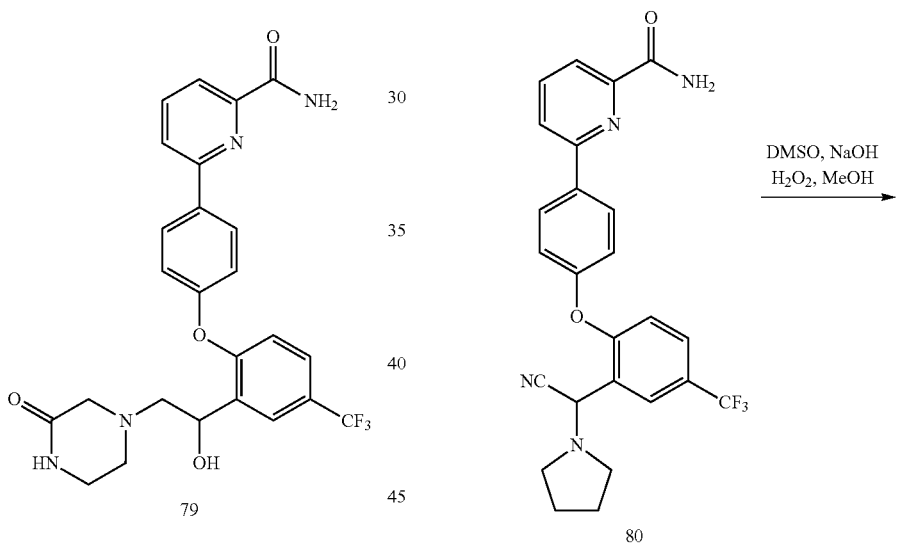

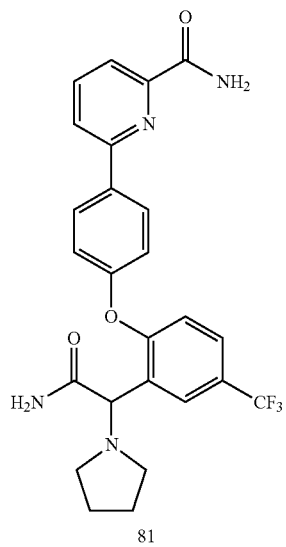

mCPBA (45 mg, 0.26 mmol) was added to a solution of Compound 76 (0.10 g, 0.26 mmol) in CHCl$_3$ (3 mL) at 0° C. The reaction mixture was stirred at 0° C. for 1 h and at RT for 36 h. The reaction was quenched with 2N NaOH (0.4 mL). The organic layer was separated, washed with saturated aq. Na$_2$SO$_3$ (1 mL), filtered over K$_2$CO$_3$ and concentrated to give crude Compound 78 (ca 0.2 g). LC/MS: m/z=401.2 [M+H]$^+$ (Calc: 400.3).

A mixture of crude Compound 78 (60 mg, 0.15 mmol) and Compound 73 (15 mg, 0.15 mmol) in 1 mL of EtOH/CHCl$_3$ (4/1) was shaken at RT for 72 h, and at 75° C. for 4 h. After cooling to RT the reaction was quenched with 0.1N HCl (1 mL), extracted with CHCl$_3$ (4 mL), concentrated and purified by reverse-phase prep HPLC (C18, 0-100% 0.1% TFA in water/0.1% TFA in ACN) to give Compound 79 as the TFA salt as a white solid (20 mg). $^1$H NMR (400 MHz, CD$_3$OD): δ 8.20 (d, J=9.2 Hz, 2H), 7.92-8.01 (m, 4H), 7.56 (dd, J=2.4, 9.2 Hz, 1H), 7.17 (d, J=8.9 Hz, 2H), 6.95 (d, J=8.8 Hz, 1H), 5.51 (dd, J=2.8, 10.4 Hz, 1H), 3.87 (d, J=3.6 Hz, 1H), 3.20-3.70 (m, 6H). LC/MS: m/z=501.2 [M+H]$^+$ (Calc: 500.5).

Pyrrolidine (74 mg, 1.0 mmol) was added to a mixture of Compound 9 (0.2 g, 0.52 mmol) and $Zn(CN)_2$ (0.12 g, 1.0 mmol) in EtOH/AcOH (3/1) (4 mL) at RT. The resulting mixture was shaken at 80° C. for 3 h. After cooling to RT the reaction was quenched by the addition of water (4 mL) and extracted with $CHCl_3$ (6 mL). The organic layer was cooled in an ice water bath, washed with water (2×3 mL) and treated with 1N NaOH to pH 10. The solvent was removed under vacuum to yield crude Compound 80 which was used directly in the next step.

Compound 80 from the previous step was dissolved in MeOH (4 mL), DMSO (40 mg), 2 N NaOH (0.4 mL) and 30% $H_2O_2$ (20 mg) were added and the resulting mixture stirred at RT for 1 h. The reaction was quenched by the addition of water and extracted with $CHCl_3$. The organic layer was washed with saturated aq. $Na_2SO_3$ (1 mL), concentrated and purified by reverse-phase prep HPLC (C18, 0-100% 0.1% TFA in water/0.1% TFA in ACN) to give Compound 81 as the TFA salt as a white solid (60 mg). $^1$H NMR (600 MHz, DMSO-$d_6$): δ 10.42 (s, 1H), 8.42 (d, J=8.9 Hz, 2H), 8.29 (s, 1H), 8.16 (d, J=7.8 Hz, 1H), 8.02 (dd, J=7.2, 8.5 Hz, 1H), 7.99 (s, 1H), 7.95 (s, 1H), 7.93 (d, J=7.8 Hz, 1H), 7.87 (s, 1H), 7.75 (d, J=7.8 Hz, 1H), 7.69 (s, 1H), 7.30 (d, J=8.4 Hz, 2H), 6.94 (d, J=8.9 Hz, 1H), 5.46 (s, 1H), 3.69 (s, 1H), 2.99-3.23 (m, 3H), 1.81-2.01 (m, 4H). LC/MS: m/z=485.1 [M+H]$^+$ (Calc: 484.5).

In a similar manner the following compounds were prepared:

6-(4-(2-(2-amino-2-oxo-1-(piperidin-1-yl)ethyl)-4-(trifluoromethyl)phenoxy)phenyl)picolinamide (Compound 82). LC/MS: m/z=499.2 [M+H]$^+$ (Calc: 498.5).

6-(4-(2-(2-amino-2-oxo-1-(propylamino)ethyl)-4-(trifluoromethyl)phenoxy)phenyl)picolinamide (Compound 83). LC/MS: m/z=473.1 [M+H]$^+$ (Calc: 472.5).

6-(4-(2-(2-amino-1-(dimethylamino)-2-oxoethyl)-4-(trifluoromethyl)phenoxy)phenyl)picolinamide (Compound 84). LC/MS: m/z=459.1 [M+H]$^+$ (Calc: 458.4).

6-(4-(2-(2-amino-1-(diethylamino)-2-oxoethyl)-4-(trifluoromethyl)phenoxy)phenyl)picolinamide (Compound 85). LC/MS: m/z=487.2 [M+H]$^+$ (Calc: 486.5).

Example 11

The following compounds were prepared in a manner similar to that described in Examples 1-10:

6-(2-chloro-4-(4-fluorophenoxy)phenyl)picolinamide (Compound 86). LC/MS, m/z=343.0 [M+H]$^+$ (Calc: 342.7).

6-(3-chloro-4-(4-fluorophenoxy)phenyl)picolinamide (Compound 87). LC/MS, m/z=343.0 [M+H]$^+$ (Calc: 342.7).

6-(3-cyano-4-(4-fluorophenoxy)phenyl)picolinamide (Compound 89). LC/MS, m/z=334.0 [M+H]$^+$ (Calc: 334.3).

6-(4-(4-fluorophenoxy)-3-(trifluoromethyl)phenyl)picolinamide (Compound 90). LC/MS, m/z=377.1 [M+H]$^+$ (Calc: 376.3).

6-(4-(4-fluorophenoxy)-2-(trifluoromethyl)phenyl)picolinamide (Compound 91). LC/MS, m/z=377.1 [M+H]$^+$ (Calc: 376.3).

6-(4-(4-fluorophenoxy)-3-(methyl(phenyl)amino)phenyl)picolinamide (Compound 92). LC/MS, m/z=414.1 [M+H]$^+$ (Calc: 413.4).

4-((5-(6-carbamoylpyridin-2-yl)-2-(4-fluorophenoxy)benzyl)(methyl)amino)benzoic acid (Compound 93). LC/MS, m/z=472.0 [M+H]$^+$ (Calc: 471.5).

6-(3-((4-chloro-2-iodophenoxy)methyl)-4-(4-fluorophenoxy)phenyl) picolinamide (Compound 94). LC/MS, m/z=575.2 [M+H]$^+$ (Calc: 574.7).

6-(3-((diethylamino)methyl)-4-(4-fluorophenoxy)phenyl)picolinamide (Compound 95). LC/MS, m/z=394.2 [M+H]$^+$ (Calc: 393.5).

6-(3-(ethoxymethyl)-4-(4-fluorophenoxy)phenyl)picolinamide (Compound 96). LC/MS, m/z=367.2 [M+H]$^+$ (Calc: 366.4).

6-(4-(4-fluorophenoxy)-3-(pyrrolidin-1-yl)phenyl)picolinamide (Compound 97). LC/MS, m/z=392.1 [M+H]$^+$ (Calc: 391.4).

6-(4-(4-fluorophenoxy)-3-(morpholinomethyl)phenyl)picolinamide (Compound 98). LC/MS, m/z=408.1 [M+H]$^+$ (Calc: 407.4).

6-(2-fluoro-4-(4-fluorophenoxy)phenyl)picolinamide (Compound 99). LC/MS, m/z=327.1 [M+H]$^+$ (Calc: 326.3).

6-(4'-chloro-6-(4-fluorophenoxy)-[1,1'-biphenyl]-3-yl)picolinamide (Compound 100). LC/MS, m/z=419.1 [M+H]$^+$ (Calc: 418.9).

6-(4-(4-fluorophenoxy)-3-(2H-tetrazol-5-yl)phenyl)picolinamide (Compound 101). LC/MS, m/z=377.1 [M+H]$^+$ (Calc: 376.3).

6-(4-(4-fluorophenoxy)-3-((methyl(phenyl)amino)methyl)phenyl)picolinamide (Compound 102). LC/MS, m/z=428.3 [M+H]$^+$ (Calc: 427.5).

6-(4-(4-fluorophenoxy)-3-(methoxymethyl)phenyl)picolinamide (Compound 103). LC/MS, m/z=353.1 [M+H]$^+$ (Calc: 352.4).

6-(4-(4-fluorophenoxy)-3-((4-fluorophenoxy)methyl)phenyl)picolinamide (Compound 104). LC/MS, m/z=433.0 [M+H]$^+$ (Calc: 432.4).

6-(3-((4-cyanophenoxy)methyl)-4-(4-fluorophenoxy)phenyl)picolinamide (Compound 105). LC/MS, m/z=440.1 [M+H]$^+$ (Calc: 439.4).

TFA salt of 6-(4-(3-((3-oxopiperazin-1-yl)methyl)-4-(trifluoromethyl)phenoxy)-phenyl)picolinamide (Compound 106): $^1$H NMR (600 MHz, DMSO-$d_6$): δ 8.34 (d, J=8.8 Hz, 2H), 8.27 (br. s., 1H), 8.11 (d, J=7.9 Hz, 1H), 7.99 (t, J=7.8 Hz, 1H), 7.91 (d, J=7.7 Hz, 1H), 7.78-7.88 (m, 1H), 7.72 (d, J=8.4 Hz, 1H), 7.65 (br. s., 1H), 7.41 (br. s., 1H), 7.19 (d, J=8.6 Hz, 2H), 7.07 (d, J=7.5 Hz, 1H), 3.49-4.05 (m, 2H), 2.91-3.35 (m, 4H), 2.48-2.88 (m, 2H). LC/MS, m/z=471.1 [M+H]$^+$ (Calc: 470.4).

TFA salt (S)-1-(6-(4-(2-(piperidin-1-ylmethyl)-4-(trifluoromethyl)phenoxy)phenyl)-pyridin-2-yl)ethane-1,2-diol (Compound 107): $^1$H NMR (400 MHz, DMSO-$d_6$): δ 7.34 (d, J=8.8 Hz, 2H), 7.21 (d, J=11.9 Hz, 2H), 7.06 (d, J=7.7 Hz, 1H), 6.98 (d, J=8.1 Hz, 1H), 6.84 (d, J=7.7 Hz, 1H), 6.53 (d, J=8.6 Hz, 2H), 6.30 (d, J=8.6 Hz, 1H), 4.07-4.15 (m, 1H), 3.74 (s, 2H), 2.95-3.21 (m, 2H), 2.79 (d, J=11.4 Hz, 2H), 2.34 (t, J=11.4 Hz, 2H), 0.88-1.31 (m, 5H), 0.75 (d, J=11.9 Hz, 1H). LC/MS, m/z=473.2 [M+H]$^+$ (Calc: 472.5).

TFA salt of 6-(4-(2-((cyclopentylamino)methyl)-4-(trifluoromethyl)phenoxy)-phenyl)-picolinamide (Compound 108): $^1$H NMR (400 MHz, DMSO-$d_6$): δ 8.93 (br. s., 2H), 8.47 (d, J=8.8 Hz, 2H), 8.34 (br. s., 1H), 8.20 (d, J=7.3 Hz, 1H), 8.04-8.13 (m, 2H), 7.95-8.03 (m, 1H), 7.68-7.87 (m, 2H), 7.33 (d, J=8.8 Hz, 2H), 7.03 (d, J=8.6 Hz, 1H), 4.37 (t, J=5.8 Hz, 2H), 3.58-3.72 (m, 1H), 1.94-2.16 (m, 2H), 1.65-1.80 (m, 4H), 1.49-1.62 (m, 2H). LC/MS, m/z=456.1 [M+H]$^+$ (Calc: 455.5).

TFA salt of 6-(4-(2-(N,N-diethylsulfamoyl)-4-(trifluoromethyl)phenoxy)phenyl)-picolinamide (Compound 109): $^1$H NMR (400 MHz, DMSO-$d_6$): δ 8.37 (d, J=8.8 Hz, 2H), 8.27 (br. s., 1H), 8.06-8.17 (m, 2H), 8.01 (t, J=7.8 Hz, 1H), 7.93 (dd, J=7.6, 1.0 Hz, 2H), 7.66 (br. s., 1H), 7.23 (d, J=8.8 Hz, 2H), 7.15 (d, J=8.6 Hz, 1H), 3.29 (q, J=7.1 Hz, 4H), 1.02 (t, J=7.0 Hz, 6H). LC/MS, m/z=494.1 [M+H]$^+$ (Calc: 493.5).

Methyl 2-(4-(6-carbamoylpyridin-2-yl)phenoxy)-5-(trifluoromethyl)benzoate (Compound 110) with the following structure:

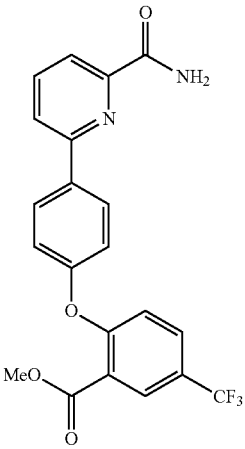

LC/MS: m/z=417.2 [M+H]+ (Calc: 416.4).

TFA salt of 6-(4-(2-(2-oxo-1,2-di(pyrrolidin-1-yl)ethyl)-4-(trifluoromethyl)phenoxy)-phenyl)picolinamide (Compound 111): $^1$H NMR (400 MHz, CD$_3$OD): δ 8.26 (d, J=8.8 Hz, 2H), 7.88-8.07 (m, 4H), 7.73 (dd, J=8.9, 1.9 Hz, 1H), 7.17-7.30 (m, 2H), 7.07 (d, J=8.8 Hz, 1H), 5.83 (s, 1H), 3.83 (br. s., 1H), 3.64-3.77 (m, 1H), 3.43-3.56 (m, 1H), 3.24-3.41 (m, 2H), 3.13 (br. s., 2H), 2.94-3.06 (m, 1H), 2.09 (br. s., 3H), 1.64-1.98 (m, 5H). LC/MS, m/z=539.2 [M+H]+ (Calc: 538.6).

TFA salt of 6-(4-(2-(2-oxo-1-(3-oxopiperazin-1-yl)-2-(pyrrolidin-1-yl)ethyl)-4-(trifluoromethyl)phenoxy)phenyl)picolinamide (Compound 112): $^1$H NMR (400 MHz, CD$_3$OD): δ 8.23 (d, J=8.8 Hz, 2H), 7.88-8.10 (m, 4H), 7.67 (dd, J=8.8, 2.0 Hz, 1H), 7.19 (d, J=8.8 Hz, 2H), 7.06 (d, J=8.8 Hz, 1H), 5.42 (s, 1H), 3.61-3.73 (m, 1H), 3.57 (d, J=16.1 Hz, 1H), 3.22-3.51 (m, 6H), 3.07-3.19 (m, 2H), 1.62-1.98 (m, 4H). LC/MS, m/z=568.2 [M+H]+ (Calc: 567.6).

TFA salt of (S)-2-(4-(6-(1,2-dihydroxyethyl)pyridin-2-yl)phenoxy)-N,N-diethyl-5-(trifluoromethyl)benzenesulfonamide (Compound 113): $^1$H NMR (400 MHz, CD$_3$OD): δ 8.27 (d, J=2.2 Hz, 1H), 8.05-8.19 (m, 3H), 7.86-7.98 (m, 2H), 7.71 (d, J=7.7 Hz, 1H), 7.31 (d, J=8.8 Hz, 2H), 7.22 (d, J=8.6 Hz, 1H), 4.92-5.02 (m, 1H), 3.79-4.00 (m, 2H), 3.45 (q, J=7.0 Hz, 4H), 1.18 (t, J=7.2 Hz, 6H). LC/MS, m/z=511.2 [M+H]+ (Calc: 510.5).

TFA salt of 6-(4-(2-((thiazol-2-ylamino)methyl)-4-(trifluoromethyl)phenoxy)-phenyl)picolinamide (Compound 114): $^1$H NMR (400 MHz, CD$_3$OD): δ 8.16 (d, J=8.8 Hz, 2H), 7.90-8.02 (m, 3H), 7.76 (d, J=2.0 Hz, 1H), 7.60 (dd, J=8.7, 2.1 Hz, 1H), 7.12 (d, J=4.4 Hz, 1H), 7.08 (d, J=8.8 Hz, 2H), 7.03 (d, J=8.6 Hz, 1H), 6.77 (d, J=4.2 Hz, 1H), 4.70 (s, 2H). LC/MS, m/z=471.1 [M+H]+ (Calc: 470.5).

(R)-1-(2-(4-(2-(pyrrolidin-1-ylmethyl)-4-(trifluoromethyl)phenoxy)phenyl)pyrimidin-4-yl)ethane-1,2-diol (Compound 115): $^1$H NMR (400 MHz, CD$_3$OD): δ 8.68 (d, J=5.1 Hz, 1H), 8.38 (d, J=8.8 Hz, 2H), 7.76 (d, J=1.5 Hz, 1H), 7.49 (dd, J=8.6, 1.8 Hz, 1H), 7.42 (d, J=5.1 Hz, 1H), 6.95-7.06 (m, 3H), 4.68 (m, 1H), 3.88 (dd, J=11.2, 4.0 Hz, 1H), 3.69-3.77 (m, 3H), 2.54 (m, 4H), 1.67-1.77 (m, 4H). LC/MS, m/z=460.2 [M+H](Calc: 459.5).

(S)-1-(2-(4-(2-(pyrrolidin-1-ylmethyl)-4-(trifluoromethyl)phenoxy)phenyl)pyrimidin-4-yl)ethane-1,2-diol (Compound 116): $^1$H NMR (400 MHz, CD$_3$OD): δ 8.68 (d, J=5.1 Hz, 1H), 8.38 (d, J=8.8 Hz, 2H), 7.76 (d, J=1.5 Hz, 1H), 7.49 (dd, J=8.6, 1.8 Hz, 1H), 7.42 (d, J=5.1 Hz, 1H), 6.95-7.06 (m, 3H), 4.68 (m, 1H), 3.88 (dd, J=11.2, 4.0 Hz, 1H), 3.69-3.77 (m, 3H), 2.54 (m, 4H), 1.67-1.77 (m, 4H). LC/MS, m/z=460.2 [M+H](Calc: 459.5).

TFA salt of 6-(4-(2-((ethyl(methyl)amino)methyl)-4-(trifluoromethyl)phenoxy)-phenyl)picolinamide (Compound 117): $^1$H NMR (400 MHz, DMSO-d$_6$): δ 8.38 (d, J=8.8 Hz, 2H), 8.12 (d, J=7.3 Hz, 1H), 7.97-8.07 (m, 2H), 7.91-7.96 (m, 1H), 7.75 (dd, J=8.7, 1.7 Hz, 1H), 7.28 (d, J=8.8 Hz, 2H), 6.99 (d, J=8.6 Hz, 1H), 4.47-4.63 (m, 1H), 4.34-4.44 (m, 1H), 3.22-3.38 (m, 1H), 3.10-3.21 (m, 1H), 2.75 (s, 3H), 1.25 (t, J=7.3 Hz, 3H). LC/MS, m/z=430.2 [M+H](Calc: 429.4).

TFA salt of 6-(4-(2-((diethylamino)methyl)-4-(trifluoromethyl)phenoxy)phenyl)-picolinamide (Compound 118): $^1$H NMR (400 MHz, DMSO-d$_6$): δ 8.38 (d, J=8.8 Hz, 2H), 8.12 (d, J=7.5 Hz, 1H), 8.04 (d, J=1.5 Hz, 1H), 8.01 (t, J=7.8 Hz, 1H), 7.92-7.97 (m, 1H), 7.75 (dd, J=8.7, 1.9 Hz, 1H), 7.27 (d, J=8.8 Hz, 2H), 7.00 (d, J=8.8 Hz, 1H), 4.46 (s, 2H), 3.10-3.27 (m, 4H), 1.24 (t, J=7.3 Hz, 6H). LC/MS, m/z=444.1 [M+H](Calc: 443.5).

TFA salt of 6-(4-(2-((ethyl(2-hydroxyethyl)amino)methyl)-4-(trifluoromethyl)-phenoxy)phenyl)picolinamide (Compound 119): $^1$H NMR (400 MHz, DMSO-d$_6$): δ 8.38 (d, J=8.8 Hz, 2H), 8.12 (d, J=7.7 Hz, 1H), 8.06 (d, J=1.8 Hz, 1H), 8.00 (t, J=7.8 Hz, 1H), 7.90-7.97 (m, 1H), 7.74 (dd, J=8.7, 1.7 Hz, 1H), 7.27 (d, J=8.8 Hz, 2H), 6.99 (d, J=8.8 Hz, 1H), 4.40-4.63 (m, 2H), 3.75 (t, J=5.2 Hz, 2H), 3.24 (q, J=7.1 Hz, 4H), 1.26 (t, J=7.3 Hz, 3H)). LC/MS, m/z=460.2 [M+H](Calc: 459.5).

TFA salt of 6-(4-(2-(((2-(dimethylamino)ethyl)(ethyl)amino)methyl)-4-(trifluoromethyl)phenoxy)phenyl)picolinamide (Compound 120): $^1$H NMR (400 MHz, DMSO-d$_6$): δ 8.35 (d, J=8.6 Hz, 2H), 8.25 (br. s., 1H), 8.11 (d, J=7.7 Hz, 1H), 8.00 (t, J=7.7 Hz, 1H), 7.87-7.95 (m, 2H), 7.67 (br. s., 2H), 7.17 (br. s., 2H), 7.01 (d, J=8.6 Hz, 1H), 3.96 (br. s., 2H), 3.30 (br. s., 2H), 2.6-2.9 (m, 10H), 0.95-1.05 (m, 3H). LC/MS, m/z=487.2 [M+H]+ (Calc: 486.5).

TFA salt of 6-(4-(2-((3-carbamoylpiperidin-1-yl)methyl)-4-(trifluoromethyl)-phenoxy)phenyl)picolinamide (Compound 121): $^1$H NMR (400 MHz, DMSO-d$_6$): δ 8.30-8.40 (m, 2H), 7.88-8.18 (m, 4H), 7.73 (d, J=9.0 Hz, 1H), 7.30 (dd, J=16.2, 8.7 Hz, 2H), 6.98 (dd, J=8.6, 5.7 Hz, 1H), 4.34-4.57 (m, 2H), 3.41-3.61 (m, 2H), 3.11-3.21 (m, 1H), 2.99-3.09 (m, 1H), 2.56-2.90 (m, 1H), 1.36-2.02 (m, 4H). LC/MS, m/z=499.2 [M+H]+ (Calc: 498.5).

(S)-6-(1,2-dihydroxyethyl)-2-(4-(2-(1-methyl-H-pyrazol-5-yl)-4-(trifluoromethyl)-phenoxy)phenyl)pyrimidine-4-carboxamide (Compound 122): $^1$H NMR (400 MHz, CD$_3$OD): δ 8.47-8.53 (m, 2H), 8.05 (s, 1H), 7.73 (dd, J=8.6, 1.8 Hz, 1H), 7.68 (d, J=2.0 Hz, 1H), 7.38 (d, J=2.0 Hz, 1H), 7.20 (d, J=8.8 Hz, 1H), 6.98-7.03 (m, 2H), 6.28 (d, J=2.0 Hz, 1H), 4.73-4.48 (m, 1H), 3.90 (dd, J=11.2, 4.0 Hz, 1H), 3.74-3.79 (m, 1H), 3.73 (s, 3H). LC/MS, m/z=500.1 [M+H]+ (Calc: 499.4).

6-(4-(2-(1-methyl-1H-pyrazol-5-yl)-4-(trifluoromethyl)phenoxy)phenyl)picolinamide (Compound 123): $^1$H NMR (400 MHz, CD$_3$OD): δ 8.18-8.28 (m, 2H), 7.99-8.10 (m, 3H), 7.77-7.85 (m, 2H), 7.53 (d, J=2.0 Hz, 1H), 7.27 (d, J=8.6 Hz, 1H), 7.10-7.19 (m, 2H), 6.43 (d, J=2.0 Hz, 1H), 3.86 (s, 3H). LC/MS, m/z=439.0 [M+H]+ (Calc: 438.4).

2-(6-carbamoyl-2-(4-(2-((diethylamino)methyl)-4-(trifluoromethyl)phenoxy)phenyl)-pyrimidin-4-yl)ethyl acetate (Compound 124): ¹H NMR (400 MHz, CD₃OD): δ 8.63 (d, J=8.8 Hz, 2H), 7.92 (d, J=1.8 Hz, 1H), 7.79 (s, 1H), 7.71 (dd, J=8.8, 2.0 Hz, 1H), 7.19-7.27 (m, 2H), 7.06 (d, J=8.6 Hz, 1H), 4.46-4.56 (m, 4H), 3.22-3.31 (m, 4H), 3.17-3.20 (m, 2H), 1.89 (s, 3H), 1.32 (t, J=7.3 Hz, 6H). LC/MS, m/z=531.2 [M+H]⁺ (Calc: 530.5).

2-(4-(2-(1-methyl-1H-pyrazol-5-yl)-4-(trifluoromethyl)phenoxy)phenyl)pyrimidine-4-carboxamide (Compound 125): ¹H NMR (400 MHz, CD₃OD): δ 8.95 (d, J=5.1 Hz, 1H), 8.43-8.53 (m, 2H), 7.82 (d, J=4.8 Hz, 1H), 7.64-7.77 (m, 2H), 7.38 (d, J=2.0 Hz, 1H), 7.21 (d, J=8.8 Hz, 1H), 6.98-7.05 (m, 2H), 6.29 (d, J=2.0 Hz, 1H), 3.73 (s, 3H). LC/MS, m/z=440.1 [M+H]⁺ (Calc: 439.4).

(S)-2-(4-(2-(1-methyl-1H-pyrazol-5-yl)-4-(trifluoromethyl)phenoxy)phenyl)-6-((2-oxopyrrolidin-3-yl)amino)pyrimidine-4-carboxamide (Compound 126): ¹H NMR (400 MHz, CD₃OD): δ 8.30-8.36 (m, 2H), 7.65-7.76 (m, 2H), 7.39 (d, J=2.0 Hz, 1H), 7.18 (d, J=8.6 Hz, 1H), 6.95-7.04 (m, 3H), 6.29 (d, J=2.0 Hz, 1H), 4.69-4.75 (m, 1H), 3.73 (s, 3H), 3.30-3.44 (m, 2H), 2.46-2.58 (m, 1H), 2.10-2.25 (m, 1H). LC/MS, m/z=538.2 [M+H]⁺ (Calc: 537.5).

6-(2-(1H-imidazol-1-yl)ethyl)-2-(4-(2-(morpholinomethyl)-4-(trifluoromethyl)-phenoxy)phenyl)pyrimidine-4-carboxamide (Compound 127): ¹H NMR (400 MHz, CD₃OD): δ 8.87 (s, 1H), 8.56-8.64 (m, 2H), 7.94 (d, J=2.0 Hz, 1H), 7.79 (s, 1H), 7.70 (dd, J=8.8, 2.0 Hz, 1H), 7.63 (t, J=1.7 Hz, 1H), 7.45 (t, J=1.7 Hz, 1H), 7.20-7.28 (m, 2H), 7.03 (d, J=8.6 Hz, 1H), 4.77-4.82 (m, 2H), 4.48 (s, 2H), 3.84 (br. s., 4H), 3.52 (t, J=6.9 Hz, 2H), 3.27-3.39 (m, 4H). LC/MS, m/z=553.2 [M+H]⁺ (Calc: 552.6).

(S)-2-(4-(2-(2-(dimethylamino)pyrimidin-5-yl)-4-(trifluoromethyl)phenoxy)phenyl)-6-((2-oxopyrrolidin-3-yl)amino)pyrimidine-4-carboxamide (Compound 128): ¹H NMR (400 MHz, CD₃OD): δ 8.52 (s, 2H), 8.33-8.39 (m, 2H), 7.74 (d, J=2.2 Hz, 1H), 7.60 (dd, J=8.7, 1.9 Hz, 1H), 7.14 (d, J=8.6 Hz, 1H), 7.01 (s, 1H), 6.93-7.00 (m, 2H), 4.72 (br. s., 1H), 3.31-3.43 (m, 2H), 3.12 (s, 6H), 2.45-2.58 (m, 1H), 2.09-2.25 (m, 1H). LC/MS, m/z=579.2 [M+H]⁺ (Calc: 578.6).

(S)-2-(4-(2-(5-(dimethylamino)pyrazin-2-yl)-4-(trifluoromethyl)phenoxy)phenyl)-6-((2-oxopyrrolidin-3-yl)amino)pyrimidine-4-carboxamide (Compound 129): ¹H NMR (400 MHz, DMSO-d₆): δ 8.70 (d, J=1.3 Hz, 1H), 8.54 (d, J=8.8 Hz, 2H), 8.29 (d, J=1.5 Hz, 2H), 8.23 (d, J=2.2 Hz, 1H), 8.09 (d, J=6.6 Hz, 1H), 7.94 (s, 1H), 7.69-7.77 (m, 2H), 7.23 (d, J=8.6 Hz, 1H), 7.15 (d, J=8.8 Hz, 2H), 7.06 (s, 1H), 4.71 (d, J=7.7 Hz, 1H), 3.29 (d, J=6.8 Hz, 2H), 3.11 (s, 6H), 2.52-2.56 (m, 1H), 1.99 (t, J=9.8 Hz, 1H). LC/MS, m/z=579.2 [M+H]⁺ (Calc: 578.5).

(S)-2-(4-(2-((diethylamino)methyl)-4-(trifluoromethyl)phenoxy)phenyl)-6-(1,2-dihydroxyethyl)pyrimidine-4-carboxamide (Compound 130): ¹H NMR (400 MHz, CD₃OD): δ 8.61-8.67 (m, 2H), 8.09 (s, 1H), 7.92 (d, J=2.0 Hz, 1H), 7.71 (dd, J=8.7, 1.9 Hz, 1H), 7.19-7.28 (m, 2H), 7.06 (d, J=8.6 Hz, 1H), 4.78 (br. s., 1H), 4.49 (s, 2H), 3.92 (dd, J=11.3, 3.9 Hz, 1H), 3.79 (dd, J=11.3, 5.8 Hz, 1H), 3.22-3.29 (m, 4H), 1.32 (t, J=7.3 Hz, 6H). LC/MS, m/z=505.2 [M+H]⁺ (Calc: 504.5).

6-Carbamoyl-2-(4-(2-((diethylamino)methyl)-4-(trifluoromethyl)phenoxy)phenyl)-pyrimidine-4-carboxylic acid (Compound 131): ¹H NMR (400 MHz, CD₃OD): δ 8.70 (d, J=8.6 Hz, 2H), 8.37 (s, 1H), 7.93 (d, J=1.8 Hz, 1H), 7.72 (dd, J=8.7, 1.9 Hz, 1H), 7.23 (d, J=8.6 Hz, 2H), 7.08 (d, J=8.6 Hz, 1H), 4.49 (s, 2H), 3.25 (q, J=7.3 Hz, 4H), 1.32 (t, J=7.3 Hz, 6H). LC/MS, m/z=489.1 [M+H](Calc: 488.5).

6-Carbamoyl-2-(4-(2-(morpholinomethyl)-4-(trifluoromethyl)phenoxy)phenyl)-pyrimidine-4-carboxylic acid (Compound 132): ¹H NMR (400 MHz, CD₃OD): δ 8.68 (d, J=8.6 Hz, 2H), 8.37 (s, 1H), 7.93 (d, J=1.8 Hz, 1H), 7.71 (dd, J=8.7, 1.9 Hz, 1H), 7.23 (d, J=8.6 Hz, 2H), 7.06 (d, J=8.8 Hz, 1H), 4.50 (s, 2H), 3.85 (br. s., 4H), 3.34 (br. s., 4H). LC/MS, m/z=503.1 [M+H]⁺ (Calc: 502.4).

(R)-2-(4-(2-((diethylamino)methyl)-4-(trifluoromethyl)phenoxy)phenyl)-6-(1,2-dihydroxyethyl)pyrimidine-4-carboxamide (Compound 133): ¹H NMR (400 MHz, CD₃OD): δ 8.62-8.66 (m, 2H), 8.09 (s, 1H), 7.95 (d, J=2.0 Hz, 1H), 7.70 (dd, J=8.7, 1.9 Hz, 1H), 7.19-7.29 (m, 2H), 7.04 (d, J=8.6 Hz, 1H), 4.79 (br. s., 1H), 4.47 (s, 2H), 3.90 (dd, J=11.3, 3.9 Hz, 1H), 3.81 (dd, J=11.3, 5.8 Hz, 1H), 3.22-3.30 (m, 4H), 1.34 (t, J=7.3 Hz, 6H). LC/MS, m/z=505.2 [M+H]⁺ (Calc: 504.5).

(S)-6-((1-amino-1-oxopropan-2-yl)amino)-2-(4-(2-(5-(dimethylamino)pyrazin-2-yl)-4-(trifluoromethyl)phenoxy)phenyl)pyrimidine-4-carboxamide (Compound 134): ¹H NMR (400 MHz, DMSO-d₆): δ 8.64 (d, J=1.5 Hz, 1H), 8.50 (d, J=8.8 Hz, 2H), 8.22 (d, J=1.3 Hz, 2H), 8.15 (d, J=2.2 Hz, 1H), 7.88 (d, J=6.4 Hz, 1H), 7.61-7.69 (m, 2H), 7.45 (br. s., 1H), 7.13 (d, J=8.6 Hz, 1H), 7.07 (d, J=8.8 Hz, 2H), 7.03 (s, 1H), 6.91 (br. s., 1H), 4.49 (t, J=6.8 Hz, 1H), 3.04 (s, 6H), 1.30 (d, J=7.0 Hz, 3H). LC/MS, m/z=567.2 [M+H]⁺ (Calc: 566.5).

(S)-4-(1,2-dihydroxyethyl)-6-(4-(2-(1-methyl-H-pyrazol-5-yl)-4-(trifluoromethyl)-phenoxy)phenyl)picolinamide (Compound 135): ¹H NMR (400 MHz, CD₃OD): δ 8.19-8.26 (m, 2H), 8.09 (d, J=7.7 Hz, 2H), 7.76-7.84 (m, 2H), 7.51 (d, J=2.0 Hz, 1H), 7.26 (d, J=8.6 Hz, 1H), 7.11-7.19 (m, 2H), 6.41 (d, J=2.0 Hz, 1H), 4.83-4.87 (m, 1H), 3.85 (s, 3H), 3.67-3.80 (m, 2H). LC/MS, m/z=499.2 [M+H](Calc: 498.5).

(S)-6-(4-(2-(1-(azetidin-3-yl)-1H-pyrazol-5-yl)-4-chlorophenoxy)phenyl)-4-(1,2-dihydroxyethyl)picolinamide (Compound 136): ¹H NMR (400 MHz, CD₃OD): δ 8.05-8.11 (m, 3H), 8.00 (s, 1H), 7.66 (d, J=1.54 Hz, 1H), 7.48 (dd, J=2.64, 8.80 Hz, 1H), 7.41 (d, J=2.42 Hz, 1H), 7.08 (d, J=8.80 Hz, 1H), 7.00 (d, J=8.58 Hz, 2H), 6.36 (d, J=1.76 Hz, 1H), 5.22 (quin, J=7.37 Hz, 1H), 4.86 (dd, J=4.40, 6.82 Hz, 1H), 4.42 (dd, J=6.71, 10.45 Hz, 2H), 4.14-4.24 (m, 2H), 3.74-3.83 (m, 1H), 3.64-3.73 (m, 1H). LC/MS, m/z=506.1 [M+H]⁺ (Calc: 505.9).

(S)-2-(4-(2-(1-(azetidin-3-yl)-1H-pyrazol-5-yl)-4-chlorophenoxy)phenyl)-6-((2-oxopyrrolidin-3-yl)amino)pyrimidine-4-carboxamide (Compound 137): ¹H NMR (400 MHz, CD₃OD): δ 8.37 (d, J=8.80 Hz, 2H), 7.70 (d, J=1.76 Hz, 1H), 7.48 (dd, J=2.42, 8.80 Hz, 1H), 7.42 (d, J=2.64 Hz, 1H), 7.13 (s, 1H), 7.07 (d, J=8.80 Hz, 1H), 6.95 (d, J=8.80 Hz, 2H), 6.39 (d, J=1.76 Hz, 1H), 5.21-5.32 (m, 1H), 4.70-4.82 (m, 1H), 4.44-4.56 (m, 4H), 3.41-3.54 (m, 2H), 2.59-2.77 (m, 1H), 2.15-2.34 (m, 1H). LC/MS, m/z=545.3 [M+H]⁺ (Calc: 545.0).

(S)-6-((1-amino-1-oxopropan-2-yl)amino)-2-(4-(2-(1-methyl-1H-pyrazol-5-yl)-4-(trifluoromethyl)phenoxy)phenyl)pyrimidine-4-carboxamide (Compound 138): ¹H NMR (400 MHz, CD₃OD): δ 8.46 (d, J=8.80 Hz, 2H), 7.66-7.77 (m, 2H), 7.50 (d, J=1.98 Hz, 1H), 7.11-7.21 (m, 2H), 7.05 (d, J=8.80 Hz, 2H), 6.38 (d, J=1.98 Hz, 1H), 4.61 (br. s., 1H), 3.86 (s, 3H), 1.55 (d, J=7.26 Hz, 3H). LC/MS, m/z=526.2 [M+H]⁺ (Calc: 525.5).

(S)-6-((1-amino-1-oxopropan-2-yl)amino)-2-(4-(2-(1-methyl-1H-pyrazol-5-yl)phenoxy)phenyl)pyrimidine-4-carboxamide (Compound 139): ¹H NMR (400 MHz, CD₃OD): δ 8.39-8.47 (m, 2H), 7.52-7.58 (m, 1H), 7.48 (dd, J=7.6, 1.7 Hz, 1H), 7.42 (d, J=2.0 Hz, 1H), 7.33-7.38 (m, 1H), 7.20

(dd, J=8.1, 0.7 Hz, 1H), 7.13 (s, 1H), 6.88-6.93 (m, 2H), 6.26 (d, J=2.0 Hz, 1H), 4.50-4.62 (m, 1H), 3.80 (s, 3H), 1.53 (d, J=7.3 Hz, 3H). LC/MS, m/z=458.3 [M+H]+ (Calc: 457.5).

(S)-6-((1-amino-1-oxopropan-2-yl)amino)-2-(4-(2-(1-methyl-1H-pyrazol-5-yl)-phenoxy)phenyl)pyrimidine-4-carboxamide (Compound 140): 1H NMR (400 MHz, CD3OD): δ 8.35-8.43 (m, 2H), 7.44-7.58 (m, 2H), 7.41 (d, J=2.0 Hz, 1H), 7.31-7.38 (m, 1H), 7.19 (d, J=8.1 Hz, 1H), 7.10 (s, 1H), 6.87-6.95 (m, 2H), 6.26 (d, J=1.8 Hz, 1H), 4.73-4.85 (m, 1H), 3.80 (s, 3H), 3.39-3.54 (m, 2H), 2.55-2.66 (m, 1H), 2.17-2.36 (m, 1H). LC/MS, m/z=470.1 [M+H]+ (Calc: 469.5).

(S)-2-(4-(4-chloro-2-(1-methyl-1H-pyrazol-5-yl)phenoxy)phenyl)-6-((2-oxopyrrolidin-3-yl)amino)pyrimidine-4-carboxamide (Compound 141): 1H NMR (400 MHz, CD3OD): δ 8.21-8.28 (m, 2H), 7.39-7.48 (m, 2H), 7.32 (d, J=2.0 Hz, 1H), 7.09 (d, J=8.8 Hz, 1H), 7.00 (s, 1H), 6.82-6.90 (m, 2H), 6.20 (d, J=2.0 Hz, 1H), 4.74 (m, 1H), 3.70 (s, 3H), 3.29-3.41 (m, 2H), 2.46-2.57 (m, 1H), 2.08-2.23 (m, 1H). LC/MS, m/z=504.1 [M+H]+ (Calc: 503.9).

(S)-1-(2-(4-(6-(2,2-dimethyl-1,3-dioxolan-4-yl)pyridin-2-yl)phenoxy)-5-fluorophenyl)-2,2,2-trifluoroethan-1-one (Compound 142) with the following structure:

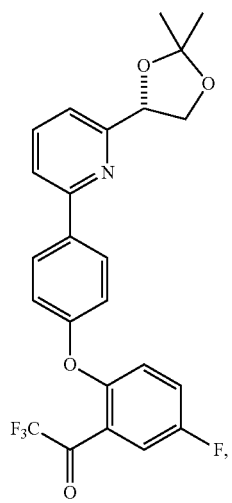

142

LC/MS, m/z=462.1 [M+H]+ (Calc: 461.4).

Methyl(S)-2-(4-(6-(2,2-dimethyl-1,3-dioxolan-4-yl)pyridin-2-yl)phenoxy)-5-(trifluoromethyl)benzoate (Compound 143) with the following structure:

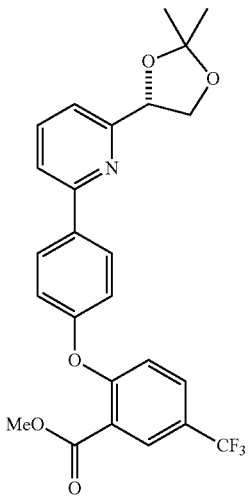

143

1H NMR (400 MHz, CDCl3): δ 8.22 (d, J=2.4 Hz, 1H), 8.04 (d, J=8.4 Hz, 2H), 7.77-7.81 (m, 1H), 7.68 (dd, J=2.8 and 8.0 Hz, 1H), 7.62 (d, J=7.6 Hz, 1H), 7.49 (d, J=7.2 Hz, 1H), 7.12 (d, J=8.8 Hz, 2H), 7.07 (d, J=8.8 Hz, 1H), 5.29 (dd, J=6.4 and 6.8 Hz, 1H), 4.08-4.16 (m, 2H), 3.9 (s, 3H), 1.58 (s, 3H), 1.53 (s, 3H). LC/MS, m/z=474.1 [M+H]+ (Calc: 473.4).

Methyl 6-(4-(2-(cyano(hydroxy)methyl)-4-(trifluoromethyl)phenoxy)phenyl)-picolinate (Compound 144): LC/MS, m/z=429.1 [M+H]+ (Calc: 428.4).

6-(4-(2-(Amino(cyano)methyl)-4-(trifluoromethyl)phenoxy)phenyl)picolinamide (Compound 145): LC/MS, m/z=413.1 [M+H]+ (Calc: 412.4).

Example 12

(S)-6-((1-amino-1-oxopropan-2-yl)amino)-2-chloropyrimidine-4-carboxamide (Compound 150)

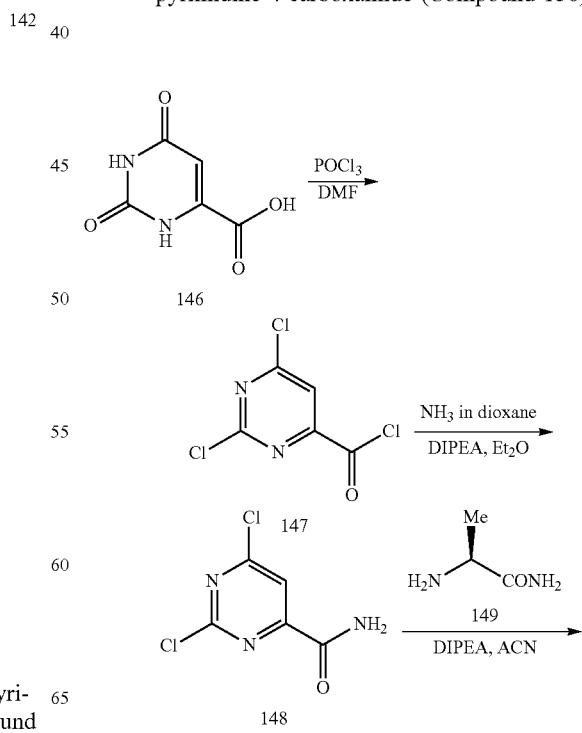

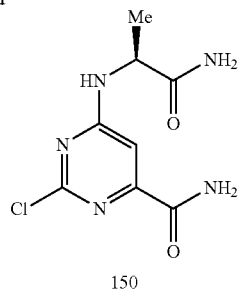

150

A mixture of 2,6-dioxo-1,2,3,6-tetrahydropyrimidine-4-carboxylic acid (Compound 146, 34.8 g, 0.20 mol, Aldrich), phosphorus oxychloride (100 mL, 1.09 mol) and 20 drops of DMF were heated at 110° C. overnight. After cooling to RT the dark mixture was diluted with hexanes (500 mL) and vigorously stirred. The hexane layer was decanted, quickly washed with water (100 mL), brine (100 mL) and dried over $MgSO_4$. The organic layer was filtered and carefully evaporated in vacuo to give 2,6-dichloropyrimidine-4-carbonyl chloride (Compound 147) as a light yellow liquid (26.13 g). Yield 62%. $^1$H NMR (400 MHz, $CDCl_3$): δ7.93 (s, 1H).

To a solution of Compound 147 (26.13 g, 123.6 mmol) in $Et_2O$ (500 mL) was added a mixture of 0.5M $NH_3$ in dioxane (250 mL, 125 mmol) and DIPEA (22 mL, 126 mmol) dropwise over 50 min. After stirring at RT overnight the reaction mixture was concentrated in vacuo to give a residue that was purified by flash chromatography ($SiO_2$, 10-50% EtOAc/hexanes). The product obtained was triturated with 10 mL 10% EtOAc/hexanes and filtered to give 2,6-dichloropyrimidine-4-carboxamide (Compound 148) as an orange crystalline solid (9.743 g). Yield 41% $^1$H NMR (400 MHz, DMSO-$d_6$): δ 8.40 (br s, 1H), 8.16 (br s, 1H), 8.10 (s, 1H). LC/MS: m/z=192.2 $[M+H]^+$ (Calc: 191.4).

To a solution of Compound 148 (4.80 g, 25.0 mmol) in ACN (100 mL) was added (S)-2-aminopropane carboxamide hydrochloride (Compound 149) (3.18 g, 25.54 mmol) and DIPEA (9.60 mL, 55.11 mmol). The mixture was heated at 50° C. overnight then concentrated. The residue was purified by flash chromatography ($SiO_2$, 20-60% acetone/hexanes) to give Compound 150 as a pale tan powder (4.81 g). Yield 79%. LC/MS: m/z=244.5 $[M+H]^+$ (Calc: 243.7).

In a similar manner the following compounds were prepared:

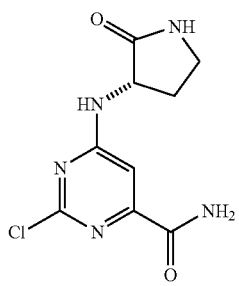

151

(S)-2-chloro-6-((2-oxopyrrolidin-3-yl)amino)pyrimidine-4-carboxamide (Compound 151): LC/MS: m/z=256.1 $[M+H]^+$ (Calc: 255.7).

Example 13

N,N-diethyl-2-fluoro-5-(trifluoromethyl)benzenesulfonamide (Compound 153)

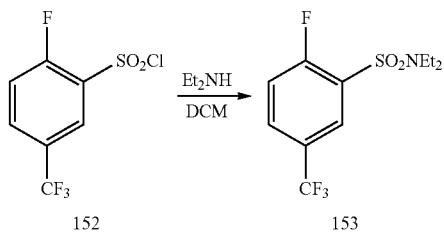

2-Fluoro-5-(trifluoromethyl)benzenesulfonyl chloride (Compound 152, 1.00 g, 3.8 mmol, Alfa Aesar) was added to a solution of $Et_2NH$ (0.60 g, 7.6 mmol) in DCM (10 mL) at 0° C. over 5 min. After stirring for 1 h at 0° C., the reaction was quenched with 2N aq. HCl (4 mL) and the layers separated. The organic layer was washed with brine, and concentrated to give Compound 153 as a colorless oil (1.00 g). Yield 88%. $^1$H NMR (400 MHz, $CDCl_3$): δ 8.22 (dd, J=6.3, 2.1 Hz, 1H), 7.82 (ddd, J=8.3, 4.1, 2.5 Hz, 1H), 7.33 (t, J=9.0 Hz, 1H), 3.39 (q, J=7.0 Hz, 4H), 1.18 (t, J=7.2 Hz, 6H).

Example 14

(Z)-6-(4-(2-((2,4-dioxothiazolidin-5-ylidene)methyl)-4-(trifluoromethyl)phenoxy)-phenyl)picolinamide (Compound 155)

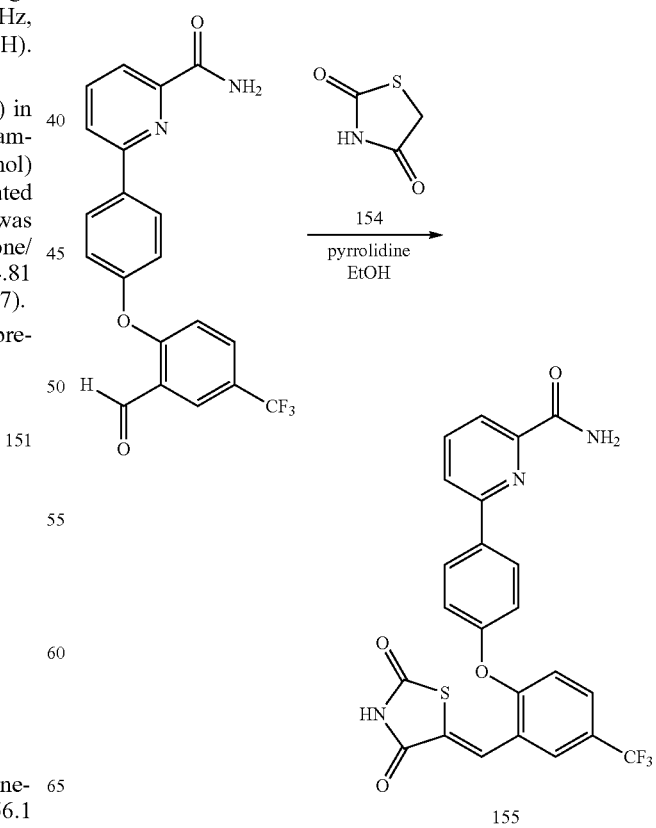

Pyrrolidine (19 mg, 0.26 mmol) in EtOH (1 mL) was added to a mixture of 6-(4-(2-formyl-4-(trifluoromethyl)phenoxy)phenyl)picolinamide (Compound 9, 100 mg, 0.26 mmol) and thiazolidine-2,4-dione (Compound 154, 91 mg, 0.78 mmol) in EtOH (4 mL) at RT. The mixture was heated at 80° C. for 2 h. After cooling to RT, the mixture was diluted with water (25 mL) and 5N aq. HCl (0.4 mL) and extracted with EtOAc. The organic extracts were washed with 10% aq. NH$_4$Cl (10 mL), satd. aq. NaHCO$_3$ (10 mL), dried over Na$_2$SO$_4$ and concentrated to give Compound 155 as a white solid (40 mg). Yield 30%. $^1$H NMR (400 MHz, DMSO-d$_6$): δ 12.70 (br. s., 1H), 8.38 (d, J=8.6 Hz, 2H), 8.29 (br. s., 1H), 8.13 (d, J=7.9 Hz, 1H), 8.00 (t, J=7.7 Hz, 1H), 7.88-7.94 (m, 2H), 7.72-7.82 (m, 2H), 7.65 (br. s., 1H), 7.25 (d, J=8.6 Hz, 2H), 7.05 (d, J=8.6 Hz, 1H). LC/MS: m/z=486.0 [M+H]$^+$ (Calc: 485.4).

Example 15

(1S)-1-(6-(4-(4-fluoro-2-(2,2,2-trifluoro-1-hydroxyethyl)phenoxy)phenyl)pyridin-2-yl)ethane-1,2-diol (Compound 156)

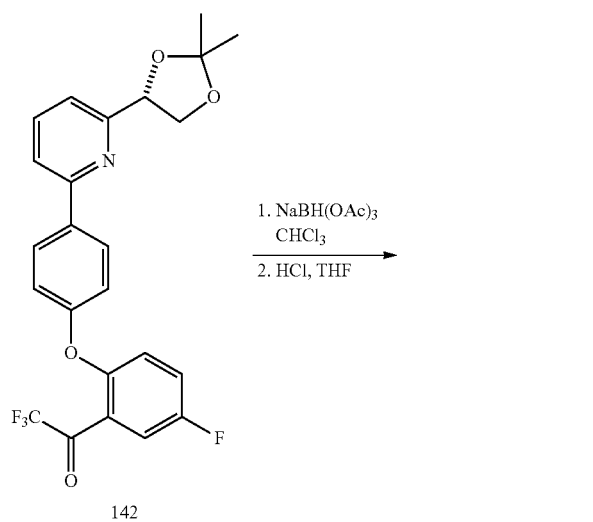

To a solution of (S)-1-(2-(4-(6-(2,2-dimethyl-1,3-dioxolan-4-yl)pyridin-2-yl)phenoxy)-5-fluorophenyl)-2,2,2-trifluoroethan-1-one (Compound 142, 50 mg, 0.11 mmol) in CHCl$_3$ (4 mL) at RT was added NaBH(OAc)$_3$ (92 mg, 0.40 mmol). The mixture was stirred at RT for 14 h, quenched by the addition of water (1 mL) and extracted with CHCl$_3$. The organic extracts were concentrated, THF (4 mL) was added followed by 1N aq. HCl (2 mL). The mixture was stirred vigorously at RT for 16 h, cooled to 0° C. and taken to pH 9 by the addition of 1N aq. NaOH. The mixture was extracted with EtOAc. The organix extracts were dried over Na$_2$SO$_4$ and concentrated. The residue was purified by flash chromatography (SiO$_2$, 10-50% EtOAc/hexanes) to give Compound 156 as a white solid (30 mg). Yield 50%. $^1$H NMR (400 MHz, CD$_3$OD): δ 8.11 (t, J=7.9 Hz, 1H), 7.79-7.95 (m, 3H), 7.66 (d, J=7.7 Hz, 1H), 7.35 (dd, J=9.1, 3.0 Hz, 1H), 7.00-7.14 (m, 3H), 6.94 (dd, J=9.0, 4.6 Hz, 1H), 5.31 (q, J=6.8 Hz, 1H), 4.88 (t, J=5.3 Hz, 1H), 3.69-3.84 (m, 2H). LC/MS: m/z=424.0 [M+H](Calc: 423.4)

Example 16

6-(4-(2-(2-oxo-2-(pyrrolidin-1-yl)acetyl)-4-(trifluoromethyl)phenoxy)phenyl)picolinamide (Compound 157) and TFA salt of 6-(4-(2-(1-hydroxy-2-oxo-2-(pyrrolidin-1-yl)ethyl)-4-(trifluoromethyl)phenoxy)phenyl)picolinamide (Compound 158)

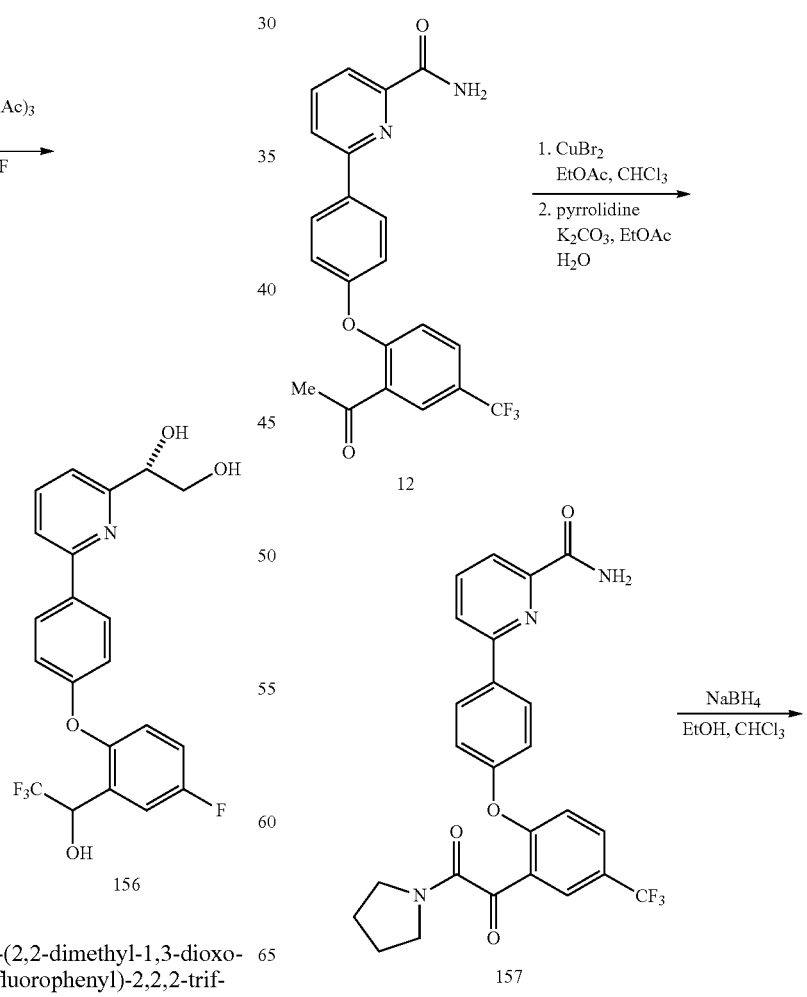

-continued

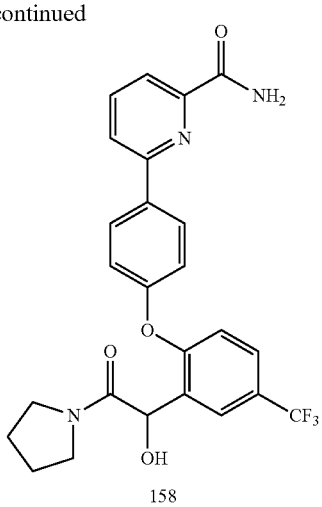

158

A mixture of CuBr₂ (67 mg, 0.30 mmol) and 6-(4-(2-acetyl-4-(trifluoromethyl)phenoxy)phenyl)picolinamide (Compound 12, 50.0 mg, 0.125 mmol) in 1:1 EtOAc/CHCl₃ (2 mL) was stirred vigorously at 80° C. for 24 h. After cooling to RT, the mixture was concentrated and the residue dissolved in 1:1 water/EtOAc (6 mL). K₂CO₃ (0.15 g, 1.0 mmol) and pyrrolidine (30 mg, 0.4 mmol) were added and the mixture stirred at RT for 16 h. The mixture was concentrated and the residue purified by column (0-100% EtOAc/hexane) to give Compound 157 as a white solid (40 mg). Yield 40% ¹H NMR (400 MHz, CDCl₃): δ 8.27 (d, J=2.2 Hz, 1H), 8.21 (dd, J=7.6, 1.0 Hz, 1H), 8.04-8.12 (m, 2H), 7.94-8.02 (m, 2H), 7.87-7.93 (m, 1H), 7.77 (dd, J=8.6, 2.0 Hz, 1H), 7.17-7.25 (m, 2H), 7.04 (d, J=8.6 Hz, 1H), 5.68 (br., 1H), 3.58 (t, J=6.7 Hz, 2H), 3.41 (t, J=6.9 Hz, 2H), 1.80-2.02 (m, 4H). LC/MS: m/z=484.2 [M+H]⁺ (Calc: 483.4).

NaBH₄ (23 mg, 0.62 mmol) was added to a solution of Compound 157 (0.10 g, 0.21 mmol) in 3:1 EtOH/CHCl₃ (4 mL). The mixture was vigorously stirred at 0° C. for 1 h. The mixture was quenched by the addition of water and extracted with EtOAc. The organic extracts were concentrated and the residue purified by reverse-phase prep HPLC (C18, 0-100% 0.1% TFA in water/0.1% TFA in ACN) to give TFA salt of Compound 158 as white solid (90 mg). ¹H NMR (400 MHz, CD₃OD): δ 8.15 (d, J=8.8 Hz, 2H), 7.81-8.02 (m, 4H), 7.53 (dd, J=8.7, 1.9 Hz, 1H), 7.05 (d, J=8.8 Hz, 2H), 6.97 (d, J=8.6 Hz, 1H), 5.68 (s, 1H), 3.52-3.66 (m, 1H), 3.25-3.36 (m, 2H), 3.08-3.20 (m, 1H), 1.66-1.90 (m, 3H), 1.51-1.65 (m, 1H). LC/MS: m/z=486.1 [M+H]⁺ (Calc: 485.4).

Example 17

2-(4-(6-carbamoylpyridin-2-yl)phenoxy)-5-(trifluoromethyl)benzoic acid (Compound 159) and 6-(4-(2-(pyrrolidine-1-carbonyl)-4-(trifluoromethyl)phenoxy) phenyl)-picolinamide (Compound 160)

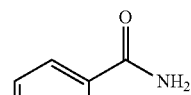

110

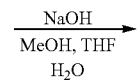

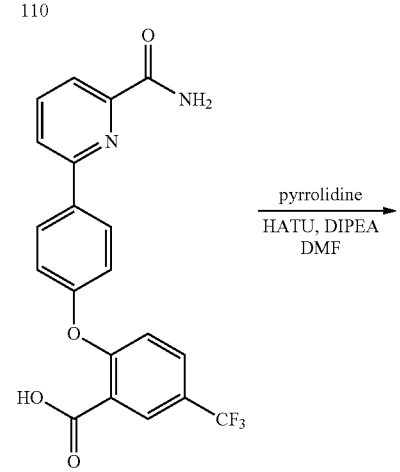

159

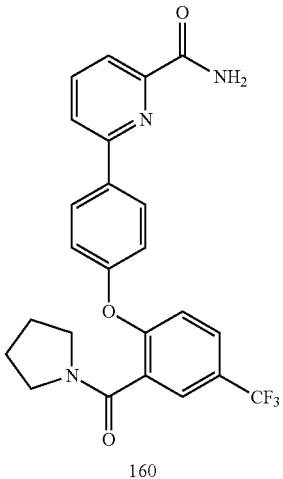

160

To a solution of Methyl 2-(4-(6-carbamoylpyridin-2-yl) phenoxy)-5-(trifluoromethyl)benzoate (Compound 110, 1.00 g, 2.40 mmol) in 2:1 MeOH/THF (9 mL) at 0° C. was added 2N aq. NaOH (1.5 mL, 3.0 mmol). The mixture was warmed to RT and stirred for 48 h. The mixture was concentrated, cooled to 0° C., and taken to pH 2 by the addition of 5N aq. HCl. The mixture was extracted with 1:1 EtOAc/CHCl$_3$ (200 mL) and the organic extracts were washed with 10% aq. NH$_4$Cl, brine and concentrated to give Compound 159 as a white solid (0.64 g). Yield 66%. $^1$H NMR (400 MHz, DMSO-d$_6$): δ 13.45 (s, 1H), 8.37 (d, J=8.8 Hz, 2H), 8.33 (s, 1H), 8.14-8.16 (m, 2H), 8.05 9 (d, J=8.0 Hz, 1H), 7.96 (d, J=8.0 Hz, 1H), 7.94 (dd, J=2.4 & 8.8 Hz, 1H), 7.71 (s, 1H), 7.23 (dd, J=7.6 & 8.4 Hz, 1H), 7.16 (d, J=8.8 Hz, 2H). LC/MS: m/z=403.0 [M+H](Calc: 402.3).

HATU (70 mg, 0.18 mmol) was added to a mixture of Compound 159 (48.3 mg, 0.12 mmol), pyrrolidine (8.5 mg, 0.12 mmol) and DIPEA (0.022 mL, 0.124 mmol) in DMF (0.5 mL) at RT. The reaction mixture was stirred at RT for 24 h, quenched with water (2 mL) and extracted with EtOAc (5 mL). The organic extracts were concentrated and purified by flash chromatography (SiO$_2$, 0-50% MeOH/DCM) to give Compound 160 as white solid (28 mg). Yield 51%. $^1$H NMR (400 MHz, DMSO-d$_6$): δ 8.29 (d, J=8.8 Hz, 2H), 8.08 (d, J=7.7 Hz, 1H), 7.88-8.01 (m, 2H), 7.62-7.76 (m, 2H), 7.15 (d, J=8.6 Hz, 2H), 7.08 (d, J=8.8 Hz, 2H), 3.37 (t, J=6.5 Hz, 2H), 3.26 (t, J=6.2 Hz, 2H), 1.64-1.87 (m, 4H).

LC/MS: m/z=456.1 [M+H]$^+$ (Calc: 455.4).

In a similar manner the following compounds were prepared:

161

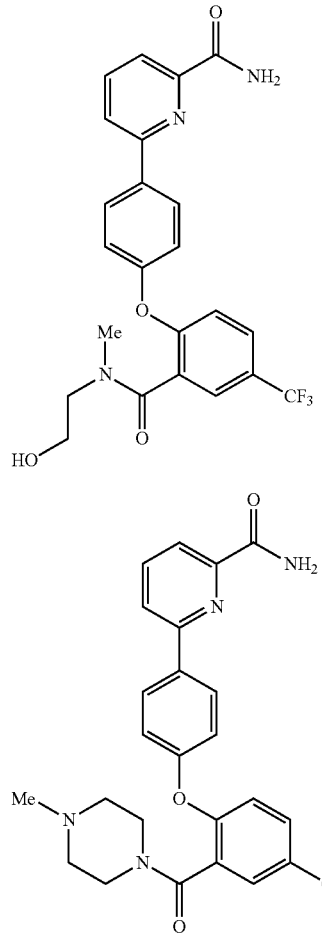

162

163

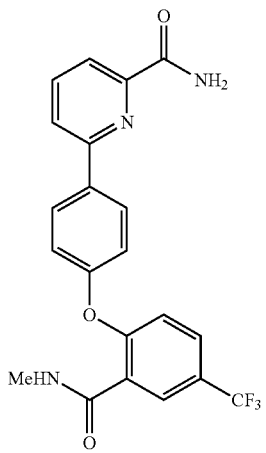

164

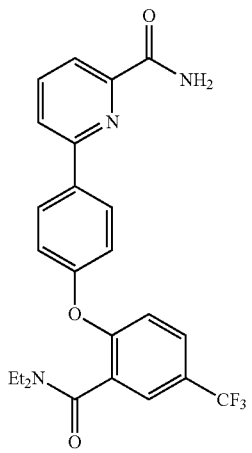

165

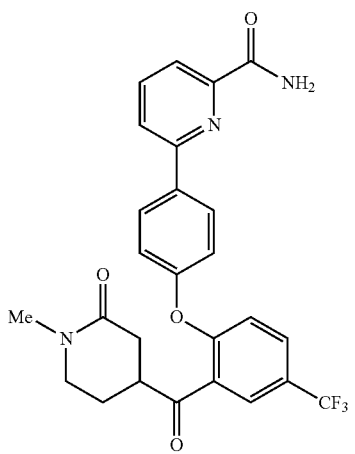

166 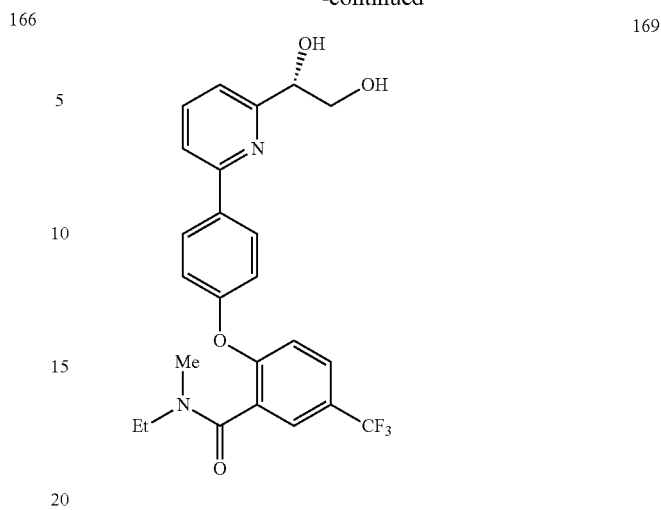
203 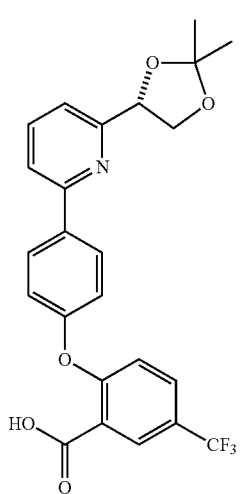
167 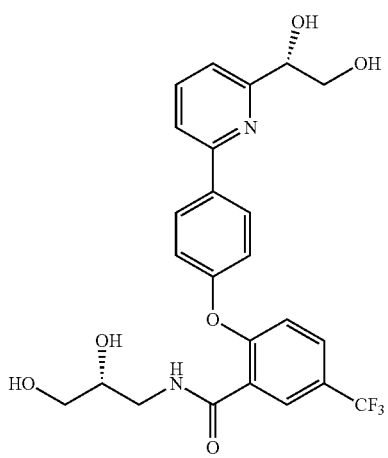
170
168 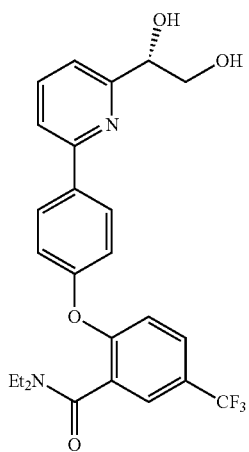
171 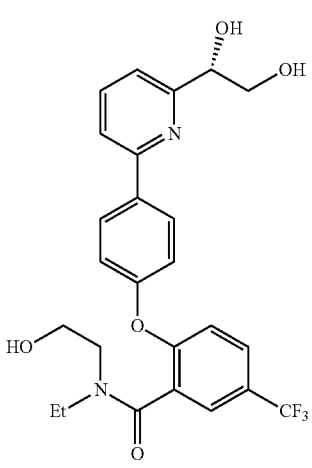
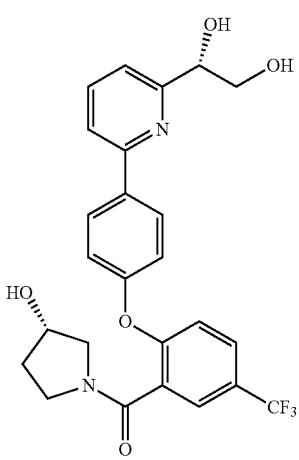

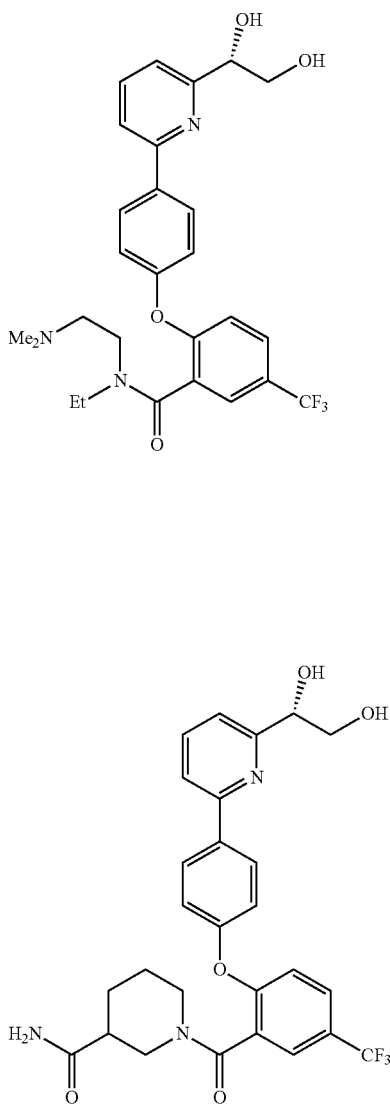
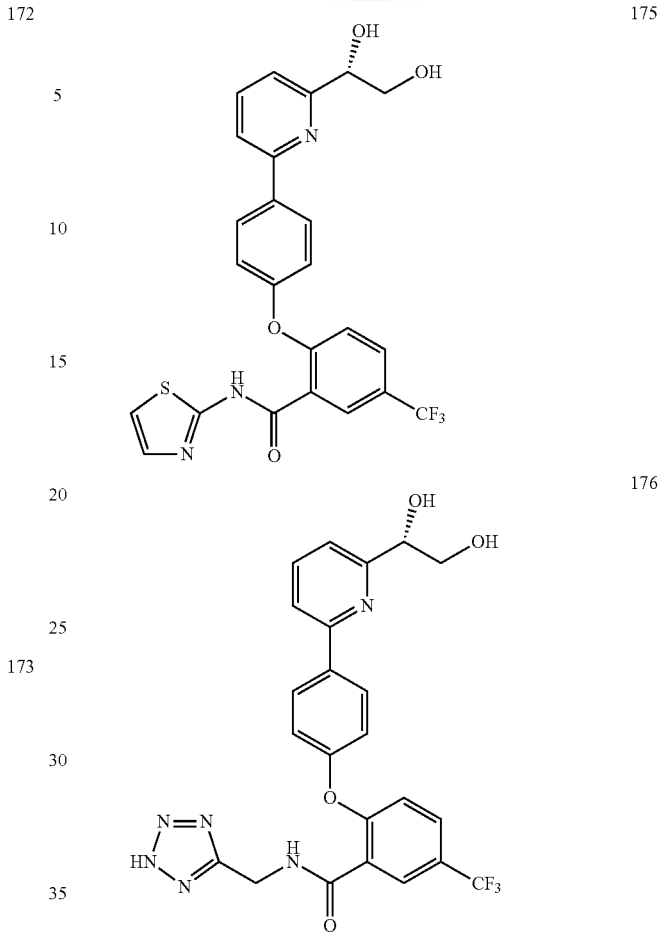

6-(4-(2-((2-Hydroxyethyl)(methyl)carbamoyl)-4-(trifluoromethyl)phenoxy)phenyl)-picolinamide (Compound 161): ¹H NMR (400 MHz, CD₃OD): δ 8.17 (d, J=8.6 Hz, 2H), 7.87-8.05 (m, 3H), 7.54-7.74 (m, 2H), 7.14 (d, J=7.3 Hz, 2H), 7.03 (dd, J=19.3, 8.7 Hz, 1H), 3.66 (br. s., 2H), 3.25-3.55 (m, 2H), 2.87-3.07 (m, 3H). LC/MS: m/z=482.1 [M+Na]⁺ (Calc: 459.4).

6-(4-(2-(4-Methylpiperazine-1-carbonyl)-4-(trifluoromethyl)phenoxy)phenyl)-picolinamide (Compound 162): ¹H NMR (400 MHz, DMSO-d₆): δ 8.33 (d, J=8.6 Hz, 2H), 8.10 (d, J=7.7 Hz, 1H), 7.87-8.03 (m, 2H), 7.69-7.83 (m, 2H), 7.22 (br. s., 2H), 7.05 (br. s., 1H), 4.56 (br. s., 1H), 3.72 (br. s., 1H), 3.24-3.58 (m, 3H), 3.09-3.21 (m, 1H), 3.05 (br. s., 2H), 2.78 (s, 3H). LC/MS: m/z=485.1 [M+H]⁺ (Calc: 484.5).

6-(4-(2-(Methylcarbamoyl)-4-(trifluoromethyl)phenoxy)phenyl)picolinamide (Compound 163): ¹H NMR (400 MHz, DMSO-d₆): δ 8.32 (d, J=8.8 Hz, 2H), 8.09 (d, J=7.7 Hz, 1H), 7.84-8.02 (m, 3H), 7.72 (dd, J=8.6, 2.0 Hz, 1H), 7.20 (d, J=8.6 Hz, 2H), 7.02 (d, J=8.6 Hz, 1H), 2.75 (s, 3H). LC/MS: m/z=416.1 [M+H]⁺ (Calc: 415.4).

6-(4-(2-(Diethylcarbamoyl)-4-(trifluoromethyl)phenoxy)phenyl)picolinamide (Compound 164): ¹H NMR (400 MHz, DMSO-d₆): δ 8.32 (d, J=8.6 Hz, 2H), 8.11 (d, J=7.7 Hz, 1H), 7.93-8.06 (m, 2H), 7.73 (d, J=8.8 Hz, 1H), 7.69 (s, 1H), 7.18 (d, J=8.6 Hz, 2H), 7.12 (d, J=8.6 Hz, 1H), 3.30-3.63 (m, 2H), 3.23 (q, J=7.2 Hz, 2H), 1.07 (dt, J=10.9, 7.1 Hz, 6H). LC/MS: m/z=458.1 [M+H]⁺ (Calc: 457.4).

6-(4-(2-(3-Oxopiperazine-1-carbonyl)-4-(trifluoromethyl)phenoxy)phenyl)-picolinamide (Compound 165): $^1$H NMR (400 MHz, DMSO-d$_6$): δ 8.23-8.38 (m, 2H), 8.05-8.15 (m, 1H), 7.88-8.02 (m, 2H), 7.68-7.82 (m, 2H), 7.10-7.27 (m, 2H), 7.07 (dd, J=13.1, 8.7 Hz, 1H), 3.40-3.92 (m, 3H), 3.00-3.29 (m, 3H). LC/MS: m/z=485.1 [M+H]$^+$ (Calc: 484.4).

(S)-2-(4-(6-(2,2-dimethyl-1,3-dioxolan-4-yl)pyridin-2-yl)phenoxy)-5-(trifluoromethyl)benzoic acid (Compound 166): $^1$H NMR (400 MHz, DMSO-d$_6$): δ 13.13-13.64 (m, 1H), 8.10-8.21 (m, 3H), 7.85-7.96 (m, 3H), 7.45 (d, J=7.3 Hz, 1H), 7.22 (d, J=8.6 Hz, 1H), 7.16 (d, J=8.8 Hz, 2H), 5.19 (t, J=6.6 Hz, 1H), 4.44 (dd, J=8.1, 6.8 Hz, 1H), 3.99 (dd, J=8.3, 6.5 Hz, 1H), 1.47 (s, 3H), 1.43 (s, 3H). LC/MS: m/z=460.1 [M+H]$^+$ (Calc: 459.4).

TFA salt of 2-(4-(6-((S)-1,2-dihydroxyethyl)pyridin-2-yl)phenoxy)-N—((R)-2,3-dihydroxypropyl)-5-(trifluoromethyl)benzamide (Compound 167): $^1$H NMR (400 MHz, CD$_3$OD): δ 8.11 (d, J=2.2 Hz, 1H), 8.00-8.07 (m, 2H), 7.73-7.81 (m, 1H), 7.62-7.71 (m, 2H), 7.41 (d, J=7.7 Hz, 1H), 7.13-7.20 (m, 2H), 7.02 (d, J=8.8 Hz, 1H), 4.73 (dd, J=6.7, 4.3 Hz, 1H), 3.85 (dd, J=11.2, 4.2 Hz, 1H), 3.62-3.73 (m, 2H), 3.48-3.57 (m, 1H), 3.42 (d, J=5.5 Hz, 2H), 3.33 (dd, J=13.8, 6.7 Hz, 1H). LC/MS: m/z=493.2 [M+H]$^+$ (Calc: 492.4).

TFA salt of (S)-2-(4-(6-(1,2-dihydroxyethyl)pyridin-2-yl)phenoxy)-N,N-diethyl-5-(trifluoromethyl)benzamide (Compound 168): $^1$H NMR (400 MHz, CD$_3$OD): δ 8.25 (t, J=7.9 Hz, 1H), 8.02-8.09 (m, 2H), 7.99 (d, J=7.9 Hz, 1H), 7.71-7.86 (m, 3H), 7.25-7.34 (m, 2H), 7.21 (d, J=8.6 Hz, 1H), 5.00 (t, J=5.4 Hz, 1H), 3.81-3.98 (m, 2H), 3.67 (br. s., 1H), 3.42-3.58 (m, 1H), 3.34-3.41 (m, 2H), 1.19 (q, J=7.3 Hz, 6H). LC/MS: m/z=475.2 [M+H]$^+$ (Calc: 474.5).

TFA salt of (S)-2-(4-(6-(1,2-dihydroxyethyl)pyridin-2-yl)phenoxy)-N-ethyl-N-methyl-5-(trifluoromethyl)benzamide (Compound 169): $^1$H NMR (400 MHz, CD$_3$OD): δ 7.98-8.08 (m, 2H), 7.73-7.80 (m, 1H), 7.57-7.68 (m, 3H), 7.40 (d, J=7.7 Hz, 1H), 7.07-7.15 (m, 2H), 7.01 (dd, J=16.4, 8.5 Hz, 1H), 4.73 (dd, J=6.5, 4.3 Hz, 1H), 3.84 (dd, J=11.2, 4.2 Hz, 1H), 3.67 (dd, J=11.3, 6.7 Hz, 1H), 3.35-3.55 (m, 1H), 3.24-3.32 (m, 1H), 2.88-3.02 (m, 3H), 1.08 (q, J=7.0 Hz, 3H). LC/MS: m/z=461.2 [M+H]$^+$ (Calc: 460.4).

TFA salt of (2-(4-(6-((S)-1,2-dihydroxyethyl)pyridin-2-yl)phenoxy)-5-(trifluoro-methyl)phenyl)((S)-3-hydroxypyrrolidin-1-yl)methanone (Compound 170): $^1$H NMR (400 MHz, CD$_3$OD): δ 8.02 (dd, J=8.7, 1.9 Hz, 2H), 7.73-7.84 (m, 1H), 7.60-7.71 (m, 2H), 7.40 (d, J=7.7 Hz, 1H), 7.12 (d, J=7.9 Hz, 2H), 6.97-7.08 (m, 1H), 4.73 (dd, J=6.7, 4.3 Hz, 1H), 4.27-4.44 (m, 1H), 3.85 (dd, J=11.2, 4.2 Hz, 1H), 3.68 (dd, J=11.2, 6.6 Hz, 1H), 3.52 (br. s., 3H), 3.32-3.49 (m, 1H), 1.78-2.08 (m, 2H). LC/MS: m/z=489.1 [M+H]$^+$ (Calc: 488.5).

TFA salt of (S)-2-(4-(6-(1,2-dihydroxyethyl)pyridin-2-yl)phenoxy)-N-ethyl-N-(2-hydroxyethyl)-5-(trifluoromethyl)benzamide (Compound 171): $^1$H NMR (400 MHz, CD$_3$OD): δ 8.02 (dd, J=8.8, 3.3 Hz, 2H), 7.74-7.83 (m, 1H), 7.55-7.70 (m, 3H), 7.40 (d, J=7.7 Hz, 1H), 7.11 (dd, J=8.8, 5.3 Hz, 2H), 7.01 (d, J=8.8 Hz, 1H), 4.73 (dd, J=6.6, 4.2 Hz, 1H), 3.85 (dd, J=11.3, 4.1 Hz, 1H), 3.45-3.76 (m, 5H), 3.29-3.41 (m, 2H), 1.09 (td, J=7.1, 3.2 Hz, 3H). LC/MS: m/z=491.1 [M+H]$^+$ (Calc: 490.5).

TFA salt of (S)-2-(4-(6-(1,2-dihydroxyethyl)pyridin-2-yl)phenoxy)-N-(2-(dimethyl-amino)ethyl)-N-ethyl-5-(trifluoromethyl)benzamide (Compound 172): $^1$H NMR (400 MHz, CD$_3$OD): δ 7.95-8.12 (m, 2H), 7.73-7.83 (m, 1H), 7.56-7.70 (m, 3H), 7.40 (d, J=7.7 Hz, 1H), 7.07-7.16 (m, 2H), 7.03 (dd, J=8.5, 5.8 Hz, 1H), 4.73 (dd, J=6.6, 4.2 Hz, 1H), 3.84 (dd, J=11.2, 4.2 Hz, 1H), 3.50-3.73 (m, 3H), 3.27 (q, J=7.2 Hz, 2H), 2.36-2.59 (m, 2H), 2.21 (s, 3H), 2.00 (s, 3H), 1.09 (dt, J=9.0, 7.2 Hz, 3H). LC/MS: m/z=518.2 [M+H]$^+$ (Calc: 517.5).

TFA salt of 1-(2-(4-(6-((S)-1,2-dihydroxyethyl)pyridin-2-yl)phenoxy)-5-(trifluoro-methyl)benzoyl)piperidine-3-carboxamide (Compound 173): $^1$H NMR (400 MHz, CD$_3$OD): δ 8.03-8.22 (m, 1H), 7.79-8.01 (m, 3H), 7.59-7.75 (m, 3H), 6.99-7.24 (m, 3H), 4.82-4.94 (m, 1H), 4.20-4.56 (m, 1H), 3.70-3.86 (m, 2H), 3.43-3.64 (m, 1H), 2.55-3.17 (m, 2H), 2.25-2.49 (m, 1H), 1.83-2.04 (m, 1H), 1.32-1.81 (m, 3H). LC/MS: m/z=530.1 [M+H]$^+$ (Calc: 529.5).

TFA salt of (S)-2-(4-(6-(1,2-dihydroxyethyl)pyridin-2-yl)phenoxy)-N-(1,3,4-thiadiazol-2-yl)-5-(trifluoromethyl)benzamide (Compound 174): $^1$H NMR (400 MHz, CD$_3$OD): δ 8.06-8.20 (m, 2H), 7.90-8.00 (m, 2H), 7.84 (d, J=7.5 Hz, 1H), 7.81 (dd, J=8.8, 2.2 Hz, 1H), 7.67 (d, J=7.7 Hz, 1H), 7.22-7.31 (m, 2H), 7.16 (d, J=8.8 Hz, 1H), 4.87 (t, J=5.4 Hz, 1H), 3.66-3.90 (m, 2H). LC/MS: m/z=503.1 [M+H]$^+$ (Calc: 502.5).

TFA salt of (S)-2-(4-(6-(1,2-dihydroxyethyl)pyridin-2-yl)phenoxy)-N-(thiazol-2-yl)-5-(trifluoromethyl)benzamide (Compound 175): $^1$H NMR (400 MHz, CD$_3$OD): δ 8.12-8.24 (m, 2H), 7.92-7.99 (m, 2H), 7.89 (d, J=7.9 Hz, 1H), 7.79 (dd, J=8.7, 2.3 Hz, 1H), 7.72 (d, J=7.9 Hz, 1H), 7.38 (d, J=3.5 Hz, 1H), 7.28 (d, J=8.6 Hz, 2H), 7.15 (d, J=8.8 Hz, 1H), 7.09 (d, J=3.5 Hz, 1H), 4.90 (t, J=5.4 Hz, 1H), 3.69-3.86 (m, 2H). LC/MS: m/z=502.0 [M+H]$^+$ (Calc: 501.5).

TFA salt of (S)—N-((1H-tetrazol-5-yl)methyl)-2-(4-(6-(1,2-dihydroxyethyl)pyridin-2-yl)phenoxy)-5-(trifluoromethyl)benzamide (Compound 176): $^1$H NMR (400 MHz, CD$_3$OD): δ 8.18 (t, J=7.9 Hz, 1H), 8.13 (d, J=2.2 Hz, 1H), 7.86-7.96 (m, 3H), 7.73 (d, J=8.1 Hz, 2H), 7.16 (d, J=8.8 Hz, 2H), 7.10 (d, J=8.8 Hz, 1H), 4.91 (t, J=5.4 Hz, 1H), 4.75 (s, 2H), 3.79 (dd, J=5.3, 2.0 Hz, 2H). LC/MS: m/z=501.1 [M+H]$^+$ (Calc: 500.4).

Example 18

Representative Compounds of the Disclosure have been tested in the FLIPR®, FLIPR$^{TETRA®}$, and/or electrophysiology (EP) assays for sodium channel blocking activity, which is described in detail above. Representative values obtained from CoroNa™ Green AM Na$^+$ dye for primary fluorescence assay and/or EP assays are presented in TABLE 4, and representative values from membrane potential dye for alternative fluorescence assays and/or EP assays for are presented in TABLE 5.

TABLE 4

Evaluation of compounds as sodium channel (Na$_v$) blockers

| Compound | Na$_v$1.7 Activity (μM) FLIPR assay IC$_{50}$ |
|---|---|
| 15 | 0.147 ± 0.016 |
| 16 | 0.104 ± 0.020 |
| 17 | 0.067 ± 0.019 |
| 18 | 0.426 ± 0.084 |
| 19 | 0.337 ± 0.006 |
| 20 | 0.124 ± 0.016 |
| 21 | 0.564 ± 0.035 |
| 22 | 0.285 ± 0.009 |
| 23 | >20 |
| 24 | 0.152 ± 0.031 |
| 25 | 0.039 ± 0.001 |

TABLE 4-continued

Evaluation of compounds as sodium channel (Na$_v$) blockers

| Compound | Na$_v$1.7 Activity (µM)<br>FLIPR assay<br>IC$_{50}$ |
|---|---|
| 26 | 0.054 ± 0.005 |
| 27 | 0.549 ± 0.085 |
| 28 | 0.101 ± 0.021 |
| 29 | 0.117 ± 0.036 |
| 30 | 0.049 ± 0.003 |
| 31 | 2.144 ± 0.432 |
| 32 | 3.046 ± 0.942 |
| 33 | 0.221 ± 0.049 |
| 34 | 1.771 ± 0.570 |
| 35 | 0.141 ± 0.022 |
| 36 | 0.432 ± 0.131 |
| 37 | 1.075 ± 0.117 |
| 38 | 1.692 ± 0.157 |
| 39 | 0.179 ± 0.034 |
| 40 | 1.680 ± 0.177 |
| 41 | 1.130 ± 0.100 |
| 42 | 1.166 ± 0.186 |
| 43 | 0.223 ± 0.018 |
| 44 | 1.157 ± 0.076 |
| 45 | 0.113 ± 0.034 |
| 46 | 2.584 ± 0.692 |
| 47 | 0.949 ± 0.168 |
| 48 | 0.913 ± 0.016 |
| 49 | 0.096 ± 0.010 |
| 50 | 0.768 ± 0.051 |
| 51 | 0.566 ± 0.062 |
| 52 | 1.104 ± 0.107 |
| 53 | 0.384 ± 0.106 |
| 54 | 0.366 ± 0.085 |
| 55 | 0.174 ± 0.018 |
| 56 | 0.173 ± 0.033 |
| 58 | 0.231 ± 0.008 |
| 59 | >20 |
| 60 | 1.848 ± 0.361 |
| 61 | 2.035 ± 0.060 |
| 62 | 0.310 ± 0.066 |
| 63 | 0.337 ± 0.056 |
| 64 | 2.136 ± 0.199 |
| 65 | 0.862 ± 0.012 |
| 74 | 0.672 ± 0.059 |
| 75 | 0.972 ± 0.114 |
| 77 | 2.448 ± 0.344 |
| 79 | >20 |
| 81 | 0.710 ± .0008 |
| 82 | 2.718 ± 0.264 |
| 83 | 6.048 ± 1.328 |
| 84 | 10-20 |
| 85 | 0.561 ± 0.024 |
| 86 | 0.490 ± 0.041 |
| 87 | 0.128 ± 0.030 |
| 89 | >20 |
| 90 | >20 |
| 91 | 0.577 ± 0.056 |
| 92 | >20 |
| 93 | >20 |
| 94 | >20 |
| 95 | 1.335 ± 0.209 |
| 96 | 1.133 ± 0.110 |
| 97 | 4.239 ± 0.919 |
| 98 | 0.961 ± 0.070 |
| 99 | 0.550 ± 0.057 |
| 100 | 0.276 ± 0.063 |
| 101 | 1.827 ± 0.383 |
| 102 | 1.299 ± 0.126 |
| 103 | 0.312 ± 0.008 |
| 104 | >20 |
| 105 | 0.362 ± 0.095 |
| 106 | 0.455 ± 0.059 |
| 107 | 0.174 ± 0.041 |
| 108 | 0.280 ± 0.009 |
| 109 | 1.302 ± 0.056 |
| 111 | 6.592 ± 0.321 |
| 112 | >20 |
| 113 | 0.249 ± 0.016 |
| 114 | 2.010 ± 0.456 |
| 115 | 0.455 ± 0.067 |
| 116 | 0.636 ± 0.065 |
| 117 | 0.066 ± 0.007 |
| 118 | 0.118 ± 0.012 |
| 119 | 0.590 ± 0.092 |
| 120 | 0.578 ± 0.098 |
| 121 | 0.716 ± 0.090 |
| 144 | 3.795 ± 0.377 |
| 145 | 3.336 ± 0.452 |
| 155 | >20 |
| 156 | 1.291 ± 0.182 |
| 157 | 2.707 ± 0.235 |
| 158 | 0.214 ± 0.029 |
| 159 | 1.258 ± 0.135 |
| 160 | 2.853 ± 0.698 |
| 161 | >20 |
| 162 | 7.954 ± 0.402 |
| 163 | >20 |
| 164 | 0.143 ± 0.023 |
| 165 | >20 |

TABLE 5

Evaluation of compounds as sodium channel (Na$_v$) blockers

| Compound | Na$_v$1.7 Activity (µM)<br>FLIPR assay<br>IC$_{50}$ |
|---|---|
| 122 | 0.079 ± 0.015 |
| 123 | 0.149 ± 0.056 |
| 124 | 0.367 ± 0.028 |
| 125 | 0.311 ± 0.006 |
| 126 | 0.288 ± 0.045 |
| 127 | 0.486 ± 0.032 |
| 128 | 0.684 ± 0.034 |
| 129 | 0.702 ± 0.035 |
| 130 | 1.280 ± 0.135 |
| 131 | >20 |
| 132 | 9.802 ± 0.365 |
| 133 | 0.699 ± 0.045 |
| 134 | 0.393 ± 0.048 |
| 135 | 0.294 ± 0.054 |
| 136 | >20 |
| 137 | >20 |
| 138 | 0.600 ± 0.077 |
| 139 | 10~20 |
| 140 | 4.229 ± 0.479 |
| 141 | 0.450 ± 0.053 |
| 167 | >20 |
| 168 | 0.519 ± 0.083 |
| 169 | 1.548 ± 0.286 |
| 170 | >20 |
| 171 | >20 |
| 172 | 7.971 ± 1.188 |
| 173 | >20 |
| 174 | 3.609 ± 0.229 |
| 175 | 1.315 ± 0.054 |
| 176 | >20 |

Having now fully described this disclosure, it will be understood by those of ordinary skill in the art that the same can be performed within a wide and equivalent range of conditions, formulations and other parameters without affecting the scope of the disclosure or any embodiment thereof.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound having Formula I:

Z-HET-E      I or a pharmaceutically acceptable salt or solvate thereof, wherein:

Z is:

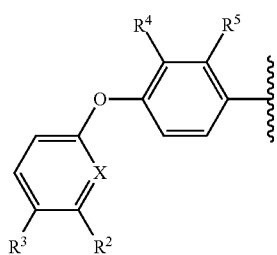

HET is a 6-membered nitrogen-containing heteroaryl selected from the group consisting of:

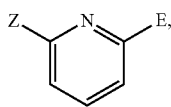 HET-1

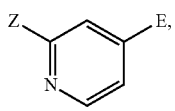 HET-2

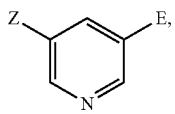 HET-3

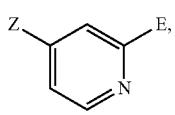 HET-4

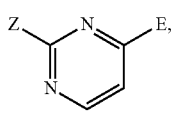 HET-5

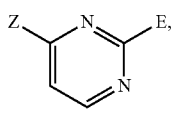 HET-6

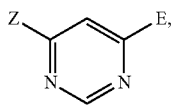 HET-7

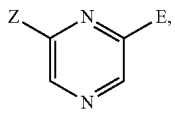 HET-8

-continued

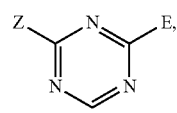 HET-9

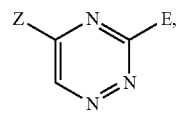 HET-10

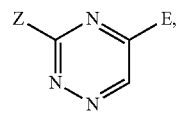 HET-11

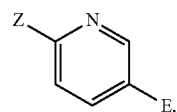 HET-12

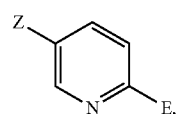 HET-13

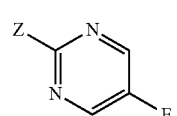 HET-14

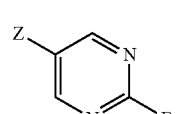 HET-15

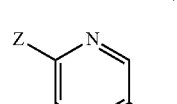 HET-16

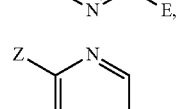 HET-17

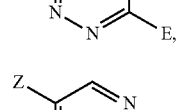 HET-18

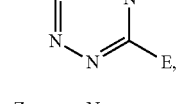 HET-19

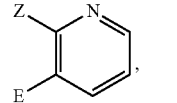 HET-20

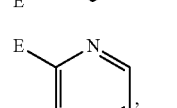,

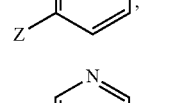,

-continued

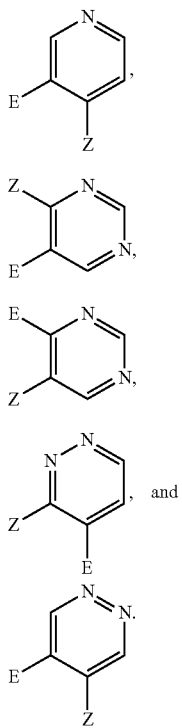

HET-22

HET-23

HET-24

HET-25

E is selected from the group consisting of:

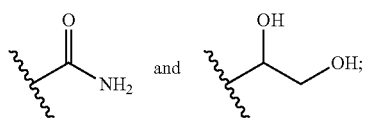

X is selected from the group consisting of N and $CR^1$;
$R^1$ is selected from the group consisting of:
  a) hydrogen;
  b) optionally substituted heteroaryl;
  c) heteroalkyl;
  d) (aralkylamino)alkyl
  e) (heterocyclo)alkyl;
  f) optionally substituted aryl;
  g) (heterocycloalkylamino)alkyl;
  h) (heterocycloamino)alkyl;
  i) alkanolamine;
  j) hydroxyalkyl;
  k) (amino)alkyl;
  l) (alkylamino)alkyl;
  m) (dialkylamino)alkyl;
  n) (cycloalkylamino)alkyl;
  o) (nitro)alkyl;
  p) (carboxamido)alkyl; and
  q) (haloalkylamino)alkyl;
$R^2$ is selected from the group consisting of:
  a) hydrogen;
  b) optionally substituted heteroaryl;
  c) heteroalkyl;
  d) (aralkylamino)alkyl
  e) (heterocyclo)alkyl;
  f) optionally substituted aryl;
  g) (heterocycloalkylamino)alkyl;
  h) (heterocycloamino)alkyl;
  i) alkanolamine;
  j) hydroxyalkyl;
  k) (amino)alkyl;
  l) (alkylamino)alkyl;
  m) (dialkylamino)alkyl;
  n) (cycloalkylamino)alkyl;
  o) (nitro)alkyl;
  p) (carboxamido)alkyl; and
  q) (haloalkylamino)alkyl;
with the proviso that at least one of $R^1$ and $R^2$ is hydrogen;
$R^3$ is selected from the group consisting of:
  a) hydrogen;
  b) halo;
  c) cyano;
  d) haloalkyl;
  e) $C_1$-$C_4$ alkyl;
  f) $C_{1-4}$ haloalkyl;
  g) $C_{1-4}$ haloalkoxy; and
  h) $C_{1-4}$ alkoxy;
$R^4$ is selected from the group consisting of:
  a) hydrogen;
  b) chloro;
  c) cyano;
  d) $C_{1-4}$ haloalkyl;
  e) arylamino;
  f) (arylamino)alkyl;
  g) (aryloxy)alkyl;
  h) (dialkylamino)alkyl;
  i) alkoxyalkyl;
  j) (heterocyclo)alkyl;
  k) optionally substituted aryl; and
  l) optionally substituted heteroaryl;
$R^5$ is selected from the group consisting of:
  a) hydrogen;
  b) chloro;
  c) cyano;
  d) $C_{1-4}$ haloalkyl;
  e) arylamino;
  f) (arylamino)alkyl;
  g) (aryloxy)alkyl;
  h) (dialkylamino)alkyl;
  i) alkoxyalkyl;
  j) (heterocyclo)alkyl;
  k) optionally substituted aryl; and
  l) optionally substituted heteroaryl,
with the provisos:
  1) when X is $CR^1$ and $R^1$ is hydrogen or hydroxyalkyl, then:
    i) $R^2$ is selected from the group consisting of optionally substituted heteroaryl; heteroalkyl; (aralkylamino)alkyl (heterocyclo)alkyl; optionally substituted aryl; (heterocycloalkylamino)alkyl; (heterocycloamino)alkyl; alkanolamine; hydroxyalkyl; (amino)alkyl; (alkylamino)alkyl; (dialkylamino)alkyl; (cycloalkylamino)alkyl; (nitro)alkyl; (carboxamido)alkyl; and (haloalkylamino)alkyl; or
    ii) $R^4$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
    iii) $R^5$ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or 2) when X is CR¹ and R² is hydrogen, then:
i) R¹ is selected from the group consisting of optionally substituted heteroaryl; heteroalkyl; (aralkylamino)alkyl; (heterocyclo)alkyl; optionally substituted aryl; (heterocycloalkylamino)alkyl; (heterocycloamino)alkyl; alkanolamine; (amino)alkyl; (alkylamino)alkyl; (dialkylamino)alkyl; (cycloalkylamino)alkyl; (nitro)alkyl; (carboxamido)alkyl; and (haloalkylamino)alkyl; or
ii) R⁴ is selected from the group consisting of arylamino; (arylamino)alkyl; (aryloxy)alkyl; (dialkylamino)alkyl; (heterocyclo)alkyl; optionally substituted aryl; and optionally substituted heteroaryl; or
iii) R⁵ is selected from the group consisting of arylamino; (arylamino)alkyl; (aryloxy)alkyl; (dialkylamino)alkyl; (heterocyclo)alkyl; optionally substituted aryl; and optionally substituted heteroaryl.

2. The compound of claim 1, or a pharmaceutically acceptable salt or solvate thereof, wherein HET is selected from the group consisting of HET-1, HET-2, HET-3, HET-4, HET-12, HET-13, HET-19, HET-20, HET-21, and HET-22.

3. The compound of claim 1 having Formula II:

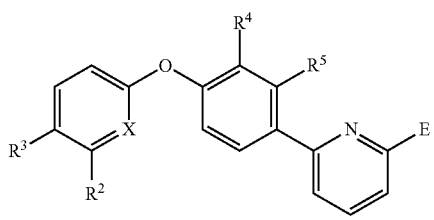

or a pharmaceutically acceptable salt or solvate thereof.

4. The compound of claim 3, or a pharmaceutically acceptable salt or solvate thereof, wherein R⁵ is selected from the group consisting of hydrogen; chloro; and $C_{1-4}$ haloalkyl.

5. The compound of claim 1, or a pharmaceutically acceptable salt or solvate thereof, having Formula III:

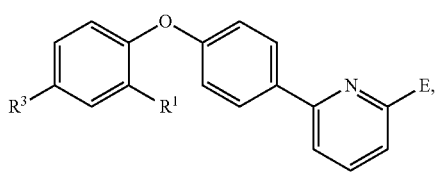

wherein:
R¹ is selected from the group consisting of:
a) optionally substituted heteroaryl;
b) heteroalkyl;
c) (aralkylamino)alkyl;
d) (heterocyclo)alkyl;
e) optionally substituted aryl;
f) (heterocycloalkylamino)alkyl;
g) (heterocycloamino)alkyl;
h) alkanolamine;
i) (amino)alkyl;
j) (alkylamino)alkyl;
k) (dialkylamino)alkyl;
l) (cycloalkylamino)alkyl;
m) (nitro)alkyl; and
n) (carboxamido)alkyl.

6. The compound of claim 5, or a pharmaceutically acceptable salt or solvate thereof, wherein R¹ is selected from the group consisting of:
a) optionally substituted heteroaryl;
b) (heterocyclo)alkyl; and
c) (dialkylamino)alkyl.

7. The compound of claim 6, or a pharmaceutically acceptable salt or solvate thereof, wherein R³ is selected from the group consisting of halo, cyano, and haloalkyl.

8. The compound of claim 1, or a pharmaceutically acceptable salt or solvate thereof, having Formula IV:

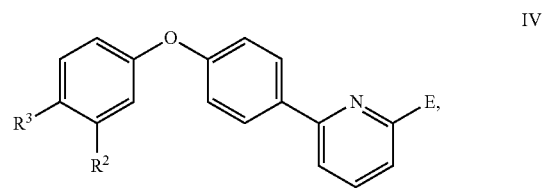

wherein R² is selected from the group consisting of heteroaryl; (heterocyclo)alkyl; and (haloalkylamino)alkyl.

9. The compound of claim 8, or a pharmaceutically acceptable salt or solvate thereof, wherein R³ is selected from the group consisting of cyano and haloalkyl.

10. The compound of claim 1, or a pharmaceutically acceptable salt or solvate thereof, having Formula V:

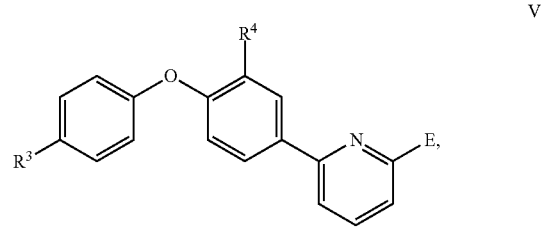

wherein R⁴ is selected from the group consisting of:
a) arylamino;
b) (arylamino)alkyl;
c) (aryloxy)alkyl;
d) (dialkylamino)alkyl;
e) (heterocyclo)alkyl;
f) optionally substituted aryl; and
g) optionally substituted heteroaryl.

11. The compound of claim 1, or a pharmaceutically acceptable salt or solvate thereof, having Formula VI:

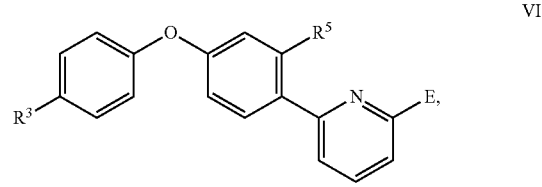

wherein R⁵ is selected from the group consisting of:
a) arylamino;
b) (arylamino)alkyl;
c) (aryloxy)alkyl;

d) (dialkylamino)alkyl;
e) (heterocyclo)alkyl;
f) optionally substituted aryl; and
g) optionally substituted heteroaryl.

12. The compound of claim 1, or a pharmaceutically acceptable salt or solvate thereof, wherein E is:

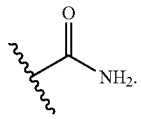

13. The compound of claim 1, or a pharmaceutically acceptable salt or solvate thereof, wherein E is selected from the group consisting of:

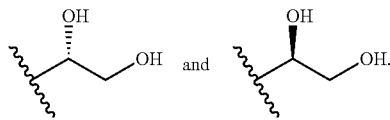 [SMILES: *[C@H](O)CO ; *[C@@H](O)CO]

14. The compound of claim 1, or a pharmaceutically acceptable salt or solvate thereof, selected from the group consisting of:
6-(2-chloro-4-(4-fluorophenoxy)phenyl)picolinamide;
6-(3-chloro-4-(4-fluorophenoxy)phenyl)picolinamide;
6-(3-cyano-4-(4-fluorophenoxy)phenyl)picolinamide;
6-(4-(4-fluorophenoxy)-3-(trifluoromethyl)phenyl)picolinamide;
6-(4-(4-fluorophenoxy)-2-(trifluoromethyl)phenyl)picolinamide;
6-(4-(4-fluorophenoxy)-3-(methyl(phenyl)amino)phenyl)picolinamide;
4-((5-(6-carbamoylpyridin-2-yl)-2-(4-fluorophenoxy)benzyl)(methyl)amino)benzoic acid;
6-(3-((4-chloro-2-iodophenoxy)methyl)-4-(4-fluorophenoxy)phenyl)picolinamide;
6-(3-((diethylamino)methyl)-4-(4-fluorophenoxy)phenyl)picolinamide;
6-(3-(ethoxymethyl)-4-(4-fluorophenoxy)phenyl)picolinamide;
6-(4-(4-fluorophenoxy)-3-(pyrrolidin-1-ylmethyl)phenyl)picolinamide;
6-(4-(4-fluorophenoxy)-3-(morpholinomethyl)phenyl)picolinamide;
6-(2-fluoro-4-(4-fluorophenoxy)phenyl)picolinamide;
6-(4'-chloro-6-(4-fluorophenoxy)-[1,1'-biphenyl]-3-yl)picolinamide;
6-(4-(4-fluorophenoxy)-3-(2H-tetrazol-5-yl)phenyl)picolinamide;
6-(4-(4-fluorophenoxy)-3-((methyl(phenyl)amino)methyl)phenyl)picolinamide;
6-(4-(4-fluorophenoxy)-3-(methoxymethyl)phenyl)picolinamide;
6-(4-(4-fluorophenoxy)-3-((4-fluorophenoxy)methyl)phenyl)picolinamide;
6-(3-((4-cyanophenoxy)methyl)-4-(4-fluorophenoxy)phenyl)picolinamide;
6-(4-cyano-2-(pyridin-4-yl)phenoxy)phenyl)picolinamide;
6-(4-(2-(((2-(dimethylamino)ethyl)amino)methyl)-4-(trifluoromethyl)phenoxy)-phenyl)picolinamide;
6-(4-(4-cyano-2-(pyridin-3-yl)phenoxy)phenyl)picolinamide;
6-(4-(2-(((4-sulfamoylphenethyl)amino)methyl)-4-(trifluoromethyl)phenoxy)-phenyl)picolinamide;
6-(4-(2-((4-methylpiperazin-1-yl)methyl)-4-(trifluoromethyl)phenoxy)phenyl) picolinamide;
6-(4-(2-(((2-(2-oxoimidazolidin-1-yl)ethyl)amino)methyl)-4-(trifluoromethyl)phenoxy)phenyl)picolinamide;
6-(4-(4-cyano-2-(1-methyl-1H-pyrrol-2-yl)phenoxy)phenyl)picolinamide;
6-(4-(2-((3-oxopiperazin-1-yl)methyl)-4-(trifluoromethyl)phenoxy)phenyl) picolinamide;
6-(4-(2-(pyrrolidin-1-ylmethyl)-4-(trifluoromethyl)phenoxy)phenyl)picolinamide;
(S)-6-(4-(2-((3-hydroxypyrrolidin-1-yl)methyl)-4-(trifluoromethyl)phenoxy)phenyl) picolinamide;
6-(4-((4'-amino-5-cyano-[1,1'-biphenyl]-2-yl)oxy)phenyl)picolinamide;
6-(4-(4-cyano-2-(thiophen-3-yl)phenoxy)phenyl)picolinamide;
6-(4-(4-cyano-2-(6-methoxypyridin-3-yl)phenoxy)phenyl)picolinamide;
6-(4-(4-cyano-3-(pyridin-4-yl)phenoxy)phenyl)picolinamide;
6-(4-(4-cyano-3-(pyridin-3-yl)phenoxy)phenyl)picolinamide;
6-(4-(4-cyano-2-(1-methyl-1H-pyrazol-4-yl)phenoxy)phenyl)picolinamide;
6-(4-(4-cyano-2-(1-methyl-1H-pyrazol-5-yl)phenoxy)phenyl)picolinamide;
6-(4-(4-cyano-2-(6-hydroxypyridin-3-yl)phenoxy)phenyl)picolinamide;
6-(4-(4-cyano-2-(2-methoxypyridin-3-yl)phenoxy)phenyl)picolinamide;
6-(4-(2-(((2-(dimethylamino)ethyl)(methyl)amino)methyl)-4-(trifluoromethyl)-phenoxy)phenyl)picolinamide;
6-(4-(4-cyano-2-(2-methoxypyridin-4-yl)phenoxy)phenyl)picolinamide;
6-(4-(2-(((3-(dimethylamino)propyl)amino)methyl)-4-(trifluoromethyl)phenoxy) phenyl)picolinamide;
6-(4-(2-((dimethylamino)methyl)-4-(trifluoromethyl)phenoxy)phenyl)picolinamide;
6-(4-(2-(((2-hydroxyethyl)amino)methyl)-4-(trifluoromethyl)phenoxy)phenyl) picolinamide;
6-(4-(2-(1-hydroxy-2-nitroethyl)-4-(trifluoromethyl)phenoxy)phenyl)picolinamide;
6-(4-(2-(aminomethyl)-4-(trifluoromethyl)phenoxy)phenyl)picolinamide;
(S)-6-(4-(2-((2-(hydroxymethyl)pyrrolidin-1-yl)methyl)-4-(trifluoromethyl)-phenoxy)phenyl) picolinamide;
(R)-6-(4-(2-((2-(hydroxymethyl)pyrrolidin-1-yl)methyl)-4-(trifluoromethyl)phenoxy) phenyl)picolinamide;
6-(4-(2-(morpholinomethyl)-4-(trifluoromethyl)phenoxy)phenyl)picolinamide
(S)-6-(4-(2-((2-carbamoylpyrrolidin-1-yl)methyl)-4-(trifluoromethyl)-phenoxy)phenyl) picolinamide;
6-(4-(2-((3,3-difluoropyrrolidin-1-yl)methyl)-4-(trifluoromethyl)phenoxy)phenyl) picolinamide;
(S)-6-(4-(2-(((2-oxopyrrolidin-3-yl)amino)methyl)-4-(trifluoromethyl)phenoxy)-phenyl)picolinamide;
6-(4-(2-((3-aminopyrrolidin-1-yl)methyl)-4-(trifluoromethyl)phenoxy)phenyl) picolinamide;
tert-butyl (1-(2-(4-(6-carbamoylpyridin-2-yl)phenoxy)-5-(trifluoromethyl)benzyl) pyrrolidin-3-yl)carbamate;

tert-butyl 3-((2-(4-(6-carbamoylpyridin-2-yl)phenoxy)-5-(trifluoromethyl)benzyl) amino)pyrrolidine-1-carboxylate;

6-(4-(2-((pyrrolidin-3-ylamino)methyl)-4-(trifluoromethyl)phenoxy)phenyl) picolinamide;

6-(4-(2-(2-amino-1-hydroxyethyl)-4-(trifluoromethyl)phenoxy)phenyl)picolinamide;

6-(4-(3-(azetidin-1-ylmethyl)-4-(trifluoromethyl)phenoxy)phenyl)picolinamide;

(S)-6-(4-(3-((3-hydroxypyrrolidin-1-yl)methyl)-4-(trifluoromethyl)phenoxy)phenyl) picolinamide;

6-(4-(4-(trifluoromethyl)-3-(((3,3,3-trifluoropropyl)amino)methyl)phenoxy)phenyl) picolinamide;

6-(4-(3-((3-oxopiperazin-1-yl)methyl)-4-(trifluoromethyl)phenoxy)-phenylpicolinamide;

6-(4-(3-(pyrrolidin-1-ylmethyl)-4-(trifluoromethyl)phenoxy)phenyl)picolinamide;

6-(4-(2-(pyridin-4-yl)-4-(trifluoromethyl)phenoxy)phenyl)picolinamide;

6-(4-(2-(pyridin-3-yl)-4-(trifluoromethyl)phenoxy)phenyl)picolinamide;

6-(4-(3-((3-aminoazetidin-1-yl)methyl)-4-(trifluoromethyl)phenoxy)phenyl) picolinamide;

(S)-4-(2-(4-(6-(1,2-dihydroxyethyl)pyridin-2-yl)phenoxy)-5-(trifluoromethyl)benzyl) piperazin-2-one;

(S)-1-(6-(4-(2-(((S)-3-hydroxypyrrolidin-1-yl)methyl)-4-(trifluoromethyl)phenoxy) phenyl)pyridin-2-yl)ethane-1,2-diol;

6-(4-(2-(1-hydroxy-2-(3-oxopiperazin-1-yl)ethyl)-4-(trifluoromethyl)phenoxy)-phenyl)picolinamide;

6-(4-(2-(2-amino-2-oxo-1-(pyrrolidin-1-yl)ethyl)-4-(trifluoromethyl)phenoxy)-phenyl)picolinamide;

(R)-6-(4-(2-(1,2-dihydroxyethyl)-4-(trifluoromethyl)phenoxy)phenyl)picolinamide;

6-(4-(2-(piperidin-1-ylmethyl)-4-(trifluoromethyl)phenoxy)phenyl)picolinamide;

6-(4-(2-(azetidin-1-ylmethyl)-4-(trifluoromethyl)phenoxy)phenyl)picolinamide;

6-(4-(2-((3-hydroxypiperidin-1-yl)methyl)-4-(trifluoromethyl)phenoxy)phenyl) picolinamide;

6-(4-(2-(((2-hydroxyethyl)(methyl)amino)methyl)-4-(trifluoromethyl)phenoxy)-phenyl)picolinamide;

6-(4-(2-(1-(pyrrolidin-1-yl)ethyl)-4-(trifluoromethyl)phenoxy)phenyl)picolinamide;

6-(4-((6-(pyrrolidin-1-ylmethyl)pyridin-2-yl)oxy)phenyl) picolinamide;

6-(4-(2-(2-amino-2-oxo-1-(piperidin-1-yl)ethyl)-4-(trifluoromethyl)phenoxy)phenyl) picolinamide;

6-(4-(2-(2-amino-2-oxo-1-(propylamino)ethyl)-4-(trifluoromethyl)phenoxy)phenyl) picolinamide;

6-(4-(2-(2-amino-1-(dimethylamino)-2-oxoethyl)-4-(trifluoromethyl)phenoxy)-phenyl)picolinamide; and 6-(4-(2-(2-amino-1-(diethylamino)-2-oxoethyl)-4-(trifluoromethyl)phenoxy)phenyl) picolinamide.

15. A pharmaceutical composition comprising the compound of claim 1, or a pharmaceutically acceptable salt or solvate thereof, and a pharmaceutically acceptable carrier.

16. A method for treating pain in a mammal, comprising administering an effective amount of a compound as claimed in claim 1, or a pharmaceutically acceptable salt or solvate thereof, to a mammal in need of such treatment.

17. The method of claim 16, wherein said pain is selected from the group consisting of chronic pain, inflammatory pain, neuropathic pain, acute pain, and surgical pain.

* * * * *